United States Patent
Buchstaller et al.

(10) Patent No.: US 9,809,598 B2
(45) Date of Patent: Nov. 7, 2017

(54) HETEROCYCLYL-BUTANAMIDE DERIVATIVES

(71) Applicant: Merck Patent GmbH, Darmstadt (DE)

(72) Inventors: Hans-Peter Buchstaller, Griesheim (DE); Dieter Dorsch, Ober-Ramstadt (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 15/308,974

(22) PCT Filed: Apr. 16, 2015

(86) PCT No.: PCT/EP2015/000793
§ 371 (c)(1),
(2) Date: Nov. 4, 2016

(87) PCT Pub. No.: WO2015/169421
PCT Pub. Date: Nov. 12, 2015

(65) Prior Publication Data
US 2017/0073347 A1    Mar. 16, 2017

(30) Foreign Application Priority Data

May 7, 2014 (EP) ..................... 14001613

(51) Int. Cl.
| C07D 487/04 | (2006.01) |
| A61K 31/517 | (2006.01) |
| C07D 491/052 | (2006.01) |
| A61K 31/502 | (2006.01) |
| A61K 31/501 | (2006.01) |
| A61K 31/4985 | (2006.01) |
| A61K 31/454 | (2006.01) |
| C07D 413/06 | (2006.01) |
| C07D 401/14 | (2006.01) |
| C07D 491/04 | (2006.01) |
| C07D 495/04 | (2006.01) |
| C07D 413/04 | (2006.01) |
| C07D 401/06 | (2006.01) |
| C07D 471/04 | (2006.01) |
| A61K 31/519 | (2006.01) |

(52) U.S. Cl.
CPC .......... *C07D 487/04* (2013.01); *A61K 31/454* (2013.01); *A61K 31/4985* (2013.01); *A61K 31/501* (2013.01); *A61K 31/502* (2013.01); *A61K 31/517* (2013.01); *A61K 31/519* (2013.01); *C07D 401/06* (2013.01); *C07D 401/14* (2013.01); *C07D 413/04* (2013.01); *C07D 413/06* (2013.01); *C07D 471/04* (2013.01); *C07D 491/04* (2013.01); *C07D 491/052* (2013.01); *C07D 495/04* (2013.01)

(58) Field of Classification Search
CPC .... A61K 31/445; A61K 38/21; A61K 31/225; A61K 39/3955; A61K 31/517; A61K 31/695; A61K 31/4545; A61K 31/498; A61K 31/4709; A61K 31/55; A61K 31/502; A61K 31/501; A61K 31/4985; A61K 31/454; A61K 31/519; C07K 16/2842; C07D 215/20; C07D 405/12; C07D 211/34; C07D 211/62; C07D 401/06; C07D 211/60; C07D 487/04; C07D 491/052; C07D 413/06; C07D 401/14; C07D 491/04; C07D 495/04; C07D 413/04; C07D 471/04; C07D 491/06
See application file for complete search history.

(56) References Cited

U.S. PATENT DOCUMENTS

| 2008/0039480 A1 | 2/2008 | Kennis et al. |
| 2015/0025070 A1 | 1/2015 | Cheung et al. |
| 2015/0225396 A1 | 8/2015 | Bregman et al. |

FOREIGN PATENT DOCUMENTS

| WO | 2006/003148 A1 | 1/2006 |
| WO | 2013/012723 A1 | 1/2013 |
| WO | 2014/036022 A1 | 3/2014 |
| WO | 2015/014442 A1 | 2/2015 |

OTHER PUBLICATIONS

Curtin, N.J., "Therapeutic applications of PARP inhibitors: anticancer therapy and beyond." Molecular aspects of medicine 34.6 (2013): 1217-1256.*
Diem, R., "Neurodegeneration and—protection in autoimmune CNS inflammation." Journal of neuroimmunology 184.1 (2007): 27-36.*

(Continued)

*Primary Examiner* — Matt Mauro
(74) *Attorney, Agent, or Firm* — Millen, White, Zelano, Branigan, P.C.

(57) ABSTRACT

Compounds of the formula I

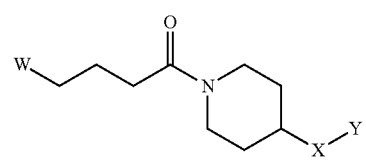

in which W, X and Y have the meanings indicated in Claim 1, are inhibitors of Tankyrase, and can be employed, inter alia, for the treatment of diseases such as cancer, cardiovascular diseases, central nervous system injury and different forms of inflammation.

20 Claims, No Drawings

(56) References Cited

OTHER PUBLICATIONS

Liu, J.K.H., "Anti-Cancer Vaccines—A One-Hit Wonder'?." The Yale journal of biology and medicine 87.4 (2014): 481-489.*
Mayo Clinic Diseases and Conditions—Multiple Sclerosis 2014; http://www.mayoclinic.org/diseases-conditions/multiple-sclerosis/basics/causes/con-20026.*
National Institute of Neurological Disorders and Stroke (NINDS) 2015; http://www.ninds.nih.gov/disorders/multiple_sclerosis/multiple_sclerosis.htm.*
International Search Report dated Jun. 25, 2015, issued in corresponding PCT/EP2015/000793, 3 pages.

* cited by examiner

HETEROCYCLYL-BUTANAMIDE DERIVATIVES

BACKGROUND OF THE INVENTION

The invention had the object of finding novel compounds having valuable properties, in particular those which can be used for the preparation of medicaments.

The present invention relates to heterocyclyl-butanamide derivatives which inhibit the activity of Tankyrases (TANKs) and poly(ADP-ribose)polymerase PARP-1. The compounds of this invention are therefore useful in treating diseases such as cancer, multiple sclerosis, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

The nuclear enzyme poly(ADP-ribose) polymerase-1 (PARP-1) is a member of the PARP enzyme family. This growing family of enzymes consist of PARPs such as, for example: PARP-1, PARP-2, PARP-3 and Vault-PARP; and Tankyrases (TANKs), such as, for example: TANK-1 and TANK-2. PARP is also referred to as poly(adenosine 5'-diphospho-ribose) polymerase or PARS (poly(ADP-ribose) synthetase).

TANK-1 seems to be required for the polymerization of mitotic spindle-associated poly(ADP-ribose). The poly (ADP-ribosyl)ation activity of TANK-1 might be crucial for the accurate formation and maintenance of spindle bipolarity. Furthermore, PARP activity of TANK-1 has been shown to be required for normal telomere separation before anaphase. Interference with tankyrase PARP activity results in aberrant mitosis, which engenders a transient cell cycle arrest, probably due to spindle checkpoint activation, followed by cell death. Inhibition of tankyrases is therefore expected to have a cytotoxic effect on proliferating tumor cells (WO 2008/107478).

PARP inhibitors are described by M. Rouleau et al. in Nature Reviews, Volume 10, 293-301 in clinical cancer studies (Table 2, page 298).

According to a review by Horvath and Szabo (Drug News Perspect 20(3), April 2007, 171-181) most recent studies demonstrated that PARP inhibitors enhance the cancer cell death primarily because they interfere with DNA repair on various levels. More recent studies have also demonstrated that PARP inhibitors inhibit angiogenesis, either by inhibiting growth factor expression, or by inhibiting growth factor-induced cellular proliferative responses. These findings might also have implications on the mode of PARP inhibitors' anticancer effects in vivo.

Also a study by Tentori et al. (Eur. J. Cancer, 2007, 43 (14) 2124-2133) shows that PARP inhibitors abrogate VEGF or placental growth factor-induced migration and prevent formation of tubule-like networks in cell-based systems, and impair angiogenesis in vivo. The study also demonstrates that growth factor-induced angiogenesis is deficient in PARP-1 knock-out mice. The results of the study provide evidence for targeting PARP for anti-angiogenesis, adding novel therapeutic implications to the use of PARP inhibitors in cancer treatment.

Defects in conserved signaling pathways are well known to play key roles in the origins and behavior of essentially all cancers (E. A. Fearon, Cancer Cell, Vol. 16, Issue 5, 2009, 366-368). The Wnt pathway is a target for anti-cancer therapy. A key feature of the Wnt pathway is the regulated proteolysis (degradation) of β-catenin by the β-catenin destruction complex. Proteins like WTX, APC or Axin are involved in the degradation process. A proper degradation of β-catenin is important to avoid an inappropriate activation of the Wnt pathway which has been observed in many cancers. Tankyrases inhibit activity of Axin and hence inhibit the degradation of β-catenin. Consequently, tankyrase inhibitors increase degradation of β-catenin. A paper in the journal Nature not only offers important new insights into proteins regulating Wnt signaling but also further supports the approach to antagonize β-catenin levels and localization via small molecules (Huang et al., 2009; Nature, Vol 461, 614-620). The compound XAV939 inhibits growth of DLD-1-cancer cells. They found that XAV9393 blocked Wnt-stimulated accumulation of β-catenin by increasing the levels of the AXIN1 and AXIN2 proteins. Subsequent work by the authors established that XAV939 regulates AXIN levels via inhibition of tankyrases 1 and 2 (TNKS1 and TNKS2), both of which are members of the poly(ADP-ribose) polymerase (PARP) protein family (S. J. Hsiao et al., Biochimie 90, 2008, 83-92).

It has been found that the compounds according to the invention and salts thereof have very valuable pharmacological properties while being well tolerated.

The present invention specifically relates to compounds of the formula I which inhibit Tankyrase 1 and 2, to compositions which comprise these compounds, and to processes for the use thereof for the treatment of TANK-induced diseases and complaints.

The compounds of the formula I can furthermore be used for the isolation and investigation of the activity or expression of TANKs. In addition, they are particularly suitable for use in diagnostic methods for diseases in connection with unregulated or disturbed TANK activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

E. Wahlberg et al., Nature Biotechnology (2012), 30(3), 283.

M. D. Shultz et al., Journal of Medicinal Chemistry 2013 (published Nov. 7, 2013)

In the same publication, the following benzoylpiperidine derivative is described as Tankyrase inhibitor:

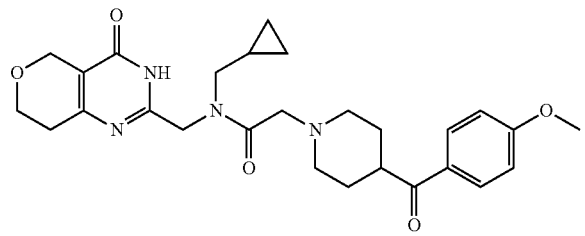 [SMILES: COc1ccc(C(=O)C2CCN(CC(=O)N(Cc3nc4c(c(=O)[nH]3)COCC4)CC3CC3)CC2)cc1]

IC$_{50}$ (TNKS1)=2 nM, IC$_{50}$ (TNKS2)=0.6 nM; cellular assay: EC$_{50}$=35 nM.

H. Bregman et al., Journal of Medicinal Chemistry (2013), 56(3), 1341

The following quinazolinone is described as Tankyrase inhibitor:

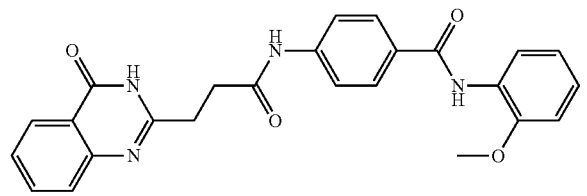 [SMILES: COc1ccccc1NC(=O)c1ccc(NC(=O)CCc2nc3ccccc3c(=O)[nH]2)cc1]

IC$_{50}$ (TNKS1)=7.4 nM, IC$_{50}$ (TNKS2)=4.4 nM; cellular assay: EC$_{50}$=320 nM.

The compounds of the present invention are significantly more active.

Other tankyrase inhibitors are described in WO 2013/012723, WO 2013/010092 and in WO 2013/008217.

Recently a patent (WO 2014/036022 A1) claiming further quinazolinones was published. One example is shown below (R=F)

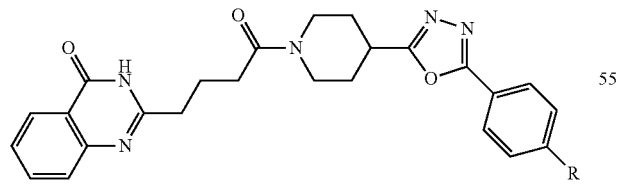

For this compound the following data are reported: IC$_{50}$ (TNKS1)=18.8 nM, IC$_{50}$(TNKS2)=2.59 nM; cellular assay: EC$_{50}$=247 nM in the patent application.

Oxoquinazolinyl-butanamide derivatives for the treatment of cancer are described in WO 2015/014442 A1.

Comparative data are given Table 3.

SUMMARY OF THE INVENTION

The invention relates to compounds of the formula I

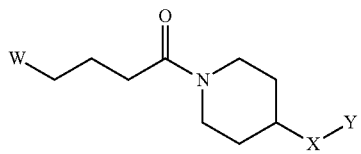

in which

W denotes

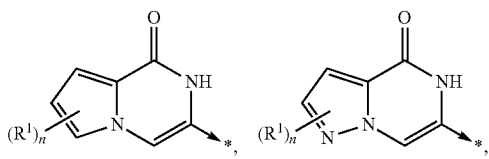

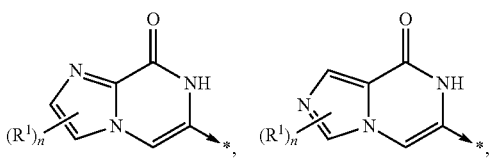

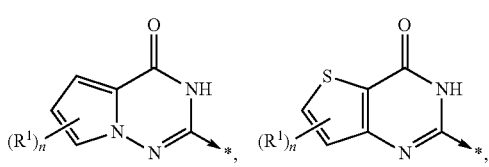

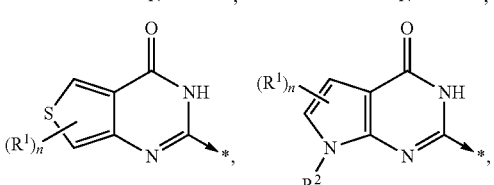

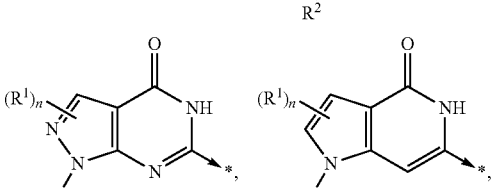

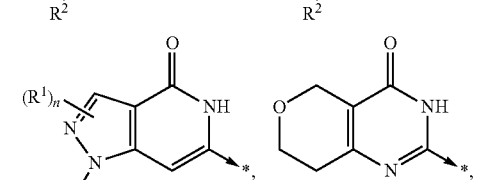

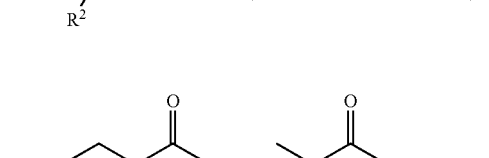

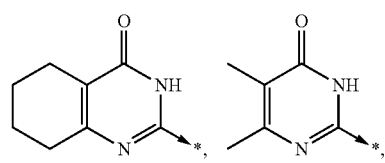

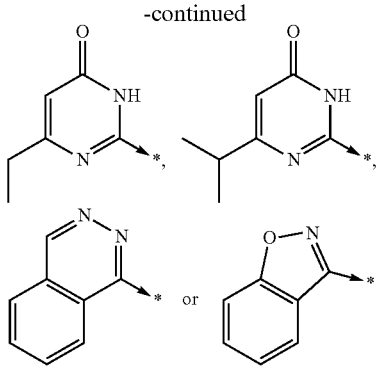

wherein * indicates the point of attachment to the propylene moiety,

X denotes O, CO or is absent,

Y denotes Ar or Het$^1$,

R$^1$ denotes H, F, Cl, CN, CH$_3$, CF$_3$, CHF$_2$, CH$_2$OH or OCH$_3$,

R$^2$ denotes H or CH$_3$,

Ar denotes phenyl, which is unsubstituted, or mono-, di- or trisubstituted by Hal, NO$_2$, CN, A, OR$^3$, S(O)$_m$R$^3$, N(R$^3$)$_2$, COA, COOR$^3$, CON(R$^3$)$_2$, SO$_2$N(R$^3$)$_2$, NR$^3$COR$^3$, NR$^3$SO$_2$A, NR$^3$CON(R$^3$)$_2$ and/or Het$^2$, Het$^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by Hal, NO$_2$, Ar$^1$, CN, A, OR$^3$, N(R$^3$)$_2$, CON(R$^3$)$_2$, Het$^2$ and/or =O, Het$^2$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by Hal, NO$_2$, Ar$^1$, CN, A, OR$^3$, N(R$^3$)$_2$, CON(R$^3$)$_2$ and/or =O, Ar$^1$ denotes phenyl, which is unsubstituted, or mono-, di- or trisubstituted by Hal, NO$_2$, CN, A, OR$^3$, S(O)$_m$R$^3$, N(R$^3$)$_2$, COA, COOR$^3$, CON(R$^3$)$_2$, NR$^3$COR$^3$ and/or NR$^3$SO$_2$A, A denotes unbranched or branched alkyl with 1-8 C-Atoms, wherein one or two non-adjacent CH- and/or CH$_2$-groups may be replaced by N- or O-atoms and wherein 1-7 H-atoms may be replaced by F, Cl and/or OH, R$^3$ denotes H or unbranched or branched alkyl with 1, 2, 3 or 4 C-Atoms, Hal denotes F, Cl, Br or I, m denotes 0, 1 or 2, n denotes 1 or 2, and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that a compound of the formula II

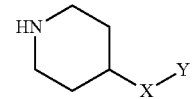

II in which X and Y have the meanings indicated in claim 1, is reacted
with a compound of formula III

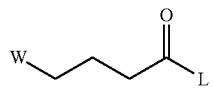

in which W has the meanings indicated in claim 1,
and L denotes Cl, Br, I or a free or reactively functionally modified OH group,
and/or
a base or acid of the formula I is converted into one of its salts.

Above and below, the radicals W, X and Y have the meanings indicated for the formula I, unless explicitely stated otherwise.

A denotes alkyl, this is unbranched (linear) or branched, and has 1, 2, 3, 4, 5, 6, 7 or 8 C atoms. A preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A very particularly preferably denotes alkyl having 2, 3, 4, 5 or 6 C atoms, preferably ethyl, propyl, isopropyl, butyl, isobutyl, sec-butyl, tert-butyl, pentyl, hexyl, trifluoromethyl, pentafluoroethyl or 1,1,1-trifluoroethyl. Moreover, A denotes preferably $CH_2OCH_3$, $CH_2CH_2OH$ or $CH_2CH_2OCH_3$.

W preferably denotes

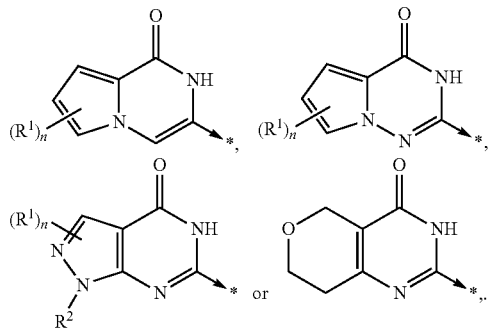

$R^1$ preferably denotes H, F, Cl, $CH_3$ or $CH_2OH$.
$R^3$ preferably denotes H or $CH_3$.
Ar preferably denotes phenyl, which is unsubstituted, or mono-, di- or trisubstituted by Hal, CN, A and/or $OR^3$.
$Het^1$ preferably denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by $Ar^1$, CN, A, $OR^3$, $N(R^3)_2$, $Het^2$ and/or =O.
$Het^2$ preferably pyrimidyl.
$Ar^1$ preferably denotes phenyl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which in Ia Ar denotes phenyl, which is unsubstituted, or mono-, di- or trisubstituted by Hal, CN, A and/or $OR^3$;

in Ib $Het^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by $Ar^1$, CN, A, $OR^3$, $N(R^3)_2$, $Het^2$ and/or =O;

in Ic $Het^2$ denotes pyrimidyl;

in Id $Ar^1$ denotes phenyl;

in Ie W denotes

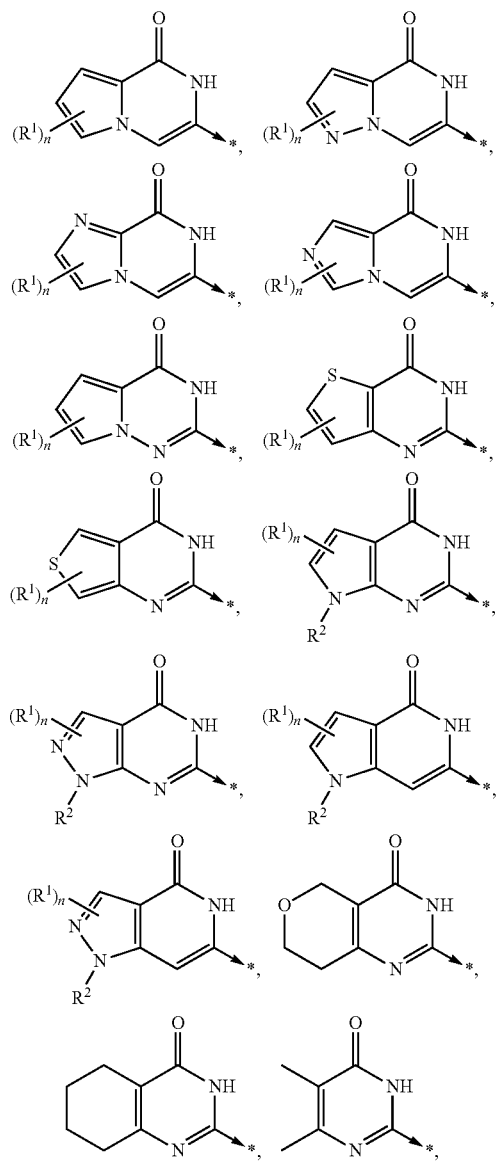

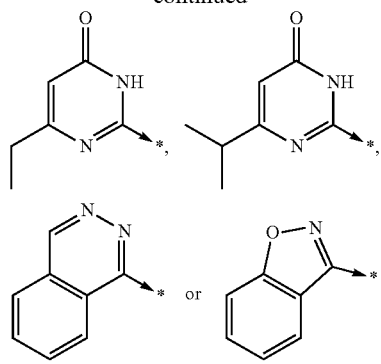

wherein * indicates the point of attachment to the propylene moiety,

X denotes O, CO or is absent,

Y denotes Ar or Het$^1$,

R$^1$ denotes H, F, Cl, CN, CH$_3$, CF$_3$, CHF$_2$, CH$_2$OH or OCH$_3$,

R$^2$ denotes H or CH$_3$,

Ar denotes phenyl, which is unsubstituted, or mono-, di- or trisubstituted by Hal, CN, A and/or OR$^3$, Het$^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by Ar$^1$, CN, A, OR$^3$, N(R$^3$)$_2$, Het$^2$ and/or =O, Het$^2$ denotes pyrimidyl, Ar$^1$ denotes phenyl, A denotes unbranched or branched alkyl with 1-8 C-Atoms, wherein one or two non-adjacent CH- and/or CH$_2$-groups may be replaced by N- or O-atoms and wherein 1-7 H-atoms may be replaced by F, Cl and/or OH, R$^3$ denotes H or unbranched or branched alkyl with 1, 2, 3 or 4 C-Atoms, Hal denotes F, Cl, Br or I, n denotes 1 or 2;

in If W denotes

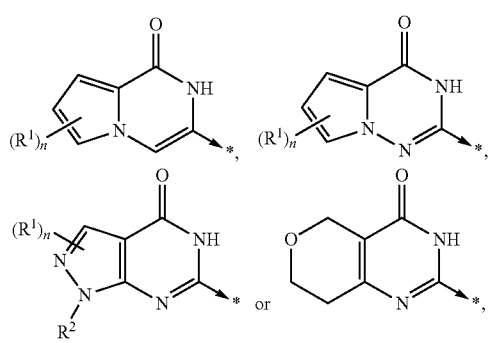

wherein * indicates the point of attachment to the propylene moiety;

in Ig W denotes

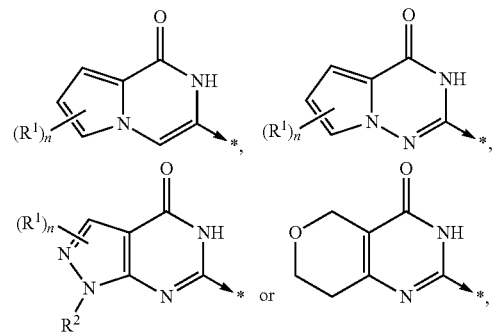

wherein * indicates the point of attachment to the propylene moiety,

X denotes CO or is absent,

Y denotes Ar or Het$^1$,

R$^1$ denotes H, F or CH$_3$,

R$^2$ denotes H or CH$_3$,

Ar denotes phenyl, which is mono- or disubstituted by Hal and/or OR$^3$,

Het$^1$ denotes pyrazolyl or pyridyl, each of which is unsubstituted or mono- or disubstituted by A, OR$^3$, N(R$^3$)$_2$ and/or Het$^2$, Het$^2$ denotes pyrimidyl, A denotes unbranched or branched alkyl with 1-8 C-Atoms, R$^3$ denotes H or unbranched or branched alkyl with 1, 2, 3 or 4 C-Atoms, Hal denotes F, Cl, Br or I, n denotes 1;

in Ih W denotes wherein * indicates the point of attachment to the propylene moiety, X denotes O, CO or is absent, Y denotes Ar or Het$^1$, R$^1$ denotes H, F, Cl, CN, CH$_3$, CF$_3$, CHF$_2$, CH$_2$OH or OCH$_3$, R$^2$ denotes H or CH$_3$, Ar denotes phenyl, which is unsubstituted, or mono-, di- or trisubstituted by Hal, CN, A and/or OR$^3$, Het$^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by Ar$^1$, CN, A, OR$^3$, N(R$^3$)$_2$, Het$^2$ and/or =O, Het$^2$ denotes pyrimidyl, Ar$^1$ denotes phenyl, A denotes unbranched or branched alkyl with 1-8 C-Atoms, wherein one or two non-adjacent CH— and/or $CH_2$-groups may be replaced by N- or O-atoms and wherein 1-7 H-atoms may be replaced by F, Cl and/or OH,
$R^3$ denotes H or unbranched or branched alkyl with 1, 2, 3 or 4 C-Atoms,
Hal denotes F, Cl, Br or I,
n denotes 1 or 2;
in Ii W denotes

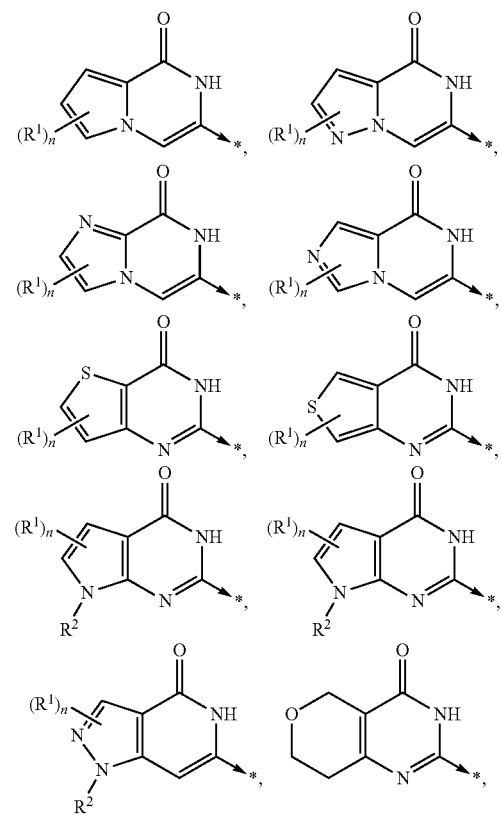

wherein * indicates the point of attachment to the propylene moiety,
X denotes O, CO or is absent,
Y denotes Ar or $Het^1$,
$R^1$ denotes H, F, Cl, CN, $CH_3$, $CF_3$, $CHF_2$, $CH_2OH$ or $OCH_3$,
$R^2$ denotes H or $CH_3$,
Ar denotes phenyl, which is unsubstituted, or mono-, di- or trisubstituted by Hal, CN, A and/or $OR^3$,
$Het^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by $Ar^1$, CN, A, $OR^3$, $N(R^3)_2$, $Het^2$ and/or $=O$,
$Het^2$ denotes pyrimidyl,
$Ar^1$ denotes phenyl,
A denotes unbranched or branched alkyl with 1-8 C-Atoms,
$R^3$ denotes H or unbranched or branched alkyl with 1, 2, 3 or 4 C-Atoms,
Hal denotes F, Cl, Br or I,
n denotes 1 or 2;
in Ij W denotes

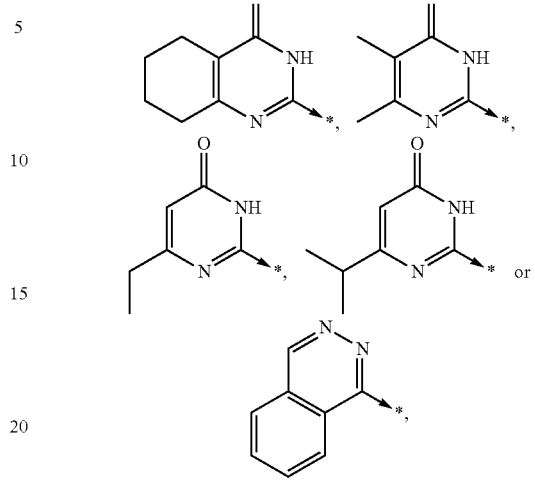

wherein * indicates the point of attachment to the propylene moiety,
X denotes O, CO or is absent,
Y denotes Ar or $Het^1$,
$R^1$ denotes H, F, Cl, CN, $CH_3$, $CF_3$, $CHF_2$, $CH_2OH$ or $OCH_3$,
$R^2$ denotes H or $CH_3$,
Ar denotes phenyl, which is unsubstituted, or mono-, di- or trisubstituted by Hal, CN, A and/or $OR^3$,
$Het^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by $Ar^1$, CN, A, $OR^3$, $N(R^3)_2$, $Het^2$ and/or $=O$,
$Het^2$ denotes pyrimidyl,
$Ar^1$ denotes phenyl,
A denotes unbranched or branched alkyl with 1-8 C-Atoms,
$R^3$ denotes H or unbranched or branched alkyl with 1, 2, 3 or 4 C-Atoms,
Hal denotes F, Cl, Br or I,
n denotes 1 or 2;
and pharmaceutically acceptable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formula II and III are generally known. If they are novel, however, they can be prepared by methods known per se.

Compounds of the formula I can preferably be obtained by reacting a compound of the formula II with a compound of the formula III. In the compounds of the formula III, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, 1,2-dichloroethane, dichloromethane and/or DMF.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other iso-topes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t1/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsiloncaprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically acceptable salts, tautomers and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, tautomers and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula (I) is an amount that inhibits a tankyrase in a cell, such as, for example, in vitro or in vivo. In some embodiments, the effective amount of the compound of formula (I) inhibits tankyrase in a cell by 10%, 20%, 30%, 40%, 50%, 60%, 70%, 80%, 90% or 99%, compared to the activity of tankyrase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of cancer, multiple sclerosis, cardiovascular diseases, central nervous system injury and different forms of inflammation.

The present invention encompasses the use of the compounds of the formula I and/or pharmaceutically acceptable salts, tautomers and stereoisomers thereof for the preparation of a medicament for the treatment or prevention of cancer, multiple sclerosis, cardiovascular diseases, central nervous system injury and different forms of inflammation.

Examples of inflammatory diseases include rheumatoid arthritis, psoriasis, contact dermatitis, delayed hypersensitivity reaction and the like.

Also encompassed is the use of the compounds of the formula I and/or pharmaceutically acceptable salts, tautomers and stereoisomers thereof for the preparation of a medicament for the treatment or prevention of a tankyrase-induced disease or a tankyrase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The expression "tankyrase-induced diseases or conditions" refers to pathological conditions that depend on the activity of one or more tankyrases. Diseases associated with tankyrase activity include cancer, multiple sclerosis, cardiovascular diseases, central nervous system injury and different forms of inflammation.

The present invention specifically relates to compounds of the formula I and pharmaceutically acceptable salts, tautomers and stereoisomers thereof, including mixtures thereof in all ratios, for the use for the treatment of diseases in which the inhibition, regulation and/or modulation inhibition of tankyrase plays a role.

The present invention specifically relates to compounds of the formula I and pharmaceutically acceptable salts, tautomers and stereoisomers thereof, including mixtures thereof in all ratios, for the use for the inhibition of tankyrase.

The present invention specifically relates to compounds of the formula I and pharmaceutically acceptable salts, tautomers and stereoisomers thereof, including mixtures thereof in all ratios, for the use for the treatment of cancer, multiple sclerosis, cardiovascular diseases, central nervous system injury and different forms of inflammation.

The present invention specifically relates to methods for treating or preventing cancer, multiple sclerosis, cardiovascular diseases, central nervous system injury and different forms of inflammation, comprising administering to a subject in need thereof an effective amount of a compound of formula I or a pharmaceutically acceptable salt, tautomer, stereoisomer or solvate thereof.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

The present invention relates to a method of treating a proliferative, autoimmune, anti inflammatory or infectious disease disorder that comprises administering to a subject in need thereof a therapeutically effective amount of a compound of formula I.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone;

apaziquone, fotemustine, glufosfamide, palifosfamide, pipobroman, trofosfamide, uramustine, TH-302[4], VAL-083[4];

Platinum Compounds such as carboplatin, cisplatin, eptaplatin, miriplatine hydrate, oxaliplatin, lobaplatin, nedaplatin, picoplatin, satraplatin;

lobaplatin, nedaplatin, picoplatin, satraplatin;

DNA Altering Agents such as amrubicin, bisantrene, decitabine, mitoxantrone, procarbazine, trabectedin, clofarabine;

amsacrine, brostallicin, pixantrone, laromustine[1,3];

Topoisomerase Inhibitors such as etoposide, irinotecan, razoxane, sobuzoxane, teniposide, topotecan;

amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;

fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;

acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1]Prop. INN (Proposed International Nonproprietary Name)
[2]Rec. INN (Recommended International Nonproprietary Names)
[3]USAN (United States Adopted Name)
[4]no INN.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethylammonium hexafluorophosphate), HPLC (High Performance Liquid Chromatography), i-PrOH (2-propanol), $K_2CO_3$ (potassium carbonate), LC (Liquid Chromatography), MeOH (methanol), MgSO$_4$ (magnesium sulfate), MS (mass spectrometry), MTBE (Methyl tert-butyl ether), NaHCO$_3$ (sodium bicarbonate), NaBH$_4$ (sodium borohydride), NMM (N-methyl morpholine), NMR (Nuclear Magnetic Resonance), PyBOP (benzotriazole-1-yl-oxy-tris-pyrrolidine-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays

Abbreviations

GST=Glutathione-S-transferase
FRET=Fluorescence resonance energy transfer
HTRF®=(homogenous time resolved fluorescence)
HEPES=4-(2-hydroxyethyl)-1-piperazine ethanesulfonic acid buffer
DTT=Dithiothreitol
BSA=bovine serum albumin
CHAPS=detergent;
CHAPS=3-[(3-cholamidopropyl)dimethylammonio]-1-propanesulfonate Streptavidin-XLent® is a high grade streptavidin-XL665 conjugate for which the coupling conditions have been optimized to yield a conjugate with enhanced performances for some assays, particularly those requiring high sensitivity.

Measurement of Cellular Inhibition of Tankyrase

Since Tankyrases have been described to modulate cellular level of Axin2 (Huang et al., 2009; Nature) the increase of Axin2 level is used as read-out for determination of cellular inhibition of Tankyrases in a Luminex based assay.

Cells of the colon carcinoma cell line DLD1 are plated in 96 well plates with $1.5 \times 10^4$ cells per well. Next day, cells are treated with a serial dilution of test compound in seven steps as triplicates with a final DMSO concentration of 0.3%. After 24 hours, cells are lysed in lysis buffer (20 mM Tris/HCl pH 8.0, 150 mM NaCl, 1% NP40, 10% Glycerol) and lysates are cleared by centrifugation through a 96 well filter plate (0.65 µm). Axin2 protein is isolated from cell lysates by incubation with a monoclonal anti-Axin2 antibody (R&D Systems #MAB6078) that is bound to fluorescent carboxybeads. Then, bound Axin2 is specifically detected with a polyclonal anti-Axin2 antibody (Cell Signaling #2151) and an appropriate PE-fluorescent secondary antibody. The amount of isolated Axin2 protein is determined in a Luminex$^{200}$ machine (Luminex Corporation) according to the manufacturer's instruction by counting 100 events per well. Inhibition of Tankyrase by test compounds results in higher levels of Axin2 which directly correlates with an increase of detectable fluorescence. As controls cells are treated with solvent alone (neutral control) and with a Tankyrase reference inhibitor IWR-2 (3E-06 M) which refers as control for maximum increase of Axin2. For analysis, the obtained data are normalized against the untreated solvent control and fitted for determination of the EC$_{50}$ values using the Assay Explorer software (Accelrys).

Description of the PARP1 Assay

Biochemical Activity Testing of PARP-1: Autoparsylation Assay

The autoparsylation assay is run in two steps: the enzymatic reaction in which His-tagged Parp-1 transfers biotinylated ADP-ribose/ADP-ribose to itself from biotinylated NAD/NAD as co-substrate and the detection reaction where a time resolved FRET between cryptate labelled anti-His antibody bound to the His tag of the enzyme and Xlent® labelled-streptavidin bound the biotin-parsylation residue is analysed. The autoparsylation activity is detectable directly via the increase in HTRF signal.

The autoparsylation assay is performed as 384-well HTRF® (Cisbio, Codolet, France) assay format in Greiner low volume nb 384-well microtiter plates. 35 nM His-tagged Parp-1 (human, recombinant, Enzo Life Sciences GmbH, Lörrach, Germany) and a mixture of 125 nM bio-NAD (Biolog, Life science Inst., Bremen, Germany) and 800 nM NAD as co-substrate are incubated in a total volume of 6 µl (100 mM Tris/HCl, 4 mM Mg-chloride, 0.01% IGEPAL® CA630, 1 mM DTT, 0.5% DMSO, pH 8, 13 ng/µl activated DNA (BPS Bioscience, San Diego, US)) in the absence or presence of the test compound (10 dilution concentrations) for 150 min at 23° C. The reaction is stopped by the addition of 4 µl of the Stop/detection solution (70 nM SA-Xlent® (Cisbio, Codolet, France), 2.5 nM Anti-His-K® (Eu-labelled anti-His, Cisbio, Codolet, France) in 50 mM HEPES, 400 mM KF, 0.1% BSA, 20 mM EDTA, pH 7.0). After 1 h incubation at room temperature the HTRF is measured with an Envision multimode reader (Perkin Elmer LAS Germany GmbH) at excitation wavelength 340 nm (laser mode) and emission wavelengths 615 nm and 665 nm. The ratio of the emission signals is determined. The full value used is the inhibitor-free reaction. The pharmacological zero value used is Olaparib (LClabs, Woburn, US) in a final concentration of 1 µM. The inhibitory values (IC50) are determined using either the program Symyx Assay Explorer® or Condosseo® from GeneData.

Description of the TNKS1 and TNKS2 ELISA Assay

Biochemical Activity Testing of TNKS 1 and 2: Activity ELISA (Autoparsylation Assay)

For analysis of autoparsylation activity of TNKS 1 and 2 an activity ELISA iss performed: In the first step GST tagged TNKS is captured on a Glutathione coated plate. Then the activity assay with biotinylated NAD is performed in the absence/presence of the compounds. During the enzymatic reaction GST tagged TNKS transfers biotinylated ADP-ribose to itself from biotinylated NAD as co-substrate. For the detection streptavidin-HRP conjugate is added that binds to the biotinylated TNKS and is thereby captured to the plates. The amount of biotinylated resp. autoparsylated TNKS is detected with a luminescence substrate for HRP. The level of the luminescence signal correlats directly with the amount of autoparsylated TNKS and therefore with activity of TNKS.

The activity ELISA is performed in 384 well Glutathione coated microtiter plates (Express capture Glutathione coated plate, Biocat, Heidelberg, Germany). The plates are pre-equilibrated with PBS. Then the plates are incubated with 50 µl 20 ng/well GST-tagged Tnks-1 (1023-1327 aa, prepared in-house), respectively GST-tagged Tnks-2 (873-1166 aa, prepared in-house) in assay buffer (50 mM HEPES, 4 mM Mg-chloride, 0.05% Pluronic F-68, 2 mM DTT, pH 7.7) overnight at 4° C. The plates are washed 3 times with PBS-Tween-20. The wells are blocked by incubation at room temperature for 20 minutes with 50 µl blocking buffer (PBS, 0.05% Tween-20, 0.5% BSA). Afterwards the plates are washed 3 times with PBS-Tween-20. The enzymatic reaction is performed in 50 µl reaction solution (50 mM HEPES, 4 mM Mg-chloride, 0.05% Pluronic F-68, 1.4 mM DTT, 0.5% DMSO, pH 7.7) with 10 µM bio-NAD (Biolog, Life science Inst., Bremen, Germany) as co-substrate in the absence or presence of the test compound (10 dilution concentrations) for 1 hour at 30° C. The reaction is stopped by 3 times washing with PBS-Tween-20. For the detection 50 µl of 20 ng/µl Streptavidin, HRP conjugate (MoBiTec, Göttingen, Germany) in PBS/0.05% Tween-20/0.01% BSA are added and the plates are incubated for 30 minutes at room temperature. After three times washing with PBS-Tween-20 50 µl of SuperSignal ELISA Femto Maximum sensitivity substrate solution (ThermoFisherScientific (Pierce), Bonn, Germany) are added. Following a 1 minute incubation at room temperature luminescence signals are measured with an Envision multimode reader (Perkin Elmer LAS Germany GmbH) at 700 nm. The full value used is the inhibitor-free reaction. The pharmacological zero value used is XAV-939 (Tocris) in a final concentration of 5 µM. The inhibitory values (IC50) are determined using either the program Symyx Assay Explorer® or Condosseo® from GeneData.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent:ethyl acetate/methanol 9:1.

Test Method Microsomal Stability (Intrinsic Clearance)

A microsomal stability assay is used to measure in vitro clearance (Clint). The assay involves measuring the rate of disappearance of a compound due to its intrinsic attitude to be metabolized ("intrinsic" meaning that the disappearance is not affected by other properties like permeability, binding etc. that play a role when quantifying in vivo clearance). The microsomal stability (intrinsic clearance, Clint) and thus metabolic stability is generally given as µl/min/mg protein. It can be visualized as the volume of solution that 1 mg of microsomes is able to clear of the compound in one minute.

Instrumentation

A Tecan Genesis workstation (RSP 150/8) was used for to perform the microsomal incubations. Analysis was carried out using a Waters ACQUITY UPLC system coupled to an ABSciex API3000 mass spectrometer. Data analysis was performed using Assay Explorer (Symyx).

UPLC Conditions

Column: Acquity UPLC BEH C18, 2.1×50 mm, 1.7 µm (Waters)

Mobile phases: A=0.1% formic acid in water; B=acetonitrile

| Gradient Time | % A | % B |
| --- | --- | --- |
| initial | 90 | 10 |
| 0.47 | 5 | 95 |
| 0.65 | 5 | 95 |
| 0.66 | 90 | 10 |

Flow rate: 0.750 mL/min; Detection: ESI, MRM; Injection: 10 µL; Column temperature: 50° C.

Chemicals

Potassium phosphate buffer: 0.05 M potassium phosphate buffer pH 7.4 containing 1 mM MgCl$_2$ NADPH (nicotinamide adenine dinucleotide phosphate): 22.5 mg NADPH-Na$_4$ in 1.8 ml potassium phosphate buffer Acetonitrile: 50 Vol % acetonitrile (1 volume acetonitrile, 1 volume water)

DMSO: 20 Vol % DMSO in water

Stock solution of 20 mg/ml human or mouse liver microsomes (protein)/ml in phosphate buffer Stock solution of 10 mM compound in 100% DMSO $^1$H NMR was recorded on Bruker DPX-300, DRX-400, AVII-400 or on a 500 MHz spectrometer, using residual signal of deuterated solvent as internal reference. Chemical shifts (δ) are reported in ppm relative to the residual solvent signal (δ=2.49 ppm for $^1$H NMR in DMSO-d$_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

HPLC Conditions:

Gradient: A:B=90:10 to 0:100 in 5.5 min; Flow rate: 2.75 ml/min

A: Water+TFA (0.01% Vol.); B: Acetonitrile+TFA (0.01% Vol.)

Column: Chromolith SpeedROD RP 18e 50-4.6

Wavelength: 220 nm

HPLC Conditions (2):

Gradient: A:B=99:1 to 0:100 in 5.5 min; Flow rate: 2.75 ml/min

A: Water+TFA (0.01% Vol.); B: Acetonitrile+TFA (0.01% Vol.)

Column: Chromolith SpeedROD RP 18e 50-4.6

Wavelength: 220 nm

HPLC/MS Conditions (A):

Gradient: A:B=96:4 to 0:100 in 3.4 min; Flow rate: 2.40 ml/min

A: Water+formic acid (0.05%); B: Acetonitrile+formic acid (0.04%)

Column: Chromolith SpeedROD RP-18e, 50×4.6 mm$^2$

Wavelength: 220 nm

HPLC/MS Conditions (B):

Gradient: 0 min: 5% B, 8 min: 100% B, 8.1 min: 100% B, 8.5 min: 5% B, 10 min 5% B flow rate: 2.0 mL/min A: Water+TFA (0.1% Vol.); B: Acetonitrile+TFA (0.1% Vol.)

Column: XBridge C8, 3.5 µm, 4.6×50 mm

Wavelength: 220 nm

HPLC/MS Conditions (C):

Gradient: 0 min: 0% B, 0.4 min: 0% B, 3.2 min: 100% B, 3.8 min: 100% B, 3.81 min: 0% B, 4.5 min 0% B; flow rate: 2.0 mL/min A: Water+formic acid (0.05%); B: Acetonitrile+formic acid (0.04%)

Column: Chromolith SpeedROD RP-18e, 100-3 mm

Wavelength: 220 nm

HPLC/MS Conditions (D):

Gradient: 0 min: 5% B, 8 min: 100% B, 8.1 min: 100% B, 8.5 min: 5% B, 10 min 5% B;

Flow rate: 1 ml/min;

A: water+10 mM NH$_4$HCO$_3$; B: ACN

Column: XBridge C8, 3.5 µm, 4.6×50 mm

HPLC/MS Conditions (E):

Gradient: 0 min: 0% B, 1.4 min: 100% B, 2.0 min: 100% B, 2.01 min: 0% B, 2.5 min 0% B; flow rate: 2.0 mL/min A: Water+formic acid (0.05%); B: Acetonitrile+formic acid (0.04%)

Column: Kinetex XB-C18 2.6 µm 50-4.6 mm

Wavelength: 220 nm

HPLC/MS Conditions (F):

Gradient: 0 min: 10% B, 2.5 min: 95% B, 4.5 min: 95% B, 4.6 min: 10% B, 6 min 10% B flow rate: 1.5 mL/min A: Water+TFA (0.1% Vol.); B: Acetonitrile+TFA (0.1% Vol.)
Column: Atlantis dC18, 4.6×50 mm, 5 μm
Wavelength: 220 nm
Pharmacological Data

TABLE 1

Inhibition of tankyrases of representative compounds of the formula I

| Compound No. | $EC_{50}$ [M] TNKS cellular assay | Compound No. | $EC_{50}$ [M] TNKS cellular assay |
|---|---|---|---|
| "C1"   | 2.60E−10 | "C11"  | 9.00E−10 |
| "C2"   | 5.00E−10 | "C12"  | 4.90E−10 |
| "C3"   | 2.90E−10 | "C13"  | 4.10E−07 |
| "C4"   | 3.40E−10 | "C15"  | 1.50E−09 |
| "C5"   | 1.20E−07 | "C22"  | 4.50E−09 |
| "C6"   | 2.80E−08 | "C31"  | 2.20E−10 |
| "C7"   | 4.70E−08 | "C33"  | 1.50E−09 |
| "C8"   | 2.80E−09 | "C34"  | 4.80E−09 |
| "C9"   | 7.20E−10 | "C35"  | 4.20E−10 |
| "C10"  | 6.70E−09 | "C36"  | 4.10E−09 |
| "C37"  | 1.00E−09 | "C47"  | 4.50E−07 |
| "C38"  | 5.40E−09 | "C48"  | 4.40E−09 |
| "C39"  | 3.10E−09 | "C49"  | 3.10E−10 |
| "C40"  | 3.20E−09 | "C50"  | 3.80E−07 |
| "C41"  | 1.80E−09 | "C52"  | 4.60E−09 |
| "C42"  | 4.80E−09 | "C54"  | 1.40E−08 |
| "C43"  | 4.30E−09 | "C55"  | 1.90E−09 |
| "C44"  | 4.00E−07 | "C56"  | 3.60E−08 |
| "C45"  | 4.90E−10 | "C57"  | 7.70E−10 |
| "C46"  | 6.60E−08 | "C62"  | 3.50E−09 |
| "C71"  | 2.90E−09 | "C119" | 3.30E−08 |
| "C78"  | 2.90E−09 | "C120" | 1.30E−09 |
| "C99"  | 1.10E−08 | "C121" | 6.80E−08 |
| "C105" | 3.90E−07 | "C123" | 3.40E−09 |
| "C113" | 2.60E−09 | "C126" | 1.30E−08 |
| "C114" | 2.50E−08 | "C128" | 3.30E−09 |
| "C115" | 4.90E−08 | "C130" | 3.30E−08 |
| "C116" | 3.60E−09 | "C131" | 1.60E−08 |
| "C117" | 1.30E−07 | "C132" | 7.70E−10 |
| "C118" | 9.10E−07 | "C133" | 6.40E−08 |
| "C135" | 3.90E−08 | "C146" | 8.70E−08 |
| "C136" | 3.60E−08 | "C147" | 8.10E−10 |
| "C137" | 1.90E−08 | "C148" | 1.40E−09 |
| "C138" | 5.20E−08 | "C149" | 3.10E−09 |
| "C139" | 3.40E−09 | "C150" | 1.10E−09 |
| "C140" | 1.00E−07 | "C151" | 1.90E−08 |
| "C141" | 6.80E−07 | "C152" | 4.80E−08 |
| "C142" | 2.00E−08 | "C153" | 1.70E−09 |
| "C143" | 1.70E−09 | "C154" | 9.70E−10 |
| "C144" | 8.30E−08 | "C155" | 1.60E−08 |
| "C157" | 2.70E−09 | "C168" | 3.40E−08 |
| "C158" | 4.40E−09 | "C169" | 2.50E−09 |
| "C159" | 3.60E−08 | "C170" | 1.90E−08 |
| "C160" | 4.90E−08 | "C171" | 4.60E−08 |
| "C161" | 9.70E−08 | "C172" | 6.80E−09 |
| "C162" | 5.00E−07 | "C173" | 8.50E−08 |
| "C163" | 2.00E−07 | "C174" | 7.80E−07 |
| "C164" | 2.50E−08 | "C175" | 3.70E−08 |
| "C165" | 1.70E−06 | "C177" | 6.70E−08 |
| "C166" | 1.80E−07 | "C179" | 1.70E−08 |
| "C180" | 3.30E−09 | "C194" | 3.10E−06 |
| "C181" | 7.30E−09 | "C195" | 3.50E−08 |
| "C182" | 2.40E−08 | "C196" | 2.00E−06 |
| "C183" | 1.00E−08 | "C197" | 3.60E−06 |
| "C184" | 4.70E−07 | "C198" | 7.50E−08 |
| "C186" | 1.40E−08 | "C199" | 3.30E−09 |
| "C190" | 1.90E−08 | "C200" | 3.70E−06 |
| "C191" | 2.00E−07 | "C202" | 2.20E−06 |
| "C192" | 4.90E−08 | "C207" | 1.10E−06 |
| "C193" | 1.00E−07 | "C208" | 5.20E−09 |
| "C209" | 1.00E−08 | "C219" | 2.40E−08 |
| "C210" | 3.60E−09 | "C220" | 4.00E−08 |
| "C211" | 1.40E−08 | "C221" | 2.70E−08 |
| "C212" | 6.10E−09 | "C222" | 2.60E−09 |
| "C213" | 8.60E−08 | "C223" | 3.30E−09 |
| "C214" | 1.50E−08 | "C224" | 1.80E−08 |

TABLE 1-continued

Inhibition of tankyrases of representative compounds of the formula I

| Compound No. | $EC_{50}$ [M] TNKS cellular assay | Compound No. | $EC_{50}$ [M] TNKS cellular assay |
|---|---|---|---|
| "C215" | 1.80E−08 | "C225" | 1.40E−08 |
| "C216" | 5.20E−08 | "C226" | 2.50E−08 |
| "C217" | 3.00E−08 | "C227" | 3.70E−09 |
| "C218" | 1.40E−07 | "C228" | 2.90E−06 |
| "C229" | 1.60E−06 | "C239" | 1.50E−08 |
| "C230" | 4.70E−08 | "C240" | 5.80E−07 |
| "C231" | 5.40E−09 | "C241" | 3.50E−08 |
| "C232" | 5.60E−08 | "C242" | 8.80E−07 |
| "C233" | 5.40E−08 | "C243" | 3.40E−08 |
| "C234" | 1.60E−08 | "C244" | 2.10E−08 |
| "C235" | 3.90E−09 | "C245" | 4.80E−09 |
| "C236" | 2.10e−08 | "C246" | 2.50E−08 |
| "C237" | 1.00E−08 | "C247" | 2.10E−08 |
| "C238" | 5.60E−08 | "C248" | 8.70E−09 |
| "C249" | 1.80E−09 | | |
| "C250" | 4.60E−08 | | |
| "C251" | 7.00E−08 | | |
| "C252" |          | | |
| "C253" | 7.00E−07 | | |
| "C254" | 2.60E−07 | | |
| "C255" | 2.70E−06 | | |
| "C256" | 2.60E−06 | | |
| "C257" | 9.30E−06 | | |
| "D1"   | 5.40E−07 | | |

The compounds shown in Table 1 are particularly preferred compounds according to the invention.

TABLE 2

Inhibition of tankyrases of representative compounds of the formula I

| Compound No. | $IC_{50}$ [M] PARP | $IC_{50}$ [M] TNKS1 ELISA | $IC_{50}$ [M] TNKS2 ELISA |
|---|---|---|---|
| "C1"  | 7.30E−07 | 1.80E−10 | 1.80E−10 |
| "C2"  |          | 2.40E−10 | 1.40E−10 |
| "C3"  | 8.20E−07 | 1.40E−10 | 1.70E−10 |
| "C4"  |          | 1.40E−10 | 1.50E−10 |
| "C5"  | 4.30E−06 | 1.30E−10 | 8.80E−09 |
| "C6"  | 3.70E−06 | 1.90E−09 | 1.30E−09 |
| "C7"  | 1.80E−06 | 2.60E−09 | 2.00E−09 |
| "C8"  | 2.90E−06 | <1.00E−10 | 1.60E−10 |
| "C9"  |          | 2.00E−10 | 1.30E−10 |
| "C10" |          | 3.20E−10 | 1.30E−10 |
| "C11" | 2.70E−06 | 1.40E−10 | 1.60E−10 |
| "C12" |          | 1.30E−10 | 1.40E−10 |
| "C13" |          | 1.20E−09 | 7.40E−10 |
| "C15" | 1.70E−06 | 2.30E−10 | 1.70E−10 |
| "C22" | 5.20E−06 | 2.50E−10 | 3.00E−10 |
| "C31" |          | 2.00E−10 | 1.70E−10 |
| "C32" | 1.70E−05 | 1.20E−10 | 1.40E−10 |
| "C33" | 5.50E−06 | 1.60E−10 | 1.20E−10 |
| "C34" | 1.10E−06 | 5.40E−10 | 3.30E−10 |
| "C35" | 1.30E−07 | 1.90E−10 | 1.10E−10 |
| "C36" | 3.50E−06 | 3.90E−10 | 2.80E−10 |
| "C37" | 6.20E−07 | <1.00E−10 | <1.00E−10 |
| "C38" | 2.40E−06 | 2.80E−10 | 1.10E−10 |
| "C39" | 2.10E−06 | 1.80E−10 | 3.70E−10 |
| "C40" | 1.60E−06 | 1.70E−10 | <1.00E−10 |
| "C41" | 6.30E−06 | 1.80E−10 | 1.30E−10 |
| "C42" | 1.20E−05 | 1.20E−10 | <1.00E−10 |
| "C43" | 1.80E−05 | 5.20E−10 | 3.50E−10 |
| "C44" | 1.80E−05 | 1.60E−09 | 9.70E−10 |
| "C45" | 3.80E−06 | 2.60E−10 | 1.90E−10 |
| "C46" | 7.20E−06 | 2.90E−09 | 2.40E−09 |
| "C47" | 4.40E−06 | 1.10E−07 | 4.10E−08 |
| "C48" | 7.30E−06 | 4.50E−10 | 3.10E−10 |
| "C49" | 9.90E−06 | 1.60E−10 | 1.40E−10 |

TABLE 2-continued

Inhibition of tankyrases of representative compounds of the formula I

| Compound No. | $IC_{50}$ [M] PARP | $IC_{50}$ [M] TNKS1 ELISA | $IC_{50}$ [M] TNKS2 ELISA |
|---|---|---|---|
| "C50" | 2.30E−05 | 1.10E−08 | 4.00E−09 |
| "C52" | 1.90E−06 | 1.40E−09 | 4.80E−10 |
| "C55" | 4.00E−07 | 1.80E−10 | 1.20E−10 |
| "C56" | 3.60E−07 | 9.50E−10 | 5.30E−10 |
| "C57" | 4.80E−10 | 1.90E−10 | 1.80E−10 |
| "C62" | 8.00E−07 | 1.60E−10 | 1.20E−10 |
| "C71" | 1.20E−06 | 2.40E−10 | 1.60E−10 |
| "C78" | 1.20E−06 | 2.40E−10 | 1.60E−10 |
| "C99" | 6.70E−06 | 3.70E−10 | 1.10E−08 |
| "C105" | 2.90E−05 | 4.30E−10 | 5.70E−10 |
| "C113" | 2.90E−05 | 3.80E−10 | 2.40E−10 |
| "C114" | 1.30E−06 | 6.80E−10 | 8.20E−10 |
| "C115" | 5.70E−07 | 9.80E−10 | 1.30E−09 |
| "C116" | 9.70E−07 | 3.70E−10 | 2.10E−10 |
| "C117" | 8.20E−07 | 8.20E−09 | 5.70E−09 |
| "C118" | 8.50E−07 | 1.10E−07 | 8.90E−08 |
| "C119" | 8.50E−07 | 9.00E−10 | 6.20E−10 |
| "C120" | 1.90E−06 | 4.00E−10 | 1.90E−10 |
| "C121" | 3.10E−06 | 4.70E−09 | 2.4E−09 |
| "C123" | 1.20E−06 | 6.70E−10 | 5.70E−10 |
| "C126" | 5.60E−07 | 2.30E−10 | 1.60E−10 |
| "C128" | 2.30E−06 | 1.10E−10 | 7.90E−10 |
| "C54" | 1.50E−06 | 4.70E−09 | 1.80E−09 |
| "C130" | 3.20E−07 | 5.00E−08 | 2.10E−08 |
| "C131" | 2.70E−07 | 3.60E−10 | 2.10E−10 |
| "C132" | 4.40E−07 | <1.00E−10 | 1.10E−10 |
| "C133" | 1.00E−06 | 2.10E−09 | 7.50E−10 |
| "C135" | 4.20E−07 | 4.90E−10 | 4.70E−10 |
| "C136" | 3.10E−06 | 2.50E−10 | 2.10E−10 |
| "C137" | 2.10E−05 | 1.50E−09 | 1.00E−09 |
| "C138" | 3.20E−06 | 2.20E−09 | 2.60E−09 |
| "C139" | 3.20E−06 | 2.30E−09 | 2.60E−09 |
| "C140" | 3.60E−06 | 1.80E−08 | 1.00E−08 |
| "C141" | 2.60E−06 | 1.00E−07 | 6.50E−08 |
| "C142" | 7.20E−06 | 1.40E−08 | 1.40E−08 |
| "C143" | 4.80E−06 | 1.90E−10 | 1.60E−10 |
| "C144" | 1.10E−05 | 7.30E−09 | 3.50E−09 |
| "C146" | | 2.20E−09 | 1.40E−09 |
| "C147" | 3.70E−07 | <1.00E−10 | <1.00E−10 |
| "C148" | 7.70E−07 | 2.80E−10 | 1.90E−10 |
| "C149" | 7.70E−07 | 3.80E−10 | 3.80E−10 |
| "C150" | 1.30E−06 | 2.30E−10 | 2.80E−10 |
| "C151" | 2.10E−06 | 1.40E−09 | 9.30E−10 |
| "C152" | 1.20E−07 | 8.50E−09 | 3.90E−09 |
| "C153" | 2.00E−06 | 1.70E−10 | 1.60E−10 |
| "C154" | 6.10E−07 | 1.60E−10 | 1.30E−10 |
| "C155" | 6.00E−07 | 5.70E−10 | 3.80E−10 |
| "C157" | 8.60E−07 | 3.10E−10 | 2.60E−10 |
| "C158" | 2.10E−06 | 4.40E−10 | 9.20E−10 |
| "C159" | 2.20E−06 | 1.20E−09 | 2.70E−09 |
| "C160" | 3.30E−06 | 1.80E−09 | 1.00E−08 |
| "C161" | 4.30E−06 | 6.20E−10 | 2.90E−09 |
| "C162" | 1.40E−06 | 2.00E−08 | 3.70E−08 |
| "C163" | 1.30E−06 | 2.10E−08 | 2.50E−08 |
| "C164" | 2.20E−06 | 7.90E−10 | 2.80E−09 |
| "C165" | 2.10E−06 | 2.20E−10 | 2.20E−10 |
| "C166" | 1.40E−06 | 1.20E−08 | 1.70E−08 |
| "C168" | 5.80E−06 | 1.00E−09 | 3.50E−09 |
| "C169" | 2.20E−06 | 1.70E−10 | 2.20E−10 |
| "C170" | 2.80E−06 | 6.70E−10 | 9.90E−10 |
| "C171" | 6.30E−06 | 1.70E−09 | 3.60E−09 |
| "C172" | 2.50E−06 | 6.10E−10 | 5.30E−10 |
| "C173" | 3.20E−06 | 1.50E−08 | 1.40e−08 |
| "C174" | 2.70E−06 | 6.40E−08 | 4.90E−08 |
| "C175" | 4.90E−06 | 4.70E−10 | 8.10E−10 |
| "C177" | 8.00E−06 | 7.10E−09 | 4.80E−09 |
| "C179" | 1.10E−05 | 5.20E−10 | 1.10E−09 |
| "C180" | 1.90E−06 | 1.80E−10 | <1.00E−10 |
| "C181" | 2.30E−06 | 6.50E−10 | 2.40E−10 |
| "C182" | 1.50E−06 | 1.30E−09 | 6.50E−10 |
| "C183" | 1.60E−06 | 5.40E−10 | 2.90E−10 |
| "C184" | 1.90E−06 | 4.70E−09 | 2.50E−09 |
| "C186" | 1.20E−06 | 4.10E−10 | 1.90E−09 |
| "C190" | 8.70E−07 | 7.10E−10 | 3.20E−10 |
| "C191" | 2.80E−06 | 8.70E−10 | 6.90E−10 |
| "C192" | 1.20E−05 | 5.60E−09 | 2.10E−09 |
| "C193" | 8.00E−06 | 7.40E−09 | 2.60E−09 |
| "C194" | 4.90E−06 | 1.50E−08 | 4.50E−09 |
| "C195" | 3.30E−06 | 2.10E−09 | 6.80E−10 |
| "C196" | 6.50E−06 | 3-10E−07 | 5.70E−08 |
| "C197" | 3.20E−06 | 5.60E−07 | 2.40E−07 |
| "C198" | 5.20E−06 | 1.20E−08 | 4.00E−09 |
| "C199" | 2.20E−06 | 2.70E−10 | 2.20E−10 |
| "C200" | | 1.70E−07 | 2.20E−08 |
| "C202" | 1.80E−05 | 8.10E−09 | 3.10E−09 |
| "C207" | | 7.10E−09 | 2.80E−09 |
| "C208" | 6.00E−06 | 2.50E−10 | 2.30E−10 |
| "C209" | 8.50E−06 | 7.60E−10 | 7.90E−10 |
| "C210" | 7.50E−06 | 3.80E−10 | 3.20E−10 |
| "C211" | 1.40E−05 | 7-00E−10 | 2.80E−10 |
| "C212" | 5.60E−06 | 3.90E−10 | 1.30E−10 |
| "C213" | 1.10E−05 | 1.20E−09 | 5.20E−10 |
| "C214" | 8.50E−06 | 2.20E−09 | 1.30E−09 |
| "C215" | 5.00E−06 | 1.50e−09 | 1.40E−09 |
| "C216" | 1.50E−06 | 2.50E−09 | 1.30E−09 |
| "C217" | 6.60E−06 | 2.00E−09 | 2.70E−09 |
| "C218" | | 2.00E−09 | 8.50E−10 |
| "C219" | 2.50E−05 | 2.00E−09 | 1.20E−09 |
| "C220" | 6.20E−06 | 4.20E−09 | 3.70E−09 |
| "C221" | 1.90E−06 | 2.10E−09 | 2.00E−09 |
| "C222" | 1.20E−06 | 2.40E−10 | 2.90E−10 |
| "C223" | 8.40E−07 | 6.00E−10 | 5.10E−10 |
| "C224" | 3.10E−06 | 8.70E−10 | 7.10E−10 |
| "C225" | 7.00E−07 | 7.30E−10 | 4.00E−10 |
| "C226" | 1.80E−06 | 1.60E−09 | 9.50E−10 |
| "C227" | 4.10E−07 | 6.60E−10 | 4.20E−10 |
| "C228" | | 1.40E−08 | 2.20E−09 |
| "C229" | 2.40E−05 | 2.30e−08 | 2.30E−09 |
| "C230" | 1.80E−06 | 5.10E−09 | 2.10E−09 |
| "C231" | 4.50E−06 | 3.60E−10 | 5.40E−10 |
| "C232" | 2.70E−06 | 2.00E−08 | 5.70E−09 |
| "C233" | 5.30E−06 | 1.20E−09 | 2.30E−09 |
| "C234" | 1.80E−05 | 6.60E−10 | 3.00E−10 |
| "C235" | 3.00E−06 | 5.70E−10 | 3.90E−10 |
| "C236" | 1.00E−05 | 4.80E−10 | 2.40E−10 |
| "C237" | 1.00E−05 | 6.60E−10 | 3.00E−10 |
| "C238" | 4.10E−06 | 1.50E−09 | 1.50E−09 |
| "C239" | 2.40E−05 | 2.60E−09 | 8.20E−10 |
| "C240" | 1.90E−05 | 1.40E−08 | 5.30E−09 |
| "C241" | | 1.10E−08 | 4.90E−09 |
| "C242" | | 2.40E−08 | 7.10E−09 |
| "C243" | 4.20E−06 | 4.70E−10 | 2.20E−10 |
| "C244" | 1.80E−06 | 8.10E−10 | 2.80E−10 |
| "C245" | 5.80E−06 | 4.10E−10 | 1.70E−10 |
| "C246" | 1.30E−05 | 6.30E−10 | 3.20E−10 |
| "C247" | 3.50E−06 | 3.30E−09 | 6.60E−10 |
| "C248" | 2.40E−06 | 7.00E−10 | 2.30E−10 |
| "C249" | 1.10E−06 | 4.20E−10 | 1.20E−10 |
| "C250" | | 2.80E−09 | 1.10E−09 |
| "C251" | | 7.80e−09 | 2.90E−09 |
| "C252" | | 3.50E−08 | 1.70E−08 |
| "C253" | | 3.10E−08 | 1.90E−08 |
| "C254" | | 2.80E−08 | 1.50E−08 |
| "C255" | | 1.10E−07 | 4.90E−08 |
| "C256" | | 1.60E−07 | 6.50E−08 |
| "C257" | | 1.10E−07 | 5.80E−08 |
| "C258" | | 1.50E−07 | 9.50E−08 |
| "C259" | | 7.30E−07 | 4.60E−07 |
| "C262" | | 7.10E−09 | 1.20E−09 |
| "C263" | | 5.10E−09 | 3.30E−10 |
| "D1" | 3.10E−06 | 1.20E−07 | 8.50E−08 |

Explanation: 3.00 E−06 means $3.00 \times 10^{-6}$

The compounds shown in Table 2 are particularly preferred compounds according to the invention.

TABLE 3

Comparative Data:

| Compound | EC$_{50}$ [M] TNKS cellular assay | Solubility pH 7.4 (mg/ml) | Microsomal stability CLint Mouse liver | Microsomal stability CLint Human |
|---|---|---|---|---|
| From WO 2015/014442 A1, page 60/61 2-{4-[4-(4-methoxy-benzoyl)-piperidin-1-yl]-4-oxo-butyl}-3H-quinazolin-4-one ("A1") | 2.00E−09 | 0.018 | 120 | 104 |
| From WO 2015/014442 A1, page 63 6,8-difluoro-2-{4-[4-(4-methoxy-benzoyl)-piperidin-1-yl]-4-oxo-butyl}-3H-quinazolin-4-one ("A5") | 2.60E−09 | 0.005 | 86 | 58 |
| "C41" | 1.80E−09 | 0.055 | 36 | 25 |
| "C43" | 4.30E−09 | 0.207 | 36 | 15 |
| "C45" | 4.90E−10 | 0.042 | 62 | 25 |
| "C48" | 4.40E−09 | 0.206 | 59 | 20 |
| "C42" | 4.80E−09 | 0.158 | 51 | 16 |
| "C52" | 4.60E−09 | 0.868 | <10 | <10 |
| "C137" | 1.90E−08 | 0.070 | 78 | 10 |
| "C157" | 2.70E−09 | 0.272 | 46 | 22 |
| "C179" | 1.70E−08 | 0.058 | 29 | 11 |
| "C199" | 3.30E−09 | 0.585 | 44 | 12 |
| "C208" | 5.20E−09 | 0.101 | 26 | <10 |
| "C214" | 1.50E−08 | 0.394 | 41 | 21 |

Compounds according to present invention show higher solubility and higher microsomal stability in comparison to "A1" and "A5" disclosed in WO 2015/014442 A1.

The compounds shown in Table 3 are particularly preferred compounds according to the invention.

Synthesis of Intermediates

6-Bromo-5-oxo-hexanoic acid methyl ester (mixture of Br— and Cl— product)

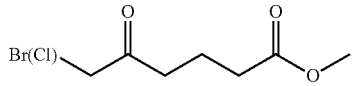

2-Acetyl-pentanedioic acid diethyl ester (99.4 g; 0.432 mol) was dissolved in dry diethyl ether (600 mL). The solution was cooled to 0° C. and bromine (22.1 mL; 0.432 mol) was added dropwise via a syringe under argon within 15 min. The yellow solution was stirred at 0° C. for 15 min, warmed to room temperature and stirred for 14 h. The reaction mixture was evaporated to dryness. The oily residue was dissolved in a mixture of glacial acetic acid (200 mL) and hydrochloric acid (37%, 200 mL), stirred at room temperature for 2 h and then warmed to 80° C. and stirred for further 4 h. The mixture was cooled to ambient temperature and evaporated to dryness. The residue was dissolved in methanol (50 mL) and sulfuric acid (98%, 1 mL) was added. The mixture was heated to reflux and stirred for 4 h, cooled to room temperature, diluted with 500 mL dichloromethane, washed twice with water, once with saturated NaHCO$_3$ solution and brine, dried with Na$_2$SO$_4$, filtered by suction and evaporated to dryness. The oily residue (69.9 g) was purified by distillation; yield: 44.2 g brown oil (Rt: 1.88 min, purity: 77.3%).

A1.1: 6-(2-Cyano-5-methyl-pyrrol-1-yl)-5-oxo-hexanoic acid methyl ester

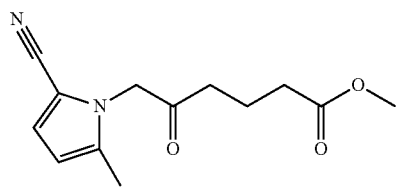 [SMILES: COC(=O)CCCC(=O)Cn1c(C)ccc1C#N]

5-Methyl-1H-pyrrole-2-carbonitrile (400 mg; 3.769 mmol) and 6-bromo-5-oxo-hexanoic acid methyl ester (1.64 g; 5.654 mmol) were dissolved in dry acetone (8 mL) and potassium carbonate (1.04 g; 7.538 mmol) was added. The reaction mixture was stirred at room temperature for 14 h. The reaction mixture was filtered by suction and the filter cake was washed with acetone. The filtrate was evaporated to dryness and the residue purified by flash-chromatography (Companion RF; 100 g C18 silica gel column). The combined fractions were evaporated to an aqueous residue, rendered basic with saturated NaHCO$_3$ solution and extracted 3 times with ethyl acetate. The combined organic layers were washed with brine, dried with Na$_2$SO$_4$, filtered and evaporated to dryness to give 882 mg (92%) light green oil (purity: 97.2%; Rt: 2.40 min).

A1.2: 4-(6-Methyl-1-oxo-1,2-dihydro-pyrrolo[1,2-a]pyrazin-3-yl)-butyric acid

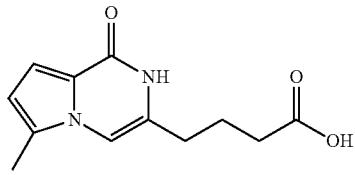 [SMILES: Cc1ccc2c(=O)[nH]c(CCCC(=O)O)cn12]

6-(2-Cyano-5-methyl-pyrrol-1-yl)-5-oxo-hexanoic acid methyl ester (500 mg; 1.957 mmol) and potassium carbonate (1.35 g; 9.787 mmol) were suspended in methanol (5 mL). Dry dimethyl sulfoxide (0.42 mL; 5.872 mmol) was added followed by the dropwise addition of hydrogen peroxide (30% in water; 0.60 mL; 5.872 mmol). The reaction mixture was stirred at 35° C. for 5 min and at room temperature for 2 h. The suspension was diluted with water, acidified with 10% citric acid solution and stirred for 10 min at room temperature. The precipitate was filtered by suction, washed with water and acetonitrile and dried under vacuum at 60° C. for 2 h; yield: 326 mg (69%) colorless solid (purity: 96.9%; Rt: 1.71 min); LC/MS (A), Rt: 1.45 min; (M+H) 235.

A2: 4-(1-Oxo-1,2-dihydro-pyrrolo[1,2-a]pyrazin-3-yl)-butyric acid

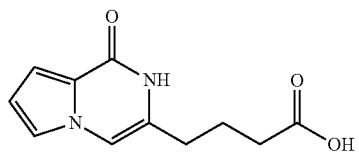

A2 was prepared according to the procedure described for A1; yield: 391 mg (84%) colorless solid (purity: 100%; Rt: 1.47 min); LC/MS (A), Rt: 1.33 min; (M+H) 221.

A3.1: 1-(5-Methoxycarbonyl-2-oxo-pentyl)-4-methyl-1H-pyrrole-2-carboxylic acid ethyl ester 4-Methyl-1H-pyrrole-2-carboxylic acid ethyl ester (500.0 mg; 3.264 mmol) and 6-bromo-5-oxo-hexanoic acid methyl ester (1.42 g; 4.896 mmol) were dissolved in dry acetone (8 mL) and potassium carbonate (0.90 g; 6.528 mmol) was added. The reaction mixture was stirred at room temperature for 1 h, at 50° C. for 14 h and at 60° C. for 7 h. The reaction mixture was diluted with water (50 mL) and extracted with ethyl acetate. The combined organic layers were washed with brine, dried with Na$_2$SO$_4$, filtered and evaporated to dryness. The crude product was purified by flash chromatography (Companion RF; 80 g Si50 silica gel column); yield: 964 mg (100%) colorless oil (purity: 100%; Rt: 2.77 min).

A3.2: 4-(7-Methyl-1-oxo-1,2-dihydro-pyrrolo[1,2-a]pyrazin-3-yl)-butyric acid methyl ester To 1-(5-Methoxycarbonyl-2-oxo-pentyl)-4-methyl-1H-pyrrole-2-carboxylic acid ethyl ester (0.96 g; 3.264 mmol) and ammonium acetate (7.00 g; 90.812 mmol) glacial acetic acid (7 mL) was added and the mixture was stirred at 110° C. for 4.5 h, cooled to ambient temperature and allowed to stand for 14 h. The reaction mixture was diluted with water (30 mL) and extracted with dichloromethane. The combined organic layers were washed with saturated NaHCO$_3$ solution and brine, dried with sodium sulfate, filtered by suction and evaporated to dryness. The oily residue was purified by flash chromatography (Companion RF; 80 g Si50 silica gel column); yield: 183 mg (22%) brown oil (purity: 99.2%; Rt: 2.06 min).

A3.3: 4-(7-Methyl-1-oxo-1,2-dihydro-pyrrolo[1,2-a]pyrazin-3-yl)-butyric acid

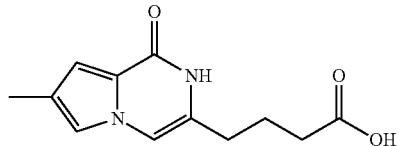 [SMILES: Cc1cc2c(=O)[nH]c(CCCC(=O)O)cn2c1]

4-(7-Methyl-1-oxo-1,2-dihydro-pyrrolo[1,2-a]pyrazin-3-yl)-butyric acid methyl ester (183.0 mg; 0.731 mmol) was suspended in dioxane (2.5 mL). Sodium hydroxide solution (2 N; 548 μL; 1.097 mmol) was added while stirring and the mixture was stirred at ambient temperature for 1 h. HCl (2 N; 550 μL; 1.100 mmol) was added and the formed precipitate was filtered by suction, washed with water, acetonitrile and diethyl ether and dried under vacuum at 50° C. for 2 h; yield: 76 mg (44%) colorless solid (purity: 100%; Rt: 1.74 min); LC/MS (A), Rt: 1.48 min; (M+H) 235.

A4.1: 5-Fluoro-1H-pyrrole-2-carboxylic acid methyl ester

1H-Pyrrole-2-carboxylic acid methyl ester (5.00 g; 38.761 mmol) was dissolved in acetonitrile (100 mL), selectfluor (15.90 g; 42.637 mmol) was added and temperature of the mixture was raised from room temperature to 60° C. within 5 min. The reaction mixture was diluted with ice water (400 mL) and extracted with dichloromethane. The combined organic layers were washed with water, dried with sodium sulfate, filtered by suction and evaporated to dryness. The residue was purified by flash chromatography (Companion RF; 330 g Si50 silica gel column); yield: 911 mg (15%) pale-yellow solid (purity: 91.9%; Rt: 1.76 min); LC/MS (A), Rt: 1.59 min; (M+H) 144.

A4.4: 4-(6-Fluoro-1-oxo-1,2-dihydro-pyrrolo[1,2-a]pyrazin-3-yl)-butyric acid

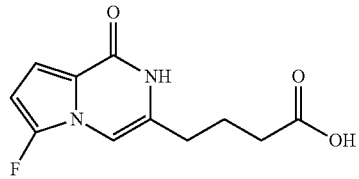 [SMILES: O=C(O)CCCc1cn2c(F)ccc2c(=O)[nH]1]

Steps A4.2-A4.4 were performed as described for A3; yield: 95 mg (30%) pale-brown solid (purity: 85.8%; Rt: 1.72 min); LC/MS (A), Rt: 1.47 min; (M+H) 239.

A5.1: (Z)-3-Dimethylamino-2-isocyano-acrylic acid ethyl ester

Isocyano-acetic acid ethyl ester (5.46 mL; 50.00 mmol) and 1-tert-butoxy-N,N,N',N'-tetramethyl-methanediamine (20.65 mL; 100.00 mmol) were stirred at room temperature for 14 h. The reaction mixture was evaporated to dryness and the residue (8.4 g, brown oil) was used in the next step without further purification.

A5.2: 1-Benzyl-1H-imidazole-4-carboxylic acid ethyl ester (Z)-3-Dimethylamino-2-isocyano-acrylic acid ethyl ester (4.87 g; 28.967 mmol) and benzylamine (3.41 mL, 31.864 mmol) were stirred at 70° C. for 14 h. The reaction mixture was evaporated to dryness and the residue purified by chromatography (330 g silica gel column; dichloromethane/methanol) to afford 3.93 g (57%) as a brown oil (purity: 97%; Rt: 2.09 min).

A5.3: 1-Benzyl-1H-imidazole-4-carboxylic acid amide

1-Benzyl-1H-imidazole-4-carboxylic acid ethyl ester (3.93 g; 17.067 mmol) and ammonium chloride (274.0 mg, 5.120 mmol) were dissolved in ammonia solution (32%; 45 mL) and heated in an autoclave at 105° C. and 6.2 bar for 14 h. The product was filtered by suction, washed with water and dried under vacuum at 50° C. for 14 h; yield: 2.13 g (63%) beige solid; (purity: 99.5%; Rt: 1.35 min).

A5.4: 4-(8-Oxo-7,8-dihydro-imidazo[1,5-a]pyrazin-6-yl)-butyric acid

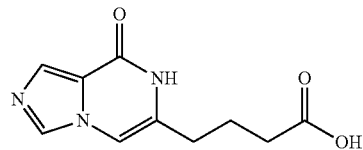 [SMILES: O=C(O)CCCc1cn2cncc2c(=O)[nH]1]

1-Benzyl-1H-imidazole-4-carboxylic acid amide (470.0 mg; 2.336 mmol) and 6-bromo-5-oxo-hexanoic acid methyl ester (1.02 g; 3.504 mmol) were dissolved in a mixture of DMF (2 mL) and acetonitrile (8 mL) and stirred at 90° C. for 14 h. The reaction mixture was cooled to ambient temperature and then evaporated to dryness. To the obtained oily residue imidazole (6.36 g; 93.428 mmol) was added and the mixture was stirred under argon at 175° C. for 4 h.

The dark-brown reaction mixture was cooled to ambient temperature and diluted with water (20 mL) and extracted with ethyl acetate. The aqueous layer was evaporated to one third of the volume and then purified by chromatography (Companion RF; 205 g RP18 silica gel column). The combined fractions were evaporated to dryness. The oily residue was dissolved in water, freeze-dried and used in the next step without further purification.

A6.1: 2-(5-Methoxycarbonyl-2-oxo-pentyl)-5-methyl-2H-pyrazole-3-carboxylic acid ethyl ester To a solution of 5-methyl-2H-pyrazole-3-carboxylic acid ethyl ester (771 mg, 5.00 mmol) and 6-bromo-5-oxo-hexanoic acid methyl ester (1.19 g, 5.35 mmol) in THF (10 ml) lithium carbonate (406 mg, 5.50 mmol) is added. The resulting suspension is stirred in a closed reaction vial at 100° C. for 15 h. The reaction mixture is allowed to reach room temperature, evaporated to dryness and the residue is purified by chromatography on a silica gel column with cyclohexane/ethyl acetate as eluent to afford 2-(5-methoxycarbonyl-2-oxo-pentyl)-5-methyl-2H-pyrazole-3-carboxylic acid ethyl ester as brown oil; HPLC/MS (C), Rt: 2.55 min; [M+H] 297; $^1$H NMR (500 MHz, DMSO-$d_6$) δ 6.71 (s, 1H), 5.31 (s, 2H), 4.23 (q, J=7.1 Hz, 2H), 3.60 (s, 3H), 2.55 (t, J=7.3 Hz, 2H), 2.33 (t, J=7.4 Hz, 2H), 2.19 (s, 3H), 1.75 (p, J=7.4 Hz, 2H), 1.26 (t, J=7.1 Hz, 3H).

In an analogous reaction using cesium carbonate instead of lithium carbonate the other isomer 1-(5-methoxycarbonyl-2-oxo-pentyl)-5-methyl-1H-pyrazole-3-carboxylic acid ethyl ester is obtained; beige solid, HPLC/MS (C), Rt: 2.37 min; [M+H] 297; $^1$H NMR (400 MHz, DMSO-$d_6$) δ 6.55 (s, 1H), 5.23 (s, 2H), 4.23 (q, J=7.1 Hz, 2H), 3.59 (s, 3H), 2.57 (t, J=7.2 Hz, 2H), 2.32 (t, J=7.4 Hz, 2H), 2.14 (s, 3H), 1.75 (p, J=7.3 Hz, 2H), 1.26 (t, J=7.1 Hz, 3H).

A6.2: 4-(2-Methyl-4-oxo-4,5-dihydro-pyrazolo[1,5-a]pyrazin-6-yl)-butyric acid methyl ester To a solution of 2-(5-methoxycarbonyl-2-oxo-pentyl)-5-methyl-2H-pyrazole-3-carboxylic acid ethyl ester (945 mg; 3.19 mmol) in acetic acid (5.83 ml) ammonium acetate (2.46 g, 31.9 mmol) is added. The suspension is heated to 100° C. and stirred at this temperature for 16 h. The reaction mixture is allowed to reach room temperature and partitioned between water and dichloromethane. The organic phase is dried over sodium sulfate and evaporated to dryness. The residue is purified by chromatography on a silica gel column with dichloromethane/methanol as eluent to afford 4-(2-methyl-4-oxo-4,5-dihydro-pyrazolo[1,5-a]pyrazin-6-yl)-butyric acid methyl ester as white solid; HPLC/MS (C), Rt: 2.02 min; [M+H] 250.

A6.3: 4-(2-Methyl-4-oxo-4,5-dihydro-pyrazolo[1,5-a]pyrazin-6-yl)-butyric acid

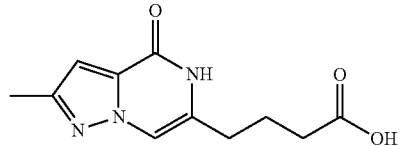 [SMILES: Cc1cc2c(=O)[nH]c(CCCC(=O)O)cn2n1]

To a solution of 4-(2-methyl-4-oxo-4,5-dihydro-pyrazolo[1,5-a]pyrazin-6-yl)-butyric acid methyl ester (189.0 mg, 0.76 mmol) in methanol (1.5 mL) aqueous sodium hydroxide solution (1 M, 1.53 ml, 1.53 mmol) is added and the reaction mixture is stirred for 4 h at room temperature. Excess water and 2 M aqueous hydrochloric acid is added to reach a pH value of 3. The resulting precipitate is filtered off, washed with water and dried under vacuum to afford 4-(2-methyl-4-oxo-4,5-dihydro-pyrazolo[1,5-a]pyrazin-6-yl)-butyric acid as colorless fluffy solid; HPLC/MS (C), Rt: 1.84 min; [M+H] 236; $^1$H NMR (400 MHz, DMSO-$d_6$) δ 12.07 (s, 1H), 11.16 (s, 1H), 7.39 (s, 1H), 6.70 (s, 1H), 2.43 (t, J=7.4 Hz, 2H), 2.32 (s, 3H), 2.24 (t, J=7.4 Hz, 2H), 1.83 (p, J=7.5 Hz, 2H).

A7: 4-(8-Oxo-7,8-dihydro-imidazo[1,2-a]pyrazin-6-yl)-butyric acid

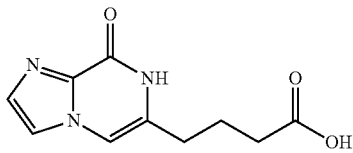

Steps A7.1-A7.3 were performed as described for A3; yield: 201 mg (54%) pale-brown solid (purity: 99.7%; Rt (2): 2.25 min); LC/MS (A), Rt: 0.79 min; (M+H) 222.

A8: 4-(7-Fluoro-1-oxo-1,2-dihydro-pyrrolo[1,2-a]pyrazin-3-yl)-butyric acid

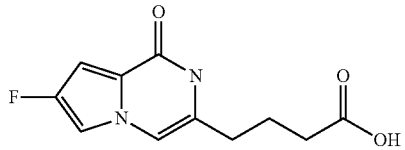 [SMILES: O=C(O)CCCc1cn2cc(F)cc2c(=O)[nH]1]

Steps A8.1-A8.3 were performed as described for A3; yield: 124 mg (100%) beige solid (purity: 97%); LC/MS (C), Rt: 1.99 min; (M+H) 239.

A9.1: 2-Methyl-1H-imidazole-4-carboxylic acid methyl ester

2-Methyl-1H-imidazole-4-carboxylic acid (5.0 g; 37.665 mmol) was dissolved in dry methanol (75 mL) and concentrated sulfuric acid (2.41 mL; 45.198 mmol) was added while stirring at room temperature. After a few minutes a clear yellow solution was formed. It was heated to reflux and stirred for 24 h. Further concentrated sulfuric acid (1 mL; 18.761 mmol) was added dropwise and the mixture was stirred for another 24 h. This was repeated once again and the reaction mixture was then worked up. The solution was cooled to ambient temperature and evaporated to a fifth of the volume. The oily residue was rendered basic (pH 9) with 2N NaOH and extracted exhaustively with dichloromethane. The combined organic layers were dried with sodium sulfate, filtered by suction and evaporated to dryness; yield: 4.15 g (78%) colorless solid (purity: 98.9%; Rt (2): 0.65 min); LC/MS (A), Rt: 0.34-0.40 min; (M+H) 141.1.

A9.2: 1-Benzyl-2-methyl-1H-imidazole-4-carboxylic acid methyl ester

2-Methyl-1H-imidazole-4-carboxylic acid methyl ester (1.50 g; 10.586 mmol) and cesium carbonate (6.90 g; 21.172 mmol) were suspended in acetonitrile (20 mL). While stirring under argon benzyl bromide (1.32 mL; 11.115 mmol) was added dropwise. The reaction mixture was stirred at room temperature for 14 h. The resulting precipitate was filtered by suction and the filtrate was evaporated to dryness. The residue (2.68 g yellow oil; purity 94.8%; Rt: 1.55 min) was used in the next step without further purification.

A9.4: 4-(3-Methyl-8-oxo-7,8-dihydro-imidazo[1,5-a]pyrazin-6-yl)-butyric acid

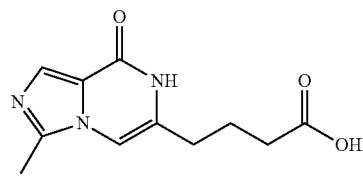 [SMILES: Cc1ncc2c(=O)[nH]c(CCCC(=O)O)cn12]

Steps A9.3-A9.4 were performed as described for A5; yield: 373 mg (57%) brown solid (purity: 94.1%; Rt (2): 2.27 min); LC/MS (A), Rt: 0.67 min; (M+H) 236.1.

A10.1: 3-Amino-4-methyl-thiophene-2-carboxylic acid

To a solution of 3-amino-4-methyl-thiophene-2-carboxylic acid methyl ester (5.00 g; 29.20 mmol) in water (75 mL) was added sodium hydroxide (5.84 g; 146.01 mmol) at room temperature. The reaction mixture was heated at 90° C. for 2 h. After completion of the reaction, the reaction mixture was cooled to 0° C. and acidified (pH 6-7) with 1.5 N HCl solution. The precipitate was filtered, washed with water and dried to afford 3-Amino-4-methyl-thiophene-2-carboxylic acid (3.0 g; 61%) as a colorless solid; $^1$H NMR (400 MHz, DMSO-$d_6$) δ [ppm] 7.18 (s, 1H), 6.38 (bs, 2H), 2.00 (s, 3H). LC/MS (B), Rt: 2.23 min.

A10.2: 3-Amino-4-methyl-thiophene-2-carboxylic acid amide

To a solution of 3-amino-4-methyl-thiophene-2-carboxylic acid (3.00 g; 19.09 mmol) in THF (60 mL) and DMF (3 mL) were added N,N-diisopropylethyl-amine (16.83 ml; 95.43 mmol), HOBt (3.95 g; 28.63 mmol) and EDCl (5.72 g; 28.63 mmol) at 0° C. The reaction mixture was stirred at room temperature for 30 min. Ammonium carbonate (9.17 g; 95.43 mmol) was added at room temperature and the reaction mixture was stirred for 15 h at room temperature. The reaction mixture was diluted with ethyl acetate, washed with water, brine, sodium sulfate and evaporated. The residue was purified by column chromatography using DCM and MeOH (9:1) as an eluent to afford 3-amino-4-methyl-thiophene-2-carboxylic acid amide (1.50 g; 47%) as a off-white solid; $^1$H NMR (400 MHz, DMSO-$d_6$) δ [ppm] 7.04 (s, 1H), 6.81 (bs, 2H), 6.27 (bs, 2H), 1.98 (s, 3H); LC/MS (D), Rt: 2.95 min; (M+H) 157.

A10.3: 4-(7-Methyl-4-oxo-3,4-dihydro-thieno[3,2-d]pyrimidin-2-yl)-butyric acid

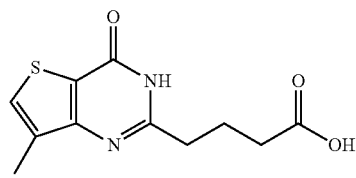 [SMILES: Cc1csc2c(=O)[nH]c(CCCC(=O)O)nc12]

To a solution of amino-4-methyl-thiophene-2-carboxylic acid amide (1.50 g; 9.60 mmol) in toluene (22.5 mL) was added dihydro-pyran-2,6-dione (1.23 g; 10.56 mmol) and refluxed for 16 h at 140° C. The solvent was removed under vacuum and the residue was crystallized with DCM and methanol, the solid was collected by filtration, washed with DCM and dried by suction to afford 4-(7-methyl-4-oxo-3,4-dihydro-thieno[3,2-d]pyrimidin-2-yl)-butyric acid (0.60 g; 24%) as a colorless solid; $^1$H NMR (400 MHz, DMSO-$d_6$) δ [ppm] 12.35 (bs, 1H), 12.07 (bs, 1H), 7.77 (s, 1H), 2.68-2.64 (t, 2H) 2.32-2.22 (m, 5H), 1.98-1.92 (m, 2H). LC/MS (B), Rt: 2.19 min; (M+H) 253.

A11.1: 5-Amino-1-methyl-1H-pyrazole-4-carbonitrile

To a mixture of methyl-hydrazine (377.0 mg; 8.255 mmol) in ethanol (20 mL) was added 2-[1-ethoxy-(E)- methylidene]-but-3-ynenitrile (1.0 g; 8.255 mmol) in portions at 25-26° C. under nitrogen atmosphere. The reaction mixture was heated to 90° C. for 2 h. The reaction mixture was cooled to 25-26° C. while a solid precipitated. The solid was filtered by suction and dried to afford the title compound (0.60 g; 60%) as a colorless solid; $^1$H NMR (400 MHz, DMSO-$d_6$) δ [ppm] 7.49 (s, 1H), 6.52 (bs, 2H), 3.50 (s, 3H); LC/MS (D), Rt: 1.95 min; (M+H) 123.

A11.2: 5-Amino-1-methyl-1H-pyrazole-4-carboxylic acid amide

5-Amino-1-methyl-1H-pyrazole-4-carbonitrile (12.0 g; 0.098 mol) was added to sulfuric acid (36 mL) in portions at room temperature and stirred for 4 h under nitrogen atmosphere. The reaction mixture was poured slowly into ice cold water. The pH of the solution was adjusted to pH 8 using aqueous ammonia solution. A precipitate formed which was filtered, washed with water (20 mL) and dried under vacuum to afford the title compound (13.0 g; 94%) as a off-white solid; $^1$H NMR (400 MHz, DMSO-$d_6$) δ [ppm] 7.50 (s, 1H), 7.13 (bs, 1H), 6.75 (bs, 1H), 6.31 (s, 2H), 3.48 (s, 3H); LC/MS (D), Rt: 0.95 min; (M+H) 141.2.

A11.3: 4-(1-Methyl-4-oxo-4,5-dihydro-1H-pyrazolo[3,4-d]pyrimidin-6-yl)-butyric acid

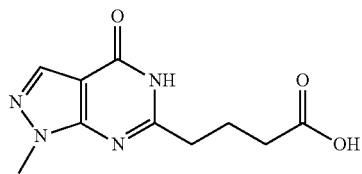 [SMILES: Cn1ncc2c(=O)[nH]c(CCCC(=O)O)nc21]

5-Amino-1-methyl-1H-pyrazole-4-carboxylic acid amide (8.00 g; 0.0566 mol) and dihydro-pyran-2,6-dione (6.59 g; 0.0566 mol) were heated to 150° C. for 6 h under nitrogen atmosphere. The reaction mixture was cooled to ambient temperature. The resulting solid was slurred with ethyl acetate (200 mL) containing methanol (20%) for 15 min, filtered by suction and dried to afford the title compound (3.00 g; 22%) as a colorless solid; $^1$H NMR (400 MHz, DMSO-$d_6$) δ [ppm] 7.96 (s, 1H), 3.85 (s, 3H), 2.66-2.63 (m, 2H), 2.31-2.29 (m, 2H), 1.97-1.91 (m, 2H); LC/MS (B), Rt: 1.54 min; (M+H) 237.3.

A12: 4-(3-Methyl-8-oxo-7,8-dihydro-imidazo[1,2-a]pyrazin-6-yl)-butyric acid

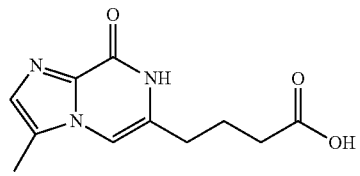 [SMILES: Cc1cnc2c(=O)[nH]c(CCCC(=O)O)cn12]

Steps A12.1-A12.3 were performed as described for A7; yield: 36 mg (58%) colorless solid (purity: 93.4%; Rt (2): 2.29 min); LC/MS (A), Rt: 0.91 min; (M+H) 236.1

A13.1: 1-Amino-5-methyl-1H-pyrrole-2-carboxylic acid ethyl ester

To a solution of 5-Methyl-1H-pyrrole-2-carboxylic acid ethyl ester (10.00 g; 62.02 mmol) in DMF (200.0 ml) lithium bis(trimethylsilyl)amide solution (1.0 M in THF; 93.03 mL; 93.03 mmol) was added dropwise at −10° C. under nitrogen. The reaction mixture was stirred at −10° C. for 1 h, then O-diphenylphosphoryl-hydroxylamine (27.40 g; 111.63 mmol) in DMF (200.0 mL) was added dropwise at −10° C. under nitrogen. The reaction mixture was slowly warmed to RT and stirred for 12 h. The reaction mixture was quenched with saturated NH$_4$Cl solution and was extracted with ethyl acetate. The organic layer was dried over sodium sulfate and concentrated under reduced pressure. The crude material was purified by flash column chromatography using 30% ethyl acetate in petrol ether to get the title compound (10.00 g; 95%). LC/MS (B), Rt: 3.42 min; (M+H) 169.0.

A13.2: 1-Amino-5-methyl-1H-pyrrole-2-carboxylic acid

To a solution of 1-Amino-5-methyl-1H-pyrrole-2-carboxylic acid ethyl ester (10.00 g; 58.74 mmol) in water (150.00 mL) sodium hydroxide (11.75 g; 293.71 mmol) was added at RT. The reaction mixture was stirred at 90° C. for 2 h. The reaction mixture was cooled to 0° C. and acidified with 1.5 N HCl solution to pH 6-7. The resultant solid was filtered, washed with water and dried to afford the title compound (4.00 g; 49%). LC/MS (B), Rt: 1.41 min; (M+H) 141.0.

A13.2: 1-Amino-5-methyl-1H-pyrrole-2-carboxylic acid amide

To a solution of 1-Amino-5-methyl-1H-pyrrole-2-carboxylic acid (4.00 g; 26.83 mmol) in THF (80.00 mL) HOBt (5.55 g; 40.25 mmol) and EDC.HCl (8.04 g; 40.25 mmol) were added at 0° C. The reaction mixture was stirred at room temperature for 15 min. Ammonium carbonate (14.32 g; 134.15 mmol) was added and the reaction mixture was stirred at room temperature for 12 h. The reaction mixture was diluted with ethyl acetate, washed with water, brine, and sodium sulfate and evaporated to dryness. The crude residue was purified by column chromatography using DCM and MeOH (9:1) as an eluent to afford 1-Amino-5-methyl-1H-pyrrole-2-carboxylic acid amide (0.80 g, 21%). LC/MS (B), Rt: 0.99 min; (M+H) 140.0.

A13.4: 4-(7-Methyl-4-oxo-3,4-dihydro-pyrrolo[2,1-f][1,2,4]triazin-2-yl)-butyric acid

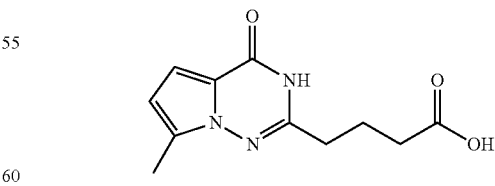

A mixture of 1-Amino-5-methyl-1H-pyrrole-2-carboxylic acid amide (100.0 mg; 0.68 mmol) and dihydro-pyran-2,6-dione (79.0 mg; 0.68 mmol) in toluene (2.00 mL) was refluxed for 16 h under nitrogen atmosphere. The solvent was evaporated under vacuum and the residue was taken up in 2 N NaOH (50 mL) and refluxed for 5 h. The reaction mass was cooled to room temperature and acidified to pH 5-6 with glacial acetic acid. The formed precipitate was collected by filtration and dried by suction to afford 4-(7-Methyl-4-oxo-3,4-dihydro-pyrrolo[2,1-f][1,2,4]triazin-2-yl)-butyric acid (120.00 mg; 74%) as a brown solid. $^1$H NMR (400 MHz, DMSO-$d_6$) δ [ppm] 12.08 (brs,1H), 11.46 (s, 1H), 6.76 (d, J=4.2 Hz, 1H), 6.30 (d, J=4.2 Hz, 1H), 2.55-2.49 (m, 2H), 2.36 (s, 3H), 2.34-2.29 (m, 2H), 1.94-1.88 (m, 2H). LC/MS (B), Rt: 2.54 min; (M+H) 236.2.

A14: 4-(6-Fluoro-4-oxo-3,4-dihydro-pyrrolo[2,1-f][1,2,4]triazin-2-yl)-butyric acid

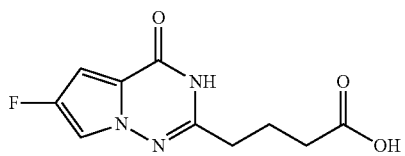 [SMILES: O=C(O)CCCc1nn2cc(F)cc2c(=O)[nH]1]

Steps A14.1-A14.4 were performed analogously to A13; yield: 1.80 g (44%) brown solid. $^1$H NMR (400 MHz, DMSO-$d_6$) δ [ppm] 12.08 (brs, 1H), 11.80 (brs, 1H), 7.64 (s, 1H), 6.69 (s, 1H), 2.29 (t, J=7.0 Hz, 2H), 1.88 (t, J=7.2 Hz, 2H). LC/MS (B), Rt: 2.47 min; (M+H) 240.0.

A15: 4-(4-Oxo-3,4-dihydro-pyrrolo[2,1-f][1,2,4]triazin-2-yl)-butyric acid

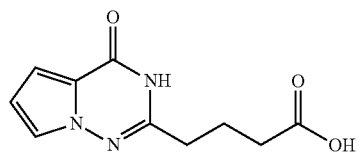 [SMILES: O=C(O)CCCc1nn2cccc2c(=O)[nH]1]

Steps A15.1-A15.4 were performed analogously to A13; yield: 2.88 g (79%) pale brown solid (purity: 97.4%; Rt: 1.41 min); LC/MS (A), Rt: 1.35 min; (M+H) 222.1.

A16: 4-(6-Methyl-4-oxo-3,4-dihydro-pyrrolo[2,1-f][1,2,4]triazin-2-yl)-butyric acid

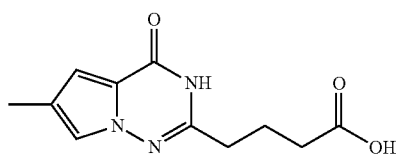

Steps A16.1-A16.4 were performed analogously to A13; yield: 0.55 g (42%) colorless solid. $^1$H NMR (400 MHz, DMSO-$d_6$) δ [ppm] 12.11 (brs, 1H), 11.62 (brs, 1H), 7.32 (s, 1H), 6.63 (s, 1H), 2.50-2.49 (m, 2H), 2.14 (s, 3H), 1.90-1.85 (m, 2H). LC/MS (B), Rt: 2.51 min; (M+H) 236.0.

A17.1: 4-(4-Oxo-3,5,7,8-tetrahydro-4H-pyrano[4,3-d]pyrimidin-2-yl)-butyric acid ethyl ester To a solution of 4-carbamimidoyl-butyric acid ethyl ester (1.80 g; 7.70 mmol) and 4-oxo-tetrahydro-pyran-3-carboxylic acid methyl ester (1.54 g; 9.24 mmol) in methanol (18.00 mL) triethylamine (2.18 mL; 15.41 mmol) was added under nitrogen atmosphere. The reaction mixture was stirred at room temperature for 18 h. The solvent was removed under vacuum and the residue was dissolved in DCM (250 mL), washed with water (2×100 mL), dried over sodium sulfate, and evaporated to dryness. The crude product was purified by column chromatography using and DCM/methanol as eluent to afford 4-(4-Oxo-3,5,7,8-tetrahydro-4H-pyrano[4,3-d]pyrimidin-2-yl)-butyric acid ethyl ester (1.20 g; 57%) as a pale yellow oil. Isolated product from chromatography containing mixture of ethyl and methyl ester was taken as such for next step.

A17.2: 4-(4-Oxo-3,5,7,8-tetrahydro-4H-pyrano[4,3-d]pyrimidin-2-yl)-butyric acid

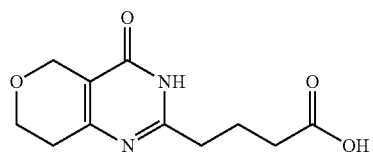 [SMILES: O=C(O)CCCc1nc2c(c(=O)[nH]1)COCC2]

To a solution of A17.1 (1.20 g; 4.41 mmol) in THF (1.44 mL), methanol (0.72 mL), and water (0.16 mL) lithium hydroxide monohydrate (0.56 g; 13.22 mmol) was added and stirred for 4 h. The reaction mixture was concentrated under vacuum, acidified to pH 5-6 with glacial acetic acid and evaporated to dryness. The residue was triturated with DCM-methanol (100 mL), filtered and dried by suction to afford 4-(4-Oxo-3,5,7,8-tetrahydro-4H-pyrano[4,3-d]pyrimidin-2-yl)-butyric acid (0.25 g; 24.0%) as a colorless solid. LC/MS (B), Rt: 0.67/0.89 min; (M+H) 239.0.

A18.1: 4-tert-Butoxycarbonylamino-5-methyl-thiophene-3-carboxylic acid methyl ester Diisopropylamine (4.863 mL; 0.034 mol) was dissolved in THF (70.0 mL) under nitrogen atmosphere and the solution was cooled to −78° C. n-Butyl-lithium (1.6 M in hexane; 18.70 mL; 0.030 mol) was added dropwise at −78° C. over a period of 30 min and the solution was warmed to −10° C. and stirred for 30 min. The solution was again cooled down to −78° C. and then 4-tert-butoxycarbonylamino-thiophene-3-carboxylic acid methyl ester (3.500 g; 0.014 mol) dissolved in THF (70.0 mL) was added dropwise over period of 30 min and the reaction mixture was stirred at −78° C. for 1 h. Iodomethane (0.941 mL; 0.015 mol) dissolved in THF (35.0 mL) was added dropwise at −78° C. and the reaction mixture was slowly warmed to 0° C. and stirred for 1 h at this temperature. The reaction mixture was cooled to −5° C. and quenched with 5% ammonium chloride solution (100 mL) and extracted with ethyl acetate. The combined organic layer was washed with water and brine, dried over sodium sulfate and concentrated. The crude mixture was purified with column chromatography using DCM containing methanol (2%) as a eluent to afford 4-tert-Butoxycarbonylamino-5-methyl-thiophene-3-carboxylic acid methyl ester (1.80 g; 0.006 mol; 47%) as a yellow solid; LC/MS (B), Rt: 4.48 min; (M+H-BOC) 172.0.

A18.2: (4-Carbamoyl-2-methyl-thiophen-3-yl)-carbamic acid tert-butyl ester

To a stirred solution of A18.1 (1.26 g; 4.64 mmol) in Methanol (13.0 mL) in an autoclave a solution of ammonia in methanol (7M; 130.0 mL) was added and the reaction mixture was heated to 70° C. for 20 h. The reaction mixture was cooled to room temperature and concentrated under vacuum. The crude product was purified by column chromatography using DCM/methanol (1%) as eluent; Yield: 0.78 g (66%) light brown solid;

A18.3: 4-Amino-5-methyl-thiophene-3-carboxylic acid amide hydrochloride

To a stirred solution of A18.2 (0.274 g; 1.07 mmol) in 1,4-dioxane (3.0 mL) at 0° C. HCl in dioxane (6.0 mL) was added and stirred at room temperature for 4 h. The reaction mixture was evaporated to dryness and the residue was triturated with ether, the solid was filtered, dried and used for the next step without further purification.

A18.4: 4-(7-Methyl-4-oxo-3,4-dihydro-thieno[3,4-d]pyrimidin-2-yl)-butyric acid

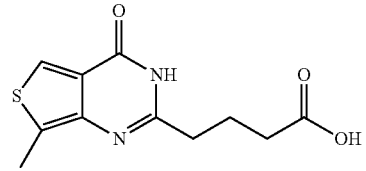 [SMILES: Cc1scc2c(=O)[nH]c(CCCC(=O)O)nc12]

The reaction was performed as described in A13.4 using triethylamine as base; yield: 0.38 g (61%) off-white solid; $^1$H NMR (400 MHz, DMSO-d$_6$) δ [ppm] 12.01 (brs, 1H), 11.47 (brs, 1H), 8.14 (s, 1H), 2.56-2.54 (m, 2H), 2.50 (s, 3H), 2.32-2.30 (m, 1H), 2.28-2.21 (m, 2H), 1.95-1.70 (m, 1H); LC/MS (F), Rt: 1.44 min; (M+H) 253.0.

A19.1: 4-(4-Oxo-3,4,5,6,7,8-hexahydro-quinazolin-2-yl)-butyric acid ethyl ester The reaction was performed as described in A13.4 using 2oxo-cyclohexane-carboxylic acid ethyl ester; yield: 2.24 g (26%) pale yellow gum; LC/MS (F), Rt: 1.62 min; (M+H) 265.2.

A19.2: 4-(4-Oxo-3,4,5,6,7,8-hexahydro-quinazolin-2-yl)-butyric acid

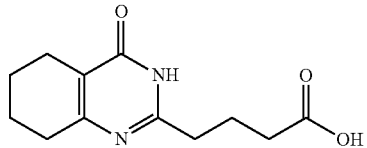 [SMILES: O=C(O)CCCc1nc2c(c(=O)[nH]1)CCCC2]

A19.1 was hydrolyzed to the corresponding acid at 100° C. for 24 h using aq. HCl (6N). The mixture was evaporated to dryness. The residue was triturated with ethyl acetate, filtered by suction and dried under vacuum; yield: 0.30 g (95%) pale yellow solid; LC/MS (F), Rt: 1.37 min; (M+H) 237.0.

A20.1: 2-Amino-1-methyl-1H-pyrrole-3-carbonitrile

To a solution of 2,2-dimethoxy-ethyl)-methyl-amine (16.40 mL; 149.86 mmol) in DCM (96 mL) malononitrile (10.00 g; 149.86 mmol) was added under nitrogen atmosphere and the reaction mixture was stirred for 10 min. Toluene-4-sulfonic acid (52.67 g; 299.72 mmol) was added and reaction mixture was stirred for 16 h at room temperature. The reaction mixture was concentrated under vacuum, rendered basic with 10% sodium bicarbonate solution and extracted with ethyl acetate. The organic layer was dried over anhydrous sodium sulfate, filtered and concentrated under vacuum. The crude was purified by column chromatography using ethyl acetate/petroleum ether; yield: 3.27 g (18.0%) pale brown solid.

A20.2: 4-(3-Cyano-1-methyl-1H-pyrrol-2-ylcarbamoyl)-butyric acid

A mixture of A20.1 (0.50 g; 3.64 mmol) and dihydropyran-2,6-dione (0.42 g; 3.64 mmol) in toluene (10.0 mL) was refluxed for 16 h under nitrogen atmosphere and the solvent evaporated under vacuum. The residue was triturated with ethyl acetate, filtered by suction and dried; yield: 0.23 g (27%) brown solid.

A20.3: 4-(7-Methyl-4-oxo-4,7-dihydro-3H-pyrrolo[2,3-d]pyrimidin-2-yl)-butyric acid

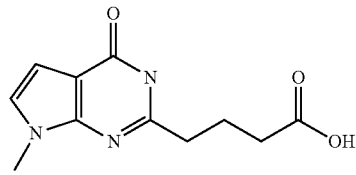 [SMILES: Cn1ccc2c(=O)[nH]c(CCCC(=O)O)nc21]

To a stirred solution of A20.2 (523.0 mg; 2.22 mmol) in 10% aqueous potassium hydroxide (20.0 mL) hydrogen peroxide (30% solution; 40.0 ml) was added at 0° C., subsequently warmed to room temperature and stirred for 30 min. The reaction mixture was heated to 75° C. for 12 h. The reaction mixture was cooled to 0° C. and acidified to pH 4 with acetic acid. The formed precipitate was filtered, triturated with n-hexane, filtered, and dried; yield: 529.0 mg (99%) colorless solid; $^1$H NMR (400 MHz, DMSO-d$_6$) δ [ppm] 12.09 (s, 1H), 11.74 (s, 1H), 7.02 (d, J=3.20 Hz, 1H), 6.39 (d, J=3.20 Hz, 1H), 3.80 (s, 3H), 2.64 (t, J=8.00 Hz, 2H), 2.31-2.34 (m, 2H), 1.94 (t, J=6.80 Hz, 2H). LC/MS (B), Rt: 1.75 min; (M+H) 236.0.

A21: 4-(6,7-Difluoro-4-oxo-3,4-dihydro-pyrrolo[2,1-f][1,2,4]triazin-2-yl)-butyric acid

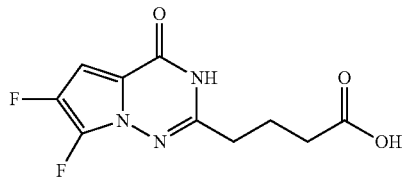 [SMILES: O=C(O)CCCc1nn2c(F)c(F)cc2c(=O)[nH]1]

A14 (100.0 mg; 0.402 mmol) was suspended in acetonitrile (3.0 mL) and acetic acid (1.0 mL; 17.485 mmol). Selectfluor (164.8 mg; 0.442 mmol) was added and the mixture was heated to 60° C. and stirred for 1.5 h. The pale brown suspension was cooled to room temperature, diluted with water and extracted with ethyl acetate. The combined organic layers were washed with brine, dried with sodium sulfate, filtered by suction and evaporated to dryness; yield: 88 mg brown solid (mixture of starting material and product). It was used without further purification; LC/MS (B), Rt: 1.61 min; (M+H) 258.1.

A22.1: 2-Methyl-3-oxo-butyramide

2-Methyl-3-oxo-butyric acid ethyl ester (5.00 g; 34.68 mmol) was taken in a pressure tube and aq. ammonia (100.0 mL) was added at room temperature, then the reaction mixture was heated in at 50° C. for 16 h. The reaction mixture was cooled to room temperature and concentrated under reduced pressure; yield: 3.27 g (82%) off-white solid.

A22.2: (Z)-3-Amino-2-methyl-but-2-enoic acid amide

A suspension of A22.1 (0.85 g; 7.38 mmol) in o-xylene (20.0 mL) was heated to 115° C. and ammonia gas was bubbled into the reaction mixture for 5 h at this temperature. The reaction mixture was cooled to room temperature, ammonia was removed by purging with nitrogen and the reaction mixture was then concentrated under reduced pressure. The residue was dried (0.30 g; off-white solid) and used for the next step without further purification.

A22.3: 4-(4,5-Dimethyl-6-oxo-1,6-dihydro-pyrimidin-2-yl)-butyric acid

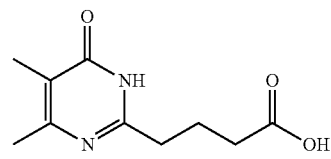

A22.2 (0.67 g; 5.83 mmol) and dihydro-pyran-2,6-dione (1.02 g; 8.74 mmol) were dissolved in toluene (6.0 mL) and heated to 130° C. for 6 h under nitrogen atmosphere. The reaction mixture was cooled to room temperature and evaporated to dryness. The crude product was triturated with petroleum ether and ethyl acetate (50:50) mixture, filtered by suction and dried; yield: 0.29 g; (24%) off white solid; $^1$H NMR (400 MHz, DMSO-$d_6$) δ [ppm] 12.0 (bs, 2H), 3.59 (s, 3H), 2.35-2.32 (m, 2H), 2.26 (s, 3H), 2.24-2.22 (m, 2H), 1.75-1.71 (m, 2H); LC/MS (F), Rt: 0.79 min; (M+H) 211.0.

A23: 4-(4-Ethyl-6-oxo-1,6-dihydro-pyrimidin-2-yl)-butyric acid

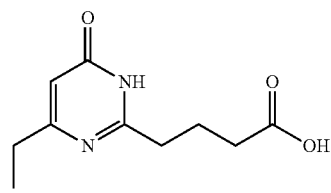

Steps A23.1-A23.3 were performed analogously to A22; yield: 0.35 g; (5%) pale brown solid. LC/MS (F), Rt: 0.81 min; (M+H) 211.0.

A24: 4-(4-Isopropyl-6-oxo-1,6-dihydro-pyrimidin-2-yl)-butyric acid

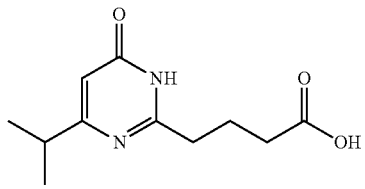 [SMILES: CC(C)c1cc(=O)[nH]c(CCCC(=O)O)n1]

Steps A24.1-A24.3 were performed analogously to A22; yield: 0.91 g; (39%) brown solid. LC/MS (F), Rt: 1.34 min; (M+H) 225.0.

A25.1: 3-Bromo-3H-isobenzofuran-1-one

A mixture of 3H-isobenzofuran-1-one (10.00 g; 73.06 mmol), 1-bromo-pyrrolidine-2,5-dione (13.79 g; 76.72 mmol) and dibenzoyl peroxide (1.05 g; 3.65 mmol) was refluxed in tetrachloro-methane (100.0 mL) under nitrogen atmosphere for 3 h. The reaction mixture was evaporated and the residue purified by chromatography; yield: 12.04 g (77%) colorless solid; LC/MS (A), Rt: 2.01 min; (M+H) 212.9/214.9.

A25.2: (3-Oxo-1,3-dihydro-isobenzofuran-1-yl)-triphenyl-phosphonium bromide

To A25.1 (1.26 g; 5.929 mmol) and triphenyl-phosphane (1.57 g; 5.929 mmol) acetonitrile (10.0 mL) was added and the mixture was stirred at 90° C. for 3 h. The reaction mixture was cooled to room temperature and evaporated to dryness. The residue was triturated with diethyl ether, filtered, washed with diethyl ether and dried in vacuo; yield: 2.71 g (96%) colorless solid; LC/MS (A), Rt: 1.71 min; (M+H) 395.1.

A25.3: 4-[3-Oxo-3H-isobenzofuran-(1E)-ylidene]-butyric acid methyl ester

A25.2 (2.71 g; 5.736 mmol) was suspended in dichloromethane (40.0 mL). While stirring 4-oxo-butyric acid methyl ester (0.67 mL; 5.736 mmol) was added under argon followed by the dropwise addition of triethylamine (874.6 µL; 6.309 mmol). The mixture was stirred at room temperature for 14 h. The reaction mixture was diluted with dichloromethane, washed twice with water, dried with sodium sulfate, filtered by suction and evaporated to dryness. The solid residue was triturated in MTB-Ether, filtered by suction, washed with MTB-Ether. The filtrate was evaporated to dryness and the residue (1.04 g, yellow solid) used in the next step without further purification.

A25.4: 4-(4-Oxo-3,4-dihydro-phthalazin-1-yl)-butyric acid methyl ester

A25.3 (1.633 g; 4.486 mmol) was dissolved in ethanol (20.0 mL) and cooled to 0-5° C. Hydrazinium hydroxide (0.44 mL; 8.973 mmol) was added dropwise over a period of 5 min and the mixture was stirred for 1 h at 0-5° C. The mixture was warmed to room temperature, stirred for 1 h and evaporated to dryness. The oily residue was dissolved in ethyl acetate, washed with water and with brine, dried with sodium sulfate, filtered by suction and evaporated to dryness. The oily residue was purified by chromatography. The combined fractions were evaporated to an aqueous residue, which was rendered basic with saturated NaHCO₃ solution and extracted 3 times with ethyl acetate. The combined organic layers were washed with brine, dried with sodium sulfate, filtered and evaporated to dryness. The residue was triturated with MTB-Ether, filtered by suction, washed with little MTB-Ether and dried; yield: 0.54 g (49%) colorless solid; LC/MS (A), Rt: 1.61 min; (M+H) 247.1.

A25.5: 4-(4-Chloro-phthalazin-1-yl)-butyric acid methyl ester

A25.4 (500.0 mg; 2.016 mmol) was suspended in acetonitrile (5.0 mL). Phosphorus oxychloride (0.37 mL; 4.032 mmol) was added under argon atmosphere and the mixture was stirred to 50° C. for 14 h. The reaction mixture was quenched with ice-water (50 mL) and extracted 3 times with ethyl acetate. The combined organic layers were washed with saturated NaHCO₃ solution and brine, dried with sodium sulfate, filtered by suction and evaporated to dryness; yield: 455 mg (85%) brown solid; LC/MS (A), Rt: 1.87 min; (M+H) 265.1/267.0.

A25.6: 4-Phthalazin-1-yl-butyric acid methyl ester

A25.5 (100.0 mg; 0.378 mmol) and trimethylamine (63.0 µL; 0.453 mmol) were dissolved in THF (10.0 mL) and hydrogenated over Pd—C (5%) at room temperature and normal pressure. The reaction mixture was filtered by suction and the residue washed with THF and methanol. The filtrate was evaporated to dryness and used in the next step without further purification.

A25.7: 4-Phthalazin-1-yl-butyric acid

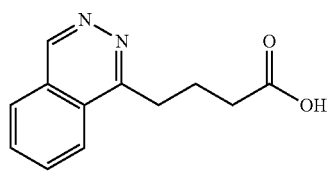 [SMILES: O=C(O)CCCc1nncc2ccccc12]

A25.6 was saponified with sodium hydroxide in 1,4-dioxane (0.60 mL) at ambient temperature for 1 h. The reaction mixture was diluted with water, acidified with hydrochloric acid and extracted with ethyl acetate. The combined organic layers were washed with brine, dried with sodium sulfate, filtered by suction and evaporated to dryness; yield: 42 mg (49%) pale brown solid; LC/MS (A), Rt: 1.08 min; (M+H) 217.3.

A26.1: 3-Benzo[d]isoxazol-3-yl-propionitrile

To a solution of 3-(2-bromo-ethyl)-benzo[d]isoxazole (2.50 g; 10.95 mmol) in DMF (100.0 mL), sodium cyanide (1.07 g; 21.90 mmol) was added at room temperature and the reaction mixture stirred at 70° C. for 18 h. The reaction mixture was diluted with ethyl acetate, washed with water and brine, dried over sodium sulfate and evaporated to dryness. The crude product was purified by flash column chromatography: yield: 1.17 g (61%); LC/MS (F), Rt: 2.37 min; (M+H) 173.0.

A26.2: 3-Benzo[d]isoxazol-3-yl-propionic acid

To a solution of potassium hydroxide (16.77 g; 269.086 mmol) in water (94 mL), A26.1 (1.17 g; 6.73 mmol) dissolved in ethanol (24 mL) was added dropwise at 0° C. under nitrogen atmosphere. The reaction mixture was heated at 75° C. for 16 h. After completion of the reaction, the mixture was concentrated under reduced pressure, acidified with conc. HCl and the precipitated product was filtered by suction, washed with dry hexane and dried; yield: 0.92 g (71%); LC/MS (F), Rt: 2.17 min; (M+H) 192.0.

A26.3: 3-Benzo[d]isoxazol-3-yl-propan-1-ol

To a solution of 3-Benzo[d]isoxazol-3-yl-propionic acid (0.92 g; 4.764 mmol) in THF (18 mL), borane dimethyl sulfide (2.44 mL; 23.820 mmol) was added dropwise at 0° C. under nitrogen atmosphere. The reaction mixture was gradually warmed to room temperature and stirred for 18 h. The reaction mixture was quenched with methanol (10 mL) at 0° C. for 5 min and then heated at 70° C. for 2 h. The reaction mixture was concentrated under reduced pressure, the residue was dissolved in dichloromethane and washed with 1M sodium carbonate solution and brine, dried over sodium sulfate and evaporated to dryness; yield: 0.47 g (55%); LC/MS (F), Rt: 2.15 min; (M+H) 178.0.

A26.4: 3-(3-Bromo-propyl)-benzo[d]isoxazole

To a solution of A26.3 (0.47 g; 2.626 mmol) in benzene (19 mL), phosphorus tri-bromide (0.50 ml; 5.252 mmol) was added dropwise at 0° C. under nitrogen atmosphere. The reaction mixture was heated at 70° C. for 18 h, cooled to room temperature and concentrated under reduced pressure. The crude product was diluted with dichloromethane, washed with 10% sodium bicarbonate solution and brine, dried over sodium sulfate and evaporated to dryness. The crude product was purified by column chromatography; yield: 0.32 g (50%); LC/MS (F), Rt: 2.92 min; (M+H) 240.0/242.0.

A26.5: 4-Benzo[d]isoxazol-3-yl-butyronitrile

To a solution of A26.4 (0.32 g; 1.319 mmol) in DMF (13 mL), sodium cyanide (0.13 g; 2.639 mmol) was added at room temperature and the mixture stirred at this temperature for 18 h. The reaction mixture was diluted with ethyl acetate, washed with water and brine, dried over sodium sulfate, filtered and evaporated to dryness. The crude product was purified by flash column chromatograpy, yield: 0.24 g (97%); LC/MS (F), Rt: 2.50 min; (M+H) 187.0.

A26.6: 4-Benzo[d]isoxazol-3-yl-butyric acid

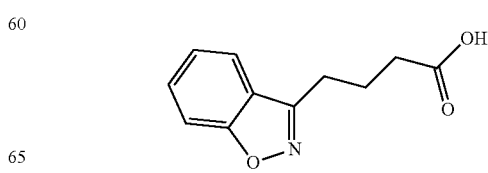

A26.5 (0.24 g; 1.276 mmol) was saponified as described for A26.2; yield: 0.20 g (76%)M $^1$H NMR (400 MHz, DMSO-d$_6$) δ [ppm] 12.16 (s, 1H), 7.91 (d, J=8.0 Hz, 1H), 7.72 (d, J=8.4 Hz, 1H), 7.70-7.62 (m, 1H), 7.42-7.38 (m, 1H), 3.03 (t, J=15.2 Hz, 2H), 2.36 (t, J=14.8 Hz, 2H), 2.07-1.98 (m, 2H). LC/MS (F), Rt: 2.26 min; (M+H) 206.0.

A27.1: 6-(4-Cyano-2-methyl-2H-pyrazol-3-yl)-hex-5-ynoic acid methyl ester

To a stirred solution of 5-bromo-1-methyl-1H-pyrazole-4-carbonitrile (1.50 g; 8.06 mmol) in dioxane (30.00 mL), hex-5-ynoic acid methyl ester (1.53 g; 12.10 mmol), ethyl-diisopropyl-amine (4.26 mL; 24.19 mmol), 1,1'-bis(diphenylphosphino)ferrocene]dichloropalladium(11), complex with dichloromethane (0.68 g; 0.81 mmol) and copper iodide (0.16 g; 0.81 mmol) were added. The reaction mixture was stirred at 100° C. for 16 h, cooled to room temperature and filtered through celite. The filtrate was concentrated under vacuum and the residue purified by column chromatography (15-25% ethyl acetate in hexane); Yield: 0.60 g (27%); LC/MS (F), Rt: 2.48 min; (M+H) 232.0.

A27.2: 6-(4-Carbamoyl-2-methyl-2H-pyrazol-3-yl)-hex-5-ynoic acid methyl ester and 6-(4-Carbamoyl-2-methyl-2H-pyrazol-3-yl)-hex-5-ynoic acid A solution of A27.1 (150.00 mg; 0.65 mmol) in sulfuric acid (1.50 mL) was stirred at ambient temperature for 12 h, poured into ice water and extracted with dichloromethane. The combined organic layer was dried over anhydrous sodium sulfate, filtered and concentrated under vacuum. The residue (160 mg) was a mixture of methyl ester and acid and was used in the next step without further purification.

A27.3: 4-(1-Methyl-4-oxo-4,5-dihydro-1H-pyrazolo[4,3-c]pyridin-6-yl)-butyric acid

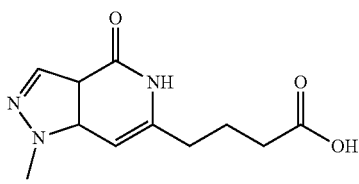 [SMILES: CN1N=CC2C(=O)NC(CCCC(=O)O)=CC21]

To a solution of A27.2 (70 mg) in ethanol (7.00 mL) potassium hydroxide (27 mg; 0.44 mmol) was added at ambient temperature. The reaction mixture was stirred at 80° C. for 16 h, extracted with dichloromethane. The aqueous layer was acidified with 1.5 N HCl solution, concentrated under vacuum. The residue was purified by column chromatography (5-10% methanol in chloroform); yield: 25.0 mg (66%) pale brown solid; $^1$H NMR (400 MHz, DMSO-d$_6$) δ 10.97 (s, 1H), 7.92 (s, 1H), 6.40 (s, 1H), 3.89 (s, 3H), 2.55-2.51 (m, 2H), 2.24 (t, J=7.20 Hz, 2H), 1.90-1.82 (m, 2H); LC/MS (F), Rt: 2.53 min; (M+H) 236.2.

Synthesis of B1: (4-Methoxy-3-methyl-phenyl)-piperidin-4-yl-methanone hydrochloride

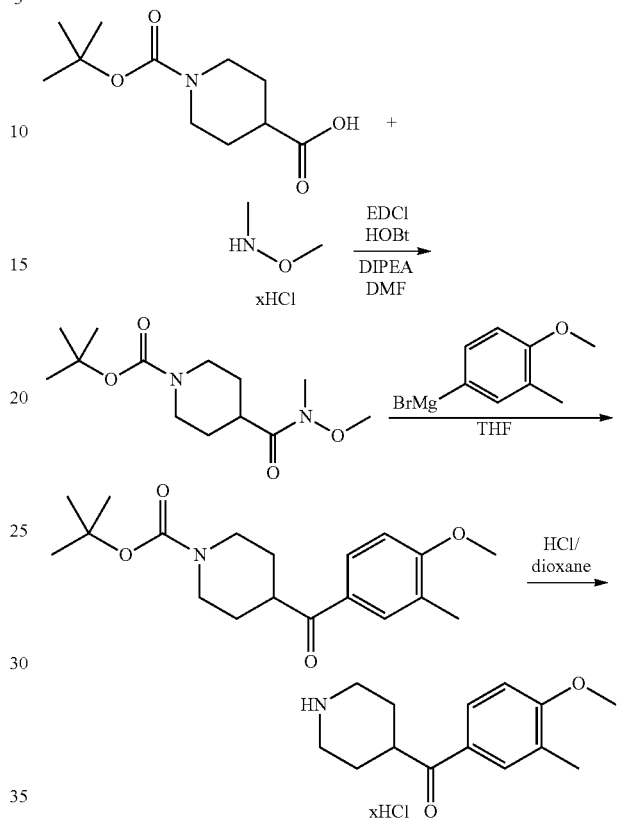

B1.1: 4-(Methoxy-methyl-carbamoyl)-piperidine-1-carboxylic acid tert-butyl ester To a solution of piperidine-1,4-dicarboxylic acid mono-tert-butyl ester (25.00 g, 107.72 mmol) in DMF (250 mL) is added N,N-diisopropyl ethylamine (57.01 mL, 323.16 mmol), 1-hydroxybenzotriazole hydrate (1.67 g, 10.77 mmol), (3-dimethylamino-propyl)-ethylcarbodiimide hydrochloride (25.03 g, 129.27 mmol) followed by the addition of O,N-dimethyl-hydroxylamine hydrochloride (11.68 g, 118.49 mmol) in small portions at 0° C. under nitrogen atmosphere. The reaction mixture is stirred at room temperature for 18 h. After completion of the reaction the solvent is evaporated under reduced pressure. The residue is dissolved in ethyl acetate (300 mL), washed with 10% sodium bicarbonate (2×200 mL), 0.5 N HCl (2×100 mL), water (200 mL) and brine (200 mL). The organic layer is dried over anhydrous Na$_2$SO$_4$ and evaporated under vacuum to afford 4-(methoxy-methyl-carbamoyl)-piperidine-1-carboxylic acid tert-butyl ester as colourless liquid;
$^1$H NMR (400 MHz, CDCl$_3$): δ 4.15-4.09 (m, 2H), 3.70 (s, 3H), 3.17 (s, 3H), 2.79-2.72 (m, 3H), 1.72-1.60 (m, 4H), 1.44 (s, 9H); LC/MS (B): 173.2 (M+H; BOC-cleaved mass), Rt: 3.54 min.

B1.2: 4-(4-Methoxy-3-methyl-benzoyl)-piperidine-1-carboxylic acid tert-butyl ester Iodine (0.93 mg) and 5 mL of 4-bromo-2-methyl anisole (5.96 g, 29.06 mmol) dissolved in THF (40 mL) were added to a suspension of magnesium turnings (0.72 g, 29.06 mmol) in dry THF (40 mL) under nitrogen atmosphere. The mixture was stirred at room temperature for 15 min and then warmed up to 50° C. The mixture was cooled to room temperature and remaining solution of 4-bromo-2-methyl anisole in THF was added dropwise during a period of 20 min. The mixture was stirred for additional 2 h at room temperature to complete dissolution of magnesium. This Grignard reagent solution was added dropwise to a solution of 4-(methoxy-methyl-carbamoyl)-piperidine-1-carboxylic acid tert-butyl ester (4.00 g, 14.53 mmol) in THF (40.00 mL) at −78° C. The reaction mixture was allowed to stir at room temperature for 15 h. Then it was cooled to 0° C., quenched with saturated ammonium chloride solution (100 mL) and extracted with ethyl acetate (2×100 mL). The organic layer was washed with 10% sodium bicarbonate (100 mL), water (100 mL) and brine (100 mL), dried over anhydrous Na$_2$SO$_4$ and evaporated under vacuum. The crude material was purified by flash chromatography using silica gel (230-400) and petrol ether/ethyl acetate (0-30%) as a gradient elution to afford 4-(4-methoxy-3-methyl-benzoyl)-piperidine-1-carboxylic acid tert-butyl ester as colourless solid; $^1$H NMR (400 MHz, CDCl$_3$): δ 7.82 (dd, J=2.2, 8.6 Hz, 1H), 7.76 (d, J=1.6 Hz, 1H), 6.86 (d, J=8.6 Hz, 1H), 4.17 (d, J=13.0 Hz, 2H), 3.90 (s, 3H), 3.41-3.34 (m, 1H), 2.93-2.86 (m, 2H), 2.26 (s, 3H), 1.83-1.80 (m, 2H), 1.76-1.65 (m, 2H), 1.45 (s, 9H); LC/MS (B): 234.3 (M+H; BOC-cleaved mass), Rt: 5.31 min.

B1.3: (4-Methoxy-3-methyl-phenyl)-piperidin-4-yl-methanone hydrochloride

A solution of 4-(4-methoxy-3-methyl-benzoyl)-piperidine-1-carboxylic acid tert-butyl ester (1.50 g, 4.36 mmol) in dioxane/HCl (3M, 14.53 mL, 43.60 mmol) was stirred at room temperature for 6 h under nitrogen atmosphere. The solvent was evaporated to dryness under reduced pressure to afford (4-methoxy-3-methyl-phenyl)-piperidin-4-yl-methanone hydrochloride as colorless solid.

$^1$H NMR (400 MHz, DMSO-d$_6$): δ 9.25 (brs, 1H), 8.92 (brs, 1H), 7.90 (dd, J=2.2, 8.6 Hz, 1H), 7.81 (d, J=1.6 Hz, 1H), 7.05 (d, J=8.6 Hz, 1H), 3.87 (s, 3H), 3.75-3.67 (m, 1H), 3.29-3.25 (m, 2H), 3.06-2.97 (m, 2H), 2.19 (s, 3H), 1.89-1.86 (m, 2H), 1.81-1.78 (m, 2H); LC/MS (B): 234.3 (M+H), Rt: 2.65 min.

Synthesis of B2:
(6-Methoxy-pyridin-3-yl)-piperidin-4-yl-methanone hydrochloride

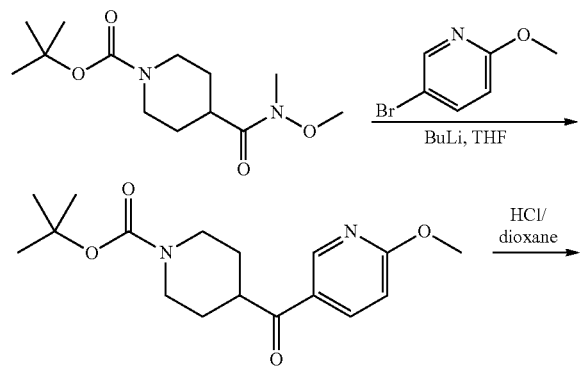

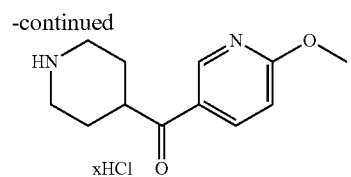

B2.1: 4-(6-Methoxy-pyridine-3-carbonyl)-piperidine-1-carboxylic acid tert-butyl ester To a solution of 5-bromo-2-methoxy-pyridine (6.60 g; 34.40 mmol) in THF (132 mL) under nitrogen atmosphere, n-butyl lithium (1.6 M in hexanes) (25.80 mL; 41.28 mmol) was added dropwise at −78° C. and stirred for 1 h at the same temperature. A solution of 4-(methoxy-methyl-carbamoyl)-piperidine-1-carboxylic acid tert-butyl ester (10.52 g; 37.84 mmol) in THF (25 mL) was added dropwise at −78° C. and stirred for 4 h at −78° C. The reaction mixture was then slowly allowed to attain room temperature and stirred for 12 h. The reaction mixture was quenched by saturated NH$_4$Cl (250 mL) and extracted with ethyl acetate (2×300 mL). The combined organic layers were washed with water (200 mL), brine (200 mL), dried over anhydrous sodium sulfate and concentrated. The crude material was purified by column chromatography using silica gel (60-120) and petrol ether/ethyl acetate as gradient elution to afford 4-(6-methoxy-pyridine-3-carbonyl)-piperidine-1-carboxylic acid tert-butyl ester (5.00 g; 44.5%) as a pale yellow oil; $^1$H NMR (400 MHz, CDCl$_3$) δ [ppm] 8.80 (d, J=2.3 Hz, 1H), 8.14 (dd, J=2.4, 8.7 Hz, 1H), 6.82 (d, J=8.8 Hz, 1H), 4.20-4.17 (m, 2H), 4.02 (s, 3H), 3.35-3.27 (m, 1H), 2.92-2.86 (m, 2H), 1.85-1.82 (m, 2H), 1.76-1.66 (m, 2H), 1.47 (s, 9H); LC/MS (B): 265 (M+H; BOC-cleaved mass), Rt: 4.64 min.

B2.2:
(6-Methoxy-pyridin-3-yl)-piperidin-4-yl-methanone hydrochloride

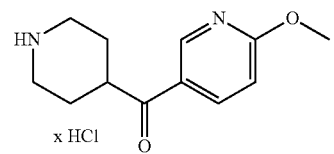

Colorless solid; LC/MS (B): 221.0 (M+H), Rt 1.84 min; $^1$H NMR (400 MHz, DMSO-d$_6$) δ [ppm] 9.21 (s, 1H), 8.91 (d, J=1.08 Hz, 2H), 8.23-8.20 (m, 1H), 6.95 (d, J=8.76 Hz, 1H), 6.55 (bs, 3H), 6.09 (bs, 2H), 3.94 (s, 3H), 3.78-3.67 (m, 1H), 3.29-3.26 (m, 2H), 3.04-2.95 (m, 2H), 1.93-1.90 (m, 2H), 1.82-1.71 (m, 2H).

B3: Azetidin-3-yl-(4-methoxy-phenyl)-methanone hydrochloride

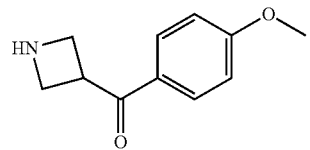

Similarly prepared as described for B1; beige solid; LC/MS (A): 228.1 (M+H), Rt: 1.12 min.

B4: (1-Methyl-1H-pyrazol-4-yl)-piperidin-4-yl-methanone hydrochloride

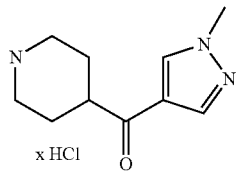

4-Iodo-1-methyl-1H-pyrazole (1.12 g; 5.385 mmol) and 4-(methoxy-methyl-carbamoyl)-piperidine-1-carboxylic acid tert-butyl ester (1.47 g; 5.385 mmol) were dissolved in dry THF (15 mL) under argon. While stirring the clear light yellow solution was cooled down to −60° C. and butyllithium (15% solution in n-hexane) (3.72 mL; 5.923 mmol) was added dropwise at this temperature over a period of 10 min. The reaction mixture was stirred for 30 min between −60 and −45° C., then slowly warmed to room temperature and stirred for 14 h. The reaction mixture was cooled to 0° C., quenched with 10% citric acid solution, diluted with ethyl acetate (70 mL) and washed with water and brine, dried with Na$_2$SO$_4$, filtered and evaporated to dryness.

The oily residue was purified by flash chromatography (Companion RF; 120 g Si50 silica gel column); yield: 999 mg (63%) light green oil (purity: 99.4; Rt: 2.33 min); $^1$H NMR (500 MHz, DMSO-d$_6$) δ [ppm] 8.42 (s, 1H), 7.94 (d, J=0.7 Hz, 1H), 3.97 (d, J=12.6 Hz, 2H), 3.87 (s, 3H), 3.15 (tt, J=11.4, 3.6 Hz, 1H), 2.93-2.75 (m, 2H), 1.76-1.67 (m, 2H), 1.33-1.46 (m, 11H); LC/MS (A), Rt: 1.93 min; 238.1 (M+H; BOC-cleaved mass);

Boc-cleavage afforded the title compound; colorless solid; LC/MS (A): 194.2 (M+H), Rt: 0.34/0.47 min.

Synthesis of B5: 6-Amino-1',2',3',4',5',6'-hexahydro-[3,4']bipyridinyl-5-carbonitrile dihydrochloride

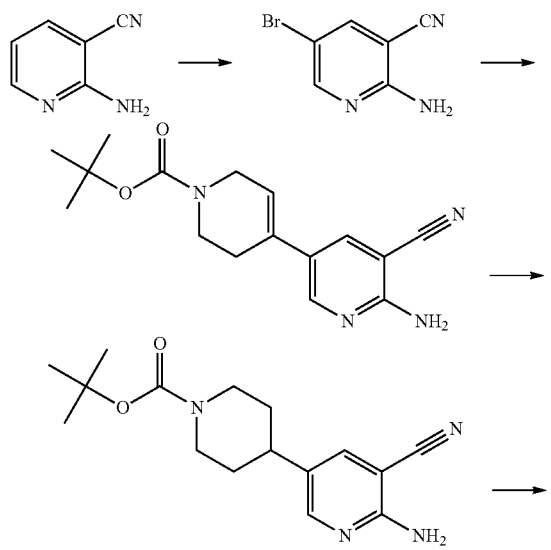

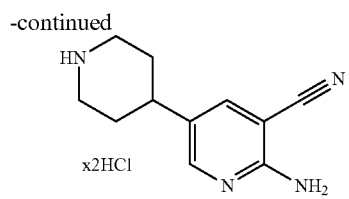

B5.1: 2-Amino-5-bromo-nicotinonitrile

To a solution of 2-amino-nicotinonitrile (0.50 g; 4.11 mmol) in acetic acid (10 mL) was added sodium carbonate (0.48 g; 4.52 mmol) at 0° C. followed by the dropwise addition of bromine (0.74 g; 4.52 mmol). The reaction mixture was stirred at ambient temperature for 2 h. The solvent was evaporated under vacuum, the residue was suspended in water (50 mL), filtered by suction and dried to afford the title compound (0.60 g; 73%). The product was used in the next step without further purification; $^1$H NMR (400 MHz, DMSO-d$_6$) δ [ppm] 8.26 (d, J=2.5 Hz, 1H), 8.14 (d, J=2.5 Hz, 1H), 7.13 (brs, 2H); LC/MS (B), Rt: 2.59 min; (M+2H) 200.

B5.2: 6-Amino-5-cyano-3',6'-dihydro-2'H-[3,4']bipyridinyl-1'-carboxylic acid tert-butyl ester To a solution of 2-amino-5-bromo-nicotinonitrile (0.60 g; 3.02 mmol) in dioxane (24 mL) and water (6 mL) 4-(4,4,5,5-tetramethyl-[1,3,2]dioxaborolan-2-yl)-3,6-dihydro-2H-pyridine-1-carboxylic acid tert-butyl ester (1.04 g; 3.32 mmol) and Na$_2$CO$_3$ (0.98 g; 9.05 mmol) were added and the mixture was degassed for 30 min. 1,1'-Bis(diphenylphosphino)ferrocene]dichloropalladium(II), complex with dichloromethane (0.13 g; 0.15 mmol) was added and the reaction mixture was heated to 90° C. for 10 h. The reaction mixture was cooled to ambient temperature, filtered through celite and the solvent was concentrated under reduced pressure. The residue was purified by flash column chromatography using petrol ether and ethyl acetate (5:5) to afford the title compound (450.0 mg; 50%) as a pale-yellow solid; $^1$H NMR (400 MHz, DMSO-d$_6$) δ [ppm] 8.32 (d, J=2.5 Hz, 1H), 7.92 (d, J=2.5 Hz, 1H), 6.92 (s, 2H), 6.08 (s, 1H), 3.94 (s, 2H), 3.49 (t, J=5.6 Hz, 2H), 2.37 (d, J=1.5 Hz, 2H), 1.40 (s, 9H); LC/MS (B), Rt: 3.50 min; (M+H) 301.2.

B5.3: 6-Amino-5-cyano-3',4',5',6'-tetrahydro-2'H-[3,4']bipyridinyl-1'-carboxylic acid tert-butyl ester 6-Amino-5-cyano-3',6'-dihydro-2'H-[3,4']bipyridinyl-1'-carboxylic acid tert-butyl ester (5.00 g; 16.63 mmol) was dissolved in methanol (150 mL) and hydrogenated with palladium on carbon (10% w/w) (1.77 g; 1.66 mmol) for 15 h. The reaction mixture was concentrated and the residue was used in the next step without further purification; yield: 4.50 g (87%) pale-yellow solid (purity: 97%); $^1$H NMR (400 MHz, DMSO-d$_6$) δ [ppm] 8.11 (d, J=2.4 Hz, 2H), 7.76 (d, J=2.4 Hz, 2H), 4.05-4.01 (m, 2H), 2.85-2.55 (m, 2H), 2.59-2.53 (m, 1H), 1.67 (d, J=12.2 Hz, 2H), 1.47-1.38 (m, 11H); LC/MS (B), Rt: 3.27 min; (M+H-t-Butyl) 247.

B5.4: 6-Amino-1',2',3',4',5',6'-hexahydro-[3,4']bipyridinyl-5-carbonitrile dihydrochloride To a solution of 6-amino-5-cyano-3',4',5',6'-tetrahydro-2'H-[3,4']bipyridinyl-1'-carboxylic acid tert-butyl ester (4.50 g; 14.43 mmol) in 1,4-dioxane (45 mL) HCl (4M in 1,4-dioxane) (10.82 ml; 43.30 mmol) was added at 0° C. and the reaction was stirred at room temperature for 2 h. The solvent was removed under reduced pressure to afford the title compound (3.50 g; 85%) as a colorless solid: $^1$H NMR (400 MHz, DMSO-$d_6$) δ [ppm] 9.22-8.95 (m, 2H), 8.15-7.98 (m, 5H), 3.38-3.29 (m, 2H), 2.95-2.87 (m, 2H), 2.85-2.70 (m, 1H), 1.92-1.81 (m, 2H), 1.80-1.58 (m, 2H); LC/MS (B), Rt: 2.13 min; (M+H) 203.2.

Synthesis of B6: 5-Pyrimidin-2-yl-1',2',3',4',5',6'-hexahydro-[3,4']bipyridinyl-6-ylamine hydrochloride

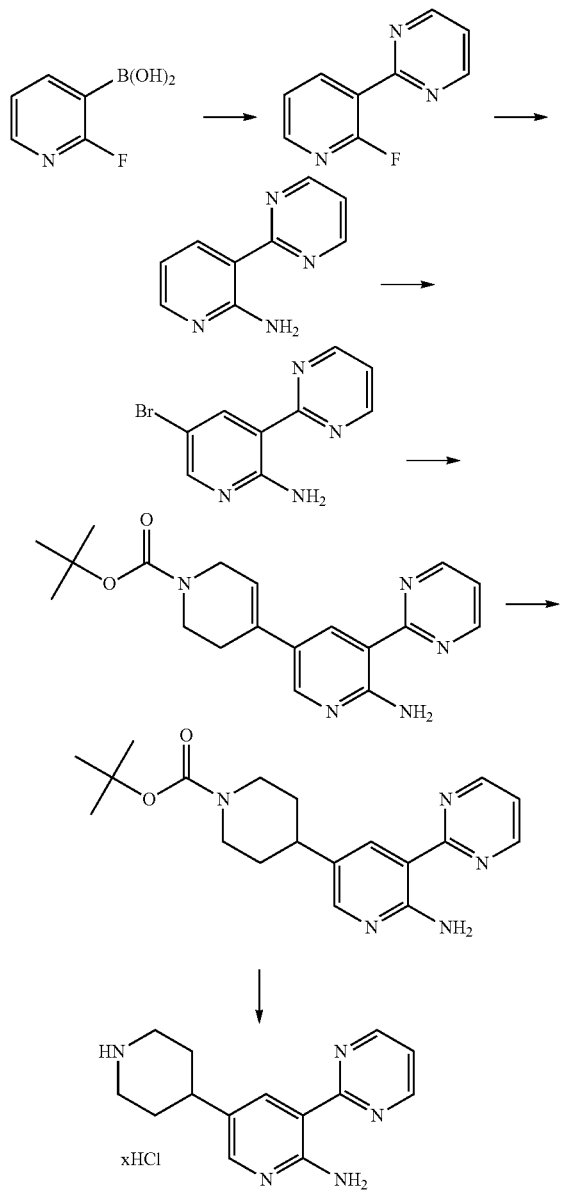

B6.1: 2-(2-Fluoro-pyridin-3-yl)-pyrimidine

To a solution of (2-fluoro-3-pyridyl)boronic acid (6.00 g; 40.45 mmol) in 1,4-dioxane (108 mL) and water (12 mL), 2-bromo-pyrimidine (6.56 g; 40.45 mmol) and Na$_2$CO$_3$ (13.12 g; 121.36 mmol) were added and the solution was degassed for 30 min. 1,1'-Bis(diphenylphosphino)ferrocene]dichloropalladium(II), complex with dichloromethane (1.70 g; 2.02 mmol) was then added and the reaction mixture was heated to 90° C. for 6 h. The reaction mixture was cooled at room temperature, filtered through celite and the solvent was concentrated under reduced pressure. The residue was purified by flash column chromatography using petrol ether-ethyl acetate (8:2) to afford the title compound (3.00 g; 42%) as an off-white solid; $^1$H NMR (400 MHz, DMSO-$d_6$) δ [ppm] 8.99 (d, J=4.9 Hz, 2H), 8.57 (t, J=9.8 Hz, 1H), 8.39 (d, J=8.0 Hz, 1H), 7.57-7.52 (m, 2H); LC/MS (B), Rt: 1.77 min; (M+H) 176.

B6.2: 3-Pyrimidin-2-yl-pyridin-2-ylamine

To a solution of 2-(2-fluoro-pyridin-3-yl)-pyrimidine (11.0 g; 62.55 mmol) in THF (110 mL), ammonia (6M in THF) (330 mL) was added at −20° C. The reaction mixture was heated to 70° C. for 40 h in autoclave. The reaction was cooled to room temperature and the solvent was removed under reduced pressure. The residue was purified by column chromatography using silica gel (230-400) and petrol ether-ethyl acetate (2:8) as eluent to afford the title compound (6.50 g; 60%) as an off-white solid; $^1$H NMR (400 MHz, DMSO-$d_6$) δ [ppm] 8.91 (d, J=4.9 Hz, 2H), 8.64 (d, J=7.8 Hz, 1H), 8.12 (d, J=6.6 Hz, 1H), 7.40 (t, J=4.8 Hz, 1H), 6.70-6.67 (m, 1H); LC/MS (B), Rt: 1.49 min; (M+H) 173.

B6.3: 5-Bromo-3-pyrimidin-2-yl-pyridin-2-ylamine

To a solution of 3-pyrimidin-2-yl-pyridin-2-ylamine (6.30 g; 36.22 mmol) in acetonitrile (315 mL), NBS (7.89 g; 43.47 mmol) was added at 0° C. over 5 min under nitrogen atmosphere. The reaction was allowed to stir at room temperature for 2 h. The reaction mixture was concentrated under reduced pressure to 50 mL followed by a hot filtration. The residue was washed with petrol ether to afford 5-bromo-3-pyrimidin-2-yl-pyridin-2-ylamine (8.50 g; 93%) as a yellow solid; $^1$H NMR (400 MHz, DMSO-$d_6$) δ [ppm] 8.93 (d, J=4.9 Hz, 2H), 8.72 (s, 1H), 8.20 (d, J=2.6 Hz, 1H), 7.46 (t, J=4.9 Hz, 1H); LC/MS (B), Rt: 2.25 min; (M+2H) 253/255.

B6.4: 6-Amino-5-pyrimidin-2-yl-3',6'-dihydro-2'H-[3,4']bipyridinyl-1'-carboxylic acid tert-butyl ester To a solution of 5-bromo-3-pyrimidin-2-yl-pyridin-2-ylamine (4.80 g; 19.03 mmol) in 1,4-dioxane (192 mL) and water (48 mL), 4-(4,4,5,5-Tetramethyl-[1,3,2]dioxaborolan-2-yl)-3,6-dihydro-2H-pyridine-1-carboxylic acid tert-butyl ester (6.54 g; 20.94 mmol) and Na$_2$CO$_3$ (6.18 g; 57.10 mmol) were added and the solution was degassed for 30 min. 1,1'-Bis(diphenylphosphino)ferrocene]-dichloropalladium(II), complex with dichloromethane (0.80 g; 0.95 mmol) was then added to reaction mixture and heated to 90° C. for 10 h. The reaction mixture was cooled to room temperature, filtered through celite and the solvent was concentrated under reduced pressure. The residue was purified by flash column chromatography using petrol ether-ethyl acetate (5:5) to afford the title compound (6.20 g; 90%) as a pale-yellow solid; $^1$H NMR (400 MHz, DMSO-$d_6$) δ [ppm] 8.93 (s, 2H), 8.70 (s, 1H), 8.27 (s, 1H), 7.94 (bs, 2H), 7.42 (t, J=4.8 Hz, 1H), 6.06 (s, 1H), 3.98-3.98 (m, 2H), 3.56-3.53 (m, 2H), 2.49-2.48 (m, 2H), 1.42 (s, 9H); LC/MS (B), Rt: 3.52 min; (M+H) 354.2.

B6.5: 6-Amino-5-pyrimidin-2-yl-3',4',5',6'-tetra-hydro-2'H-[3,4']bipyridinyl-1'-carboxylic acid tert-butyl ester 6-Amino-5-pyrimidin-2-yl-3',6'-dihydro-2'H-[3,4']bi-pyridinyl-1'-carboxylic acid tert-butyl ester (1.20 g; 3.31 mmol) was dissolved in methanol (36 mL) and hydrogenated with palladium on carbon (10% w/w) (0.24 g; 0.23 mmol) at room temperature for 10 h. The reaction mixture was evaporated to dryness to afford the title compound (1.00 g; 77%) as a pale-yellow solid; LC/MS (B), Rt: 3.51 min; (M+H) 356.3.

B6.6: 5-Pyrimidin-2-yl-1',2',3',4',5',6'-hexahydro-[3,4']bipyridinyl-6-ylamine hydrochloride

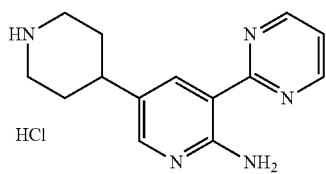 [SMILES: Cl ; Nc1ncc(C2CCNCC2)cc1-c1ncccn1]

To a solution of 6-amino-5-pyrimidin-2-yl-3',4',5',6'-tetrahydro-2'H-[3,4']bipyridinyl-1'-carboxylic acid tert-butyl ester (1.00 g; 2.54 mmol) in 1,4-dioxane (10 mL) was HCl (4M in 1,4-dioxane) (5.00 ml; 20.00 mmol) was added at 0° C. and the reaction was stirred at room temperature for 2 h. The solvent was removed under reduced pressure to afford 5-pyrimidin-2-yl-1',2',3',4',5',6'-hexahydro-[3,4']bipyridinyl-6-ylamine hydrochloride (0.80 g; 94%) as a yellow solid; $^1$H NMR (400 MHz, DMSO-d$_6$) δ [ppm] 9.15-9.14 (m, 1H), 9.05-9.02 (m, 3H), 8.95-8.92 (m, 1H), 8.14 (s, 1H), 7.62 (t, J=4.9 Hz, 1H), 3.38-3.35 (m, 1H), 2.98-2.93 (m, 3H), 2.01-1.98 (m, 2H), 1.92-1.82 (m, 2H); LC/MS (B), Rt: 1.31 min; (M+H) 256.2.

B7: (3-Fluoro-4-methoxy-phenyl)-piperidin-4-yl-methanone hydrochloride

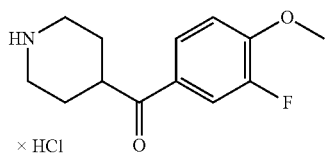

Preparation as described for B1; colorless solid; LC/MS (B): 238.0 (M+H), Rt 2.38 min;
$^1$H NMR (400 MHz, DMSO-d$_6$) δ [ppm] 9.29 (brs, 1H), 8.98 (brs, 1H), 7.89-7.81 (m, 2H), 7.32-7.28 (t, 16.8 Hz, 1H), 3.92 (s, 3H), 3.79-3.67 (m, 1H), 3.31-3.22 (m, 2H), 3.06-2.95 (m, 2H), 1.95-1.84 (m, 2H), 1.83-1.70 (m, 2H).

B8: Piperidin-4-yl-p-tolyl-methanone hydrochloride

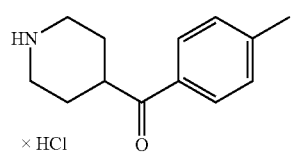

Preparation as described for B1; colorless solid; LC/MS (F): 204.2 (M+H), Rt 2.26 min;
$^1$H NMR (400 MHz, DMSO-d$_6$) δ [ppm] 9.29 (brs, 1H), 8.97 (brs, 1H), 7.92 (d, J=8.4 Hz, 2H), 7.36 (d, J=8.0 Hz, 2H), 3.80-3.70 (m, 1H), 3.35-3.23 (m, 2H), 3.10-2.98 (m, 2H), 2.39 (s, 3H), 1.98-1.87 (m, 2H), 1.85-1.73 (m, 2H).

B9: [4-(1-Hydroxy-1-methyl-ethyl)-phenyl]-piperidin-4-yl-methanone hydrochloride

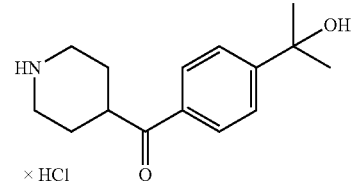

Preparation similar to B1; colorless solid; LC/MS (F): 248.3 (M+H), Rt 1.50 min;
$^1$H NMR (400 MHz, DMSO-d$_6$) δ [ppm] 9.02 (brs, 1H), 8.71 (brs, 1H), 7.93 (d, J=8.5 Hz, 2H), 7.61 (d, J=8.5 Hz, 2H), 5.20 (s, 1H), 3.79-3.69 (m, 1H), 3.35-3.24 (m, 2H), 3.08-2.96 (m, 2H), 1.94-1.88 (m, 2H), 1.80-1.68 (m, 2H), 1.43 (s, 6H).

B10: [4-(1-Hydroxy-1-methyl-ethyl)-phenyl]-piperidin-4-yl-methanone hydrochloride

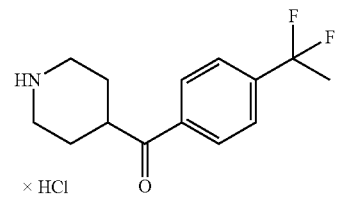

Preparation similar to B1; off-white solid; LC/MS (A): 254.1 (M+H), Rt 1.38 min.

B11: (1-Ethyl-1H-pyrazol-4-yl)-piperidin-4-yl-methanone hydrochloride

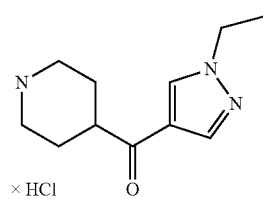

Preparation as described for B4; off-white solid; LC/MS (B): 208.2 (M+H), Rt: 1.26 min;
$^1$H NMR (400 MHz, DMSO-d$_6$) δ [ppm] 9.27 (brs, 1H), 8.75 (brs, 1H), 8.49 (s, 1H), 7.99 (s, 1H), 4.20-4.11 (m, 2H), 3.31-3.22 (m, 3H), 2.99-2.88 (m, 2H), 1.93-1.68 (m, 4H), 1.42-1.31 (m, 3H).

B12: (1-Isopropyl-1H-pyrazol-4-yl)-piperidin-4-yl-methanone hydrochloride

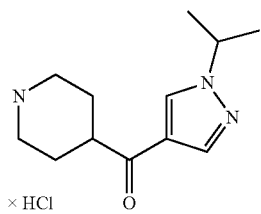

Preparation as described for B4; off-white solid; LC/MS (F): 222.2 (M+H), Rt: 1.54 min.

EXAMPLES

3-{4-[4-(4-Methoxy-benzoyl)-piperidin-1-yl]-4-oxo-butyl}-6-methyl-2H-pyrrolo[1,2-a]pyrazin-1-one ("C1")

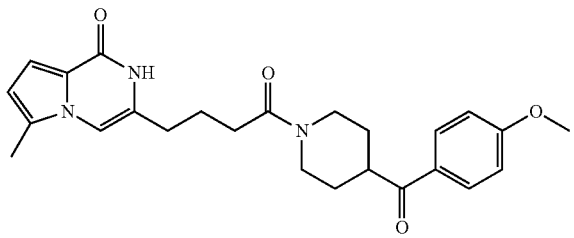 [SMILES: COc1ccc(C(=O)C2CCN(C(=O)CCCc3cn4c(C)ccc4c(=O)[nH]3)CC2)cc1]

A1 (50.0 mg; 0.207 mmol), (4-methoxy-phenyl)-piperidin-4-yl-methanone hydrochloride (68.8 mg; 0.269 mmol), N-(3-dimethylaminopropyl)-N'-ethylcarbodiimide hydrochloride (67.4 mg; 0.352 mmol) and benzotriazol-1-ol hydrate (41.2 mg; 0.269 mmol) were suspended in DMF (0.5 mL). 4-Methylmorpholine (91 µl; 0.827 mmol) was added and the mixture was stirred at room temperature for 1.5 h. The reaction mixture was diluted with saturated NaHCO$_3$ solution (10 mL) and water (20 mL) and extracted with ethyl acetate. A colorless precipitate formed between the layers, which was filtered by suction, washed with water and acetonitrile and dried under vacuum at 60° C. for 2 h; yield: 57 mg (63%) colorless solid (purity: 98.9%; Rt: 2.46 min); $^1$H NMR (400 MHz, DMSO-d$_6$) δ 10.38 (s, 1H), 8.13-7.86 (m, 2H), 7.19-6.99 (m, 2H), 6.90 (s, 1H), 6.74 (d, J=3.9 Hz, 1H), 6.27 (d, J=3.9 Hz, 1H), 4.54-4.25 (m, 1H), 3.98-3.75 (m, 4H), 3.74-3.52 (m, 1H), 3.25-3.08 (m, 1H), 2.80-2.69 (m, 1H), 2.43-2.27 (m, 7H), 1.93-1.70 (m, 4H), 1.59-1.26 (m, 2H); LC/MS (A), Rt: 2.01 min; (M+H) 436.

3-{4-[4-(4-Methoxy-benzoyl)-piperidin-1-yl]-4-oxo-butyl}-2H-pyrrolo[1,2-a]-pyrazin-1-one ("C2")

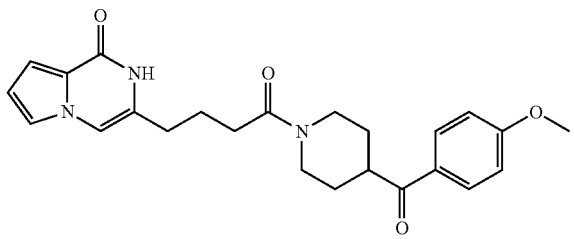 [SMILES: COc1ccc(C(=O)C2CCN(C(=O)CCCc3cn4cccc4c(=O)[nH]3)CC2)cc1]

"C2" was prepared as described for "C1" using A2; yield: 38 mg (39%) colorless solid (purity: 98.4%; Rt: 2.37 min); $^1$H NMR (400 MHz, DMSO-d$_6$) δ 10.45 (s, 1H), 8.11-7.88 (m, 2H), 7.39-7.32 (m, 1H), 7.13 (s, 1H), 7.11-6.97 (m, 2H), 6.84-6.78 (m, 1H), 6.49 (dd, J=4.0, 2.5 Hz, 1H), 4.57-4.32 (m, 1H), 4.04-3.78 (m, 4H), 3.77-3.57 (m, 1H), 3.25-3.09 (m, 1H), 2.82-2.68 (m, 1H), 2.45-2.26 (m, 4H), 1.90-1.69 (m, 4H), 1.61-1.26 (m, 2H); LC/MS (A), Rt: 1.93 min; (M+H) 422.

3-{4-[4-(4-Methoxy-3-methyl-benzoyl)-piperidin-1-yl]-4-oxo-butyl}-6-methyl-2H-pyrrolo[1,2-a]pyrazin-1-one ("C3")

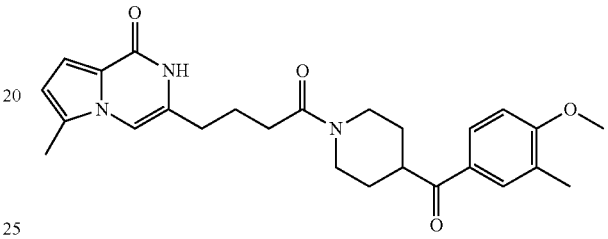

A1 (50.0 mg; 0.207 mmol), B1 (61.4 mg; 0.228 mmol) and [dimethylamino-([1,2,3]triazolo[4,5-b]pyridin-3-yloxy)-methylene]-dimethylammonium hexafluoro phosphate (118.0 mg; 0.310 mmol) were suspended in DMF (2 ml). N-Ethyldiisopropylamine (0.11 mL; 0.620 mmol) was added (pH of the solution was alkaline) and the reaction mixture was stirred at room temperature for 30 min. A yellow suspension was formed. The precipitate was filtered by suction. The residue was washed with water, acetonitrile and diethyl ether and dried under vacuum at 50° C. for 3 h; yield: 74 mg (78%) colorless powder (purity: 98.6%; Rt: 2.61 min); $^1$H NMR (400 MHz, DMSO-d$_6$) δ 10.38 (s, 1H), 7.89 (dd, J=8.6, 2.3 Hz, 1H), 7.80 (d, 1H), 7.05 (d, J=8.6 Hz, 1H), 6.91 (s, 1H), 6.74 (d, J=3.8 Hz, 1H), 6.27 (d, J=3.6 Hz, 1H), 4.48-4.34 (m, 1H), 3.96-3.80 (m, 4H), 3.74-3.56 (m, 1H), 3.25-3.09 (m, 1H), 2.83-2.69 (m, 1H), 2.44-2.27 (m, 7H), 2.20 (s, 3H), 1.91-1.68 (m, 4H), 1.58-1.22 (m, 2H); LC/MS (A), Rt: 2.14 min; (M+H) 450.

3-{4-[4-(4-Methoxy-3-methyl-benzoyl)-piperidin-1-yl]-4-oxo-butyl}-2H-pyrrolo[1,2-a]pyrazin-1-one ("C4")

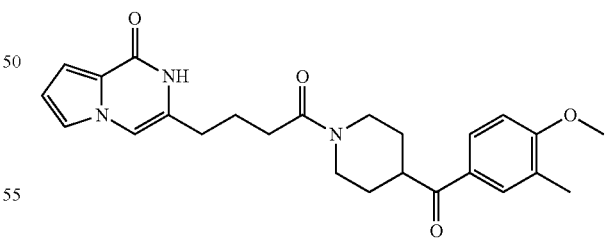

"C4" was prepared as described for "C3" using A2 and B1; yield: 66 mg (66%) colorless powder (purity: 100%; Rt: 2.51 min); $^1$H NMR (400 MHz, DMSO-d$_6$) δ 10.44 (s, 1H), 7.89 (dd, J=8.5, 2.3 Hz, 1H), 7.81 (dd, J=2.2, 1.0 Hz, 1H), 7.35 (dd, J=2.5, 1.5 Hz, 1H), 7.12 (s, 1H), 7.05 (d, J=8.6 Hz, 1H), 6.81 (ddd, J=3.9, 1.5, 0.7 Hz, 1H), 6.48 (dd, J=4.0, 2.5 Hz, 1H), 4.55-4.29 (m, 1H), 4.00-3.78 (m, 4H), 3.74-3.59 (m, 1H), 3.23-3.10 (m, 1H), 2.82-2.70 (m, 1H), 2.44-2.27 (m, 4H), 2.20 (s, 3H), 1.89-1.67 (m, 4H), 1.59-1.26 (m, 2H); LC/MS (A), Rt: 2.07 min; (M+H) 436.

4-{1-[4-(1-Oxo-1,2-dihydro-pyrrolo[1,2-a]pyrazin-3-yl)-butyryl]-piperidin-4-yloxy}-benzonitrile ("C5")

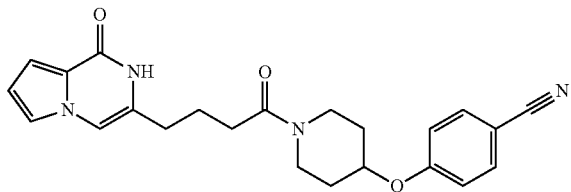 [SMILES: N#Cc1ccc(OC2CCN(C(=O)CCCc3cn4cccc4c(=O)[nH]3)CC2)cc1]

"C5" was prepared as described for "C3" using A2 and 4-(piperidin-4-yloxy)-benzonitrile hydrochloride; yield: 26 mg (29%) colorless solid (purity: 100%; Rt: 2.38 min); $^1$H NMR (400 MHz, DMSO-$d_6$) δ 10.44 (s, 1H), 7.86-7.67 (m, 2H), 7.35 (dd, J=2.5, 1.5 Hz, 1H), 7.22-7.06 (m, 3H), 6.80 (ddd, J=4.0, 1.5, 0.7 Hz, 1H), 6.47 (dd, J=3.9, 2.5 Hz, 1H), 4.86-4.65 (m, 1H), 3.98-3.79 (m, 1H), 3.79-3.60 (m, 1H), 3.36-3.13 (m, 2H), 2.44-2.29 (m, 4H), 2.03-1.87 (m, 2H), 1.81 (p, 2H), 1.70-1.41 (m, 2H); LC/MS (A), Rt: 1.95 min; (M+H) 405.

3-{4-Oxo-4-[4-(5-phenyl-[1,3,4]oxadiazol-2-yl)-piperidin-1-yl]-butyl}-2H-pyrrolo[1,2-a]pyrazin-1-one ("C6")

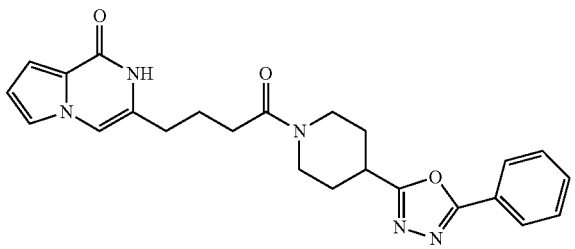 [SMILES: O=C(CCCc1cn2cccc2c(=O)[nH]1)N1CCC(c2nnc(-c3ccccc3)o2)CC1]

"C6" was prepared as described for "C3" using A2 and 4-(5-phenyl-[1,3,4]oxadiazol-2-yl)-piperidine; yield: 63 mg (65%) colorless powder (purity: 100%; Rt: 2.25 min); $^1$H NMR (500 MHz, DMSO-$d_6$) δ 10.42 (s, 1H), 8.04-7.95 (m, 2H), 7.67-7.54 (m, 3H), 7.33 (dd, J=2.4 Hz, 1.6, 1H), 7.12 (s, 1H), 6.85-6.71 (m, 1H), 6.45 (dd, J=3.9, 2.5 Hz, 1H), 4.35-4.23 (m, 1H), 3.93-3.79 (m, 1H), 3.41-3.30 (m, 1H), 3.28-3.20 (m, 1H), 2.95-2.84 (m, 1H), 2.43-2.29 (m, 4H), 2.15-2.00 (m, 2H), 1.83 (d, J=7.4 Hz, 2H), 1.79-1.52 (m, 2H); LC/MS (A), Rt: 1.84 min; (M+H) 432.

4-{1-[4-(6-Methyl-1-oxo-1,2-dihydro-pyrrolo[1,2-a]pyrazin-3-yl)-butyryl]-piperidin-4-yloxy}-benzonitrile ("C7")

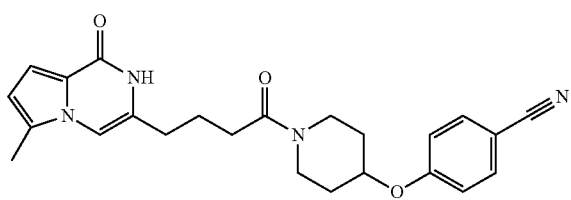 [SMILES: Cc1ccc2c(=O)[nH]c(CCCC(=O)N3CCC(Oc4ccc(C#N)cc4)CC3)cn12]

"C7" was prepared as described for "C3" using A1 and 4-(piperidin-4-yloxy)-benzonitrile hydrochloride. The isolated product was further purified by chromatography (prep. Agilent 1260 HPLC; Column: Waters SunFire C18 5 µm 30×150 mm). The combined fractions were evaporated to an aqueous residue, rendered basic with saturated NaHCO$_3$ solution and extracted with dichloromethane. The combined organic layers were washed with brine and evaporated to dryness. The solid residue was suspended in water/acetonitrile—1/1 (5 mL), filtered by suction, washed with water, acetonitrile and diethyl ether and dried under vacuum at 60° C. for 2 h; yield: 48 mg (55%) colorless powder (purity: 100%; Rt: 2.47 min); $^1$H NMR (400 MHz, DMSO-$d_6$) δ 10.38 (s, 1H), 7.85-7.63 (m, 2H), 7.26-7.05 (m, 2H), 6.90 (s, 1H), 6.74 (d, J=3.9 Hz, 1H), 6.27 (dd, J=3.9, 0.9 Hz, 1H), 4.84-4.69 (m, 1H), 3.96-3.82 (m, 1H), 3.76-3.63 (m, 1H), 3.38-3.31 (m, 1H), 3.26-3.13 (m, 1H), 2.44-2.23 (m, 7H), 2.03-1.74 (m, 4H), 1.67-1.42 (m, 2H); LC/MS (A), Rt: 2.02 min; (M+H) 419.

3-{4-[4-(4-Methoxy-benzoyl)-piperidin-1-yl]-4-oxo-butyl}-7-methyl-2H-pyrrolo[1,2-a]pyrazin-1-one ("C8")

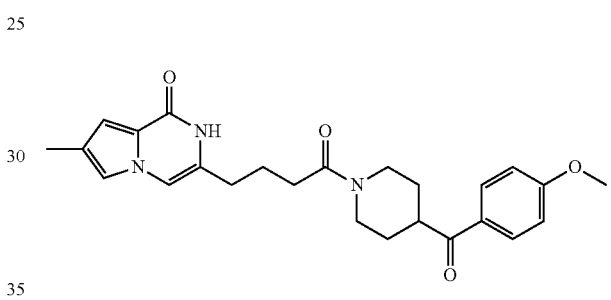

"C8" was prepared as described for "C3" using A3. The usual work-up provided 36 mg. Further product was obtained from the filtrate by chromatography (Companion RF; 55 g C18 silica gel column); yield: 50 mg (84%) colorless powder (purity: 100%; Rt: 2.47 min); $^1$H NMR (400 MHz, DMSO-$d_6$) δ 10.36 (s, 1H), 7.98 (d, J=8.4 Hz, 2H), 7.22-6.88 (m, 4H), 6.60 (s, 1H), 4.55-4.28 (m, 1H), 4.00-3.74 (m, 4H), 3.74-3.55 (m, 1H), 3.24-3.07 (m, 1H), 2.83-2.61 (m, 1H), 2.43-2.21 (m, 4H), 2.14 (s, 3H), 1.92-1.66 (m, 4H), 1.61-1.24 (m, 2H); LC/MS (A), Rt: 2.03 min; (M+H) 436.

6-Fluoro-3-{4-[4-(4-methoxy-benzoyl)-piperidin-1-yl]-4-oxo-butyl}-2H-pyrrolo[1,2-a]pyrazin-1-one ("C9")

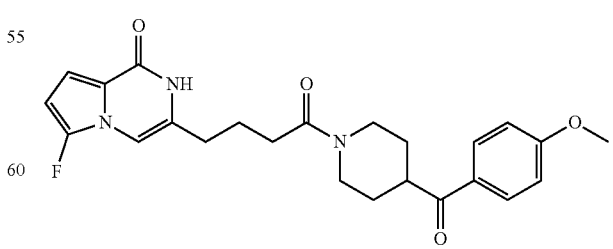

"C9" was prepared as described for "C3" using A4. The reaction mixture was purified by chromatography (prep. Agilent 1260 HPLC; Column: Waters SunFire C18 5 µm 30×150 mm). The combined fractions were evaporated to an aqueous residue, rendered basic with saturated NaHCO$_3$ solution and extracted with ethyl acetate. The combined organic layers were washed with brine, dried with Na$_2$SO$_4$, filtered and evaporated to dryness. The solid residue was triturated with diethyl ether/ethyl acetate (9:1), filtered by suction, washed with little acetonitrile and diethyl ether and dried under vacuum at 60° C. for 2 h; yield: 30 mg (54%) colorless powder (purity: 100%; Rt: 2.49 min); $^1$H NMR (500 MHz, DMSO-d$_6$) δ 10.51 (s, 1H), 8.05-7.87 (m, 2H), 7.12-7.00 (m, 2H), 6.95 (s, 1H), 6.82-6.70 (m, 1H), 6.23-6.11 (m, 1H), 4.50-4.29 (m, 1H), 3.96-3.78 (m, 4H), 3.65 (tt, J=11.3, 3.7 Hz, 1H), 3.18 (td, J=13.0, 2.7 Hz, 1H), 2.75 (td, J=12.6, 2.8 Hz, 1H), 2.45-2.28 (m, 4H), 1.90-1.69 (m, 4H), 1.60-1.43 (m, 1H), 1.43-1.27 (m, 1H); LC/MS (A), Rt. 2.03 min; (M+H) 440.2.

6-{4-[4-(4-Methoxy-benzoyl)-piperidin-1-yl]-4-oxo-butyl}-7H-imidazo[1,5-a]-pyrazin-8-one ("C10")

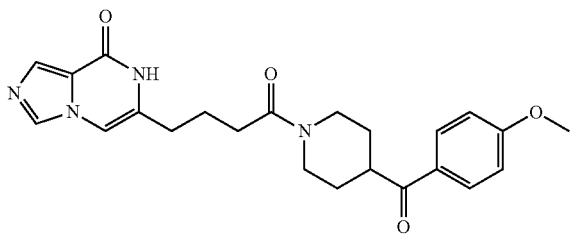 [SMILES: COc1ccc(C(=O)C2CCN(C(=O)CCCc3cn4cncc4c(=O)[nH]3)CC2)cc1]

Example 10 was prepared as described for "C3" using A5; yield: 16 mg (11%) colorless solid (purity: 98.5%; Rt: 1.99 min); $^1$H NMR (500 MHz, DMSO-d$_6$) δ 10.64 (s, 1H), 8.17 (s, 1H), 7.98 (d, J=8.9 Hz, 2H), 7.68 (s, 1H), 7.23 (s, 1H), 7.05 (d, J=8.9 Hz, 2H), 4.48-4.31 (m, 1H), 3.98-3.79 (m, 4H), 3.70-3.59 (m, 1H), 3.22-3.11 (m, 1H), 2.80-2.69 (m, 1H), 2.43-2.30 (m, 4H), 1.86-1.69 (m, 4H), 1.58-1.42 (m, 1H), 1.42-1.28 (m, 1H); LC/MS (A), Rt: 1.64 min; (M+H) 423.

6-Chloro-3-{4-[4-(4-methoxy-benzoyl)-piperidin-1-yl]-4-oxo-butyl}-2H-pyrrolo[1,2-a]pyrazin-1-one ("C11")

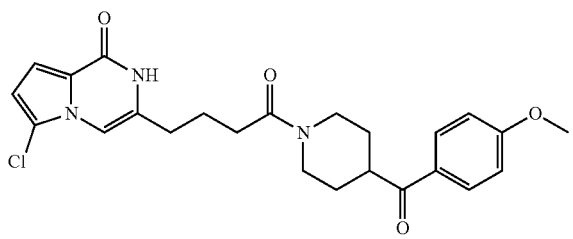 [SMILES: COc1ccc(C(=O)C2CCN(C(=O)CCCc3cn4c(Cl)ccc4c(=O)[nH]3)CC2)cc1]

"C11" was prepared as described for "C9"; purity: 97%; Rt: 2.59 min; $^1$H NMR (500 MHz, DMSO-d$_6$) δ 10.73 (s, 1H), 8.02-7.95 (m, 2H), 7.10-7.02 (m, 2H), 6.99 (s, 1H), 6.90 (dd, J=4.2, 0.6 Hz, 1H), 6.60 (d, J=4.2 Hz, 1H), 4.45-4.34 (m, 1H), 3.96-3.79 (m, 4H), 3.64 (tt, J=11.2, 3.6 Hz, 1H), 3.23-3.13 (m, 1H), 2.80-2.68 (m, 1H), 2.43 (t, J=7.4 Hz, 2H), 2.40-2.28 (m, 2H), 1.88-1.71 (m, 4H), 1.56-1.42 (m, 1H), 1.36 (ddt, J=20.5, 12.5, 3.0 Hz, 1H); LC/MS (A), Rt: 2.03 min; (M+H) 456/458.

6-{4-[4-(4-Methoxy-benzoyl)-piperidin-1-yl]-4-oxo-butyl}-2-methyl-5H-pyrazolo[1,5-a]pyrazin-4-one ("C12")

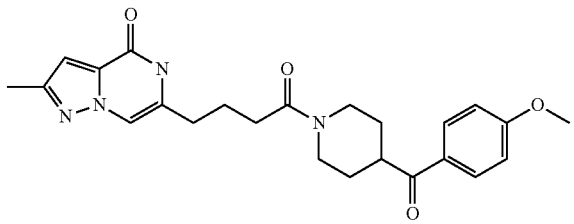

"C12" was prepared as described for "C3" using A6. The residue was crystallized from 2-propanol; yield: 58 mg (32%) colorless powder; $^1$H NMR (500 MHz, DMSO-d$_6$) δ 11.15 (s, 1H), 7.98 (d, J=8.9 Hz, 2H), 7.38 (s, 1H), 7.05 (d, J=8.9 Hz, 2H), 6.69 (s, 1H), 4.39 (dt, J=13.1, 3.7 Hz, 1H), 3.93-3.86 (m, 1H), 3.85 (s, 3H), 3.64 (tt, J=11.2, 3.7 Hz, 1H), 3.17 (td, J=13.1, 2.7 Hz, 1H), 2.78-2.71 (m, 1H), 2.43 (t, J=7.4 Hz, 2H), 2.35 (td, J=7.4, 5.0 Hz, 2H), 2.31 (s, 3H), 1.83 (q, J=7.4 Hz, 2H), 1.81-1.71 (m, 2H), 1.57-1.43 (m, 1H), 1.43-1.26 (m, 1H); LC/MS (C), Rt: 2.40 min; [M+H] 437.

6-{4-[4-(4-Methoxy-benzoyl)-piperidin-1-yl]-4-oxo-butyl}-7H-imidazo[1,2-a]-pyrazin-8-one ("C13")

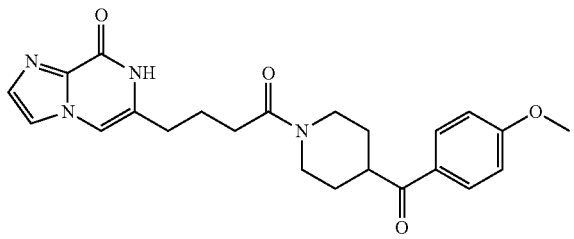

"C13" was prepared as described for "C3" using A7; yield: 41 mg (43%) colorless solid (purity: 98.6%; Rt: 2.01 min); $^1$H NMR (400 MHz, DMSO-d$_6$) δ 11.15 (s, 1H), 8.11-7.87 (m, 2H), 7.74 (s, 1H), 7.42 (s, 1H), 7.33 (s, 1H), 7.19-6.98 (m, 2H), 4.53-4.29 (m, 1H), 4.01-3.77 (m, 4H), 3.75-3.54 (m, 1H), 3.26-3.09 (m, 1H), 2.84-2.66 (m, 1H), 2.47-2.28 (m, 4H), 1.95-1.68 (m, 4H), 1.62-1.26 (m, 2H); LC/MS (A), Rt: 1.66 min; (M+H) 423.

7-Fluoro-3-{4-[4-(4-methoxy-benzoyl)-piperidin-1-yl]-4-oxo-butyl}-2H-pyrrolo[1,2-a]pyrazin-1-one ("C31")

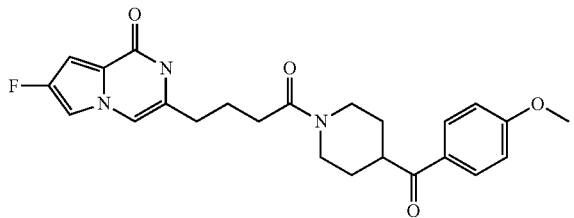 [SMILES: COc1ccc(C(=O)C2CCN(C(=O)CCCc3cn4cc(F)cc4c(=O)[nH]3)CC2)cc1]

The compound was prepared as described for "C3" using A8; yield: 145 mg (63%) colorless solid (purity: 96%); $^1$H NMR (400 MHz, DMSO-$d_6$) δ [ppm] 10.68 (s, 1H), 7.98 (d, J=8.4 Hz, 2H), 7.38 (s, 1H), 7.16-6.94 (m, 3H), 6.62 (s, 1H), 4.49-4.32 (m, 1H), 3.97-3.78 (m, 4H), 3.64 (t, J=11.3 Hz, 1H), 3.17 (t, J=13.1 Hz, 1H), 2.83-2.65 (m, 1H), 2.45-2.26 (m, 4H), 1.91-1.69 (m, 4H), 1.28-1.57 (m, 2H); LC/MS (C), Rt. 2.51 min; (M+H) 440.1.

6-{4-[4-(4-Methoxy-benzoyl)-piperidin-1-yl]-4-oxo-butyl}-3-methyl-7H-imidazo[1,5-a]pyrazin-8-one ("C33")

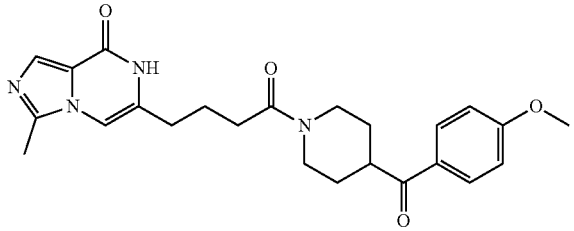 [SMILES: COc1ccc(C(=O)C2CCN(C(=O)CCCc3cn4c(C)ncc4c(=O)[nH]3)CC2)cc1]

"C33" was prepared as described for "C3" using A9; yield: 68 mg (65%) pale-brown solid (purity: 98.5%, Rt: 1.91 min); $^1$H NMR (400 MHz, DMSO-$d_6$) δ [ppm]10.57 (s, 1H), 8.13-7.92 (m, 2H), 7.58 (s, 1H), 7.16-6.94 (m, 3H), 4.56-4.32 (m, 1H), 3.97-3.78 (m, 4H), 3.74-3.58 (m, 1H), 3.24-3.12 (m, 1H), 2.83-2.68 (m, 1H), 2.49 (s, 3H), 2.44-2.32 (m, 4H), 1.93-1.70 (m, 4H), 1.60-1.43 (m, 1H), 1.43-1.27 (m, 1H); LC/MS (A), Rt: 1.55 min; (M+H) 437.2.

3-{4-[3-(4-Methoxy-benzoyl)-azetidin-1-yl]-4-oxo-butyl}-2H-pyrrolo[1,2-a]pyrazin-1-one ("D1")

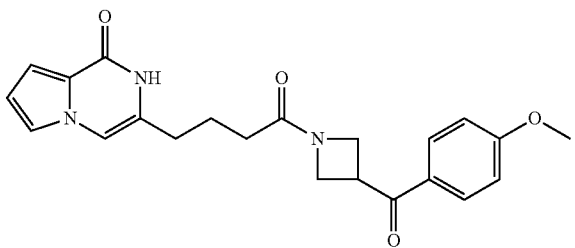 [SMILES: COc1ccc(C(=O)C2CN(C(=O)CCCc3cn4cccc4c(=O)[nH]3)C2)cc1]

"D1" was prepared as described for "C3" using A2 and B3; yield: 54 mg (50%) colorless solid (purity: 95.2%, Rt: 2.21 min); $^1$H NMR (500 MHz, DMSO-$d_6$) δ [ppm] 10.40 (s, 1H), 7.86 (d, J=8.9 Hz, 2H), 7.33 (dd, J=2.4, 1.6 Hz, 1H), 7.11 (s, 1H), 7.06 (d, J=8.9 Hz, 2H), 6.83-6.75 (m, 1H), 6.46 (dd, J=3.9, 2.5 Hz, 1H), 4.44-4.29 (m, 2H), 4.28-4.15 (m, 1H), 4.17-4.05 (m, 1H), 3.97-3.87 (m, 1H), 3.85 (s, 3H), 2.33 (t, J=7.4 Hz, 2H), 2.08 (t, J=7.4 Hz, 2H), 1.85-1.71 (m, 2H); LC/MS (A), Rt: 1.82 min; (M+H) 394.2.

3-{4-[4-(1-Methyl-1H-pyrazole-4-carbonyl)-piperidin-1-yl]-4-oxo-butyl}-2H-pyrrolo[1,2-a]pyrazin-1-one ("C22")

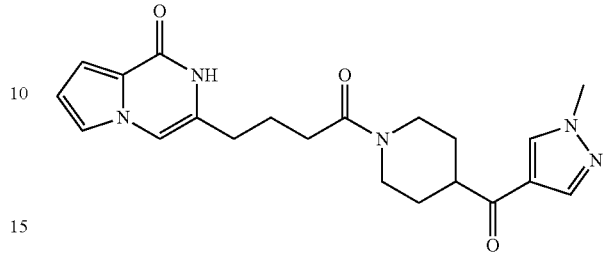

"C22" was prepared as described for "C3" using A2 and B4; yield: 64 mg (71%) colorless solid (purity: 99.5%, Rt: 1.84 min); $^1$H NMR (400 MHz, DMSO-$d_6$) δ [ppm] 10.41 (s, 1H), 8.42 (s, 1H), 7.95 (s, 1H), 7.34 (dd, J=2.5, 1.6 Hz, 1H), 7.11 (s, 1H), 6.86-6.71 (m, 1H), 6.46 (dd, J=4.0, 2.5 Hz, 1H), 4.51-4.30 (m, 1H), 3.96-3.78 (m, 4H), 3.25-3.17 (m, 1H), 3.16-3.01 (m, 1H), 2.74-2.60 (m, 1H), 2.43-2.24 (m, 4H), 1.89-1.67 (m, 4H), 1.59-1.42 (m, 1H), 1.42-1.27 (m, 1H); LC/MS (A), Rt: 1.53 min; (M+H) 396.2.

2-{4-[4-(4-Methoxy-benzoyl)-piperidin-1-yl]-4-oxo-butyl}-7-methyl-3H-thieno-[3,2-d]pyrimidin-4-one ("C35")

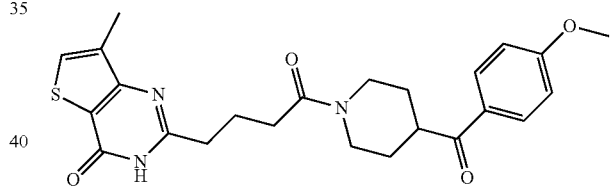

To a solution of 4-(7-methyl-4-oxo-3,4-dihydro-thieno[3,2-d]pyrimidin-2-yl)-butyric acid (150.00 mg; 0.59 mmol) and (4-methoxy-phenyl)-piperidin-4-yl-methanone hydrochloride (151.41 mg; 0.59 mmol) in DMF (3 mL) was added triethylamine (0.25 ml; 1.76 mmol) followed by the dropwise addition of T3P (50% in ethyl acetate) (644.06 mg; 0.88 mmol) at 0° C. under nitrogen atmosphere. The reaction mixture was stirred at room temperature for 15 h. The solvent was evaporated under vacuum, the residue was dissolved in DCM (50 mL), washed with 10% sodium bicarbonate (2×50 mL), water (50 mL), dried over anhydrous sodium sulfate and evaporated under vacuum. The crude material was purified by recrystallisation with acetonitrile to afford 2-{4-[4-(4-methoxy-benzoyl)-piperidin-1-yl]-4-oxo-butyl}-7-methyl-3H-thieno[3,2-d]-pyrimidin-4-one (220 mg; 81%) as colorless solid; $^1$H NMR (400 MHz, DMSO-$d_6$) δ 11.51 (bs, 1H), 8.14 (s, 1H), 7.98 (d, J=9.0 Hz, 2H), 7.06 (d, J=9.0 Hz, 2H), 4.42-4.32 (m, 1H), 3.94-3.89 (m, 1H), 3.84 (s, 3H), 3.66-3.60 (m, 1H), 3.23-3.14 (m, 1H), 2.76-2.69 (m, 1H), 2.57 (s, 3H), 2.56-2.51 (m, 2H), 2.44-2.39 (m, 2H), 1.99-1.90 (m, 2H), 1.82-1.70 (m, 2H), 1.58-1.45 (m, 1H), 1.40-1.30 (m, 1H); LC/MS (B), Rt: 3.75 min; (M+H) 454.2.

7-Methyl-2-{4-oxo-4-[4-(5-phenyl-[1,3,4]oxadiazol-2-yl)-piperidin-1-yl]-butyl}-3H-thieno[3,2-d]pyrimidin-4-one ("C54")

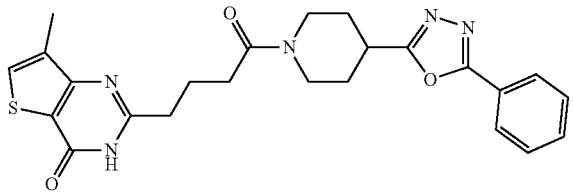 [SMILES: Cc1csc2c(=O)[nH]c(CCCC(=O)N3CCC(c4nnc(-c5ccccc5)o4)CC3)nc12]

Preparation as described for "C35": yield: 185 mg (67%) colorless solid; $^1$H (400 MHz, DMSO-d$_6$) δ 12.35 (s, 1H), 7.99 (dd, J=1.4, 7.8 Hz, 2H), 7.75 (d, J=1.0 Hz, 1H), 7.62-7.56 (m, 3H), 4.30 (d, J=13.2 Hz, 1H), 3.91 (d, J=13.7 Hz, 1H), 3.43-3.34 (m, 1H), 3.28-3.21 (m, 1H), 2.91-2.82 (m, 1H), 2.70-2.54 (m, 2H), 2.48-2.41 (m, 2H), 2.28 (s, 3H), 2.14-2.05 (m, 2H), 2.02-1.93 (m, 2H), 1.81-1.71 (m, 1H), 1.68-1.54 (m, 1H); LC/MS (B), Rt: 3.50; (M+H) 464.2.

6-{4-[4-(4-Methoxy-benzoyl)-piperidin-1-yl]-4-oxo-butyl}-1-methyl-1,5-dihydro-pyrazolo[3,4-d]pyrimidin-4-one ("C41")

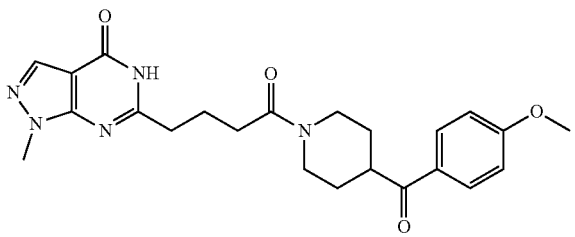 [SMILES: COc1ccc(C(=O)C2CCN(C(=O)CCCc3nc4c(cnn4C)c(=O)[nH]3)CC2)cc1]

"C41" was prepared as described for "C35" using A11; yield: 185 mg (52%) colorless solid; $^1$H NMR (400 MHz, DMSO-d$_6$) δ 12.00 (s, 1H), 8.01-7.95 (m, 3H), 7.05 (d, J=8.9 Hz, 2H), 4.39 (d, J=13.1 Hz, 1H), 3.91 (d, J=13.6 Hz, 1H), 3.86-3.83 (m, 6H), 3.69-3.61 (m, 1H), 3.16 (t, J=12.5 Hz, 1H), 2.74-2.71 (m, 1H), 2.70-2.64 (m, 2H), 2.45-2.38 (m, 2H), 2.00-1.91 (m, 2H), 1.81-1.71 (m, 2H), 1.56-1.43 (m, 1H), 1.38-1.28 (m, 1H); LC/MS (B), Rt: 3.21 min; (M+H) 438.3.

The following compounds were prepared analogously:

6-{4-[4-(6-Methoxy-pyridine-3-carbonyl)-piperidin-1-yl]-4-oxo-butyl}-1-methyl-1,5-dihydro-pyrazolo[3,4-d]pyrimidin-4-one ("C43")

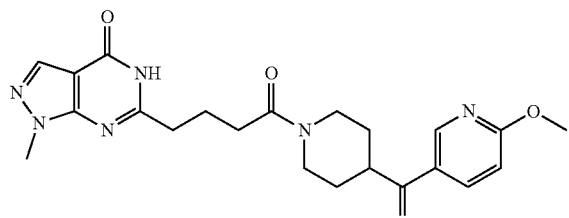

Yield: 120 mg (34%) colorless solid; $^1$H NMR (400 MHz, DMSO-d$_6$) δ 12.01 (s, 1H), 8.90 (s, 1H), 8.22 (dd, J=2.4, 8.7 Hz, 1H), 7.96 (s, 1H), 6.92 (d, J=8.8 Hz, 1H), 4.39 (d, J=13.1 Hz, 1H), 3.94-3.87 (m, 4H), 3.86 (s, 3H), 3.70-3.62 (m, 1H), 3.16 (t, J=11.8 Hz, 1H), 2.78-2.63 (m, 3H), 2.48-2.36 (m, 2H), 1.98-1.91 (m, 2H), 1.84-1.74 (m, 2H), 1.55-1.45 (m, 1H), 1.39-1.29 (m, 1H); LC/MS (B), Rt: 2.88 min; (M+H) 439.3.

6-Amino-1'-[4-(1-methyl-4-oxo-4,5-dihydro-1H-pyrazolo[3,4-d]pyrimidin-6-yl)-butyryl]-1',2',3',4',5',6'-hexahydro-[3,4']bipyridinyl-5-carbonitrile ("C44")

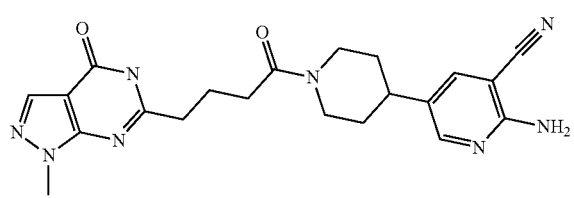 [SMILES: Cn1ncc2c(=O)[nH]c(CCCC(=O)N3CCC(c4cnc(N)c(C#N)c4)CC3)nc21]

Yield: 200 mg (57%) colorless solid; $^1$H NMR (400 MHz, DMSO-d$_6$) δ 12.01 (s, 1H), 8.11 (s, 1H), 7.97 (s, 1H), 7.76 (s, 1H), 6.70 (s, 2H), 4.50 (d, J=12.9 Hz, 1H), 3.95 (d, J=13.4 Hz, 1H), 3.86 (s, 3H), 3.05 (t, J=12.8 Hz, 1H), 2.70-2.62 (m, 3H), 2.60-2.56 (m, 1H), 2.46-2.38 (m, 2H), 2.01-1.91 (m, 2H), 1.78-1.67 (m, 2H), 1.59-1.48 (m, 1H), 1.43-1.34 (m, 1H); LC/MS (B), Rt: 1.97 min; (M+H) 421.3.

6-[4-(6-Amino-5-pyrimidin-2-yl-3',4',5',6'-tetrahydro-2'H-[3,4']bipyridinyl-1'-yl)-4-oxo-butyl]-1-methyl-1,5-dihydro-pyrazolo[3,4-d]pyrimidin-4-one ("C45")

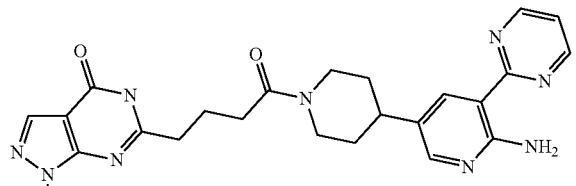

Yield: 70 mg (23%) pale-yellow solid; $^1$H NMR (400 MHz, DMSO-d$_6$) δ 12.02 (s, 1H), 8.90 (d, J=4.9 Hz, 2H), 8.50 (s, 1H), 8.04 (s, 1H), 7.97 (s, 1H), 7.65 (brs, 2H), 7.39 (t, J=4.9 Hz, 1H), 4.54 (d, J=12.6 Hz, 1H), 3.99 (d, J=13.0 Hz, 1H), 3.86 (s, 3H), 3.09 (t, J=12.5 Hz, 1H), 2.78-2.65 (m, 3H), 2.63-2.57 (m, 1H), 2.46-2.40 (m, 2H), 2.03-1.94 (m, 2H), 1.85-1.76 (m, 2H), 1.62-1.50 (m, 1H), 1.44-1.36 (m, 1H); LC/MS (B), Rt: 2.30 min; (M+H) 474.2.

1-Methyl-6-{4-oxo-4[4-(5-phenyl-[1,3,4]oxadiazol-2-yl)-piperidin-1-yl]-butyl}-1,5-dihydro-pyrazolo[3,4-d]pyrimidin-4-one ("C46")

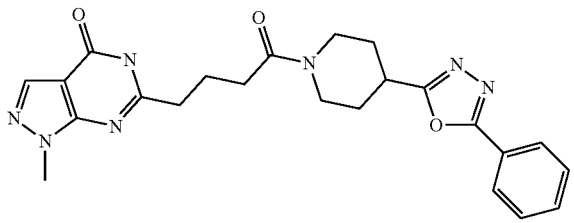 [SMILES: Cn1ncc2c(=O)[nH]c(CCCC(=O)N3CCC(c4nnc(-c5ccccc5)o4)CC3)nc21]

Yield: 35 mg (13%) pale-yellow solid; $^1$H NMR (400 MHz, DMSO-d$_6$) δ 12.02 (s, 1H), 8.04-7.97 (m, 3H), 7.64-7.57 (m, 3H), 4.30 (d, J=12.8 Hz, 1H), 3.91 (d, J=13.4 Hz, 1H), 3.86 (s, 3H), 3.37-3.32 (m, 1H), 3.27-3.21 (m, 1H), 2.86 (t, J=11.2 Hz, 1H), 2.71-2.65 (m, 2H), 2.48-2.40 (m, 2H), 2.14-2.05 (m, 2H), 2.01-1.91 (m, 2H), 1.80-1.71 (m, 1H), 1.68-1.58 (m, 1H); LC/MS (B), Rt: 3.03 min; (M+H) 448.2.

4-{1-[4-(1-Methyl-4-oxo-4,5-dihydro-1H-pyrazolo[3,4-d]pyrimidin-6-yl)-butyryl]-piperidin-4-yloxy}-benzonitrile ("C47")

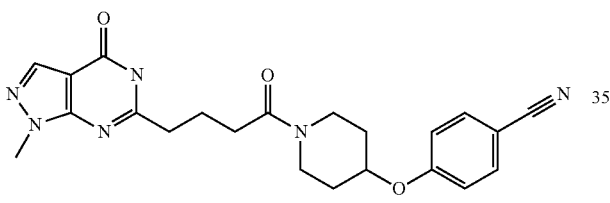

Yield: 220 mg (64%) colorless solid; $^1$H NMR (400 MHz, DMSO-d$_6$) δ [ppm] 12.01 (s, 1H), 7.97 (s, 1H), 7.76 (d, J=6.88 Hz, 2H), 7.15 (d, J=6.92 Hz, 2H), 4.79-4.71 (m, 1H), 3.91-3.85 (m, 4H), 3.74-3.67 (m, 1H), 3.37-3.35 (m, 1H), 3.22-3.16 (m, 1H), 2.70-2.62 (m, 2H), 2.44-2.38 (m, 2H), 2.02-1.84 (m, 4H), 1.64-1.53 (m, 1H), 1.52-1.43 (m, 1H); LC/MS (B), Rt: 3.26 min; (M+H) 421.3.

6-{4-[4-(4-Fluoro-benzoyl)-piperidin-1-yl]-4-oxo-butyl}-1-methyl-1,5-dihydro-pyrazolo[3,4-d]pyrimidin-4-one ("C48")

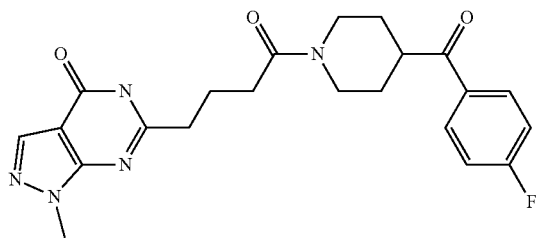 [SMILES: Cn1ncc2c(=O)[nH]c(CCCC(=O)N3CCC(C(=O)c4ccc(F)cc4)CC3)nc21]

Yield: 280 mg (81%) colorless solid; $^1$H NMR (400 MHz, DMSO-d$_6$) δ [ppm] 12.01 (s, 1H), 8.12-8.06 (m, 2H), 7.96 (s, 1H), 7.39-7.33 (m, 2H), 4.39 (d, J=13.0 Hz, 1H), 3.91 (d, J=13.5 Hz, 1H), 3.86 (s, 3H), 3.73-3.64 (m, 1H), 3.16 (t, J=11.9 Hz, 1H), 2.76-2.62 (m, 3H), 2.44-2.35 (m, 2H), 1.98-1.91 (m, 2H), 1.85-1.74 (m, 2H), 1.55-1.42 (m, 1H), 1.37-1.26 (m, 1H); LC/MS (B), Rt: 3.38 min; (M+H) 426.2.

6-{4-[4-(4-Methoxy-3-methyl-benzoyl)-piperidin-1-yl]-4-oxo-butyl}-1-methyl-1,5-dihydro-pyrazolo[3,4-d]pyrimidin-4-one ("C49")

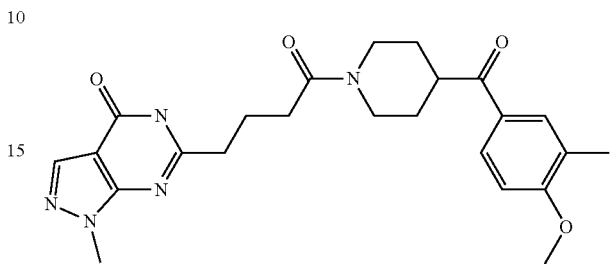

Yield: 200 mg (55%) colorless solid; $^1$H NMR (400 MHz, DMSO-d$_6$) δ [ppm] 12.01 (s, 1H), 7.96 (s, 1H), 7.89 (d, J=8.6 Hz, 1H), 7.80 (s, 1H), 7.05 (d, J=8.6 Hz, 1H), 4.39 (d, J=13.0 Hz, 1H), 3.95-3.83 (m, 7H), 3.69-3.61 (m, 1H), 3.21-3.12 (m, 1H), 2.78-2.63 (m, 3H), 2.46-2.37 (m, 2H), 2.19 (s, 3H), 2.00-1.91 (m, 2H), 1.80-1.71 (m, 2H), 1.54-1.42 (m, 1H), 1.37-1.25 (m, 1H); LC/MS (B), Rt: 3.65 min; (M+H) 452.2.

2-{4-[4-(3-Fluoro-4-methoxy-benzoyl)-piperidin-1-yl]-4-oxo-butyl}-7-methyl-3H-thieno[3,2-d]pyrimidin-4-one ("C55")

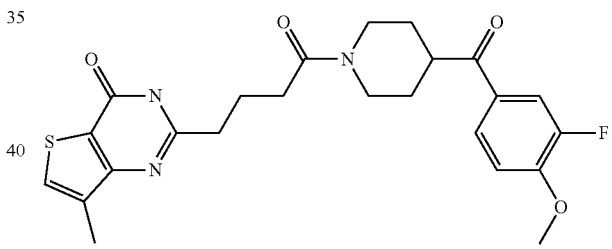

Yield: 200 mg (50%) off-white solid; $^1$H NMR (400 MHz, DMSO-d$_6$) δ [ppm] 12.35 (s, 1H), 7.88-7.77 (m, 3H), 7.29 (t, J=8.5 Hz, 1H), 4.45-4.38 (m, 1H), 3.94 (s, 3H), 3.92-3.88 (m, 1H), 3.65-3.42 (m, 1H), 3.19-2.98 (m, 1H), 2.79-2.70 (m, 3H), 2.69-2.64 (m, 2H), 2.27 (s, 3H), 2.00-1.95 (m, 2H), 1.79-1.71 (m, 2H), 1.52-1.47 (m, 1H), 1.37-1.27 (m, 1H); LC/MS (B), Rt: 3.80 min; (M+H) 472.2.

6-Amino-1'-[4-(7-methyl-4-oxo-3,4-dihydro-thieno[3,2-d]pyrimidin-2-yl)-butyryl]-1',2',3',4',5',6'-hexahydro-[3,4']bipyridinyl-5-carbonitrile ("C56")

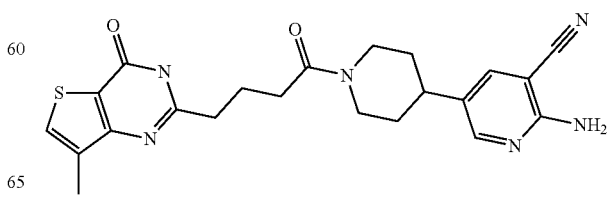

Yield: 150 mg (43%) colorless solid; ¹H NMR (400 MHz, DMSO-d₆) δ [ppm] 12.35 (s, 1H), 8.11 (d, J=2.8 Hz, 2H), 7.76 (dd, J=1.1, 8.6 Hz, 2H), 6.70 (s, 2H), 4.50 (d, J=12.3 Hz, 1H), 3.98-3.87 (m, 1H), 3.09-2.98 (m, 1H), 2.76-2.60 (m, 3H), 2.48-2.37 (m, 2H), 2.28 (s, 3H), 2.05-1.89 (m, 2H), 1.78-1.61 (m, 2H), 1.58-1.47 (m, 1H), 1.39-1.33 (m, 1H); LC/MS (B), Rt: 2.52 min; (M+H) 437.3.

2-Methyl-6-{4-[4-(1-methyl-1H-pyrazole-4-carbonyl)-piperidin-1-yl]-4-oxo-butyl}-5H-pyrazolo[1,5-a]pyrazin-4-one ("C209")

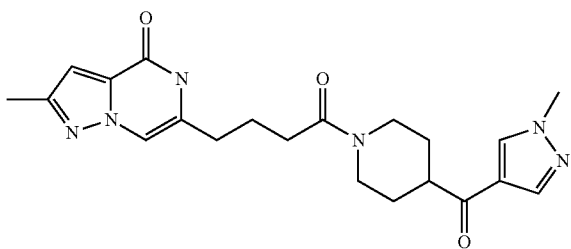 [SMILES: Cc1cc2c(=O)[nH]c(CCCC(=O)N3CCC(C(=O)c4cnn(C)c4)CC3)cn2n1]

Yield: 91 mg (75%) colorless solid;
¹H NMR (400 MHz, DMSO-d₆) δ 11.14 (s, 1H), 8.42 (s, 1H), 7.95 (s, 1H), 7.37 (s, 1H), 6.68 (s, 1H), 4.39 (d, J=13.1 Hz, 1H), 3.88 (s, 3H), 3.21 (tt, J=11.3, 3.6 Hz, 1H), 3.15-3.05 (m, 1H), 2.67 (t, J=12.2 Hz, 1H), 2.43 (t, J=7.4 Hz, 2H), 2.38-2.32 (m, 2H), 2.31 (s, 3H), 1.88-1.71 (m, 5H), 1.49 (m, 1H), 1.35 (m, 1H); LC/MS (C), Rt: 2.03 min; (M+H) 411.1.

4-{{1-[4-(7-Methyl-4-oxo-3H-thieno[3,2-d]pyrimidin-2-yl)butanoyl]-4-piperidyl}-oxy}benzonitrile ("C130")

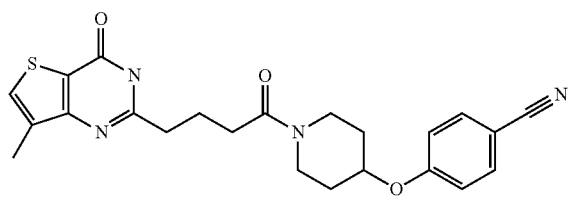 [SMILES: Cc1csc2c(=O)[nH]c(CCCC(=O)N3CCC(Oc4ccc(C#N)cc4)CC3)nc12]

Yield: 250 mg (70%) colorless solid
¹H NMR (400 MHz, DMSO-d₆) δ 12.35 (s, 1H), 7.99 (dd, J=1.4, 7.8 Hz, 2H), 7.75 (d, J=1.0 Hz, 1H), 7.62-7.56 (m, 3H), 4.30 (d, J=13.2 Hz, 1H), 3.91 (d, J=13.7 Hz, 1H), 3.43-3.34 (m, 1H), 3.28-3.21 (m, 1H), 2.91-2.82 (m, 1H), 2.70-2.54 (m, 2H), 2.48-2.41 (m, 2H), 2.28 (s, 3H), 2.14-2.05 (m, 2H), 2.02-1.93 (m, 2H), 1.81-1.71 (m, 1H), 1.68-1.54 (m, 1H); LC/MS (B), Rt: 3.82 min; (M+H) 437.3.

2-{4-[4-(4-Fluorobenzoyl)-1-piperidyl]-4-oxo-butyl}-7-methyl-3H-thieno[3,2-d]pyrimidin-4-one ("C131")

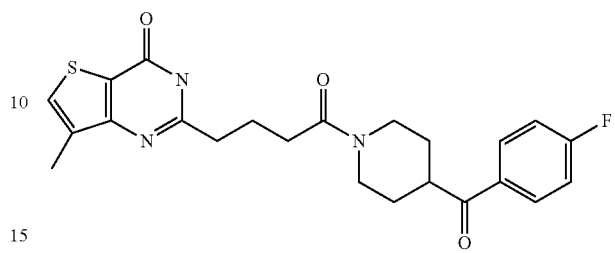

Yield: 220 mg (60%) colorless solid;
¹H NMR (400 MHz, DMSO-d₆) δ 12.33 (s, 1H), 8.07 (dd, J=3.4, 6.8 Hz, 2H), 7.77 (s, 1H), 7.36 (t, J=8.8 Hz, 2H), 4.48-4.33 (m, 1H), 3.99-3.82 (m, 1H), 3.71-3.61 (m, 1H), 3.22-3.08 (m, 1H), 2.72-2.61 (m, 3H), 2.48-2.39 (m, 2H), 2.27 (s, 3H), 2.00-1.89 (m, 2H), 1.81-1.70 (m, 2H), 1.58-1.41 (m, 1H), 1.39-1.29 (m, 1H); LC/MS (B), Rt: 3.88 min; (M+H) 442.3.

2-{4-[4-(4-Methoxy-3-methyl-benzoyl)-1-piperidyl]-4-oxo-butyl}-7-methyl-3H-thieno[3,2-d]pyrimidin-4-one ("C132")

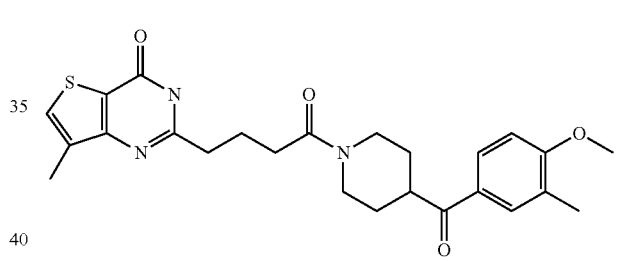

Yield: 100 mg (26%) colorless solid,
¹H NMR (400 MHz, DMSO-d₆) δ 12.35 (s, 1H), 7.88 (dd, J=2.0, 8.4 Hz, 1H), 7.80-7.77 (m, 2H), 7.04 (d, J=8.8 Hz, 1H), 4.48-4.32 (m, 1H), 3.96-3.89 (m, 1H), 3.86 (s, 3H), 3.69-3.59 (m, 1H), 3.28-3.04 (m, 1H), 2.79-2.61 (m, 3H), 2.47-2.33 (m, 2H), 2.28 (s, 3H), 2.19 (s, 3H), 2.01-1.90 (m, 2H), 1.82-1.71 (m, 2H), 1.57-1.43 (m, 1H), 1.38-1.28 (m, 1H); LC/MS (B), Rt: 3.88 min; (M+H) 442.3.

2-{4-{4-[4-(1-Hydroxy-1-methyl-ethyl)benzoyl]-1-piperidyl}-4-oxo-butyl}-7-methyl-3H-thieno[3,2-d]pyrimidin-4-one ("C133")

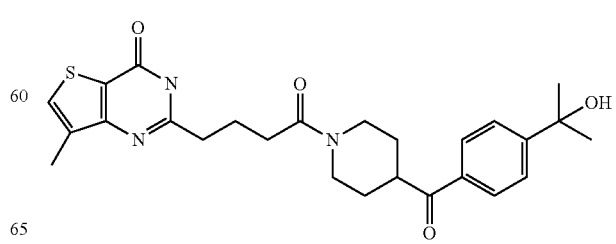

Yield: 85 mg (43%) colorless solid;
¹H NMR (400 MHz, DMSO-d₆) δ 12.35 (bs, 1H), 7.93 (d, J=8.2 Hz, 2H), 7.77 (s, 1H), 7.60 (d, J=8.4 Hz, 2H), 5.30 (bs, 1H), 4.44-4.33 (m, 1H), 3.98-3.85 (m, 1H), 3.69-3.61 (m, 1H), 3.29-3.11 (m, 1H), 2.79-2.61 (m, 3H), 2.48-2.31 (m, 2H), 2.28 (s, 3H), 2.00-1.91 (m, 2H), 1.81-1.73 (m, 2H), 1.55-1.45 (m, 1H), 1.43 (s, 6H), 1.38-1.31 (m, 1H); LC/MS (B), Rt: 3.35 min; (M+H) 482.2.

6-{4-[4-(3-Fluoro-4-methoxy-benzoyl)-piperidin-1-yl]-4-oxo-butyl}-1-methyl-1,5-dihydro-pyrazolo[3,4-d]pyrimidin-4-one ("C42")

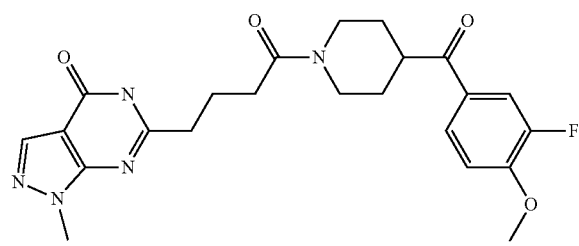 [SMILES: COc1ccc(C(=O)C2CCN(C(=O)CCCc3nc4c(cnn4C)c(=O)[nH]3)CC2)cc1F]

Yield: 172 mg (47%) colorless solid;
¹H NMR (400 MHz, DMSO-d₆) δ 11.02 (brs, 1H), 7.96 (s, 1H), 7.89-7.86 (m, 1H), 7.83-7.80 (m, 1H), 7.29 (t, J=8.4 Hz, 1H), 4.40-4.37 (m, 1H), 3.92-3.86 (m, 7H), 3.69-3.63 (m, 1H), 3.19-3.13 (m, 1H), 2.75-2.65 (m, 3H), 2.40-2.38 (m, 2H), 1.98-1.90 (m, 2H), 1.77-1.74 (m, 2H), 1.52-1.43 (m, 1H), 1.35-1.27 (m, 1H); LC/MS (B), Rt: 3.39 min; (M+H) 456.2.

6-{4-{4-[4-(1-Hydroxy-1-methyl-ethyl)benzoyl]-1-piperidyl}-4-oxo-butyl}-1-methyl-5H-pyrazolo[3,4-d]pyrimidin-4-one ("C50")

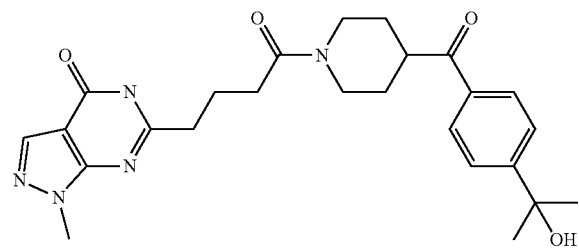 [SMILES: Cn1ncc2c(=O)[nH]c(CCCC(=O)N3CCC(C(=O)c4ccc(C(C)(C)O)cc4)CC3)nc21]

Yield: 175 mg (46%) colorless solid;
¹H NMR (400 MHz, DMSO-d₆) δ 12.01 (s, 1H), 7.97-7.92 (m, 3H), 7.61 (d, J=8.4 Hz, 2H), 5.18 (s, 1H), 4.48 (d, J=12.9 Hz, 1H), 3.92-3.84 (m, 4H), 3.71-3.63 (m, 1H), 3.17 (t, J=12.0 Hz, 1H), 2.76-2.62 (m, 3H), 2.42-2.36 (m, 2H), 1.98-1.89 (m, 2H), 1.80-1.71 (m, 2H), 1.55-1.45 (m, 1H), 1.43 (s, 6H), 1.35-1.25 (m, 1H); LC/MS (B), Rt: 2.95 min; (M+H) 466.2.

2-{4-[4-(6-Methoxypyridine-3-carbonyl)-1-piperidyl]-4-oxo-butyl}-7-methyl-3H-thieno[3,2-d]pyrimidin-4-one ("C126")

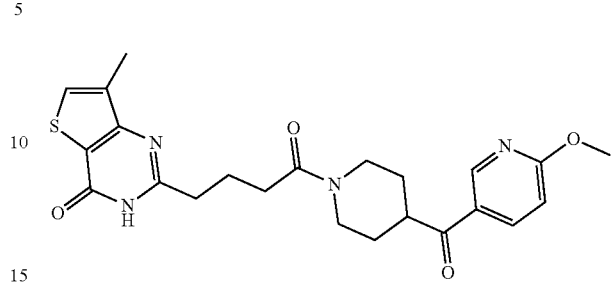

Yield: 90 mg (24%) colorless solid;
¹H NMR (400 MHz, DMSO-d₆) δ 12.35 (s, 1H), 8.90 (d, J=2.8 Hz, 1H), 8.21 (dd, J=2.4, 8.8 Hz, 1H), 7.77 (s, 1H), 6.94 (d, J=8.8 Hz, 1H), 4.44-4.35 (m, 1H), 3.94 (s, 3H), 3.93-3.89 (m, 1H), 3.69-3.60 (m, 1H), 3.22-3.01 (m, 1H), 2.79-2.61 (m, 3H), 2.48-2.33 (m, 2H), 2.28 (s, 3H), 2.01-1.89 (m, 2H), 1.79-1.62 (m, 2H), 1.51-1.42 (m, 1H), 1.40-1.23 (m, 1H); LC/MS (B), Rt: 3.39 min; (M+H) 455.3.

2-{4-[4-(6-Amino-5-pyrimidin-2-yl-3-pyridyl)-1-piperidyl]-4-oxo-butyl}-7-methyl-3H-thieno[3,2-d]pyrimidin-4-one ("C128")

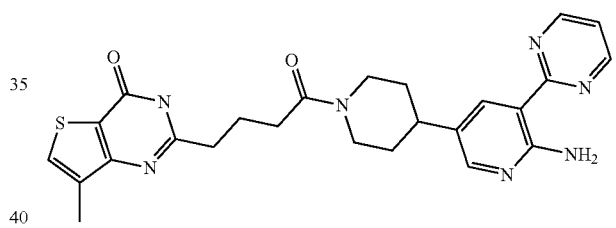

Yield: 120 mg (29%) off-white solid;
¹H NMR (400 MHz, DMSO-d₆) δ 8.89 (d, J=4.8 Hz, 2H), 8.50 (d, J=2.4 Hz, 1H), 8.04 (d, J=2.4 Hz, 1H), 7.76 (d, J=1.1 Hz, 1H), 7.60 (bs, 2H), 7.39 (t, J=4.8 Hz, 1H), 4.59-4.51 (m, 1H), 4.08-3.94 (m, 1H), 3.22-3.05 (m, 1H), 2.78-2.62 (m, 4H), 2.48-2.39 (m, 2H), 2.27 (s, 3H), 2.05-1.91 (m, 2H), 1.85-1.74 (m, 2H), 1.61-1.52 (m, 1H), 1.48-1.35 (m, 1H); LC/MS (B), Rt: 2.66 min; (M+H) 490.2.

6-{4-[4-(1-Methylpyrazole-4-carbonyl)-1-piperidyl]-4-oxo-butyl}-7H-imidazo[1,5-a]pyrazin-8-one ("C207")

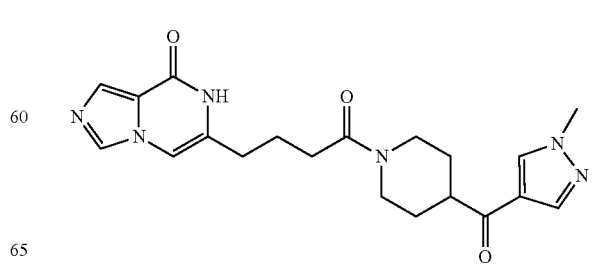

Yield: 17 mg (16%) colorless solid (purity: 98.4%; Rt: 1.28 min);

¹H NMR (400 MHz, DMSO-d₆) δ 10.63 (s, 1H), 8.42 (s, 1H), 8.18-8.15 (m, 1H), 7.96-7.93 (m, 1H), 7.67 (s, 1H), 7.22 (s, 1H), 4.45-4.33 (m, 1H), 3.96-3.80 (m, 4H), 3.28-3.16 (m, 1H), 3.16-3.04 (m, 1H), 2.72-2.60 (m, 1H), 2.42-2.32 (m, 4H), 1.86-1.71 (m, 4H), 1.56-1.41 (m, 1H), 1.41-1.27 (m, 1H); LC/MS (A), Rt: 0.34 min; (M+H) 397.2.

6-{4-[4-(4-Methoxybenzoyl)-1-piperidyl]-4-oxo-butyl}-3-methyl-7H-imidazo[1,2-a]pyrazin-8-one ("C32")

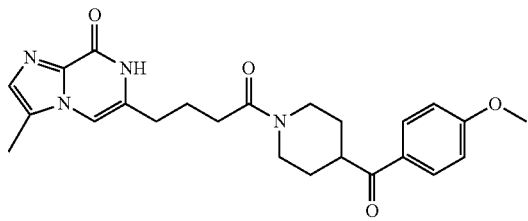

Yield: 47 mg (74%) colorless solid (purity: 98.9%; Rt: 2.01 min);

¹H NMR (500 MHz, DMSO-d₆) δ 11.10 (s, 1H), 8.03-7.97 (m, 2H), 7.25-7.18 (m, 1H), 7.11 (s, 1H), 7.09-7.01 (m, 2H), 4.45-4.36 (m, 1H), 3.95-3.81 (m, 4H), 3.66 (tt, J=11.2, 3.4 Hz, 1H), 3.23-3.13 (m, 1H), 2.80-2.71 (m, 1H), 2.46 (t, J=7.4 Hz, 2H), 2.42-2.32 (m, 5H), 1.86 (q, J=7.3 Hz, 2H), 1.82-1.73 (m, 2H), 1.59-1.42 (m, 1H), 1.42-1.28 (m, 1H); LC/MS (A), Rt: 1.62 min; (M+H) 437.2.

7-Fluoro-3-{4-[4-(1-methyl-1H-pyrazole-4-carbonyl)-piperidin-1-yl]-4-oxo-butyl}-2H-pyrrolo[1,2-a]pyrazin-1-one ("C78")

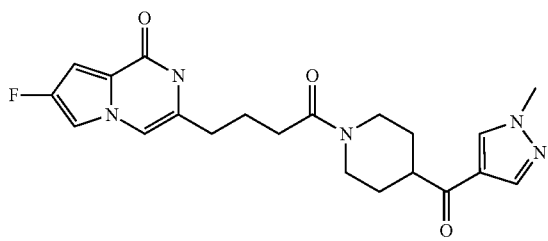 [SMILES: Cn1cc(C(=O)C2CCN(C(=O)CCCc3cn4cc(F)cc4c(=O)[nH]3)CC2)cn1]

Yield: 173 mg (63%) colorless solid (purity: 95%);

¹H NMR (500 MHz, DMSO-d₆) δ 10.68 (s, 1H), 8.43 (s, 1H), 7.96 (s, 1H), 7.38 (dd, J=3.3, 1.9 Hz, 1H), 7.05 (s, 1H), 6.62 (d, J=1.8 Hz, 1H), 4.40 (d, J=13.0 Hz, 1H), 3.92-3.84 (m, 4H), 3.22 (tt, J=11.4, 3.7 Hz, 1H), 3.10 (t, J=12.1 Hz, 1H), 2.67 (t, J=11.8 Hz, 1H), 2.43-2.27 (m, 4H), 1.87-1.70 (m, 4H), 1.55-1.42 (m, 1H), 1.39-1.29 (m, 1H); LC/MS (E), Rt: 1.17 min; (M+H) 414.1.

6-Methyl-3-{4-[4-(1-methyl-1H-pyrazole-4-carbonyl)-piperidin-1-yl]-4-oxo-butyl}-2H-pyrrolo[1,2-a]pyrazin-1-one ("C62")

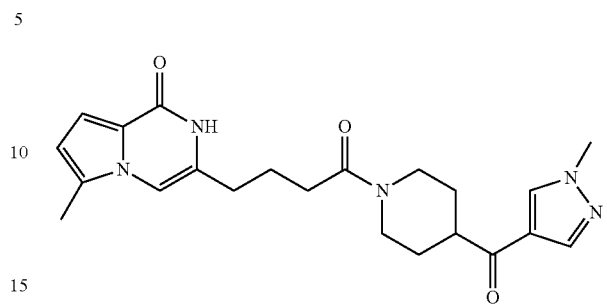

Yield: 74 mg (87%) colorless powder (purity: 100%; Rt: 1.99 min);

¹H NMR (400 MHz, DMSO-d₆) δ 10.36 (s, 1H), 8.42 (s, 1H), 7.96-7.94 (m, 1H), 6.90 (s, 1H), 6.74 (d, J=3.8 Hz, 1H), 6.29-6.25 (m, 1H), 4.40 (d, J=13.2 Hz, 1H), 3.93-3.84 (m, 4H), 3.27-3.17 (m, 1H), 3.16-3.06 (m, 1H), 2.73-2.63 (m, 1H), 2.42-2.31 (m, 7H), 1.87-1.72 (m, 4H), 1.55-1.28 (m, 2H); LC/MS (A), Rt: 1.60 min; (M+H) 410.2.

3-Methyl-6-{4-[4-(1-methyl-1H-pyrazole-4-carbonyl)-piperidin-1-yl]-4-oxo-butyl}-7H-imidazo[1,5-a]pyrazin-8-one ("C105")

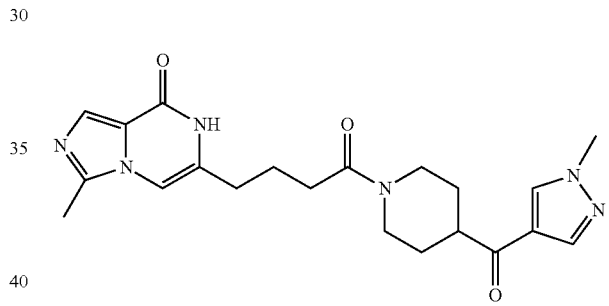

Yield: 50 mg (56%) colorless solid (purity: 98.5%; Rt (2): 2.53 min);

¹H NMR (400 MHz, DMSO-d₆) δ 10.55 (s, 1H), 8.42 (s, 1H), 7.97-7.93 (m, 1H), 7.57 (s, 1H), 7.04 (s, 1H), 4.44-4.35 (m, 1H), 3.94-3.82 (m, 4H), 3.27-3.16 (m, 1H), 3.15-3.05 (m, 1H), 2.72-2.62 (m, 1H), 2.48 (s, 3H), 2.42-2.31 (m, 4H), 1.88-1.71 (m, 4H), 1.56-1.27 (m, 2H); LC/MS (A), Rt: 1.16 min; (M+H) 411.1.

2-{4-[4-(4-Methoxybenzoyl)-piperidin-1-yl]-4-oxo-butyl}-7-methyl-3H-pyrrolo[2,1-f][1,2,4]triazin-4-one ("C37")

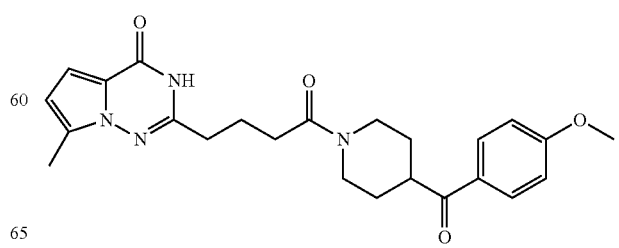

Yield: 68 mg (73%) pale yellow solid;

¹H NMR (400 MHz, DMSO-d₆) δ 11.46 (s, 1H), 7.98 (d, J=8.9 Hz, 2H), 7.04 (d, J=8.9 Hz, 2H), 6.75 (d, J=4.2 Hz, 1H), 6.30 (d, J=3.8 Hz, 1H), 4.39 (d, J=13.0 Hz, 1H), 3.98-3.85 (m, 1H), 3.84 (s, 3H), 3.69-3.59 (m, 1H), 3.38-3.10 (m, 1H), 2.79-2.66 (m, 1H), 2.59-2.50 (m, 2H), 2.49-2.43 (m, 2H), 2.42-2.31 (m, 3H), 2.02-1.90 (m, 2H), 1.89-1.71 (m, 2H), 1.58-1.32 (m, 1H), 1.31-0.82 (m, 1H); LC/MS (B), Rt: 4.0 min; (M+H) 437.3.

2-{4-[4-(3-Fluoro-4-methoxy-benzoyl)-piperidin-1-yl]-4-oxo-butyl}-7-methyl-3H-pyrrolo[2,1-f][1,2,4]triazin-4-one ("C147")

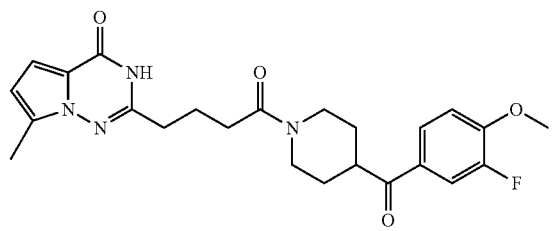

Yield: 45 mg (47%) pale yellow solid;

¹H NMR (400 MHz, DMSO-d₆) δ 11.46 (s, 1H), 7.87 (d, J=8.7 Hz, 1H), 7.81 (dd, J=2.0, 12.3 Hz, 1H), 7.29 (t, J=8.6 Hz, 1H), 6.75 (d, J=4.2 Hz, 1H), 6.31-6.28 (m, 1H), 4.58-4.29 (m, 1H), 3.92 (s, 3H), 3.90-3.83 (m, 1H), 3.71-3.60 (m, 1H), 3.38-3.11 (m, 1H), 2.78-2.61 (m, 1H), 2.59-2.50 (m, 2H), 2.49-2.39 (m, 2H), 2.36 (s, 3H), 2.02-1.82 (m, 2H), 1.79-1.71 (m, 2H), 1.50-1.42 (m, 1H), 1.39-1.19 (m, 1H); LC/MS (B), Rt: 4.1 min; (M+H) 455.3.

7-Methyl-2-{4-oxo-4-[4-(5-phenyl-[1,3,4]oxadiazol-2-yl)-piperidin-1-yl]-butyl}-3H-pyrrolo[2,1-f][1,2,4]triazin-4-one ("C151")

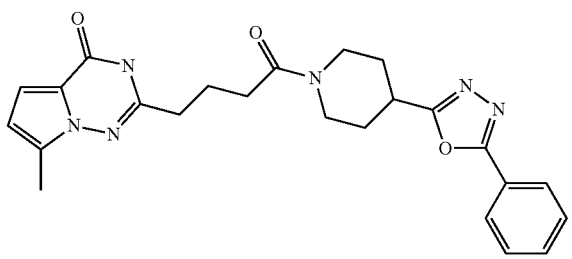 [SMILES: Cc1ccc2c(=O)[nH]c(CCCC(=O)N3CCC(c4nnc(-c5ccccc5)o4)CC3)nn12]

Yield: 50 mg (56%) pale yellow solid;

¹H NMR (400 MHz, DMSO-d₆) δ 11.46 (s, 1H), 8.06-7.92 (m, 2H), 7.68-7.51 (m, 3H), 6.75 (d, J=4.4 Hz, 1H), 6.29 (dd, J=0.4, 4.2 Hz, 1H), 4.29 (d, J=13.5 Hz, 1H), 3.90 (d, J=13.8 Hz, 1H), 3.41-3.30 (m, 1H), 3.29-3.11 (m, 1H), 2.86-2.79 (m, 1H), 2.59-2.50 (m, 2H), 2.49-2.40 (m, 2H), 2.35 (s, 3H), 2.18-2.00 (m, 2H), 1.97-1.94 (m, 2H), 1.93-1.91 (m, 1H), 1.89-1.72 (m, 1H); LC/MS (B), Rt: 3.87 min; (M+H) 447.3.

4-{1-[4-(7-Methyl-4-oxo-3,4-dihydro-pyrrolo[2,1-f][1,2,4]triazin-2-yl)-butyryl]-piperidin-4-yloxy}-benzonitrile ("C152")

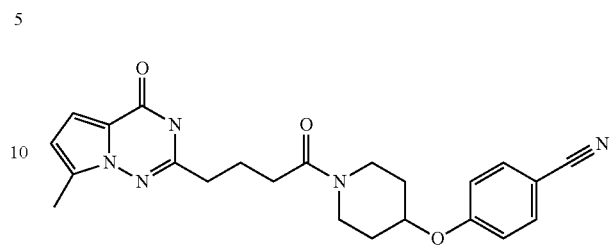

Yield: 45 mg (52%) off-white solid;

¹H NMR (400 MHz, DMSO-d₆) δ 11.46 (s, 1H), 7.79-7.70 (m, 2H), 7.17-7.13 (m, 2H), 6.75 (d, J=4.2 Hz, 1H), 6.29 (dd, J=0.7, 4.2 Hz, 1H), 4.79-4.70 (m, 1H), 3.91-3.80 (m, 1H), 3.78-3.61 (m, 1H), 3.35 (s, 3H), 3.38-3.20 (m, 1H), 3.19-3.11 (m, 1H), 2.59-2.50 (m, 2H), 2.49-2.39 (m, 2H), 2.36 (s, 3H), 2.09-1.81 (m, 1H), 1.59-1.50 (m, 1H), 1.49-1.18 (m, 1H); LC/MS (B), Rt: 4.16 min; (M+H) 420.2.

2-{4-[4-(4-Fluoro-benzoyl)-piperidin-1-yl]-4-oxo-butyl}-7-methyl-3H-pyrrolo[2,1-f][1,2,4]triazin-4-one ("C153")

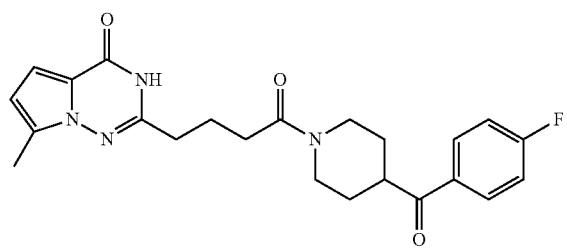 [SMILES: Cc1ccc2c(=O)[nH]c(CCCC(=O)N3CCC(C(=O)c4ccc(F)cc4)CC3)nn12]

Yield: 69 mg (80%) off-white solid;

¹H NMR (400 MHz, DMSO-d₆) δ 11.45 (s, 1H), 8.12-7.95 (m, 2H), 7.38-7.34 (m, 2H), 6.75 (d, J=4.2 Hz, 1H), 6.31-6.28 (m, 1H), 4.38 (d, J=12.8 Hz, 1H), 3.90 (d, J=13.3 Hz, 1H), 3.74-3.63 (m, 1H), 3.19-3.13 (m, 1H), 2.76-2.68 (m, 1H), 2.55-2.51 (m, 2H), 2.45-2.37 (m, 2H), 2.35 (s, 3H), 1.94-1.86 (m, 2H), 1.82-1.73 (m, 2H), 1.53-1.42 (m, 1H), 1.38-1.26 (m, 1H); LC/MS (B), Rt: 4.13 min; (M+H) 425.2.

2-{4-[4-(4-Methoxy-3-methyl-benzoyl)-piperidin-1-yl]-4-oxo-butyl}-7-methyl-3H-pyrrolo[2,1-f][1,2,4]triazin-4-one ("C154")

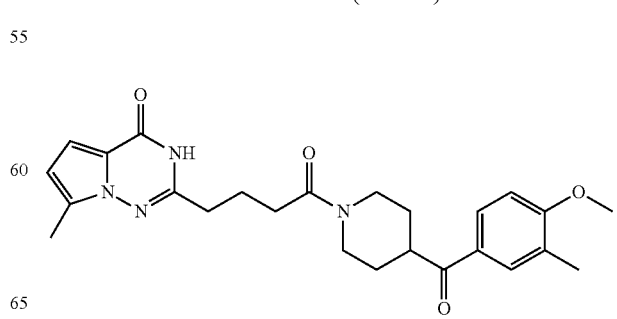

Yield: 62 mg (67%) off-white solid;

$^1$H NMR (400 MHz, DMSO-$d_6$) δ 11.45 (s, 1H), 7.88 (d, J=8.5 Hz, 1H), 7.80 (s, 1H), 7.04 (d, J=8.7 Hz, 1H), 6.75 (d, J=4.2 Hz, 1H), 6.30 (d, J=4.2 Hz, 1H), 4.39 (d, J=12.5 Hz, 1H), 3.92-3.86 (m, 4H), 3.67-3.61 (m, 1H), 3.22-3.13 (m, 1H), 2.76-2.64 (m, 1H), 2.55-2.51 (m, 2H), 2.49-2.39 (m, 2H), 2.36 (s, 3H), 2.19 (s, 3H), 1.97-1.86 (m, 2H), 1.79-1.72 (m, 2H), 1.49-1.41 (m, 1H), 1.36-1.26 (m, 1H); LC/MS (B), Rt: 4.45 min; (M+H) 451.2.

2-(4-{4-[4-(1-Hydroxy-1-methyl-ethyl)-benzoyl]-piperidin-1-yl}-4-oxo-butyl)-7-methyl-3H-pyrrolo[2,1-f][1,2,4]triazin-4-one ("C155")

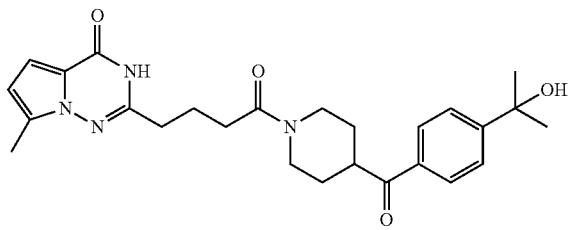 [SMILES: Cc1ccc2c(=O)[nH]c(CCCC(=O)N3CCC(C(=O)c4ccc(C(C)(C)O)cc4)CC3)nn12]

Yield: 33 mg (36%) pale yellow solid;

$^1$H NMR (400 MHz, DMSO-$d_6$) δ 11.46 (s, 1H), 7.93 (d, J=8.5 Hz, 2H), 7.60 (d, J=8.5 Hz, 2H), 6.75 (d, J=4.2 Hz, 1H), 6.29 (d, J=4.1 Hz, 1H), 5.18 (s, 1H), 4.38 (d, J=13.0 Hz, 1H), 3.90 (d, J=13.2 Hz, 1H), 3.72-3.64 (m, 1H), 3.17-3.14 (m, 1H), 2.73 (t, J=12.4 Hz, 1H), 2.54-2.51 (m, 2H), 2.47-2.38 (m, 2H), 2.36 (s, 3H), 1.96-1.86 (m, 2H), 1.80-1.71 (m, 2H), 1.54-1.45 (m, 1H), 1.43 (s, 6H), 1.34-1.24 (m, 1H); LC/MS (B), Rt: 3.64 min; (M+H) 465.2.

6-Fluoro-2-{4-[4-(4-methoxy-benzoyl)-piperidin-1-yl]-4-oxo-butyl}-3H-pyrrolo[2,1-f][1,2,4]triazin-4-one ("C39")

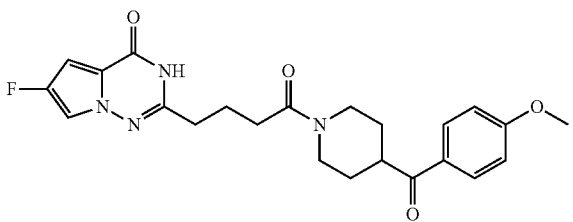 [SMILES: COc1ccc(C(=O)C2CCN(C(=O)CCCc3nn4cc(F)cc4c(=O)[nH]3)CC2)cc1]

Yield: 65 mg (57%) colorless solid;

$^1$H NMR (400 MHz, DMSO-$d_6$) δ 11.79 (s, 1H), 7.98 (d, J=7.0 Hz, 2H), 7.63-7.62 (m, 1H), 7.04 (d, J=9.0 Hz, 2H), 6.68 (d, J=2.1 Hz, 1H), 4.38 (d, J=13.5 Hz, 1H), 3.92-3.84 (m, 1H), 3.81 (s, 3H), 3.67-3.61 (m, 1H), 3.18-3.12 (m, 1H), 2.74-2.68 (m, 1H), 2.53-2.51 (m, 2H), 2.41-2.36 (m, 2H), 1.92-1.86 (m, 2H), 1.80-1.70 (m, 2H), 1.52-1.44 (m, 1H), 1.36-1.28 (m, 1H); LC/MS (B), Rt: 3.97 min; (M+H) 441.2.

6-Fluoro-2-{4-[4-(3-fluoro-4-methoxy-benzoyl)-piperidin-1-yl]-4-oxo-butyl}-3H-pyrrolo[2,1-f][1,2,4]triazin-4-one ("C169")

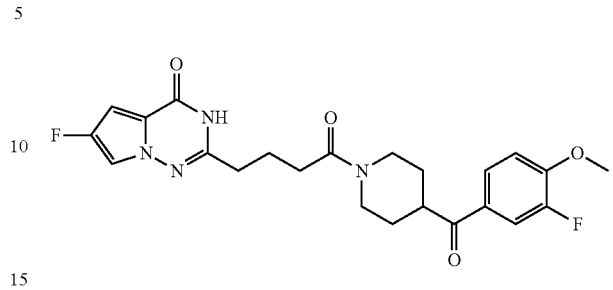

Yield: 60 mg (52%) colorless solid;

$^1$H NMR (400 MHz, DMSO-$d_6$) δ 7.87 (d, J=8.7 Hz, 1H), 7.83-7.78 (m, 1H), 7.62 (s, 1H), 7.29 (t, J=8.6 Hz, 1H), 6.68 (s, 1H), 4.37 (d, J=13.1 Hz, 1H), 3.93-3.86 (m, 4H), 3.69-3.62 (m, 1H), 3.15 (t, J=12.0 Hz, 1H), 2.74-2.64 (m, 1H), 2.55-2.51 (m, 2H), 2.41-2.34 (m, 2H), 1.92-1.84 (m, 2H), 1.79-1.60 (m, 2H), 1.54-1.42 (m, 1H), 1.36-1.26 (m, 1H); LC/MS (B), Rt: 4.17 min; (M+H) 459.2.

6-Fluoro-3-{4-[4-(1-methyl-1H-pyrazole-4-carbonyl)-piperidin-1-yl]-4-oxo-butyl}-2H-pyrrolo[1,2-a]pyrazin-1-one ("C208")

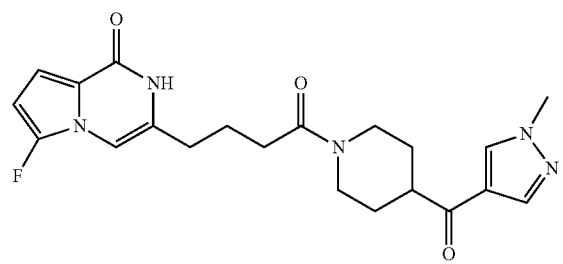 [SMILES: Cn1cc(C(=O)C2CCN(C(=O)CCCc3cn4c(F)ccc4c(=O)[nH]3)CC2)cn1]

Yield: 43 mg (61%) colorless powder (purity: 98.9%; Rt: 1.98 min);

$^1$H NMR (400 MHz, DMSO-$d_6$) δ 10.57 (s, 1H), 8.49 (s, 1H), 8.02 (s, 1H), 7.00 (s, 1H), 6.82 (t, J=4.7 Hz, 1H), 6.22 (t, J=4.1 Hz, 1H), 4.59-4.34 (m, 1H), 4.06-3.84 (m, 4H), 3.33-3.22 (m, 1H), 3.22-3.08 (m, 1H), 2.82-2.65 (m, 1H), 2.51-2.29 (m, 4H), 1.96-1.75 (m, 4H), 1.65-1.48 (m, 1H), 1.48-1.32 (m, 1H); LC/MS (A), Rt: 1.61 min; (M+H) 414.2.

2-{4-[4-(4-Methoxy-benzoyl)-piperidin-1-yl]-4-oxo-butyl}-3H-pyrrolo[2,1-f][1,2,4]triazin-4-one ("C36")

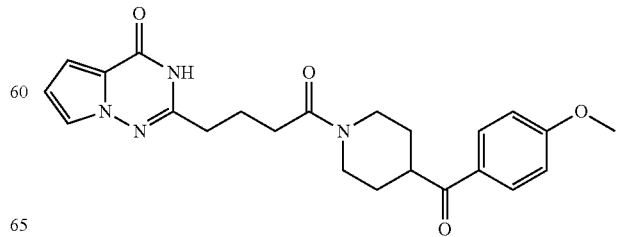

Yield: 25 mg (34%) colorless solid;
$^1$H NMR (400 MHz, DMSO-d$_6$) δ 11.55 (s, 1H), 7.98 (d, J=8.9 Hz, 2H), 7.52 (dd, J=1.6, 2.6 Hz, 1H), 7.02 (d, J=8.9 Hz, 2H), 6.80 (dd, J=1.6, 4.3 Hz, 1H), 6.51-6.43 (m, 1H), 4.39 (d, J=12.4 Hz, 1H), 3.90 (d, J=14.0 Hz, 1H), 3.84 (s, 3H), 3.64 (t, J=11.6 Hz, 1H), 3.16 (t, J=11.0 Hz, 1H), 2.79-2.62 (m, 1H), 2.60-2.46 (m, 2H), 2.45-2.33 (m, 2H), 1.99-1.81 (m, 2H), 1.78-1.63 (m, 2H), 1.56-1.45 (m, 1H), 1.39-1.22 (m, 1H); LC/MS (B), Rt: 3.71 min; (M+H) 423.3.

2-{4-[4-(3-Fluoro-4-methoxy-benzoyl)-piperidin-1-yl]-4-oxo-butyl}-3H-pyrrolo[2,1-f][1,2,4]triazin-4-one ("C136")

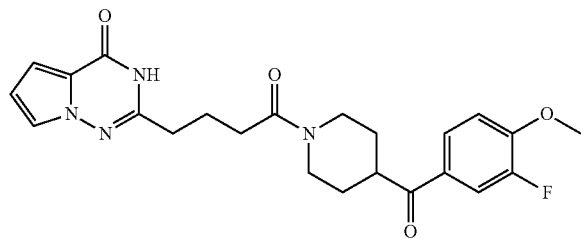 [SMILES: COc1ccc(C(=O)C2CCN(C(=O)CCCc3nn4cccc4c(=O)[nH]3)CC2)cc1F]

Yield: 100 mg (50%) colorless solid;
$^1$H NMR (400 MHz, DMSO-d$_6$) δ 11.56 (s, 1H), 7.95-7.80 (m, 2H), 7.52 (t, J=2.3 Hz, 1H), 7.29 (t, J=8.6 Hz, 1H), 6.88-6.81 (m, 1H), 6.48 (dd, J=2.6, 4.2 Hz, 1H), 4.38 (d, J=13.1 Hz, 1H), 3.91 (s, 3H), 3.98-3.82 (m, 1H), 3.66 (t, J=11.7 Hz, 1H), 3.16 (t, J=12.2 Hz, 1H), 2.78-2.69 (m, 1H), 2.59-2.43 (m, 2H), 2.45-2.33 (m, 2H), 2.01-1.83 (m, 2H), 1.89-1.71 (m, 2H), 1.51-1.42 (m, 1H), 1.39-1.20 (m, 1H); LC/MS (B), Rt: 3.85 min; (M+H) 441.2.

2-{4-[4-(6-Methoxy-pyridine-3-carbonyl)-piperidin-1-yl]-4-oxo-butyl}-3H-pyrrolo[2,1-f][1,2,4]triazin-4-one ("C137")

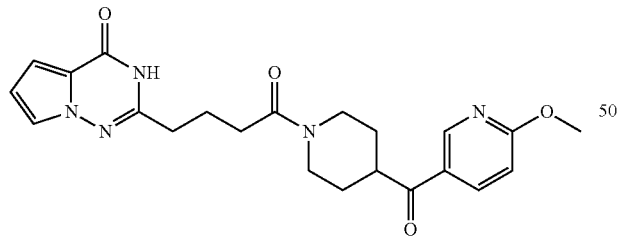

Yield: 50 mg (43%) colorless solid;
$^1$H NMR (400 MHz, DMSO-d$_6$) δ 11.56 (s, 1H), 8.90 (d, J=2.0 Hz, 1H), 8.22 (dd, J=2.4, 8.8 Hz, 1H), 7.52 (dd, J=1.7, 2.6 Hz, 1H), 6.97-6.92 (m, 1H), 6.82 (dd, J=1.7, 4.3 Hz, 1H), 6.48 (dd, J=2.6, 4.3 Hz, 1H), 4.38 (d, J=12.8 Hz, 1H), 3.94 (s, 3H), 3.92-3.90 (m, 1H), 3.69-3.60 (m, 1H), 3.16 (t, J=10.9 Hz, 1H), 2.78-2.64 (m, 1H), 2.59-2.45 (m, 2H), 2.43-2.32 (m, 2H), 2.01-1.90 (m, 2H), 1.88-1.73 (m, 2H), 1.55-1.43 (m, 1H), 1.38-1.20 (m, 1H); LC/MS (B), Rt: 3.41 min; (M+H) 424.0.

6-Amino-1'-[4-(4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile ("C138")

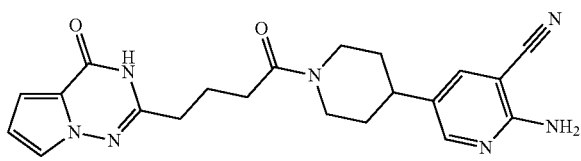 [SMILES: N#Cc1cc(C2CCN(C(=O)CCCc3nn4cccc4c(=O)[nH]3)CC2)cnc1N]

Yield: 45 mg (40%) colorless solid;
$^1$H NMR (400 MHz, DMSO-d$_6$) δ 11.57 (s, 1H), 8.11 (d, J=2.4 Hz, 1H), 7.75 (d, J=2.40 Hz, 1H), 7.52 (dd, J=1.7, 2.6 Hz, 1H), 6.83 (dd, J=1.7, 4.3 Hz, 1H), 6.70 (s, 2H), 6.48 (dd, J=2.6, 4.3 Hz, 1H), 4.50 (d, J=13.7 Hz, 1H), 3.94 (d, J=12.6 Hz, 1H), 3.08-2.91 (m, 1H), 2.71-2.46 (m, 3H), 2.45-2.41 (m, 1H), 2.40-2.39 (m, 2H), 1.99-1.83 (m, 2H), 1.70 (t, J=13.4 Hz, 2H), 1.58-1.42 (m, 1H), 1.47-1.18 (m, 1H); LC/MS (B), Rt: 2.44 min; (M+H) 406.0.

2-{4-Oxo-4-[4-(5-phenyl-[1,3,4]oxadiazol-2-yl)-piperidin-1-yl]-butyl}-3H-pyrrolo[2,1-f][1,2,4]triazin-4-one ("C140")

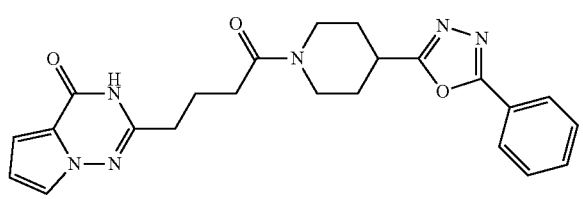 [SMILES: O=C(CCCc1nn2cccc2c(=O)[nH]1)N1CCC(c2nnc(-c3ccccc3)o2)CC1]

Yield: 40 mg (53%) colorless solid;
$^1$H NMR (400 MHz, DMSO-d$_6$) δ 11.56 (s, 1H), 8.04-7.94 (m, 2H), 7.65-7.54 (m, 3H), 7.50 (d, J=1.7 Hz, 1H), 6.82 (dd, J=1.7, 4.3 Hz, 1H), 6.46 (dd, J=2.6, 4.2 Hz, 1H), 4.29 (d, J=13.6 Hz, 1H), 3.90 (d, J=13.4 Hz, 1H), 3.39-3.26 (m, 1H), 3.23-3.19 (m, 1H), 2.86 (t, J=10.6 Hz, 1H), 2.58-2.45 (m, 2H), 2.43-2.39 (m, 2H), 2.30-1.99 (m, 2H), 1.97-1.84 (m, 2H), 1.80-1.72 (m, 1H), 1.69-1.51 (m, 1H); LC/MS (B), Rt: 3.50 min; (M+H) 433.3.

4-{1-[4-(4-Oxo-3,4-dihydro-pyrrolo[2,1-f][1,2,4]triazin-2-yl)-butyryl]-piperidin-4-yloxy}-benzonitrile ("C141")

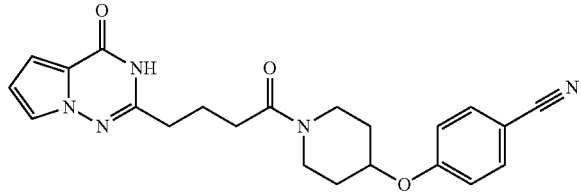 [SMILES: N#Cc1ccc(OC2CCN(C(=O)CCCc3nn4cccc4c(=O)[nH]3)CC2)cc1]

Yield: 40 mg (56%) off-white solid;
$^1$H NMR (400 MHz, DMSO-d$_6$) δ 11.57 (s, 1H), 7.76 (dd, J=2.0, 6.8 Hz, 2H), 7.52 (dd, J=1.7, 2.6 Hz, 1H), 7.19-7.11 (m, 2H), 6.82 (dd, J=1.6, 4.3 Hz, 1H), 6.48 (dd, J=2.6, 4.3

Hz, 1H), 4.80-4.71 (m, 1H), 3.91-3.81 (m, 1H), 3.79-3.62 (m, 1H), 3.37-3.23 (m, 1H), 3.22-3.12 (m, 1H), 2.58-2.44 (m, 2H), 2.41 (t, J=7.3 Hz, 2H), 2.11-1.85 (m, 4H), 1.69-1.53 (m, 1H), 1.51-1.40 (m, 1H); LC/MS (B), Rt: 3.77 min; (M+H) 406.2.

2-{4-[4-(4-Fluoro-benzoyl)-piperidin-1-yl]-4-oxo-butyl}-3H-pyrrolo[2,1-f][1,2,4]triazin-4-one ("C142")

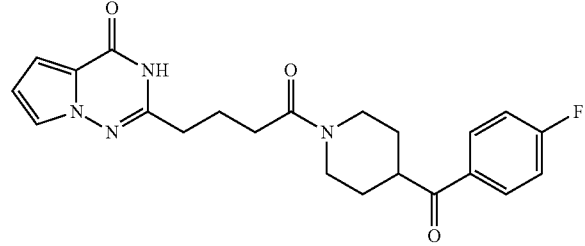 [SMILES: O=C(c1ccc(F)cc1)C1CCN(C(=O)CCCc2nn3cccc3c(=O)[nH]2)CC1]

Yield: 45 mg (64%) colorless solid;
$^1$H NMR (400 MHz, DMSO-d$_6$) δ 11.55 (s, 1H), 8.08 (dd, J=5.6, 8.8 Hz, 2H), 7.52 (s, 1H), 7.36 (t, J=8.8 Hz, 2H), 6.82 (dd, J=1.6, 4.3 Hz, 1H), 6.48 (dd, J=2.6, 4.2 Hz, 1H), 4.38 (d, J=12.4 Hz, 1H), 3.90 (d, J=12.3 Hz, 1H), 3.69 (t, J=11.4 Hz, 1H), 3.16 (t, J=11.4 Hz, 1H), 2.79-2.69 (m, 1H), 2.58-2.43 (m, 2H), 2.40-2.32 (m, 2H), 1.98-1.83 (m, 2H), 1.79-1.69 (m, 2H), 1.59-1.43 (m, 1H), 1.39-1.29 (m, 1H); LC/MS (B), Rt: 3.83 min; (M+H) 411.2.

2-{4-[4-(4-Methoxy-3-methyl-benzoyl)-piperidin-1-yl]-4-oxo-butyl}-3H-pyrrolo[2,1-f][1,2,4]triazin-4-one ("C143")

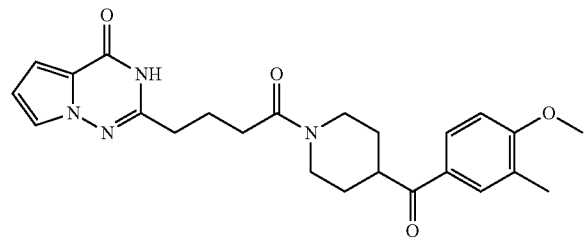

Yield: 35 mg (46%) colorless solid;
$^1$H NMR (400 MHz, DMSO-d$_6$) δ 11.55 (s, 1H), 7.89 (dd, J=2.1, 8.6 Hz, 1H), 7.80 (s, 1H), 7.53 (dd, J=1.7, 2.6 Hz, 1H), 7.05 (d, J=8.7 Hz, 1H), 6.82 (dd, J=1.6, 4.2 Hz, 1H), 6.48 (dd, J=2.6, 4.3 Hz, 1H), 4.39 (d, J=12.8 Hz, 1H), 3.91 (s, 3H), 3.90-3.82 (m, 1H), 3.64 (t, J=11.2 Hz, 1H), 3.16 (t, J=13.8 Hz, 1H), 2.72 (t, J=12.5 Hz, 1H), 2.59-2.45 (m, 2H), 2.44-2.31 (m, 2H), 2.19 (s, 3H), 1.99-1.82 (m, 2H), 1.79-1.69 (m, 2H), 1.58-1.41 (m, 1H), 1.39-1.21 (m, 1H); LC/MS (B), Rt: 4.08 min; (M+H) 437.3.

2-(4-{4-[4-(1-Hydroxy-1-methyl-ethyl)-benzoyl]-piperidin-1-yl}-4-oxo-butyl)-3H-pyrrolo[2,1-f][1,2,4]triazin-4-one ("C144")

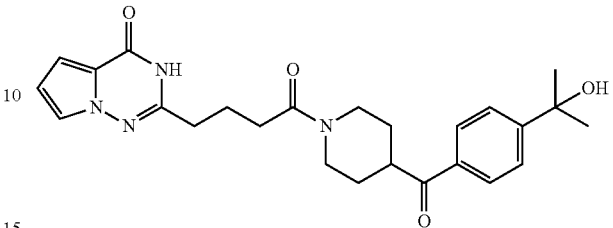

Yield: 90 mg (46%) off-white solid;
$^1$H NMR (400 MHz, DMSO-d$_6$) δ 11.56 (s, 1H), 7.93 (d, J=8.5 Hz, 2H), 7.61 (d, J=8.5 Hz, 2H), 7.52 (dd, J=1.7, 2.6 Hz, 1H), 6.82 (dd, J=1.6, 4.3 Hz, 1H), 6.48 (dd, J=2.6, 4.3 Hz, 1H), 5.18 (s, 1H), 4.38 (d, J=13.0 Hz, 1H), 3.97-3.88 (m, 1H), 3.78-3.61 (m, 1H), 3.17 (t, J=11.3 Hz, 1H), 2.73 (t, J=10.8 Hz, 1H), 2.59-2.42 (m, 2H), 2.40-2.32 (m, 2H), 2.01-1.95 (m, 2H), 1.94-1.88 (m, 2H), 1.86-1.48 (m, 1H), 1.43 (s, 6H), 1.39-1.18 (m, 1H); LC/MS (B), Rt: 3.38 min; (M+H) 451.2.

4-{1-[4-(6-Fluoro-4-oxo-3,4-dihydro-pyrrolo[2,1-f][1,2,4]triazin-2-yl)-butyryl]-piperidin-4-yloxy}-benzonitrile ("C174")

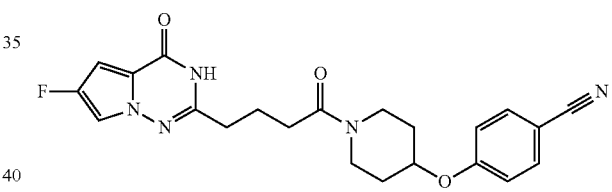

Yield: 30 mg (33%) colorless solid;
$^1$H NMR (400 MHz, DMSO-d$_6$) δ 11.80 (s, 1H), 7.76 (d, J=8.9 Hz, 2H), 7.64-7.62 (m, 1H), 7.15 (d, J=9.0 Hz, 2H), 6.70-6.68 (m, 1H), 4.78-4.74 (m, 1H), 3.89-3.82 (m, 1H), 3.74-3.67 (m, 1H), 3.35-3.32 (m, 1H), 3.21-3.16 (m, 1H), 2.55-2.51 (m, 2H), 2.42-2.36 (m, 2H), 1.99-1.74 (m, 4H), 1.64-1.55 (m, 1H), 1.51-1.41 (m, 1H); LC/MS (B), Rt: 4.09 min; (M+H) 424.2.

6-Fluoro-2-{4-[4-(4-fluoro-benzoyl)-piperidin-1-yl]-4-oxo-butyl}-3H-pyrrolo[2,1-f][1,2,4]triazin-4-one ("C175")

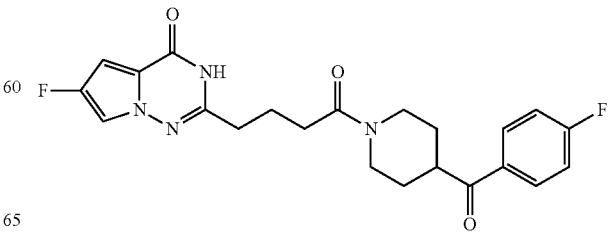

Yield: 37 mg (41%) colorless solid;
$^1$H NMR (400 MHz, DMSO-d$_6$) δ 11.80 (s, 1H), 8.12-8.06 (m, 2H), 7.64-7.61 (m, 1H), 7.39-7.34 (m, 2H), 6.68 (s, 1H), 4.38 (d, J=12.0 Hz, 1H), 3.89 (d, J=13.1 Hz, 1H), 3.72-3.66 (m, 1H), 3.18-3.11 (m, 1H), 2.75-2.66 (m, 1H), 2.54-2.51 (m, 2H), 2.42-2.36 (m, 2H), 1.94-1.85 (m, 2H), 1.80-1.72 (m, 2H), 1.54-1.46 (m, 1H), 1.37-1.23 (m, 1H); LC/MS (B), Rt: 4.16 min; (M+H) 429.2.

6-Fluoro-2-{4-[4-(4-methoxy-3-methyl-benzoyl)-piperidin-1-yl]-4-oxo-butyl}-3H-pyrrolo[2,1-f][1,2,4]triazin-4-one ("C176")

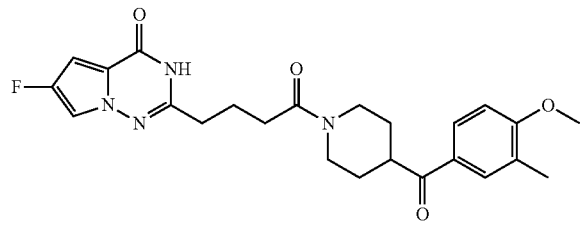 [SMILES: COc1ccc(C(=O)C2CCN(C(=O)CCCc3nn4cc(F)cc4c(=O)[nH]3)CC2)cc1C]

Yield: 44 mg (37%) colorless solid;
$^1$H NMR (400 MHz, DMSO-d$_6$) δ 11.80 (s, 1H), 7.89 (dd, J=2.2, 8.6 Hz, 1H), 7.80 (d, J=1.5 Hz, 1H), 7.64-7.62 (m, 1H), 7.05 (d, J=8.7 Hz, 1H), 6.68 (d, J=2.1 Hz, 1H), 4.38 (d, J=12.5 Hz, 1H), 3.87-3.75 (m, 4H), 3.66-3.61 (m, 1H), 3.19-3.11 (m, 1H), 2.74-2.66 (m, 1H), 2.54-2.51 (m, 2H), 2.41-2.32 (m, 2H), 2.19 (s, 3H), 1.93-1.84 (m, 2H), 1.78-1.71 (m, 2H), 1.52-1.42 (m, 1H), 1.33-1.23 (m, 1H); LC/MS (B), Rt: 4.36 min; (M+H) 455.3.

1-Methyl-5-{4-[4-(1-methyl-1H-pyrazole-4-carbonyl)-piperidin-1-yl]-4-oxo-butyl}-1,6-dihydro-pyrazolo[4,3-d]pyrimidin-7-one ("C191")

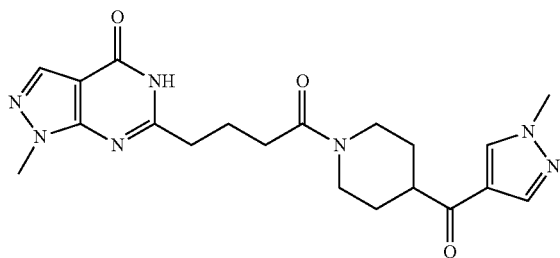 [SMILES: Cn1cc(C(=O)C2CCN(C(=O)CCCc3nc4c(cnn4C)c(=O)[nH]3)CC2)cn1]

Yield: 165 mg (65%) colorless solid;
$^1$H NMR (400 MHz, DMSO-d$_6$) δ 12.01 (s, 1H), 8.44 (s, 1H), 7.97-7.95 (m, 2H), 4.38 (d, J=12.0 Hz, 1H), 3.94-3.86 (m, 7H), 3.67-3.62 (m, 1H), 3.19-3.13 (m, 1H), 2.80 (s, 3H), 2.48-2.39 (m, 2H), 1.98-1.90 (m, 2H), 1.78-1.72 (m, 2H), 1.53-1.45 (m, 1H), 1.38-1.24 (m, 1H); LC/MS (B), Rt: 2.20 min; (M+H) 412.3.

7-Methyl-2-{4-[4-(1-methyl-1H-pyrazole-4-carbonyl)-piperidin-1-yl]-4-oxo-butyl}-3H-thieno[3,2-d]pyrimidin-4-one ("C135")

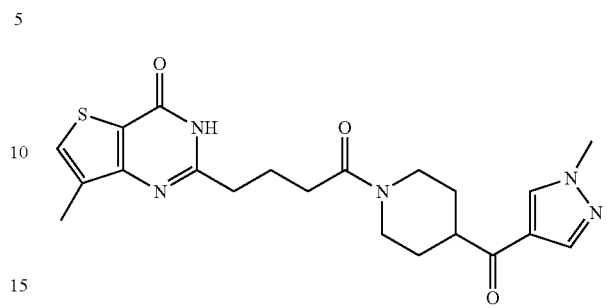

Yield: 180 mg (56%) colorless solid;
$^1$H NMR (400 MHz, DMSO-d$_6$) δ 12.34 (s, 1H), 8.43 (s, 1H), 7.96 (s, 1H), 7.77 (s, 1H), 4.39 (d, J=13.1 Hz, 1H), 3.93-3.87 (m, 4H), 3.28-3.23 (m, 1H), 3.22-3.07 (m, 1H), 2.69-2.63 (m, 3H), 2.48-2.39 (m, 2H), 2.28 (s, 3H), 1.99-1.93 (m, 2H), 1.78-1.71 (m, 2H), 1.49-1.42 (m, 1H), 1.34-1.26 (m, 1H); LC/MS (B), Rt: 2.71 min; (M+H) 428.3.

2-[4-(6-Amino-5-pyrimidin-2-yl-3',4',5',6'-tetrahydro-2'H-[3,4']bipyridinyl-1'-yl)-4-oxo-butyl]-3H-pyrrolo[2,1-f][1,2,4]triazin-4-one ("C139")

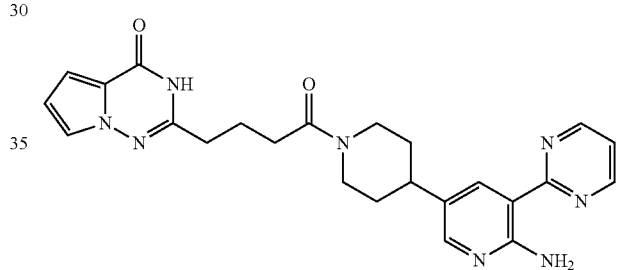

Yield: 55 mg (46%) colorless solid;
$^1$H NMR (400 MHz, DMSO-d$_6$) δ 11.58 (s, 1H), 8.90 (d, J=4.9 Hz, 2H), 8.50 (d, J=2.4 Hz, 1H), 8.05 (d, J=2.4 Hz, 1H), 7.52 (dd, J=1.7, 2.6, 2H), 7.39 (d, J=4.9, 1 H), 6.82 (dd, J=1.6, 4.3 Hz, 1H), 6.47 (dd, J=2.6, 4.3 Hz, 1H), 4.53 (d, J=13.1 Hz, 1H), 3.98 (d, J=12.7 Hz, 1H), 3.08 (t, J=10.92 Hz, 1H), 2.79-2.68 (m, 1H), 2.64-2.50 (m, 1H), 2.49-2.44 (m, 3H), 2.43-2.39 (m, 2H), 1.99-1.73 (m, 2H), 1.58-1.50 (m, 2H), 1.48-1.40 (m, 1H), 1.38-1.20 (m, 1H); LC/MS (B), Rt: 2.71 min; (M+H) 459.0.

2-{4-[4-(4-Methoxy-benzoyl)-piperidin-1-yl]-4-oxo-butyl}-6-methyl-3H-pyrrolo[2,1-f][1,2,4]triazin-4-one ("C38")

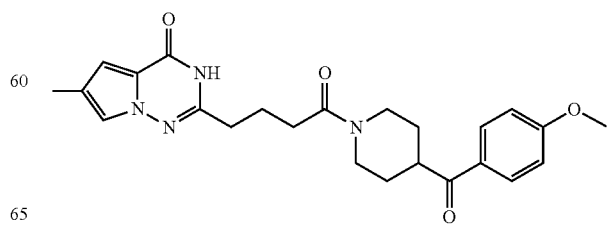

Yield: 65 mg (73%) colorless solid;
¹H NMR (400 MHz, DMSO-d₆) δ 11.48 (s, 1H), 7.98 (d, J=7.0 Hz, 2H), 7.33-7.31 (m, 1H), 7.05 (d, J=7.0 Hz, 2H), 6.63-6.61 (m, 1H), 4.39 (d, J=13.2 Hz, 1H), 3.92-3.86 (m, 1H), 3.84 (s, 3H), 3.69-3.61 (m, 1H), 3.15 (t, J=12.8 Hz, 1H), 2.75-2.68 (m, 1H), 2.54-2.51 (m, 2H), 2.40-2.36 (m, 2H), 2.13 (s, 3H), 1.90-1.83 (m, 2H), 1.79-1.70 (m, 2H), 1.55-1.42 (m, 1H), 1.38-1.23 (m, 1H); LC/MS (B), Rt: 3.97 min; (M+H) 437.3.

2-{4-[4-(3-Fluoro-4-methoxy-benzoyl)-piperidin-1-yl]-4-oxo-butyl}-6-methyl-3H-pyrrolo[2,1-f][1,2,4]triazin-4-one ("C158")

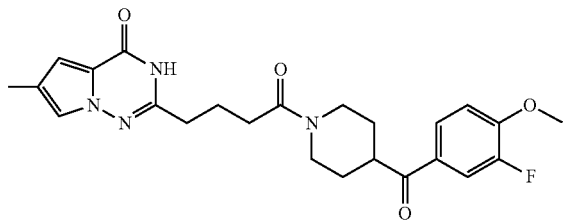

Yield: 90 mg (48%) colorless solid;
¹H NMR (400 MHz, DMSO-d₆) δ 11.48 (s, 1H), 7.88 (dd, J=1.6, 8.6 Hz, 1H), 7.82 (dd, J=2.4, 12.2 Hz, 1H), 7.33-7.27 (m, 2H), 6.63-6.61 (m, 1H), 4.38 (d, J=13.0 Hz, 1H), 3.94-3.84 (m, 4H), 3.70-3.62 (m, 1H), 3.20-3.11 (m, 1H), 2.77-2.68 (m, 1H), 2.48-2.46 (m, 2H), 2.42-2.35 (m, 2H), 2.13 (s, 3H), 1.94-1.83 (m, 2H), 1.80-1.72 (m, 2H), 1.54-1.42 (m, 1H), 1.38-1.22 (m, 1H); LC/MS (B), Rt: 4.01 min; (M+H) 455.3.

2-{4-[4-(6-Methoxy-pyridine-3-carbonyl)-piperidin-1-yl]-4-oxo-butyl}-6-methyl-3H-pyrrolo[2,1-f][1,2,4]triazin-4-one ("C159")

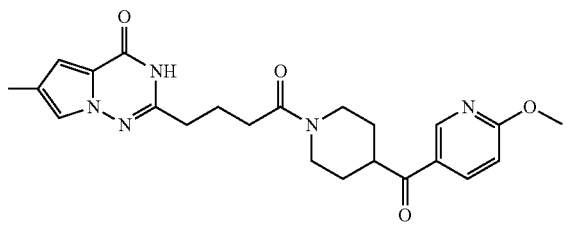

Yield: 30 mg (16%) off-white solid;
¹H NMR (400 MHz, CDCl₃) δ 10.53 (s, 1H), 8.82 (s, 1H), 8.16 (d, J=7.2 Hz, 1H), 7.18-7.21 (m, 1H), 6.87-6.83 (m, 2H), 4.61 (d, J=12.2 Hz, 1H), 4.04 (s, 3H), 4.01-3.95 (m, 1H), 3.49-3.41 (m, 1H), 3.28 (t, J=12.7 Hz, 1H), 2.91 (t, J=11.5 Hz, 1H), 2.68-2.62 (m, 2H), 2.59-2.51 (m, 2H), 2.24 (s, 3H), 2.16-2.05 (m, 2H), 1.98-1.82 (m, 3H), 1.73-1.60 (m, 1H); LC/MS (D), Rt: 4.94 min; (M+H) 438.2.

6-Amino-1'-[4-(6-methyl-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile ("C160")

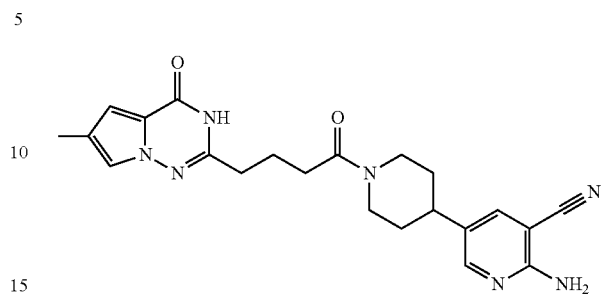

Yield: 78 mg (45%) colorless solid;
¹H NMR (400 MHz, DMSO-d₆) δ 11.49 (s, 1H), 8.11 (d, J=2.4 Hz, 1H), 7.76 (d, J=2.4 Hz, 1H), 7.29-7.33 (m, 1H), 6.70 (s, 2H), 6.64-6.61 (m, 1H), 4.49 (d, J=12.7 Hz, 1H), 3.93 (d, J=13.9 Hz, 1H), 3.02 (t, J=12.8 Hz, 1H), 2.68-2.59 (m, 1H), 2.56-2.51 (m, 3H), 2.39 (t, J=7.3 Hz, 2H), 2.13 (s, 3H), 1.90 (t, J=7.3 Hz, 2H), 1.75-1.66 (m, 2H), 1.56-1.47 (m, 1H), 1.40-1.33 (m, 1H); LC/MS (B), Rt: 2.69 min; (M+H) 420.2.

2-[4-(6-Amino-5-pyrimidin-2-yl-3',4',5',6'-tetrahydro-2'H-[3,4']bipyridinyl-1'-yl)-4-oxo-butyl]-6-methyl-3H-pyrrolo[2,1-f][1,2,4]triazin-4-one ("C161")

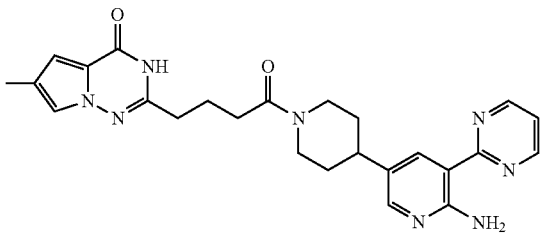 [SMILES: Cc1cc2c(=O)[nH]c(CCCC(=O)N3CCC(c4cnc(N)c(-c5ncccn5)c4)CC3)nn2c1]

Yield: 100 mg (51%) colorless solid;
¹H NMR (400 MHz, DMSO-d₆) δ 11.49 (s, 1H), 8.90 (d, J=4.9 Hz, 2H), 8.51 (d, J=2.3 Hz, 1H), 8.04 (d, J=2.3 Hz, 1H), 7.58 (brs, 2H), 7.39 (t, J=4.9 Hz, 1H), 7.31 (s, 1H), 6.62 (d, J=1.1 Hz, 1H), 4.54 (d, J=12.8 Hz, 1H), 3.97 (d, J=13.7 Hz, 1H), 3.08 (t, J=12.2 Hz, 1H), 2.74 (t, J=11.7 Hz, 1H), 2.62-2.53 (m, 3H), 2.45-2.37 (m, 2H), 2.11 (s, 3H), 1.95-1.88 (m, 2H), 1.85-1.74 (m, 2H), 1.58-1.51 (m, 1H), 1.40-1.32 (m, 1H); LC/MS (B), Rt: 2.87 min; (M+H) 473.2.

6-Methyl-2-{4-oxo-4-[4-(5-phenyl-[1,3,4]oxadiazol-2-yl)-piperidin-1-yl]-butyl}-3H-pyrrolo[2,1-f][1,2,4]triazin-4-one ("C162")

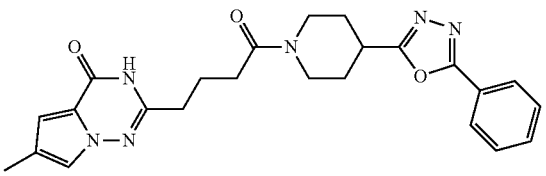 [SMILES: Cc1cc2c(=O)[nH]c(CCCC(=O)N3CCC(c4nnc(-c5ccccc5)o4)CC3)nn2c1]

Yield: 60 mg (33%) colorless solid;
<sup>1</sup>H NMR (400 MHz, DMSO-d$_6$) δ 11.49 (s, 1H), 7.99 (dd, J=1.9, 7.9 Hz, 2H), 7.63-7.56 (m, 3H), 7.30 (d, J=0.8 Hz, 1H), 6.62 (d, J=1.2 Hz, 1H), 4.29 (d, J=13.4 Hz, 1H), 3.89 (d, J=13.8 Hz, 1H), 3.38-3.34 (m, 1H), 3.22 (t, J=11.3 Hz, 1H), 2.86 (t, J=10.8 Hz, 1H), 2.53-2.51 (m, 2H), 2.43-2.38 (m, 2H), 2.14-2.02 (m, 5H), 1.95-1.86 (m, 2H), 1.80-1.68 (m, 1H), 1.66-1.54 (m, 1H); LC/MS (B), Rt: 3.75 min; (M+H) 447.3.

4-{1-[4-(6-Methyl-4-oxo-3,4-dihydro-pyrrolo[2,1-f][1,2,4]triazin-2-yl)-butyryl]-piperidin-4-yloxy}-benzonitrile ("C163")

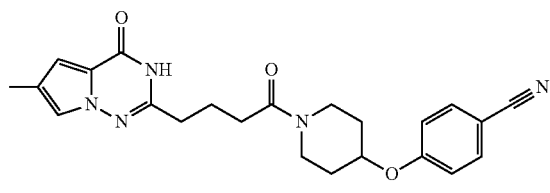 [SMILES: Cc1cc2c(=O)[nH]c(CCCC(=O)N3CCC(Oc4ccc(C#N)cc4)CC3)nn2c1]

Yield: 45 mg (52%) colorless solid;
<sup>1</sup>H NMR (400 MHz, DMSO-d$_6$) δ 11.49 (s, 1H), 7.75 (d, J=8.8 Hz, 2H), 7.31 (s, 1H), 7.15 (d, J=8.8 Hz, 2H), 6.62 (s, 1H), 4.79-4.70 (m, 1H), 3.91-3.82 (m, 1H), 3.72-3.67 (m, 1H), 3.36-3.32 (m, 1H), 3.23-3.16 (m, 1H), 2.53-2.51 (m, 2H), 2.41-2.36 (m, 2H), 2.13 (s, 3H), 1.97-1.81 (m, 4H), 1.62-1.52 (m, 1H), 1.51-1.42 (m, 1H); LC/MS (D), Rt: 5.32 min; (M+H) 420.2.

2-{4-[4-(4-Fluoro-benzoyl)-piperidin-1-yl]-4-oxo-butyl}-6-methyl-3H-pyrrolo[2,1-f][1,2,4]triazin-4-one ("C164")

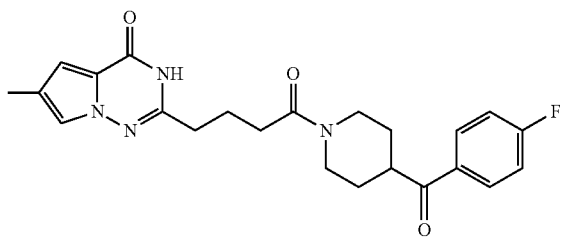 [SMILES: Cc1cc2c(=O)[nH]c(CCCC(=O)N3CCC(C(=O)c4ccc(F)cc4)CC3)nn2c1]

Yield: 26 mg (31%) colorless solid;
<sup>1</sup>H NMR (400 MHz, CDCl$_3$) δ 10.74 (s, 1H), 8.02-7.96 (m, 2H), 7.20-7.15 (m, 3H), 6.86 (s, 1H), 4.58 (d, J=13.0 Hz, 1H), 3.97 (d, J=13.0 Hz, 1H), 3.52-3.47 (m, 1H), 2.91 (t, J=11.5 Hz, 1H), 2.67 (t, J=7.0 Hz, 2H), 2.58-2.53 (m, 2H), 2.23 (s, 3H), 2.21-2.20 (m, 1H), 2.14-2.07 (m, 2H), 1.97-1.78 (m, 3H), 1.67-1.58 (m, 1H); LC/MS (B), Rt: 4.11 min; (M+H) 425.0.

2-{4-[4-(4-Methoxy-3-methyl-benzoyl)-piperidin-1-yl]-4-oxo-butyl}-6-methyl-3H-pyrrolo[2,1-f][1,2,4]triazin-4-one ("C165")

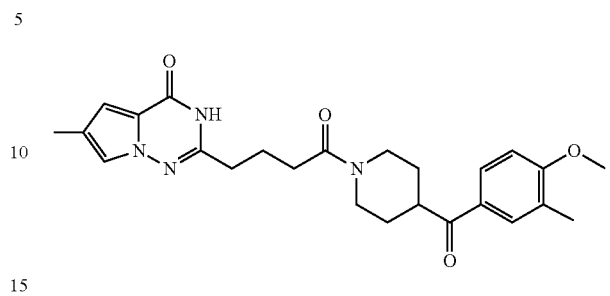

Yield: 48 mg (52%) colorless solid;
<sup>1</sup>H NMR (400 MHz, DMSO-d$_6$) δ 11.48 (s, 1H), 7.89 (dd, J=2.2, 8.6 Hz, 1H), 7.82-7.78 (m, 1H), 7.33-7.30 (m, 1H), 7.05 (d, J=8.8 Hz, 1H), 6.63-6.61 (m, 1H), 4.38 (d, J=12.8 Hz, 1H), 3.92-3.87 (m, 4H), 3.67-3.61 (m, 1H), 3.16 (t, J=12.4 Hz, 1H), 2.75-2.68 (m, 1H), 2.54-2.51 (m, 2H), 2.41-2.35 (m, 2H), 2.19 (s, 3H), 2.13 (s, 3H), 1.92-1.85 (m, 2H), 1.76-1.70 (m, 2H), 1.52-1.42 (m, 1H), 1.37-1.26 (m, 1H); LC/MS (B), Rt: 4.42 min; (M+H) 451.2.

2-(4-{4-[4-(1-Hydroxy-1-methyl-ethyl)-benzoyl]-piperidin-1-yl}-4-oxo-butyl)-6-methyl-3H-pyrrolo[2,1-f][1,2,4]triazin-4-one ("C166")

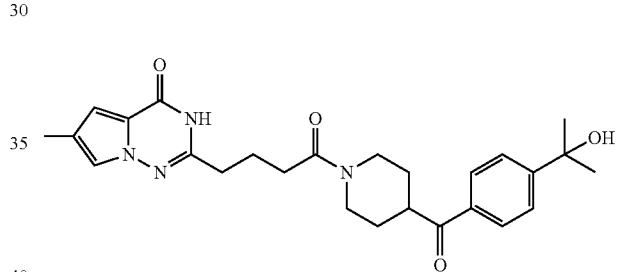

Yield: 98 mg (51%) colorless solid;
<sup>1</sup>H NMR (400 MHz, DMSO-d$_6$) δ 11.48 (s, 1H), 7.93 (d, J=8.4 Hz, 2H), 7.61 (d, J=8.4 Hz, 2H), 7.31 (s, 1H), 6.62 (s, 1H), 5.18 (s, 1H), 4.38 (d, J=12.8 Hz, 1H), 3.89 (d, J=13.6 Hz, 1H), 3.70-3.62 (m, 1H), 3.16 (t, J=12.0 Hz, 1H), 2.76-2.66 (m, 1H), 2.54-2.51 (m, 2H), 2.40-2.32 (m, 2H), 2.13 (s, 3H), 1.90-1.82 (m, 2H), 1.78-1.72 (m, 2H), 1.54-1.48 (m, 1H), 1.43 (s, 6H), 1.36-1.24 (m, 1H); LC/MS (B), Rt: 3.61 min; (M+H) 465.2.

6-Fluoro-2-{4-[4-(6-methoxy-pyridine-3-carbonyl)-piperidin-1-yl]-4-oxo-butyl}-3H-pyrrolo[2,1-f][1,2,4]triazin-4-one ("C170")

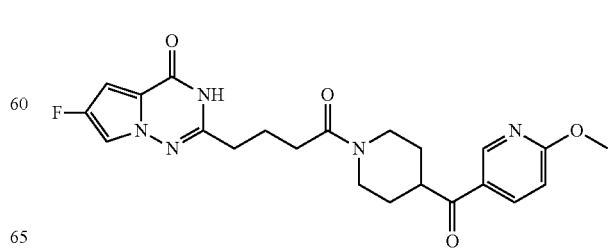

Yield: 135 mg (34%) colorless solid;
¹H NMR (400 MHz, DMSO-d₆) δ 11.80 (s, 1H), 8.90 (s, 1H), 8.22 (d, J=8.8 Hz, 1H), 7.62 (s, 1H), 6.94 (d, J=8.7 Hz, 1H), 6.69 (s, 1H), 4.38 (d, J=13.4 Hz, 1H), 3.94 (s, 3H), 3.89 (d, J=13.6 Hz, 1H), 3.65 (t, J=11.6 Hz, 1H), 3.15 (t, J=11.8 Hz, 1H), 2.74-2.66 (m, 1H), 2.55-2.51 (m, 2H), 2.44-2.41 (m, 2H), 1.91-1.85 (m, 2H), 1.83-1.74 (m, 2H), 1.53-1.42 (m, 1H), 1.41-1.21 (m, 1H); LC/MS (B), Rt: 3.65 min; (M+H) 442.3.

2-[4-(6-Amino-5-pyrimidin-2-yl-3',4',5',6'-tetra-hydro-2'H-[3,4']bipyridinyl-1'-yl)-4-oxo-butyl]-6-fluoro-3H-pyrrolo[2,1-f][1,2,4]triazin-4-one ("C172")

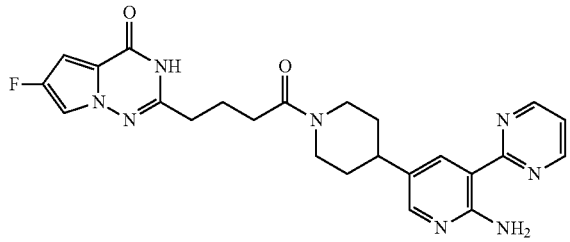 [SMILES: Nc1ncc(C2CCN(C(=O)CCCc3nn4cc(F)cc4c(=O)[nH]3)CC2)cc1-c1ncccn1]

Yield: 70 mg (17%) brown solid;
¹H NMR (400 MHz, DMSO-d₆) δ 11.80 (s, 1H), 8.90 (d, J=4.9 Hz, 2H), 8.51 (d, J=2.2 Hz, 1H), 8.05 (d, J=2.3 Hz, 1H), 7.65-7.63 (m, 3H), 7.40 (t, J=4.9 Hz, 1H), 6.69 (t, J=1.0 Hz, 1H), 4.53 (d, J=12.6 Hz, 1H), 3.97 (d, J=12.9 Hz, 1H), 3.08 (t, J=13.3 Hz, 1H), 2.76-2.67 (m, 1H), 2.60-2.53 (m, 3H), 2.45-2.42 (m, 2H), 1.95-1.88 (m, 2H), 1.82-1.76 (m, 2H), 1.59-1.50 (m, 1H), 1.49-1.30 (m, 1H); LC/MS (B), Rt: 2.88 min; (M+H) 477.2.

6-Fluoro-2-{4-oxo-4-[4-(5-phenyl-[1,3,4]oxadiazol-2-yl)-piperidin-1-yl]-butyl}-3H-pyrrolo[2,1-f][1,2,4]triazin-4-one ("C173")

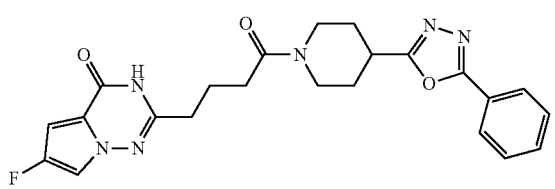 [SMILES: O=C(CCCc1nn2cc(F)cc2c(=O)[nH]1)N1CCC(c2nnc(-c3ccccc3)o2)CC1]

Yield: 185 mg (50%) colorless solid;
¹H NMR (400 MHz, DMSO-d₆) δ 11.80 (s, 1H), 8.00-7.98 (m, 2H), 7.62-7.56 (m, 4H), 6.69 (s, 1H), 4.29 (d, J=13.1 Hz, 1H), 3.90 (d, J=12.8 Hz, 1H), 3.37-3.32 (m, 1H), 3.22 (t, J=12.4 Hz, 1H), 2.86 (t, J=11.8 Hz, 1H), 2.57-2.51 (m, 2H), 2.45-2.40 (m, 2H), 2.12-2.01 (m, 2H), 1.89-1.81 (m, 2H), 1.79-1.66 (m, 1H), 1.56-1.45 (m, 1H); LC/MS (B), Rt: 3.74 min; (M+H) 451.2.

6-Fluoro-2-(4-{4-[4-(1-hydroxy-1-methyl-ethyl)-benzoyl]-piperidin-1-yl}-4-oxo-butyl)-3H-pyrrolo[2,1-f][1,2,4]triazin-4-one ("C177")

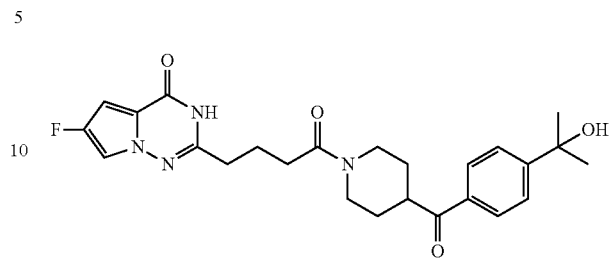

Yield: 166 mg (42%) colorless solid;
¹H NMR (400 MHz, DMSO-d₆) δ 11.80 (s, 1H), 7.93 (d, J=8.5 Hz, 2H), 7.64-7.58 (m, 3H), 6.69 (s, 1H), 5.18 (s, 1H), 4.38 (d, J=13.1 Hz, 1H), 3.89 (d, J=13.8 Hz, 1H), 3.72-3.64 (m, 1H), 3.16 (t, J=12.4 Hz, 1H), 2.73 (t, J=10.8 Hz, 1H), 2.54-2.52 (m, 2H), 2.42-2.37 (m, 2H), 1.93-1.85 (m, 2H), 1.82-1.73 (m, 2H), 1.54-1.47 (m, 1H), 1.43 (s, 6H), 1.34-1.27 (m, 1H); LC/MS (B), Rt: 3.65 min; (M+H) 469.0.

2-{4-[4-(1-Methyl-1H-pyrazole-4-carbonyl)-piperidin-1-yl]-4-oxo-butyl}-3H-pyrrolo[2,1-f][1,2,4]triazin-4-one ("C146")

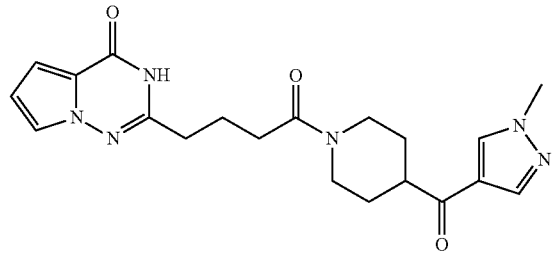 [SMILES: Cn1cc(C(=O)C2CCN(C(=O)CCCc3nn4cccc4c(=O)[nH]3)CC2)cn1]

Yield: 55 mg (54%) colorless solid;
¹H NMR (400 MHz, DMSO-d₆) δ 11.56 (s, 1H), 8.44 (s, 1H), 7.96 (s, 1H), 7.53-7.51 (m, 1H), 6.82 (d, J=4.3 Hz, 1H), 6.48 (d, J=4.3 Hz, 1H), 4.39 (d, J=12.8 Hz, 1H), 3.91-3.82 (m, 4H), 3.23-3.21 (m, 1H), 3.19-3.14 (m, 1H), 3.12-3.03 (m, 1H), 2.66-2.53 (m, 1H), 2.52-2.49 (m, 1H), 2.48-2.32 (m, 2H), 1.93-1.88 (m, 2H), 1.78-1.71 (m, 2H), 1.51-1.47 (m, 1H), 1.35-1.22 (m, 1H); LC/MS (B), Rt: 2.70 min; (M+H) 397.0.

6-Methyl-2-{4-[4-(1-methyl-1H-pyrazole-4-carbonyl)-piperidin-1-yl]-4-oxo-butyl}-3H-pyrrolo[2,1-f][1,2,4]triazin-4-one ("C168")

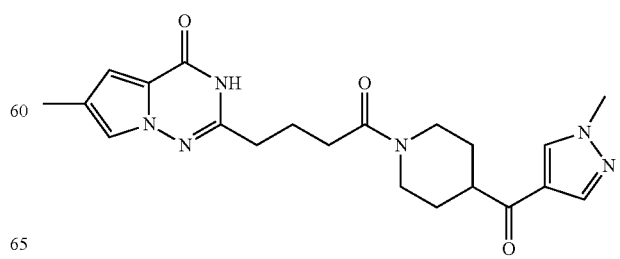

Yield: 85 mg (49%) pale brown solid;
¹H NMR (400 MHz, DMSO-d₆) δ 11.48 (s, 1H), 8.43 (s, 1H), 7.96 (s, 1H), 7.33-7.30 (m, 1H), 6.62 (d, J=1.2 Hz, 1H), 4.39 (d, J=13.2 Hz, 1H), 3.92-3.82 (m, 4H), 3.25-3.22 (m, 1H), 3.21-3.06 (m, 1H), 2.68-2.65 (m, 1H), 2.62-2.51 (m, 2H), 2.40-2.35 (m, 2H), 2.13 (s, 3H), 1.92-1.82 (m, 2H), 1.78-1.69 (m, 2H), 1.55-1.40 (m, 1H), 1.38-1.22 (m, 1H); LC/MS (B), Rt: 2.93 min; (M+H) 411.2.

6-Fluoro-2-{4-[4-(1-methyl-1H-pyrazole-4-carbonyl)-piperidin-1-yl]-4-oxo-butyl}-3H-pyrrolo[2,1-f][1,2,4]triazin-4-one ("C179")

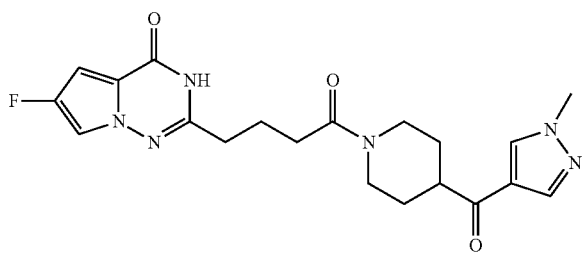 [SMILES: Cn1cc(C(=O)C2CCN(C(=O)CCCc3nn4cc(F)cc4c(=O)[nH]3)CC2)cn1]

Yield: 190 mg (53%) colorless solid;
¹H NMR (400 MHz, DMSO-d₆) δ 11.50 (s, 1H), 8.43 (s, 1H), 7.96 (s, 1H), 7.64 (s, 1H), 6.69 (s, 1H), 4.38 (d, J=12.9 Hz, 1H), 3.92-3.87 (m, 4H), 3.32-3.23 (m, 1H), 3.22-3.06 (m, 1H), 2.70-2.60 (m, 1H), 2.55-2.49 (m, 2H), 2.39-2.35 (m, 2H), 1.92-1.85 (m, 2H), 1.80-1.70 (m, 2H), 1.55-1.44 (m, 1H), 1.39-1.25 (m, 1H); LC/MS (B), Rt: 2.98 min; (M+H) 415.0.

6-Amino-1'-[4-(6-fluoro-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile ("C171")

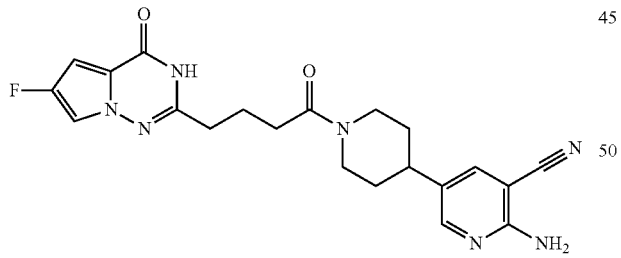

Yield: 190 mg (53%) colorless solid;
¹H NMR (400 MHz, DMSO-d₆) δ 11.75 (brs, 1H), 8.12 (d, J=2.0 Hz, 1H), 7.76 (d, J=4.0 Hz, 1H), 7.62-7.58 (m, 1H), 6.69 (s, 2H), 6.64 (s, 1H), 4.49 (d, J=11.3 Hz, 1H), 3.94 (d, J=14.5 Hz, 1H), 3.02 (t, J=12.3 Hz, 1H), 2.61-2.56 (m, 4H), 2.44-2.38 (m, 2H), 1.94-1.86 (m, 2H), 1.76-1.67 (m, 2H), 1.57-1.47 (m, 1H), 1.45-1.30 (m, 1H); LC/MS (B), Rt: 2.66 min; (M+H) 424.2.

2-{4-[4-(4-Methoxy-benzoyl)-piperidin-1-yl]-4-oxo-butyl}-3,5,7,8-tetrahydro-pyrano[4,3-d]pyrimidin-4-one ("C52")

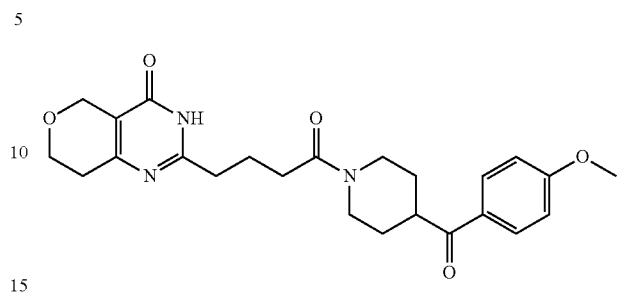

Yield: 30 mg (32%) off-white solid;
¹H NMR (400 MHz, DMSO-d₆) δ 12.31 (s, 1H), 7.98 (d, J=7.0 Hz, 2H), 7.05 (d, J=6.9 Hz, 2H), 4.39 (d, J=13.1 Hz, 1H), 4.33 (s, 2H), 3.90 (d, J=11.4 Hz, 1H), 3.85-3.81 (m, 5H), 3.68-3.62 (m, 1H), 3.17-3.13 (m, 2H), 2.76-2.70 (m, 1H), 2.55-2.51 (m, 3H), 2.38-2.31 (m, 2H), 1.91-1.84 (m, 2H), 1.82-1.72 (m, 2H), 1.55-1.43 (m, 1H), 1.39-1.28 (m, 1H); LC/MS (B), Rt: 2.94 min; (M+H) 440.2.

2-{4-[4-(3-Fluoro-4-methoxy-benzoyl)-piperidin-1-yl]-4-oxo-butyl}-3,5,7,8-tetrahydro-pyrano[4,3-d]pyrimidin-4-one ("C192")

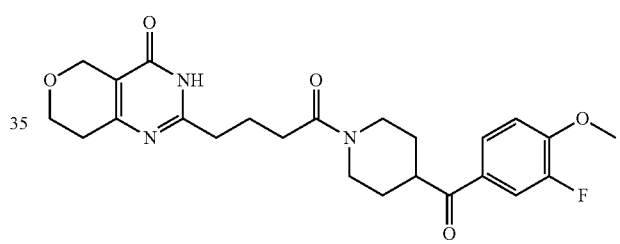

Yield: 85 mg (71%) pale yellow solid;
¹H NMR (400 MHz, DMSO-d₆) δ 12.31 (s, 1H), 7.88 (dd, J=1.2, 8.6 Hz, 1H), 7.82 (dd, J=2.1, 12.3 Hz, 1H), 7.30 (t, J=8.6 Hz, 1H), 4.38 (d, J=12.1 Hz, 1H), 4.33 (s, 2H), 3.94-3.88 (m, 4H), 3.82 (t, J=5.6 Hz, 2H), 3.69-3.62 (m, 1H), 3.29-3.20 (m, 1H), 2.76-2.66 (m, 1H), 2.54-2.51 (m, 4H), 2.39-2.31 (m, 2H), 1.88-1.82 (m, 2H), 1.79-1.71 (m, 2H), 1.51-1.41 (m, 1H), 1.36-1.28 (m, 1H); LC/MS (B), Rt: 3.04 min; (M+H) 458.3.

2-{4-[4-(6-Methoxy-pyridine-3-carbonyl)-piperidin-1-yl]-4-oxo-butyl}-3,5,7,8-tetrahydro-pyrano[4,3-d]pyrimidin-4-one ("C193")

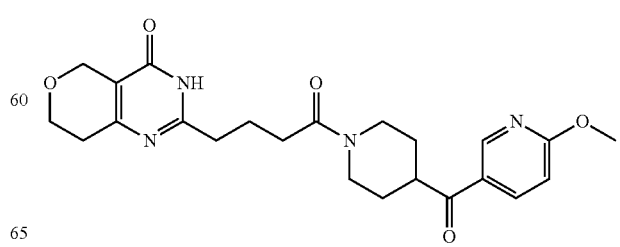

Yield: 10 mg (11%) off-white solid;

$^1$H NMR (400 MHz, DMSO-$d_6$) δ 12.31 (s, 1H), 8.90 (s, 1H), 8.90 (d, J=2.1 Hz, 1H), 8.22 (dd, J=2.5, 8.8 Hz, 1H), 6.94 (dd, J=0.4, 8.8 Hz, 1H), 4.39 (d, J=13.0 Hz, 1H), 4.33 (s, 2H), 3.96-3.87 (m, 4H), 3.82 (t, J=5.6 Hz, 2H), 3.70-3.62 (m, 1H), 3.21-3.11 (m, 1H), 2.77-2.68 (m, 1H), 2.54-2.51 (m, 4H), 2.40-2.32 (m, 2H), 1.91-1.84 (m, 2H), 1.82-1.74 (m, 2H), 1.54-1.44 (m, 1H), 1.39-1.27 (m, 1H); LC/MS (B), Rt: 2.60 min; (M+H) 441.2.

6-Amino-1'-[4-(4-oxo-3,5,7,8-tetrahydro-4H-pyrano[4,3-d]pyrimidin-2-yl)-butyryl]-1',2',3',4',5',6'-hexahydro-[3,4']bipyridinyl-5-carbonitrile ("C194")

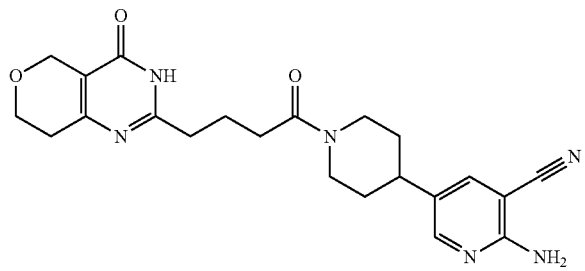 [SMILES: N#Cc1cc(C2CCN(C(=O)CCCc3nc4c(c(=O)[nH]3)COCC4)CC2)cnc1N]

Yield: 35 mg (39%) off-white solid;

$^1$H NMR (400 MHz, DMSO-$d_6$) δ 12.32 (s, 1H), 8.12 (d, J=2.4 Hz, 1H), 7.76 (d, J=2.4 Hz, 1H), 6.70 (s, 2H), 4.50 (d, J=12.8 Hz, 1H), 4.33 (s, 2H), 3.95 (d, J=13.8 Hz, 1H), 3.82 (t, J=5.6 Hz, 2H), 3.03 (t, J=12.8 Hz, 1H), 2.69-2.62 (m, 1H), 2.58-2.52 (m, 5H), 2.36 (t, J=7.4 Hz, 2H), 1.92-1.84 (m, 2H), 1.76-1.67 (m, 2H), 1.58-1.45 (m, 1H), 1.44-1.32 (m, 1H); LC/MS (B), Rt: 3.39 min; (M+H) 423.0.

2-[4-(6-Amino-5-pyrimidin-2-yl-3',4',5',6'-tetrahydro-2'H-[3,4']bipyridinyl-1'-yl)-4-oxo-butyl]-3,5,7,8-tetrahydro-pyrano[4,3-d]pyrimidin-4-one ("C195")

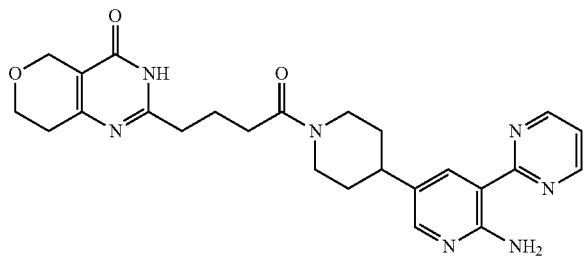 [SMILES: Nc1ncc(C2CCN(C(=O)CCCc3nc4c(c(=O)[nH]3)COCC4)CC2)cc1-c1ncccn1]

Yield: 35 mg (34%) pale yellow solid;

$^1$H NMR (400 MHz, DMSO-$d_6$) δ 12.33 (s, 1H), 8.90 (d, J=4.9 Hz, 2H), 8.50 (d, J=2.4 Hz, 1H), 8.04 (d, J=2.4 Hz, 1H), 7.60 (brs, 2H), 7.40 (t, J=4.9 Hz, 1H), 4.54 (d, J=13.6 Hz, 1H), 4.33 (s, 2H), 3.98 (d, J=13.6 Hz, 1H), 3.81 (t, J=5.6 Hz, 2H), 3.08 (t, J=12.4 Hz, 1H), 2.78-2.70 (m, 1H), 2.63-2.51 (m, 5H), 2.42-2.36 (m, 2H), 1.94-1.87 (m, 2H), 1.85-1.76 (m, 2H), 1.60-1.51 (m, 1H), 1.48-1.36 (m, 1H); LC/MS (B), Rt: 2.13 min; (M+H) 476.0.

2-{4-Oxo-4-[4-(5-phenyl-[1,3,4]oxadiazol-2-yl)-piperidin-1-yl]-butyl}-3,5,7,8-tetrahydro-pyrano[4,3-d]pyrimidin-4-one ("C196")

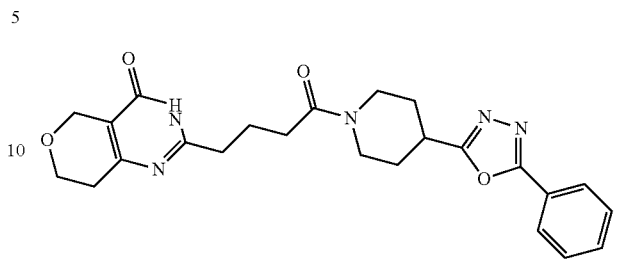

Yield: 50 mg (53%) off-white solid;

$^1$H NMR (400 MHz, DMSO-$d_6$) δ 12.32 (s, 1H), 8.02-7.97 (m, 2H), 7.63-7.55 (m, 3H), 4.35-4.27 (m, 3H), 3.95-3.86 (m, 1H), 3.81 (t, J=5.6 Hz, 2H), 3.37-3.34 (m, 1H), 3.28-3.18 (m, 1H), 2.87 (t, J=10.7 Hz, 1H), 2.54-2.51 (m, 4H), 2.41-2.36 (m, 2H), 2.14-2.04 (m, 2H), 1.93-1.84 (m, 2H), 1.80-1.72 (m, 1H), 1.68-1.58 (m, 1H); LC/MS (B), Rt: 2.77 min; (M+H) 450.2.

4-{1-[4-(4-Oxo-3,5,7,8-tetrahydro-4H-pyrano[4,3-d]pyrimidin-2-yl)-butyryl]-piperidin-4-yloxy}-benzonitrile ("C197")

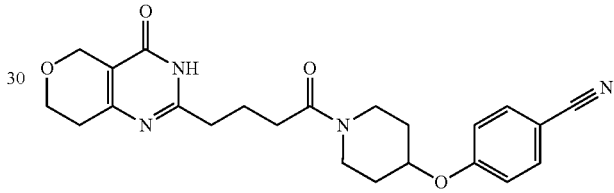

Yield: 75 mg (42%) brown solid;

$^1$H NMR (400 MHz, DMSO-$d_6$) δ 12.32 (s, 1H), 7.76 (d, J=8.9 Hz, 2H), 7.15 (d, J=8.9 Hz, 2H), 4.79-4.73 (m, 1H), 4.33 (s, 2H), 3.92-3.86 (m, 1H), 3.82 (t, J=5.6 Hz, 2H), 3.73-3.67 (m, 1H), 3.29-3.27 (m, 1H), 3.24-3.17 (m, 1H), 2.54-2.51 (m, 4H), 2.37 (t, J=7.3 Hz, 2H), 2.02-1.82 (m, 4H), 1.64-1.56 (m, 1H), 1.54-1.46 (m, 1H); LC/MS (B), Rt: 2.98 min; (M+H) 423.3.

2-{4-[4-(4-Fluoro-benzoyl)-piperidin-1-yl]-4-oxo-butyl}-3,5,7,8-tetrahydro-pyrano[4,3-d]pyrimidin-4-one ("C198")

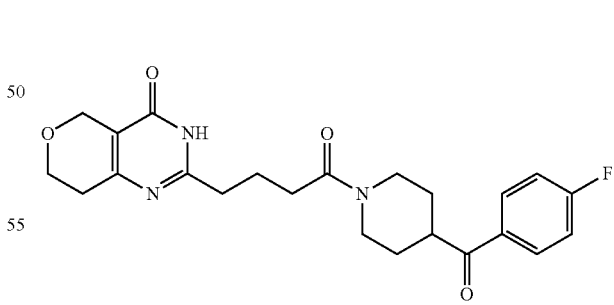

Yield: 89 mg (54%) colorless solid;

$^1$H NMR (400 MHz, DMSO-$d_6$) δ 12.31 (s, 1H), 8.12-8.06 (m, 2H), 7.36 (t, J=8.8 Hz, 2H), 4.39 (d, J=13.6 Hz, 1H), 4.33 (s, 2H), 3.90 (d, J=13.6 Hz, 1H), 3.82 (t, J=5.6 Hz, 2H), 3.74-3.65 (m, 1H), 3.20-3.11 (m, 1H), 2.76-2.68 (m, 1H), 2.54-2.51 (m, 4H), 2.38-2.33 (m, 2H), 1.90-1.74 (m, 4H), 1.54-1.42 (m, 1H), 1.38-1.26 (m, 1H); LC/MS (B), Rt: 3.08 min; (M+H) 428.0.

2-{4-[4-(4-Methoxy-3-methyl-benzoyl)-piperidin-1-yl]-4-oxo-butyl}-3,5,7,8-tetrahydro-pyrano[4,3-d]pyrimidin-4-one ("C199")

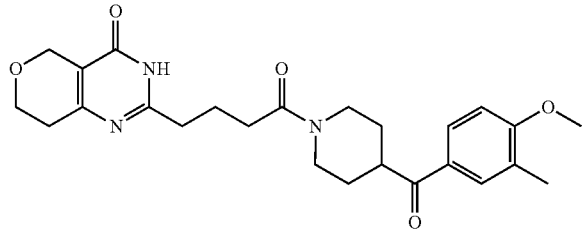 [SMILES: COc1ccc(C(=O)C2CCN(C(=O)CCCc3nc4c(c(=O)[nH]3)COCC4)CC2)cc1C]

Yield: 100 mg (52%) brown solid;
$^1$H NMR (400 MHz, DMSO-d$_6$) δ 12.31 (s, 1H), 7.89 (dd, J=2.4, 8.6 Hz, 1H), 7.80 (s, 1H), 7.05 (d, J=8.7 Hz, 1H), 4.40 (d, J=12.8 Hz, 1H), 4.33 (s, 2H), 3.93-3.86 (m, 4H), 3.82 (t, J=5.6 Hz, 2H), 3.69-3.61 (m, 1H), 3.19-3.12 (m, 1H), 2.76-2.68 (m, 1H), 2.55-2.51 (m, 4H), 2.39-2.31 (m, 2H), 2.19 (s, 3H), 1.90-1.83 (m, 2H), 1.79-1.72 (m, 2H), 1.54-1.42 (m, 1H), 1.38-1.28 (m, 1H); LC/MS (B), Rt: 3.31 min; (M+H) 454.2.

2-(4-{4-[4-(1-Hydroxy-1-methyl-ethyl)-benzoyl]-piperidin-1-yl}-4-oxo-butyl)-3,5,7,8-tetrahydro-pyrano[4,3-d]pyrimidin-4-one ("C200")

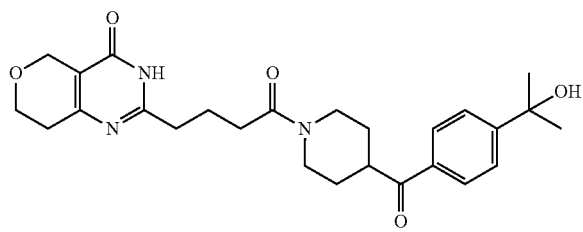 [SMILES: CC(C)(O)c1ccc(C(=O)C2CCN(C(=O)CCCc3nc4c(c(=O)[nH]3)COCC4)CC2)cc1]

Yield: 110 mg (63%) colorless solid;
$^1$H NMR (400 MHz, DMSO-d$_6$) δ 12.31 (s, 1H), 7.93 (d, J=8.5 Hz, 2H), 7.61 (d, J=8.5 Hz, 2H), 5.19 (s, 1H), 4.39 (d, J=12.9 Hz, 1H), 4.33 (s, 2H), 3.90 (d, J=13.4 Hz, 1H), 3.82 (t, J=5.6 Hz, 2H), 3.72-3.64 (m, 1H), 3.17 (t, J=12.1 Hz, 1H), 2.74 (t, J=12.3 Hz, 1H), 2.55-2.51 (m, 4H), 2.39-2.33 (m, 2H), 1.90-1.84 (m, 2H), 1.82-1.76 (m, 2H), 1.54-1.45 (m, 1H), 1.43 (s, 6H), 1.36-1.27 (m, 1H); LC/MS (B), Rt: 2.62 min; (M+H) 468.2.

2-{4-[4-(1-Methyl-1H-pyrazole-4-carbonyl)-piperidin-1-yl]-4-oxo-butyl}-3,5,7,8-tetrahydro-pyrano[4,3-d]pyrimidin-4-one ("C202")

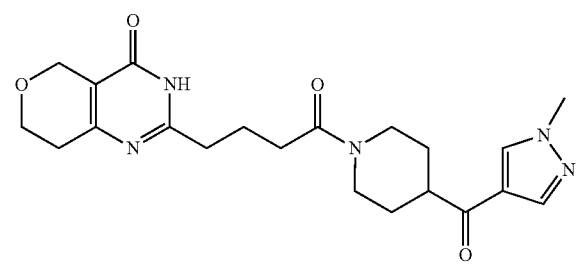 [SMILES: Cn1cc(C(=O)C2CCN(C(=O)CCCc3nc4c(c(=O)[nH]3)COCC4)CC2)cn1]

Yield: 90 mg (59%) off-white solid;
$^1$H NMR (400 MHz, DMSO-d$_6$) δ 12.31 (s, 1H), 8.44 (s, 1H), 7.96 (s, 1H), 4.39 (d, J=13.0 Hz, 1H), 4.33 (s, 2H), 3.92-3.87 (m, 4H), 3.86-3.80 (m, 2H), 3.23-3.19 (m, 1H), 3.14-3.06 (m, 1H), 2.66-2.63 (m, 1H), 2.54-2.51 (m, 4H), 2.37-2.33 (m, 2H), 1.87-1.82 (m, 2H), 1.78-1.71 (m, 2H) 1.53-1.45 (m, 1H), 1.35-1.26 (m, 1H); LC/MS (B), Rt: 1.93 min; (M+H) 414.2.

2-{4-[4-(6-Methoxy-pyridine-3-carbonyl)-piperidin-1-yl]-4-oxo-butyl}-7-methyl-3H-pyrrolo[2,1-f][1,2,4]triazin-4-one ("C148")

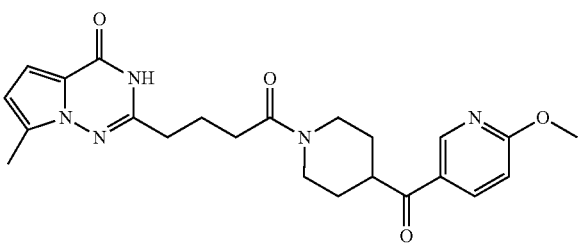 [SMILES: COc1ccc(C(=O)C2CCN(C(=O)CCCc3nn4c(C)ccc4c(=O)[nH]3)CC2)cn1]

Yield: 10 mg (10%) pale yellow solid;
$^1$H NMR (400 MHz, DMSO-d$_6$) δ 11.46 (s, 1H), 8.90 (d, J=2.2 Hz, 1H), 8.22 (dd, J=2.4, 8.7 Hz, 1H), 6.94 (d, J=8.7 Hz, 1H), 6.75 (d, J=4.2 Hz, 1H), 6.30 (d, J=4.1 Hz, 1H), 4.39 (d, J=13.1 Hz, 1H), 3.94 (s, 3H), 3.93-3.89 (m, 1H), 3.64 (t, J=11.3 Hz, 1H), 3.16 (t, J=12.6 Hz, 1H), 2.72 (t, J=11.8 Hz, 1H), 2.58-2.51 (m, 2H), 2.49-2.39 (m, 2H), 2.36 (s, 3H), 1.98-1.82 (m, 2H), 1.80-1.71 (m, 2H), 1.58-1.42 (m, 1H), 1.40-1.26 (m, 1H); LC/MS (D), Rt: 3.67 min; (M+H) 438.3.

6-Amino-1'-[4-(7-methyl-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile ("C149")

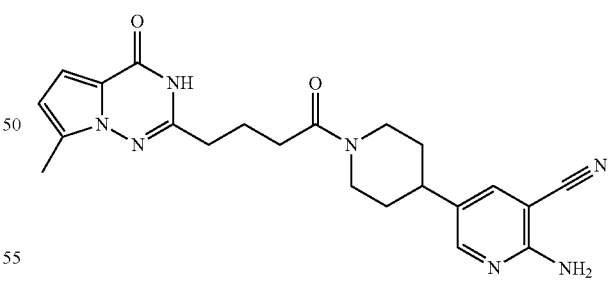

Yield: 30 mg (35%) colorless solid;
$^1$H NMR (400 MHz, DMSO-d$_6$) δ 11.50 (s, 1H), 8.11 (d, J=2.4 Hz, 1H), 7.75 (d, J=2.4 Hz, 1H), 6.76 (d, J=4.2 Hz, 1H), 6.70 (s, 2H), 6.30 (dd, J=0.7, 4.3 Hz, 1H), 4.50 (d, J=12.5 Hz, 1H), 3.95 (d, J=13.5 Hz, 1H), 3.03 (t, J=13.0 Hz, 1H), 2.69-2.59 (m, 1H), 2.57-2.47 (m, 3H), 2.45-2.37 (m, 2H), 2.35 (s, 3H), 1.99-1.79 (m, 2H), 1.75-1.63 (t, J=12.2 Hz, 2H), 1.59-1.43 (m, 1H), 1.42-1.31 (m, 1H); LC/MS (B), Rt: 2.72 min; (M+H) 420.2.

2-[4-(6-Amino-5-pyrimidin-2-yl-3',4',5',6'-tetra-hydro-2'H-[3,4']bipyridinyl-1'-yl)-4-oxo-butyl]-7-methyl-3H-pyrrolo[2,1-f][1,2,4]triazin-4-one ("C150")

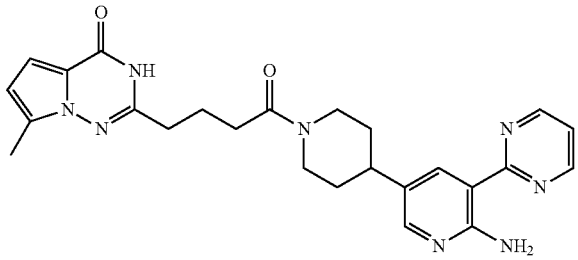 [SMILES: Cc1ccc2c(=O)[nH]c(CCCC(=O)N3CCC(c4cnc(N)c(-c5ncccn5)c4)CC3)nn12]

Yield: 16 mg (16%) colorless solid;
¹H NMR (400 MHz, DMSO-d₆) δ 11.47 (s, 1H), 8.90 (d, J=4.9 Hz, 1H), 8.50 (d, J=2.4 Hz, 1H), 8.04 (d, J=2.4 Hz, 1H), 7.61 (brs, 2H), 7.39 (t, J=4.9 Hz, 1H), 6.76 (d, J=4.2 Hz, 1H), 6.30 (dd, J=0.6, 4.2 Hz, 1H), 4.53 (d, J=13.1 Hz, 1H), 3.98 (d, J=14.2 Hz, 1H), 3.12-3.04 (m 1H), 2.79-2.69 (m, 1H), 2.60-2.52 (m, 3H), 2.50-2.39 (m, 2H), 2.36 (s, 3H), 2.01-1.90 (m, 2H), 1.898-1.73 (m, 2H), 1.60-1.54 (m, 2H), 1.48-1.33 (m, 1H); LC/MS (B), Rt: 2.91 min; (M+H) 473.2.

7-Methyl-2-{4-[4-(1-methyl-1H-pyrazole-4-carbonyl)-piperidin-1-yl]-4-oxo-butyl}-3H-pyrrolo[2,1-f][1,2,4]triazin-4-one ("C157")

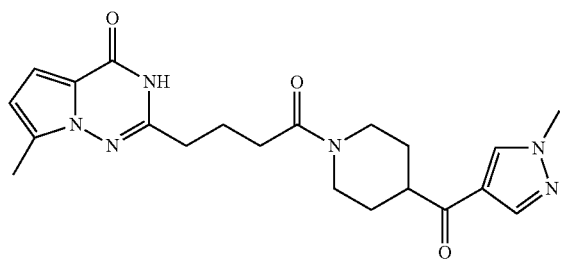

Yield: 30 mg (37%) colorless solid;
¹H NMR (400 MHz, DMSO-d₆) δ 11.46 (s, 1H), 8.44 (s, 1H), 7.96 (s, 1H), 6.76 (d, J=4.2 Hz, 1H), 6.30 (d, J=4.1 Hz, 1H), 4.38 (d, J=12.8 Hz, 1H), 3.92-3.87 (m, 4H), 3.24-3.16 (m, 1H), 3.09 (t, J=12.8 Hz, 1H), 2.69-2.61 (m, 1H), 2.54-2.51 (m, 2H), 2.46-2.42 (m, 2H), 2.36 (s, 3H), 1.95-1.89 (m, 2H), 1.78-1.71 (m, 2H), 1.52-1.43 (m, 1H), 1.36-1.22 (m, 1H); LC/MS (B), Rt: 2.94 min; (M+H) 411.2.

3-{4-[4-(1-Isopropyl-1H-pyrazole-4-carbonyl)-piperidin-1-yl]-4-oxo-butyl}-2H-pyrrolo[1,2-a]pyrazin-1-one ("C210")

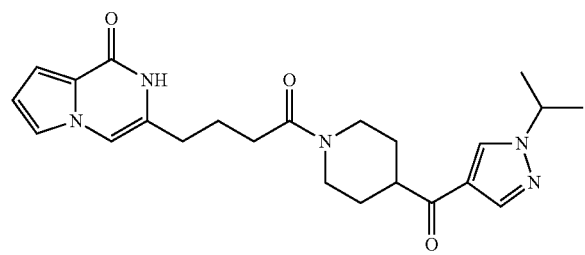

Yield: 23 mg (31%) colorless solid;
¹H NMR (400 MHz, DMSO-d₆) δ 10.43 (s, 1H), 8.49 (s, 1H), 7.98 (s, 1H), 7.35 (dd, J=2.5, 1.6 Hz, 1H), 7.13 (s, 1H), 6.85-6.78 (m, 1H), 6.48 (dd, J=3.9, 2.5 Hz, 1H), 4.55 (hept, J=6.7 Hz, 1H), 4.47-4.36 (m, 1H), 3.94-3.82 (m, 1H), 3.32-3.22 (m, 1H), 3.18-3.07 (m, 1H), 2.75-2.62 (m, 1H), 2.42-2.31 (m, 4H), 1.88-1.72 (m, 4H), 1.56-1.28 (m, 8H); LC/MS (A), Rt: 1.69 min; (M+H) 424.3.

3-{4-[4-(1-Isopropyl-1H-pyrazole-4-carbonyl)-piperidin-1-yl]-4-oxo-butyl}-6-methyl-2H-pyrrolo[1,2-a]pyrazin-1-one ("C211")

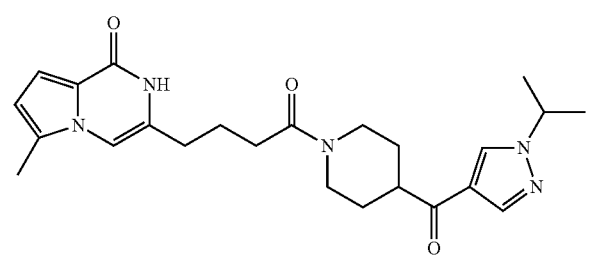 [SMILES: Cc1ccc2c(=O)[nH]c(CCCC(=O)N3CCC(C(=O)c4cnn(C(C)C)c4)CC3)cn12]

Yield: 40 mg (53%) colorless solid;
¹H NMR (400 MHz, DMSO-d₆) δ 10.38 (s, 1H), 8.50 (s, 1H), 7.98 (s, 1H), 6.91 (s, 1H), 6.76 (d, J=3.8 Hz, 1H), 6.30-6.27 (m, 1H), 4.55 (hept, J=6.7 Hz, 1H), 4.46-4.37 (m, 1H), 3.95-3.85 (m, 1H), 3.32-3.22 (m, 1H), 3.18-3.06 (m, 1H), 2.74-2.64 (m, 1H), 2.43-2.32 (m, 7H), 1.89-1.74 (m, 4H), 1.57-1.29 (m, 8H); LC/MS (A), Rt: 1.77 min; (M+H) 438.3.

3-{4-[4-(6-Methoxy-pyridine-3-carbonyl)-piperidin-1-yl]-4-oxo-butyl}-2H-pyrrolo[1,2-a]pyrazin-1-one ("C15")

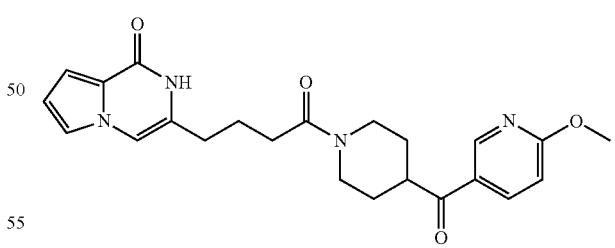

Yield: 41 mg (61%) colorless solid;
¹H NMR (400 MHz, DMSO-d₆) δ 10.41 (s, 1H), 8.90 (d, J=1.9 Hz, 1H), 8.22 (dd, J=8.7, 2.2 Hz, 1H), 7.34 (s, 1H), 7.11 (s, 1H), 6.94 (d, J=8.8 Hz, 1H), 6.79 (d, J=3.5 Hz, 1H), 6.56-6.38 (m, 1H), 4.49-4.29 (m, 1H), 3.95 (s, 3H), 3.92-3.80 (m, 1H), 3.73-3.57 (m, 1H), 3.24-3.07 (m, 1H), 2.82-2.66 (m, 1H), 2.44-2.23 (m, 4H), 1.92-1.71 (m, 4H), 1.58-1.42 (m, 1H), 1.42-1.25 (m, 1H); LC/MS (A), Rt: 1.81 min; (M+H) 423.2.

3-{4-[4-(6-Methoxy-pyridine-3-carbonyl)-piperidin-1-yl]-4-oxo-butyl}-6-methyl-2H-pyrrolo[1,2-a]pyrazin-1-one ("C57")

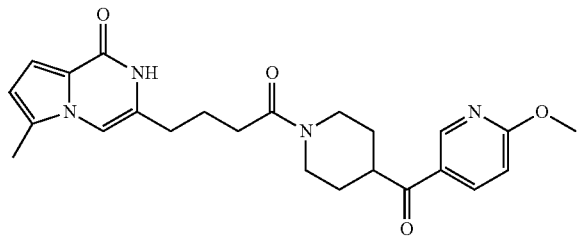

Yield: 43 mg (64%) colorless solid;
$^1$H NMR (400 MHz, DMSO-$d_6$) δ 10.36 (s, 1H), 8.90 (d, J=2.2 Hz, 1H), 8.22 (dd, J=8.7, 2.4 Hz, 1H), 6.94 (d, J=8.8 Hz, 1H), 6.90 (s, 1H), 6.74 (d, J=3.8 Hz, 1H), 6.27 (d, J=3.7 Hz, 1H), 4.48-4.33 (m, 1H), 3.95 (s, 3H), 3.93-3.81 (m, 1H), 3.72-3.58 (m, 1H), 3.24-3.10 (m, 1H), 2.82-2.68 (m, 1H), 2.45-2.28 (m, 7H), 1.88-1.73 (m, 4H), 1.58-1.43 (m, 1H), 1.43-1.28 (m, 1H); LC/MS (A), Rt: 1.89 min; (M+H) 437.2.

6-Fluoro-3-{4-[4-(1-isopropyl-1H-pyrazole-4-carbonyl)-piperidin-1-yl]-4-oxo-butyl}-2H-pyrrolo[1,2-a]pyrazin-1-one ("C212")

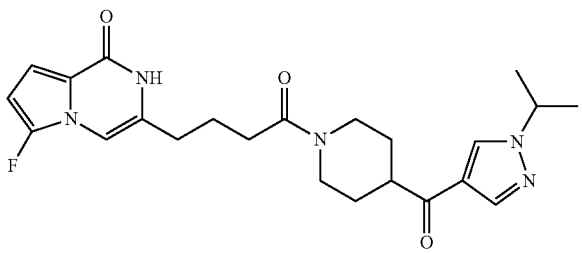

Yield: 16 mg (25%) yellow solid;
$^1$H NMR (400 MHz, DMSO-$d_6$) δ 10.49 (s, 1H), 8.49 (s, 1H), 7.96 (s, 1H), 6.93 (s, 1H), 6.75 (t, J=4.8 Hz, 1H), 6.15 (t, J=4.1 Hz, 1H), 4.55 (hept, J=6.7 Hz, 1H), 4.45-4.33 (m, 1H), 3.97-3.82 (m, 1H), 3.33-3.18 (m, 1H), 3.18-3.04 (m, 1H), 2.76-2.60 (m, 1H), 2.43-2.28 (m, 4H), 1.90-1.71 (m, 4H), 1.61-1.27 (m, 8H); LC/MS (A), Rt: 1.79 min; (M+H) 442.2.

6-{4-[4-(6-Methoxy-pyridine-3-carbonyl)-piperidin-1-yl]-4-oxo-butyl}-3-methyl-7H-imidazo[1,5-a]pyrazin-8-one ("C99")

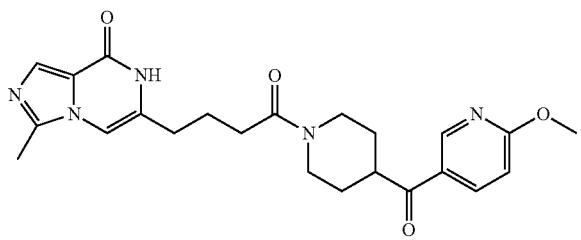 [SMILES: COc1ccc(C(=O)C2CCN(C(=O)CCCc3cn4c(C)ncc4c(=O)[nH]3)CC2)cn1]

Yield: 42 mg (53%) colorless solid;
$^1$H NMR (400 MHz, DMSO-$d_6$) δ 10.56 (s, 1H), 8.90 (d, J=2.2 Hz, 1H), 8.22 (dd, J=8.7, 2.4 Hz, 1H), 7.57 (s, 1H), 7.04 (s, 1H), 6.94 (d, J=8.7 Hz, 1H), 4.46-4.34 (m, 1H), 3.95 (s, 3H), 3.93-3.85 (m, 1H), 3.71-3.60 (m, 1H), 3.21-3.05 (m, 1H), 2.79-2.66 (m, 1H), 2.48 (s, 3H), 2.42-2.28 (m, 4H), 1.89-1.71 (m, 4H), 1.61-1.42 (m, 1H), 1.42-1.18 (m, 1H); LC/MS (A), Rt: 1.40 min; (M+H) 438.2.

7-Methyl-3-{4-[4-(1-methyl-1H-pyrazole-4-carbonyl)-piperidin-1-yl]-4-oxo-butyl}-2H-pyrrolo[1,2-a]pyrazin-1-one ("C212")

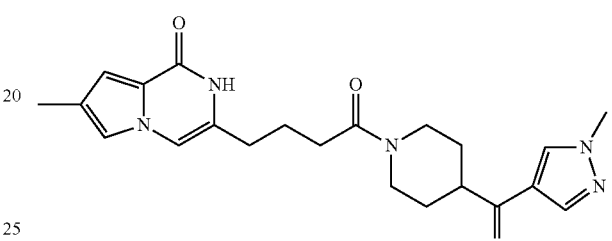

Yield: 13 mg (28%) off-white solid;
$^1$H NMR (500 MHz, DMSO-$d_6$) δ 10.34 (s, 1H), 8.43 (s, 1H), 7.95 (s, 1H), 7.14-7.10 (m, 1H), 7.01 (s, 1H), 6.62-6.58 (m, 1H), 4.40 (d, J=13.0 Hz, 1H), 3.92-3.83 (m, 4H), 3.22 (tt, J=11.3, 3.7 Hz, 1H), 3.14-3.06 (m, 1H), 2.71-2.63 (m, 1H), 2.37-2.29 (m, 4H), 2.13 (s, 3H), 1.83-1.72 (m, 4H), 1.53-1.42 (m, 1H), 1.39-1.29 (m, 1H); LC/MS (A), Rt: 1.61 min; (M+H) 410.2.

2-{4-[4-(3-Fluoro-4-methoxy-benzoyl)-piperidin-1-yl]-4-oxo-butyl}-7-methyl-3H-thieno[3,4-d]pyrimidin-4-one ("C113")

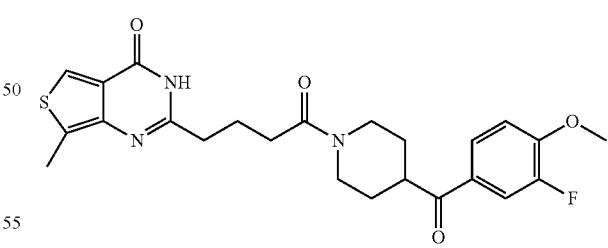

Yield: 40 mg (28%) colorless solid;
$^1$H NMR (400 MHz, DMSO-$d_6$) δ 11.47 (s, 1H), 8.13 (s, 1H), 7.87 (d, J=10.4 Hz, 1H), 7.81 (dd, J=2.3, 12.4 Hz, 1H), 7.28 (t, J=8.6 Hz, 1H), 4.45-4.37 (m, 1H), 3.92 (s, 3H), 3.95-3.85 (m, 1H), 3.69-3.62 (m, 1H), 3.21-3.12 (m, 1H), 2.79-2.70 (m, 1H), 2.54 (s, 3H), 2.58-2.48 (m, 2H), 2.41-2.35 (m, 2H), 1.99-1.86 (m, 2H), 1.80-1.70 (m, 2H), 1.52-1.40 (m, 1H), 1.34-1.24 (m, 1H); LC/MS (B), Rt: 3.60 min; (M+H) 472.0.

2-(4-{4-[4-(1-Hydroxy-1-methyl-ethyl)-benzoyl]-piperidin-1-yl}-4-oxo-butyl)-7-methyl-3H-thieno[3,4-d]pyrimidin-4-one ("C121")

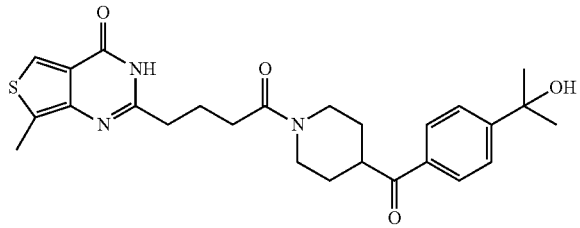 [SMILES: Cc1scc2c(=O)[nH]c(CCCC(=O)N3CCC(C(=O)c4ccc(C(C)(C)O)cc4)CC3)nc12]

Yield: 33 mg (38%) colorless solid;
¹H NMR (400 MHz, DMSO-d₆) δ 11.47 (s, 1H), 8.13 (s, 1H), 7.92 (d, J=8.4 Hz, 2H), 7.60 (d, J=8.4 Hz, 2H), 5.18 (s, 1H), 4.38 (d, J=12.8 Hz, 1H), 3.92-3.83 (m, 1H), 3.75-3.61 (m, 1H), 3.23-3.12 (m, 1H), 2.79-2.69 (m, 1H), 2.54 (s, 3H), 2.52-2.45 (m, 2H), 2.43-2.35 (m, 2H), 1.99-1.90 (m, 2H), 1.81-1.71 (m, 2H), 1.61-1.49 (m, 1H), 1.41 (s, 6H), 1.40-1.35 (m, 1H); LC/MS (B), Rt: 3.16 min; (M+H) 482.0.

2-{4-[4-(4-Methoxy-benzoyl)-piperidin-1-yl]-4-oxo-butyl}-7-methyl-3H-thieno[3,4-d]pyrimidin-4-one ("C34")

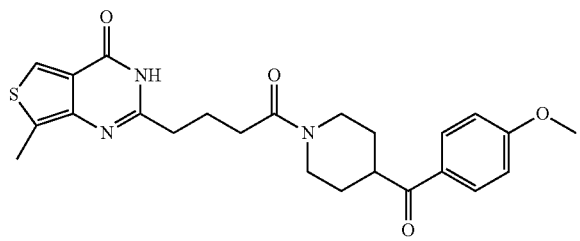 [SMILES: COc1ccc(C(=O)C2CCN(C(=O)CCCc3nc4c(C)scc4c(=O)[nH]3)CC2)cc1]

Yield: 25 mg (36%) off-white solid;
¹H NMR (400 MHz, DMSO-d₆) δ 11.52 (s, 1H), 8.14 (s, 1H), 7.97 (d, J=9.0 Hz, 2H), 7.04 (d, J=9.0 Hz, 2H), 4.42-4.32 (m, 1H), 3.93-3.89 (m, 1H), 3.83 (s, 3H), 3.66-3.60 (m, 1H), 3.23-3.13 (m, 1H), 2.76-2.69 (m, 1H), 2.57 (s, 3H), 2.56-2.50 (m, 2H), 2.43-2.38 (m, 2H), 1.99-1.89 (m, 2H), 1.81-1.69 (m, 2H), 1.58-1.45 (m, 1H), 1.39-1.30 (m, 1H); LC/MS (B), Rt: 3.47 min; (M+H) 454.2.

2-[4-(6-Amino-5-pyrimidin-2-yl-3',4',5',6'-tetrahydro-2'H-[3,4']bipyridinyl-1'-yl)-4-oxo-butyl]-7-methyl-3H-thieno[3,4-d]pyrimidin-4-one ("C116")

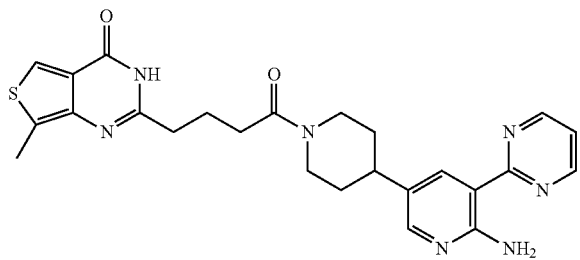 [SMILES: Cc1scc2c(=O)[nH]c(CCCC(=O)N3CCC(c4cnc(N)c(-c5ncccn5)c4)CC3)nc12]

Yield: 29 mg (29%) off-white solid;
¹H NMR (400 MHz, DMSO-d₆) δ 11.49 (s, 1H), 8.91 (t, J=4.9 Hz, 2H), 8.50 (d, J=2.4 Hz, 1H), 8.14 (s, 2H), 8.05 (d, J=2.4 Hz, 1H), 7.78 (bs, 1H), 7.40 (t, J=4.8 Hz, 1H), 4.55 (d, J=10.3 Hz, 1H), 4.00 (d, J=13.4 Hz, 1H), 3.10 (t, J=12.5 Hz, 1H), 2.81-2.70 (m, 1H), 2.59 (s, 3H), 2.61-2.48 (m, 3H), 2.44-2.38 (m, 2H), 2.08-1.82 (m, 2H), 1.80 (t, J=11.6 Hz, 2H), 1.66-1.51 (m, 1H), 1.49-1.35 (m, 1H); LC/MS (B), Rt: 2.59 min; (M+H) 490.0.

7-Methyl-2-{4-oxo-4-[4-(5-phenyl-[1,3,4]oxadiazol-2-yl)-piperidin-1-yl]-butyl}-3H-thieno[3,4-d]pyrimidin-4-one ("C117")

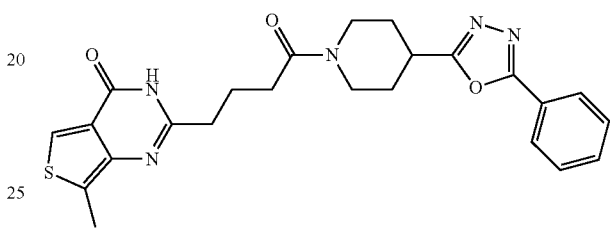

Yield: 32 mg (35%) off-white solid;
¹H NMR (400 MHz, DMSO-d₆) δ 11.52 (s, 1H), 8.16 (s, 1H), 8.00 (dd, J=1.6, 7.6 Hz, 2H), 7.63-7.60 (m, 3H), 4.26 (d, J=12.0 Hz, 1H), 3.92 (d, J=9.7 Hz, 1H), 3.53-3.42 (m, 1H), 3.41-3.38 (m, 1H), 3.30-3.24 (m, 1H), 2.94-2.81 (m, 1H), 2.67 (s, 3H), 2.64-2.51 (m, 1H), 2.49-2.30 (m, 2H), 2.18-2.00 (m, 2H), 1.99-1.91 (m, 2H), 1.84-1.71 (m, 1H), 1.69-1.54 (m, 1H); LC/MS (B), Rt: 3.29 min; (M+H) 464.2.

2-{4-[4-(4-Fluoro-benzoyl)-piperidin-1-yl]-4-oxo-butyl}-7-methyl-3H-thieno[3,4-d]pyrimidin-4-one ("C119")

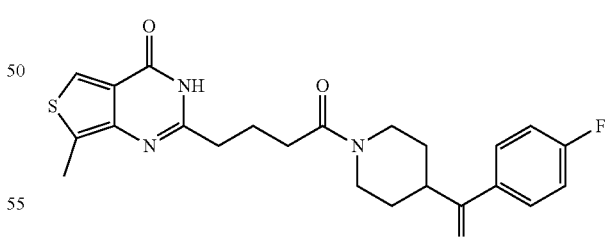

Yield: 25 mg (37%) pale brown gum;
¹H NMR (400 MHz, DMSO-d₆) δ 11.49 (s, 1H), 8.13 (s, 1H), 8.08 (dd, J=5.6, 8.8 Hz, 2H), 7.36 (t, J=9.0 Hz, 2H), 4.42-4.33 (m, 1H), 3.98-3.88 (m, 1H), 3.72-3.61 (m, 1H), 3.25-3.11 (m, 1H), 2.78-2.68 (m, 1H), 2.55 (s, 3H), 2.51-2.50 (m, 2H), 2.48-2.39 (m, 2H), 1.98-1.88 (m, 2H), 1.82-1.72 (m, 2H), 1.55-1.42 (m, 1H), 1.38-1.25 (m, 1H); LC/MS (B), Rt: 3.59 min; (M+H) 442.0.

2-{4-[4-(4-Methoxy-3-methyl-benzoyl)-piperidin-1-yl]-4-oxo-butyl}-7-methyl-3H-thieno[3,4-d]pyrimidin-4-one ("C120")

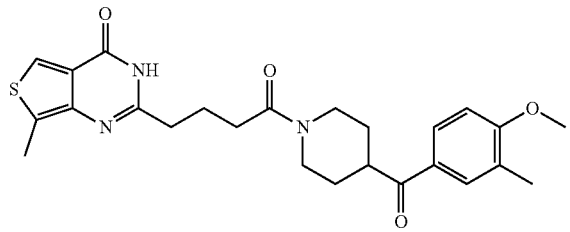 [SMILES: COc1ccc(C(=O)C2CCN(C(=O)CCCc3nc4c(C)scc4c(=O)[nH]3)CC2)cc1C]

Yield: 33 mg (53%) pale brown gum;
$^1$H NMR (400 MHz, DMSO-d$_6$) δ 11.51 (s, 1H), 8.14 (s, 1H), 7.89 (dd, J=1.6, 7.6 Hz, 1H), 7.80 (d, J=1.4 Hz, 1H), 7.04 (d, J=8.6 Hz, 1H), 4.46-4.33 (m, 1H), 3.97-3.91 (m, 1H), 3.86 (s, 3H), 3.69-3.58 (m, 1H), 3.20-3.11 (m, 1H), 2.72 (t, J=12.1 Hz, 1H), 2.58-2.44 (m, 5H), 2.41-2.39 (m, 2H), 2.19 (s, 3H), 1.99-1.87 (m, 2H), 1.78-1.70 (m, 2H), 1.54-1.46 (m, 1H), 1.41-1.26 (m, 1H); LC/MS (B), Rt: 3.84 min; (M+H) 468.0.

7-Fluoro-3-{4-[4-(6-methoxy-pyridine-3-carbonyl)-piperidin-1-yl]-4-oxo-butyl}-2H-pyrrolo[1,2-a]pyrazin-1-one ("C71")

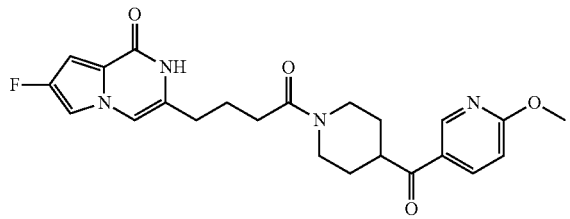 [SMILES: COc1ccc(C(=O)C2CCN(C(=O)CCCc3cn4cc(F)cc4c(=O)[nH]3)CC2)cn1]

Yield: 69 mg (75%) colorless solid;
$^1$H NMR (500 MHz, DMSO-d$_6$) δ 10.68 (s, 1H), 8.90 (d, J=2.3 Hz, 1H), 8.22 (dd, J=8.7, 2.4 Hz, 1H), 7.37 (dd, J=3.1, 2.0 Hz, 1H), 7.04 (s, 1H), 6.94 (d, J=8.7 Hz, 1H), 6.62 (d, J=1.7 Hz, 1H), 4.48-4.31 (m, 1H), 3.95 (s, 3H), 3.92-3.83 (m, 1H), 3.65 (tt, J=11.2, 3.4 Hz, 1H), 3.22-3.07 (m, 1H), 2.81-2.67 (m, 1H), 2.43-2.27 (m, 4H), 1.88-1.70 (m, 4H), 1.57-1.42 (m, 1H), 1.42-1.27 (m, 1H); LC/MS (A), Rt: 1.90 min; (M+H) 441.2.

2-{4-[4-(4-Methoxy-3-methyl-benzoyl)-piperidin-1-yl]-4-oxo-butyl}-7-methyl-3H-thieno[3,4-d]pyrimidin-4-one ("C114")

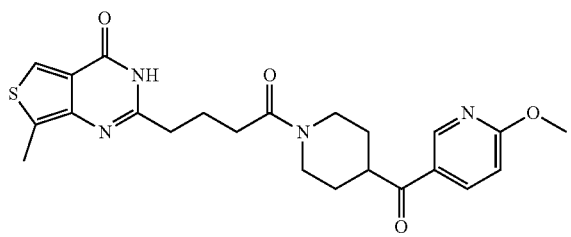 [SMILES: COc1ccc(C(=O)C2CCN(C(=O)CCCc3nc4c(C)scc4c(=O)[nH]3)CC2)cn1]

Yield: 22 mg (24%) off-white solid;
$^1$H NMR (400 MHz, DMSO-d$_6$) δ 11.30 (s, 1H), 8.67 (d, J=2.1 Hz, 1H), 7.99 (dd, J=2.4, 8.7 Hz, 1H), 7.92 (s, 1H), 6.71 (d, J=9.1 Hz, 1H), 4.15 (d, J=12.6 Hz, 1H), 3.71 (s, 3H) 3.69-3.56 (m, 1H), 3.49-3.39 (m, 1H), 2.98-2.88 (m, 1H), 2.54-2.43 (m, 1H), 2.32 (s, 3H), 2.28-2.15 (m, 2H), 1.77-1.65 (m, 2H), 1.61-1.50 (m, 2H), 1.32-1.20 (m, 1H), 1.18-1.03 (m, 1H); LC/MS (B), Rt: 3.15 min; (M+H) 455.3.

6-Amino-1'-[4-(7-methyl-4-oxo-3,4-dihydro-thieno[3,4-d]pyrimidin-2-yl)-butyryl]-1',2',3',4',5',6'-hexahydro-[3,4']bipyridinyl-5-carbonitrile trifluoroacetate ("C115")

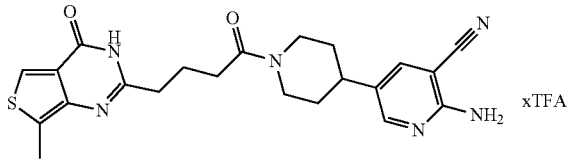 [SMILES: Cc1scc2c(=O)[nH]c(CCCC(=O)N3CCC(c4cnc(N)c(C#N)c4)CC3)nc12]

Yield: 35 mg (28%) pale brown solid;
$^1$H NMR (400 MHz, DMSO-d$_6$) δ 11.60 (s, 1H), 8.16 (s, 1H), 8.11 (d, J=2.4 Hz, 1H), 7.80 (d, J=2.4 Hz, 1H), 6.80 (bs, 2H), 4.50 (d, J=12.8 Hz, 1H), 3.96 (d, J=9.2 Hz, 1H), 3.04 (t, J=12.7 Hz, 1H), 2.69-2.61 (m, 1H), 2.60-2.50 (m, 6H), 2.48-2.38 (m, 2H), 2.01-1.90 (m, 2H), 1.78-1.63 (m, 2H), 1.56-1.48 (m, 1H), 1.46-1.31 (m, 1H); LC/MS (B), Rt: 2.29 min; (M+H) 437.3.

4-{1-[4-(7-Methyl-4-oxo-3,4-dihydro-thieno[3,4-d]pyrimidin-2-yl)-butyryl]-piperidin-4-yloxy}-benzonitrile ("C118")

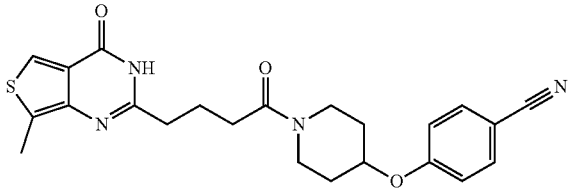 [SMILES: Cc1scc2c(=O)[nH]c(CCCC(=O)N3CCC(Oc4ccc(C#N)cc4)CC3)nc12]

Yield: 24 mg (29%) off-white solid;
$^1$H NMR (400 MHz, DMSO-d$_6$) δ 11.53 (s, 1H), 8.14 (s, 1H), 7.75 (d, J=8.8 Hz, 2H), 7.15 (t, J=8.8 Hz, 1H), 4.84-4-69 (m, 1H), 3.99-3.72 (m, 1H), 3.71-3.62 (m, 1H), 3.38-3.33 (m, 1H), 3.26-3.12 (m, 1H), 2.63-2.11 (m, 6H), 2.48-2.38 (m, 2H), 2.01-1.85 (m, 4H), 1.64-1.53 (m, 1H), 1.52-1.42 (m, 1H); LC/MS (B), Rt: 3.52 min; (M+H) 437.3.

7-Methyl-2-{4-[4-(1-methyl-1H-pyrazole-4-carbonyl)-piperidin-1-yl]-4-oxo-butyl}-3H-thieno[3,4-d]pyrimidin-4-one ("C123")

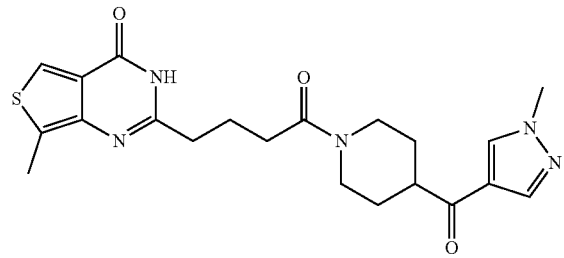 [SMILES: Cc1scc2c(=O)[nH]c(CCCC(=O)N3CCC(C(=O)c4cnn(C)c4)CC3)nc12]

Yield: 20 mg (24%) colorless solid;
<sup>1</sup>H NMR (400 MHz, DMSO-d<sub>6</sub>) δ 11.47 (s, 1H), 8.43 (s, 1H), 8.13 (s, 1H), 7.95 (s, 1H), 4.39 (d, J=13.6 Hz, 1H), 3.93-3.90 (m, 1H), 3.87 (s, 3H) 3.29-3.21 (m, 1H), 3.19-3.09 (m, 1H), 2.60-2.50 (m, 6H), 2.46-2.38 (m, 2H), 1.99-1.89 (m, 2H), 1.80-1.70 (m, 2H), 1.52-1.41 (m, 1H), 1.39-1.23 (m, 1H); LC/MS (B), Rt: 2.51 min; (M+H) 428.0.

6-{4-[4-(1-Ethyl-1H-pyrazole-4-carbonyl)-piperidin-1-yl]-4-oxo-butyl}-1-methyl-1,5-dihydro-pyrazolo[3,4-d]pyrimidin-4-one ("C213")

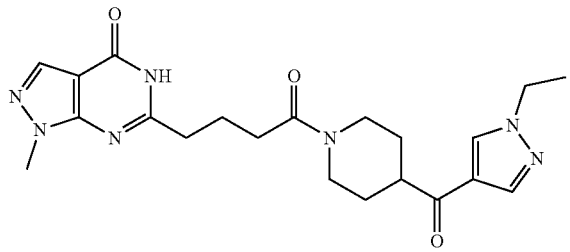 [SMILES: CCn1cc(C(=O)C2CCN(C(=O)CCCc3nc4c(cnn4C)c(=O)[nH]3)CC2)cn1]

Yield: 105 mg (60%) colorless solid;
<sup>1</sup>H NMR (400 MHz, DMSO-d<sub>6</sub>) δ 12.00 (s, 1H), 8.48 (s, 1H), 7.97-7.95 (m, 2H), 4.39 (d, J=12.9 Hz, 1H), 4.15 (q, J=7.3 Hz, 2H), 3.92-3.88 (m, 1H), 3.86 (s, 3H), 3.26-3.19 (m, 1H), 3.12-3.06 (m, 1H), 2.69-2.62 (m, 3H), 2.42-2.36 (m, 2H), 1.97-1.90 (m, 2H), 1.78-1.71 (m, 2H), 1.55-1.42 (m, 1H), 1.38 (t, J=7.3 Hz, 3H), 1.37-1.25 (m, 1H); LC/MS (B), Rt: 2.46 min; (M+H) 426.2.

2-{4-[4-(1-Ethyl-1H-pyrazole-4-carbonyl)-piperidin-1-yl]-4-oxo-butyl}-3H-pyrrolo[2,1-f][1,2,4]triazin-4-one ("C214")

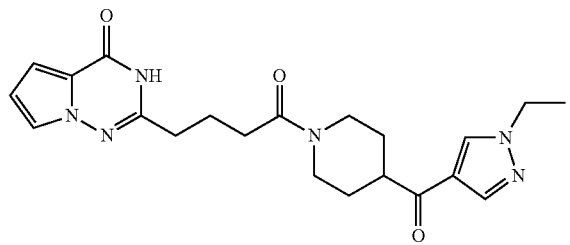 [SMILES: CCn1cc(C(=O)C2CCN(C(=O)CCCc3nn4cccc4c(=O)[nH]3)CC2)cn1]

Yield: 70 mg (38%) colorless solid;
<sup>1</sup>H NMR (400 MHz, DMSO-d<sub>6</sub>) δ 11.56 (s, 1H), 8.48 (s, 1H), 7.97 (s, 1H), 7.52 (dd, J=1.8, 2.5 Hz, 1H), 6.81 (dd, J=1.7, 4.3 Hz, 1H), 6.48 (dd, J=2.6, 4.3 Hz, 1H), 4.39 (d, J=13.0 Hz, 1H), 4.16 (q, J=7.3 Hz, 2H), 3.89 (d, J=13.6 Hz, 1H), 3.26-3.18 (m, 1H), 3.12-3.06 (m, 1H), 2.68-2.61 (m, 1H), 2.54-2.51 (m, 2H), 2.42-2.36 (m, 2H), 1.93-1.86 (m, 2H), 1.78-1.71 (m, 2H), 1.54-1.44 (m, 1H), 1.38 (t, J=7.3 Hz, 3H), 1.36-1.26 (m, 1H); LC/MS (B), Rt: 2.90 min; (M+H) 411.2.

2-{4-[4-(1-Ethyl-1H-pyrazole-4-carbonyl)-piperidin-1-yl]-4-oxo-butyl}-6-fluoro-3H-pyrrolo[2,1-f][1,2,4]triazin-4-one ("C215")

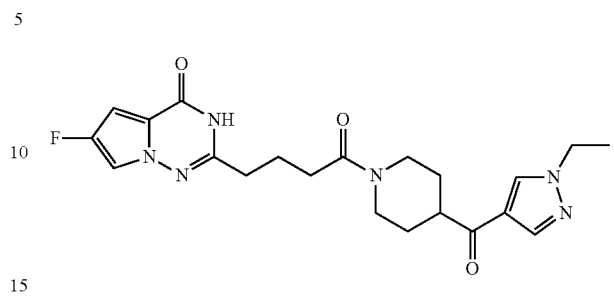

Yield: 75 mg (43%) colorless solid
<sup>1</sup>H NMR (400 MHz, DMSO-d<sub>6</sub>) δ 11.79 (s, 1H), 8.48 (s, 1H), 7.97 (s, 1H), 7.63 (dd, J=2.2, 3.2 Hz, 1H), 6.68 (d, J=2.1 Hz, 1H), 4.38 (d, J=13.2 Hz, 1H), 4.16 (q, J=7.3 Hz, 2H), 3.88 (d, J=13.5 Hz, 1H), 3.26-3.20 (m, 1H), 3.12-3.06 (m, 1H), 2.68-2.62 (m, 1H), 2.54-2.51 (m, 2H), 2.40-2.36 (m, 2H), 1.90-1.82 (m, 2H), 1.78-1.71 (m, 2H), 1.54-1.46 (m, 1H), 1.38 (t, J=7.3 Hz, 3H), 1.34-1.26 (m, 1H); LC/MS (B), Rt: 3.22 min; (M+H) 429.0.

2-{4-[4-(1-Ethyl-1H-pyrazole-4-carbonyl)-piperidin-1-yl]-4-oxo-butyl}-7-methyl-3H-thieno[3,4-d]pyrimidin-4-one ("C216")

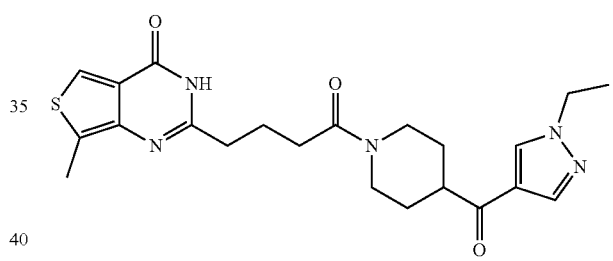

Yield: 100 mg (60%) colorless solid;
<sup>1</sup>H NMR (400 MHz, DMSO-d<sub>6</sub>) δ 12.34 (s, 1H), 8.48 (s, 1H), 7.97 (s, 1H), 7.77 (s, 1H), 4.39 (d, J=13.2 Hz 1H), 4.10 (q, J=7.2 Hz, 2H), 3.91 (d, J=13.2 Hz, 1H), 3.25-3.19 (m, 1H), 3.10 (t, J=11.6 Hz, 1H), 2.68-2.61 (m, 3H), 2.43-2.36 (m, 2H), 2.27 (s, 3H), 1.98-1.91 (m, 2H), 1.78-1.71 (m, 2H), 1.54-1.46 (m, 1H), 1.37 (t, J=7.2 Hz, 3H), 1.32-1.26 (m, 1H); LC/MS (B), Rt: 3.00 min; (M+H) 442.0.

6-{4-[4-(1-Isopropyl-1H-pyrazole-4-carbonyl)-piperidin-1-yl]-4-oxo-butyl}-2-methyl-5H-pyrazolo[1,5-a]pyrazin-4-one ("C217")

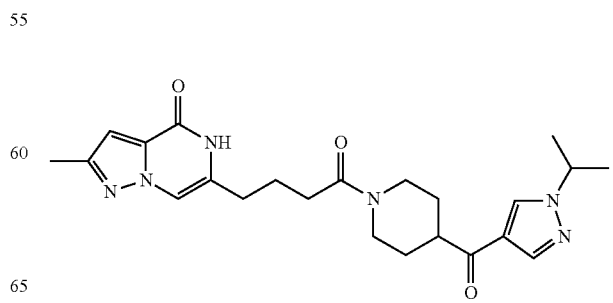

Yield: 28 mg (42%) pale yellow solid;
¹H NMR (500 MHz, DMSO-d₆) δ 11.15 (s, 1H), 8.49 (s, 1H), 7.96 (s, 1H), 7.37 (s, 1H), 6.68 (s, 1H), 4.54 (hept, J=6.7 Hz, 1H), 4.46-4.33 (m, 1H), 3.95-3.81 (m, 1H), 3.29-3.19 (m, 1H), 3.19-3.02 (m, 1H), 2.75-2.60 (m, 1H), 2.47-2.39 (m, 2H), 2.40-2.30 (m, 2H), 2.31 (s, 3H), 1.89-1.79 (m, 2H), 1.77-1.71 (m, 2H), 1.55-1.45 (m, 1H), 1.44 (d, J=6.7 Hz, 6H), 1.40-1.27 (m, 1H); LC/MS (A), Rt: 1.66 min; (M+H) 439.2.

6-{4-[4-(1-Isopropyl-1H-pyrazole-4-carbonyl)-piperidin-1-yl]-4-oxo-butyl}-1-methyl-1,5-dihydropyrazolo[3,4-d]pyrimidin-4-one ("C218")

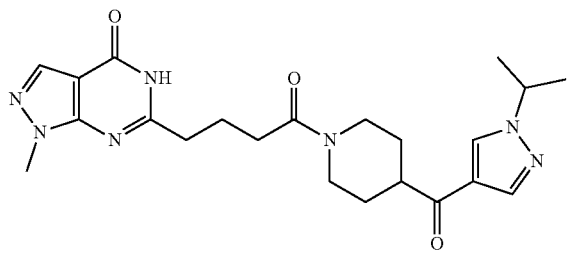 [SMILES: CC(C)n1cc(C(=O)C2CCN(C(=O)CCCc3nc4c(cnn4C)c(=O)[nH]3)CC2)cn1]

Yield: 67 mg (54%) colorless solid;
¹H NMR (400 MHz, DMSO-d₆) δ 12.01 (s, 1H), 8.50 (s, 1H), 7.98-7.96 (m, 2H), 4.58-4.50 (m, 1H), 4.40 (d, J=13.5 Hz, 1H), 3.92-3.84 (m, 4H), 3.29-3.22 (m, 1H), 3.14-3.07 (m, 1H), 2.69-2.61 (m, 3H), 2.42-2.36 (m, 2H), 1.98-1.91 (m, 2H), 1.83-1.71 (m, 2H), 1.54-1.46 (m, 1H), 1.42 (d, J=6.7 Hz, 6H), 1.34-1.25 (m, 1H); LC/MS (B), Rt: 2.71 min; (M+H) 440.2.

2-{4-[4-(1-Isopropyl-1H-pyrazole-4-carbonyl)-piperidin-1-yl]-4-oxo-butyl}-3H-pyrrolo[2,1-f][1,2,4]triazin-4-one ("C219")

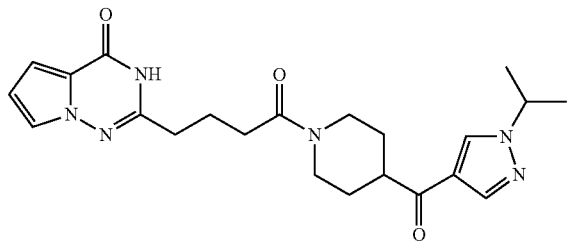 [SMILES: CC(C)n1cc(C(=O)C2CCN(C(=O)CCCc3nn4cccc4c(=O)[nH]3)CC2)cn1]

Yield: 92 mg (70%) off-white solid;
¹H NMR (400 MHz, DMSO-d₆) δ 11.57 (s, 1H), 8.50 (s, 1H), 7.97 (s, 1H), 7.52 (s, 1H), 6.82 (d, J=4.0 Hz, 1H), 6.49-6.46 (m, 1H), 4.57-4.50 (m, 1H), 4.40 (d, J=13.3 Hz, 1H), 3.89 (d, J=12.7 Hz, 1H), 3.26-3.20 (m, 1H), 3.10 (t, J=12.5 Hz, 1H), 2.69-2.61 (m, 1H), 2.54-2.51 (m, 2H), 2.41-2.36 (m, 2H), 1.94-1.86 (m, 2H), 1.83-1.71 (m, 2H), 1.54-1.46 (m, 1H), 1.44 (d, J=6.6 Hz, 6H), 1.36-1.26 (m, 1H); LC/MS (B), Rt: 3.17 min; (M+H) 425.2.

2-{4-[4-(1-Isopropyl-1H-pyrazole-4-carbonyl)-piperidin-1-yl]-4-oxo-butyl}-6-methyl-3H-pyrrolo[2,1-f][1,2,4]triazin-4-one ("C220")

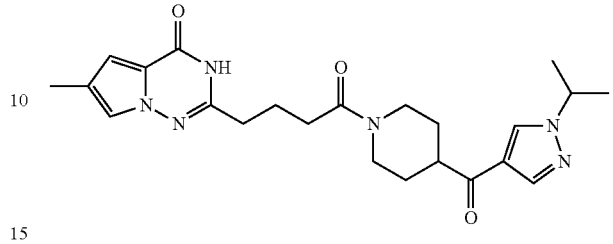

Yield: 20 mg (22%) colorless solid;
¹H NMR (400 MHz, DMSO-d₆) δ 11.49 (s, 1H), 8.50 (s, 1H), 7.97 (s, 1H), 7.32 (s, 1H), 6.62 (s, 1H), 4.57-4.50 (m, 1H), 4.39 (d, J=13.2 Hz, 1H), 3.89 (d, J=13.4 Hz, 1H), 3.26-3.21 (m, 2H), 3.12-3.06 (m, 1H), 2.69-2.61 (m, 2H), 2.41-2.32 (m, 2H), 2.13 (s, 3H), 1.90-1.83 (m, 2H), 1.83-1.71 (m, 2H), 1.54-1.46 (m, 1H), 1.42 (d, J=6.6 Hz, 6H), 1.34-1.26 (m, 1H); LC/MS (B), Rt: 3.77 min; (M+H) 439.0.

6-Fluoro-2-{4-[4-(1-isopropyl-1H-pyrazole-4-carbonyl)-piperidin-1-yl]-4-oxo-butyl}-3H-pyrrolo[2,1-f][1,2,4]triazin-4-one ("C221")

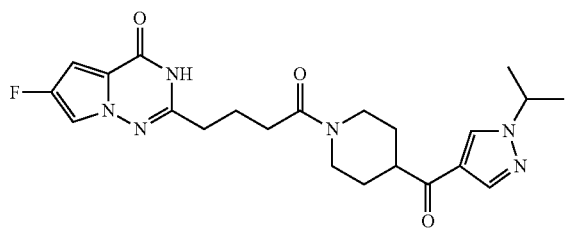 [SMILES: CC(C)n1cc(C(=O)C2CCN(C(=O)CCCc3nn4cc(F)cc4c(=O)[nH]3)CC2)cn1]

Yield: 85 mg (65%) colorless solid;
¹H NMR (400 MHz, DMSO-d₆) δ 11.80 (s, 1H), 8.50 (s, 1H), 7.97 (s, 1H), 7.65-7.63 (m, 1H), 6.69-6.68 (m, 1H), 4.58-4.50 (m, 1H), 4.38 (d, J=13.4 Hz, 1H), 3.89 (d, J=13.5 Hz, 1H), 3.29-3.22 (m, 1H), 3.10 (t, J=12.0 Hz, 1H), 2.69-2.62 (m, 1H), 2.54-2.51 (m, 2H), 2.41-2.38 (m, 2H), 1.92-1.85 (m, 2H), 1.79-1.71 (m, 2H), 1.54-1.46 (m, 1H), 1.43 (d, J=6.7 Hz, 6H), 1.34-1.26 (m, 1H); LC/MS (B), Rt: 3.56 min; (M+H) 443.0.

2-{4-[4-(1-Ethyl-1H-pyrazole-4-carbonyl)-piperidin-1-yl]-4-oxo-butyl}-7-methyl-3H-pyrrolo[2,1-f][1,2,4]triazin-4-one ("C222")

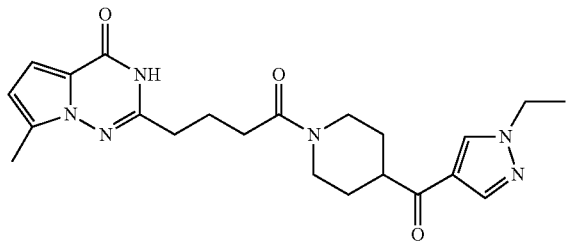 [SMILES: CCn1cc(C(=O)C2CCN(C(=O)CCCc3nn4c(C)ccc4c(=O)[nH]3)CC2)cn1]

Yield: 35 mg (32%) colorless solid;
¹H NMR (400 MHz, DMSO-d₆) δ 11.46 (s, 1H), 8.48 (s, 1H), 7.97 (s, 1H), 6.76 (d, J=4.2 Hz, 1H), 6.30 (d, J=4.2 Hz, 1H), 4.39 (d, J=13.4 Hz, 1H), 4.16 (q, J=7.2 Hz, 2H), 3.90 (d, J=13.4 Hz, 1H), 3.27-3.21 (m, 1H), 3.13-3.07 (m, 1H), 2.69-2.63 (m, 1H), 2.54-2.51 (m, 2H), 2.44-2.40 (m, 2H), 2.36 (s, 3H), 1.95-1.87 (m, 2H), 1.79-1.71 (m, 2H), 1.54-1.46 (m, 1H), 1.38 (t, J=7.3 Hz, 3H), 1.34-1.26 (m, 1H); LC/MS (B), Rt: 3.53 min; (M+H) 425.0.

2-{4-[4-(1-Isopropyl-1H-pyrazole-4-carbonyl)-piperidin-1-yl]-4-oxo-butyl}-7-methyl-3H-pyrrolo[2,1-f][1,2,4]triazin-4-one ("C223")

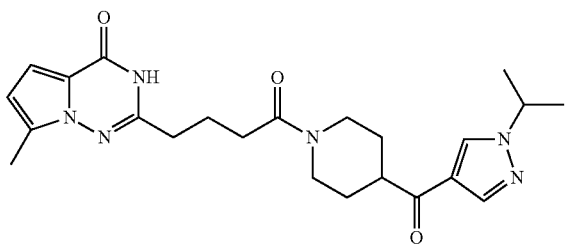 [SMILES: Cc1ccc2c(=O)[nH]c(CCCC(=O)N3CCC(C(=O)c4cnn(C(C)C)c4)CC3)nn12]

Yield: 45 mg (40%) colorless solid;
¹H NMR (400 MHz, DMSO-d₆) δ 11.46 (s, 1H), 8.50 (s, 1H), 7.97 (s, 1H), 6.76 (d, J=4.2 Hz, 1H), 6.30 (d, J=4.1 Hz, 1H), 4.59-4.51 (m, 1H), 4.40 (d, J=13.1 Hz, 1H), 3.91 (d, J=13.4 Hz, 1H), 3.29-3.21 (m, 1H), 3.10 (t, J=12.0 Hz, 1H), 2.66 (t, J=11.0 Hz, 1H), 2.56-2.51 (m, 2H), 2.43-2.38 (m, 2H), 2.36 (s, 3H), 1.95-1.87 (m, 2H), 1.78-1.71 (m, 2H), 1.50-1.42 (m, 1H), 1.43 (d, J=6.6 Hz, 6H), 1.34-1.26 (m, 1H); LC/MS (B), Rt: 3.82 min; (M+H) 438.9.

2-{4-[4-(1-Ethyl-1H-pyrazole-4-carbonyl)-piperidin-1-yl]-4-oxo-butyl}-7-methyl-3H-thieno[3,2-d]pyrimidin-4-one trifluoroacetate ("C224")

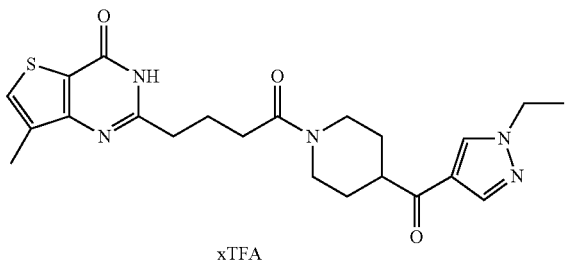 [SMILES: CCn1cc(C(=O)C2CCN(C(=O)CCCc3nc4c(C)csc4c(=O)[nH]3)CC2)cn1]

xTFA

Yield: 45 mg (41%) off-white solid;
¹H NMR (400 MHz, DMSO-d₆) δ 11.58 (s, 1H), 8.50 (s, 1H), 8.17 (s, 1H), 7.98 (s, 1H), 7.11 (s, 1H), 4.42-4.20 (m 1H), 4.20-4.10 (m, 2H), 3.95-3.59 (m, 1H), 3.26-3.22 (m, 1H), 3.17-3.09 (m, 1H), 2.67-2.61 (m, 1H), 2.55-2.51 (m, 5H), 2.43-2.33 (m, 2H), 1.96-1.88 (m, 2H), 1.78-1.71 (m, 2H), 1.54-1.46 (m, 1H), 1.38 (t, J=7.3 Hz, 3H), 1.37-1.26 (m, 1H); LC/MS (B), Rt: 2.74 min; (M+H) 442.0.

2-{4-[4-(1-Isopropyl-1H-pyrazole-4-carbonyl)-piperidin-1-yl]-4-oxo-butyl}-7-methyl-3H-thieno[3,2-d]pyrimidin-4-one ("C225")

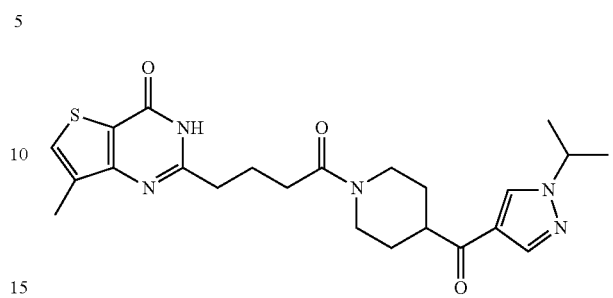

Yield: 87 mg (68%) colorless solid;
¹H NMR (400 MHz, DMSO-d₆) δ 12.34 (s, 1H), 8.50 (s, 1H), 7.97 (s, 1H), 7.77 (s, 1H), 4.57-4.50 (m, 1H), 4.39 (d, J=13.2 Hz, 1H), 3.91 (d, J=13.6 Hz, 1H), 3.28-3.21 (m, 1H), 3.11 (t, J=12.4 Hz, 1H), 2.69-2.61 (m, 3H), 2.43-2.36 (m, 2H), 2.28 (s, 3H), 1.99-1.92 (m, 2H), 1.78-1.71 (m, 2H), 1.53-1.46 (m, 1H), 1.42 (d, J=6.8 Hz, 6H), 1.35-1.26 (m, 1H); LC/MS (B), Rt: 3.19 min; (M+H) 456.0.

2-{4-[4-(1-Isopropyl-1H-pyrazole-4-carbonyl)-piperidin-1-yl]-4-oxo-butyl}-7-methyl-3H-thieno[3,4-d]pyrimidin-4-one ("C226")

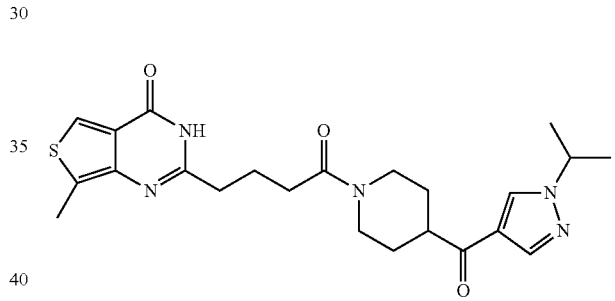

Yield: 19 mg (15%) pale brown solid;
¹H NMR (400 MHz, DMSO-d₆) δ 11.47 (s, 1H), 8.50 (s, 1H), 8.13 (s, 1H), 7.97 (s, 1H), 4.57-4.49 (m, 1H), 4.39 (d, J=12.8 Hz, 1H), 3.92 (d, J=12.8 Hz, 1H), 3.26-3.21 (m, 1H), 3.16-3.08 (m, 1H), 2.69-2.61 (m, 1H), 2.56-2.51 (m, 5H), 2.43-2.36 (m, 2H), 1.96-1.89 (m, 2H), 1.78-1.72 (m, 2H), 1.54-1.46 (m, 1H), 1.42 (d, J=6.8 Hz, 6H), 1.34-1.26 (m, 1H); LC/MS (B), Rt: 2.96 min; (M+H) 456.2.

2-{4-[4-(4-Methoxy-benzoyl)-piperidin-1-yl]-4-oxo-butyl}-5,6,7,8-tetrahydro-3H-quinazolin-4-one ("C227")

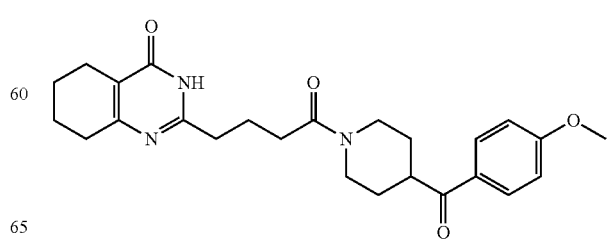

Yield: 30 mg (26%) colorless solid;
¹H NMR (400 MHz, DMSO-d₆) δ 12.09 (s, 1H), 7.98 (d, J=8.8 Hz, 2H), 7.5 (d, J=8.8 Hz, 2H), 4.43-4.37 (m, 1H), 3.93-3.81 (m, 4H), 3.69-3.60 (m, 1H), 3.21-3.11 (m, 1H), 2.78-2.68 (m, 1H), 2.49-2.40 (m, 4H), 2.46-2.35 (m, 2H), 2.34-2.26 (m, 2H), 1.90-1.58 (m, 8H), 1.54-1.42 (m, 1H), 1.39-1.25 (m, 1H); LC/MS (B), Rt: 3.14 min; (M+H) 438.3.

2-{4-[4-(1-Ethyl-1H-pyrazole-4-carbonyl)-piperidin-1-yl]-4-oxo-butyl}-3,5,7,8-tetrahydro-pyrano[4,3-d]pyrimidin-4-one ("C228")

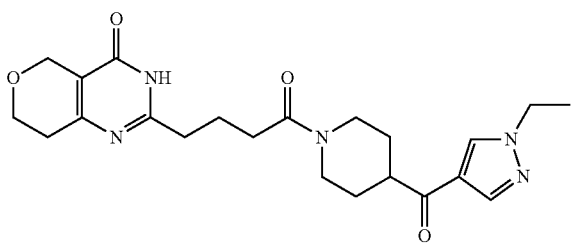 [SMILES: CCn1cc(C(=O)C2CCN(C(=O)CCCc3nc4c(c(=O)[nH]3)COCC4)CC2)cn1]

Yield: 55 mg (30%) pale brown solid;
¹H NMR (400 MHz, DMSO-d₆) δ 12.32 (s, 1H), 8.48 (s, 1H), 7.97 (s, 1H), 4.40 (d, J=13.2 Hz, 1H), 4.33 (s, 2H), 4.15 (q, J=7.2 Hz, 2H), 3.90 (d, J=13.2 Hz, 1H), 3.82 (t, J=5.6 Hz, 2H), 3.28-3.18 (m, 1H), 3.14-3.06 (m, 1H), 2.68-2.61 (m, 1H), 2.54-2.51 (m, 3H), 2.36-2.28 (m, 2H), 1.88-1.81 (m, 2H), 1.78-1.71 (m, 2H), 1.54-1.46 (m, 2H), 1.41-1.30 (m, 4H); LC/MS (B), Rt: 2.15 min; (M+H) 428.3.

2-{4-[4-(1-Isopropyl-1H-pyrazole-4-carbonyl)-piperidin-1-yl]-4-oxo-butyl}-3,5,7,8-tetrahydro-pyrano[4,3-d]pyrimidin-4-one ("C229")

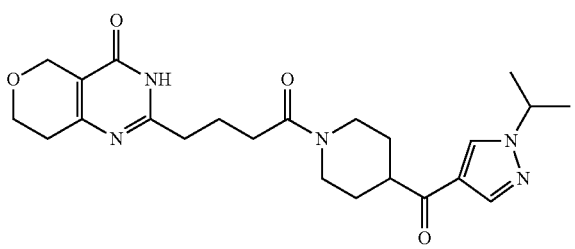 [SMILES: CC(C)n1cc(C(=O)C2CCN(C(=O)CCCc3nc4c(c(=O)[nH]3)COCC4)CC2)cn1]

Yield: 39 mg (23%) pale brown solid;
¹H NMR (400 MHz, DMSO-d₆) δ 12.32 (s, 1H), 8.50 (s, 1H), 7.97 (s, 1H), 4.57-4.51 (m, 1H), 4.39 (d, J=13.2 Hz, 1H), 4.33 (s, 2H), 3.85 (d, J=13.2 Hz, 1H), 3.81 (t, J=5.6 Hz, 2H), 3.29-3.20 (m, 1H), 3.12-3.06 (m, 1H), 2.67-2.61 (m, 1H), 2.57-2.51 (m, 4H), 2.36-2.28 (m, 3H), 1.87-1.81 (m, 2H), 1.78-1.71 (m, 2H), 1.54-1.46 (m, 1H), 1.43-1.41 (m, 6H), 1.34-1.26 (m, 1H); LC/MS (B), Rt: 2.43 min; (M+H) 442.3.

2-{4-[4-(1-Methyl-1H-pyrazole-4-carbonyl)-piperidin-1-yl]-4-oxo-butyl}-5,6,7,8-tetrahydro-3H-quinazolin-4-one ("C230")

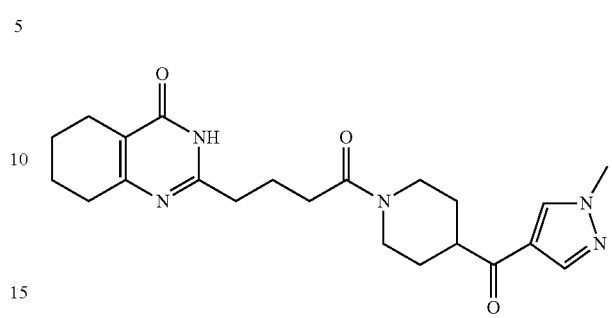

Yield: 6 mg (7%) pale yellow gum;
¹H NMR (400 MHz, DMSO-d₆) δ 8.50 (s, 1H), 7.96 (s, 1H), 4.41-4.36 (m, 1H), 3.23-3.12 (m, 4H), 2.68-2.60 (m, 2H), 2.50-2.59 (m, 1H), 2.49-2.28 (m, 4H), 1.95-1.84 (m, 2H), 1.80-1.60 (m, 6H), 1.55-1.42 (m, 1H), 1.38-1.26 (m, 1H); LC/MS (B), Rt: 2.16 min; (M+H) 412.3.

6-{4-[4-(6-Methoxy-pyridine-3-carbonyl)-piperidin-1-yl]-4-oxo-butyl}-2-methyl-5H-pyrazolo[1,5-a]pyrazin-4-one ("C231")

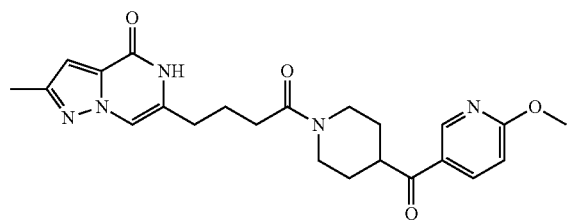

Yield: 63 mg (67%) pale yellow solid;
¹H NMR (400 MHz, DMSO-d₆) δ 11.16 (s, 1H), 8.90 (d, J=2.4 Hz, 1H), 8.22 (dd, J=8.7, 2.5 Hz, 1H), 7.38 (s, 1H), 6.94 (d, J=8.7 Hz, 1H), 6.69 (s, 1H), 4.42-4.34 (m, 1H), 3.95 (s, 3H), 3.91-3.84 (m, 1H), 3.64 (tt, J=11.1, 3.6 Hz, 1H), 3.21-3.11 (m, 1H), 2.78-2.68 (m, 1H), 2.43 (t, J=7.4 Hz, 2H), 2.38-2.32 (m, 2H), 2.31 (s, 3H), 1.87-1.74 (m, 4H), 1.56-1.43 (m, 1H), 1.40-1.28 (m, 1H); LC/MS (A), Rt: 1.77 min; (M+H) 438.2.

6-Amino-1'-[4-(4-oxo-3,4,5,6,7,8-hexahydro-quinazolin-2-yl)-butyryl]-1',2',3',4',5',6'-hexahydro-[3,4']bipyridinyl-5-carbonitrile ("C232")

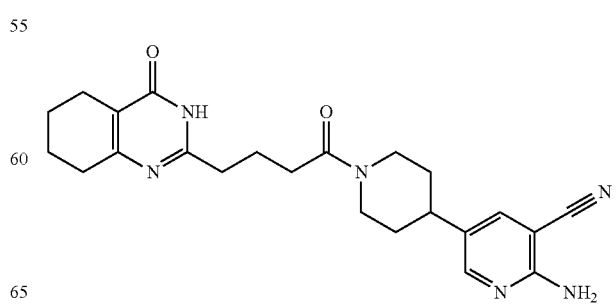

Yield: 4 mg (4%) pale yellow gum;
$^1$H NMR (400 MHz, DMSO-$d_6$) δ 8.11 (d, J=2.4 Hz, 1H), 7.77 (d, J=2.4 Hz, 1H), 7.76 (brs, 2H), 4.52-4.48 (m, 1H), 3.99-3.90 (m, 1H), 3.15-2.85 (m, 3H), 2.70-2.55 (m, 5H), 2.45-2.25 (m, 4H), 1.95-1.85 (m, 2H), 1.78-1.61 (m, 6H), 1.58-1.44 (m, 1H), 1.42-1.30 (m, 1H); LC/MS (B), Rt: 1.97 min; (M+H) 421.3.

2-{4-[4-(1-Ethyl-1H-pyrazole-4-carbonyl)-piperidin-1-yl]-4-oxo-butyl}-6-methyl-3H-pyrrolo[2,1-f][1,2,4]triazin-4-one ("C233")

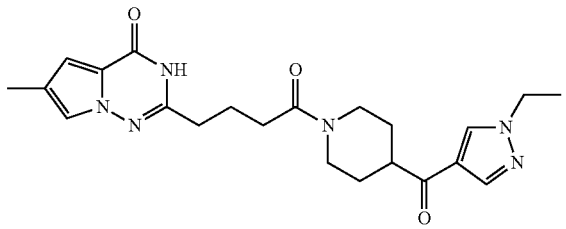 [SMILES: CCn1cc(C(=O)C2CCN(C(=O)CCCc3nn4cc(C)cc4c(=O)[nH]3)CC2)cn1]

Yield: 25 mg (19%) off-white solid;
$^1$H NMR (400 MHz, DMSO-$d_6$) δ 8.55 (s, 1H), 8.04 (s, 1H), 7.39 (d, 1H), 6.69 (s, 1H), 4.51-4.43 (m, 1H), 4.28-4.20 (m, 2H), 4.01-3.92 (m, 1H), 3.39-3.28 (m, 1H), 3.22-3.12 (m, 1H), 2.76-2.68 (m, 2H), 2.46-2.31 (m, 2H) 2.20 (s, 3H), 1.99-1.91 (m, 3H), 1.88-1.78 (m, 2H), 1.62-1.48 (m, 1H), 1.46 (t, J=8.0 Hz, 3H), 1.43-1.30 (m, 1H); LC/MS (B), Rt: 3.17 min; (M+H) 425.2.

2-{4-[4-(4-Methoxy-benzoyl)-piperidin-1-yl]-4-oxo-butyl}-7-methyl-3,7-dihydro-pyrrolo[2,3-d]pyrimidin-4-one ("C40")

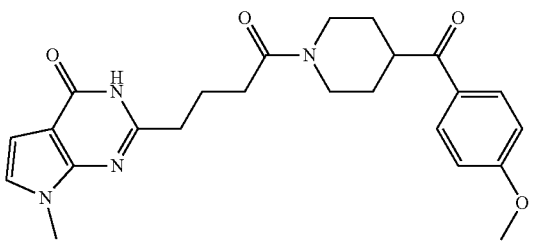 [SMILES: COc1ccc(C(=O)C2CCN(C(=O)CCCc3nc4c(ccn4C)c(=O)[nH]3)CC2)cc1]

Yield: 87 mg (50%) colorless solid;
$^1$H NMR (400 MHz, DMSO-$d_6$) δ 11.74 (s, 1H), 8.01 (d, J=7.0 Hz, 2H), 7.06 (d, J=7.0 Hz, 2H), 7.02 (d, J=3.2 Hz, 1H), 6.39 (d, J=3.2 Hz, 1H), 4.43 (d, J=13.2 Hz, 1H), 3.92 (d, J=13.2 Hz, 1H), 3.88 (s, 3H), 3.72-3.62 (m, 4H), 3.16 (t, J=11.6 Hz, 1H), 2.78-2.70 (m, 1H), 2.68-2.58 (m, 2H), 2.48-2.32 (m, 2H), 2.00-1.91 (m, 2H), 1.85-1.75 (m, 2H), 1.56-1.42 (m, 1H), 1.39-1.26 (m, 1H); LC/MS (B), Rt: 3.38 min; (M+H) 437.3.

2-{4-[4-(4-Fluoro-benzoyl)-piperidin-1-yl]-4-oxo-butyl}-7-methyl-3,7-dihydro-pyrrolo[2,3-d]pyrimidin-4-one ("C186")

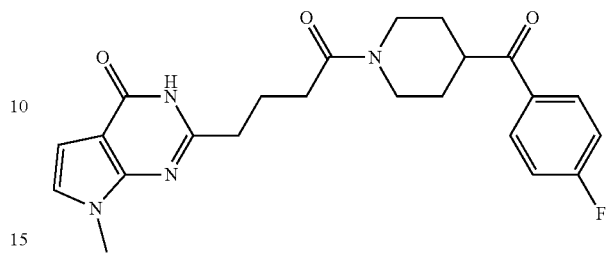

Yield: 79 mg (43%) colorless solid;
$^1$H NMR (400 MHz, DMSO-$d_6$) δ 11.74 (s, 1H), 8.12-8.09 (m, 2H), 7.34-7.30 (m, 2H), 7.00 (d, J=4.2 Hz, 1H), 6.38 (d, J=4.4 Hz, 1H), 4.42-4.35 (m, 1H), 3.95-3.89 (m, 1H), 3.75-7.63 (m, 4H), 3.24-3.15 (m, 1H), 2.80-2.60 (m, 3H), 2.47-2.32 (m, 2H), 1.99-1.89 (m, 2H), 1.84-1.77 (m, 2H), 1.58-1.43 (m, 1H), 1.40-1.26 (m, 1H); LC/MS (B), Rt: 3.48 min; (M+H) 425.2.

2-{4-[4-(3-Fluoro-4-methoxy-benzoyl)-piperidin-1-yl]-4-oxo-butyl}-7-methyl-3,7-dihydro-pyrrolo[2,3-d]pyrimidin-4-one ("C180")

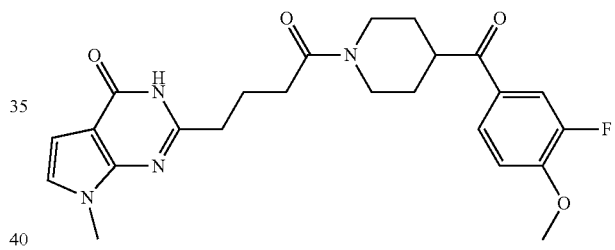

Yield: 140 mg (76%) colorless solid;
$^1$H NMR (400 MHz, DMSO-$d_6$) δ 11.74 (s, 1H), 7.89 (d, J=8.8 Hz, 1H), 7.83 (dd, J=2.0, 12.4 Hz, 1H), 7.31 (t, J=8.4 Hz, 1H), 7.02 (d, J=3.6 Hz, 1H), 6.39 (d, J=3.2 Hz, 1H), 4.40 (d, J=13.2 Hz, 1H), 3.99-3.88 (m, 4H), 3.73-3.62 (m, 4H), 3.22-3.12 (m, 1H), 2.77-2.71 (m, 1H), 2.68-2.61 (m, 2H), 2.41-2.36 (m, 2H), 1.98-1.92 (m, 2H), 1.82-1.74 (m, 2H) 1.55-1.46 (m, 1H), 1.40-1.26 (m, 1H); LC/MS (B), Rt: 3.49 min; (M+H) 455.3.

2-{4-[4-(6-Methoxy-pyridine-3-carbonyl)-piperidin-1-yl]-4-oxo-butyl}-7-methyl-3,7-dihydro-pyrrolo[2,3-d]pyrimidin-4-one ("C181")

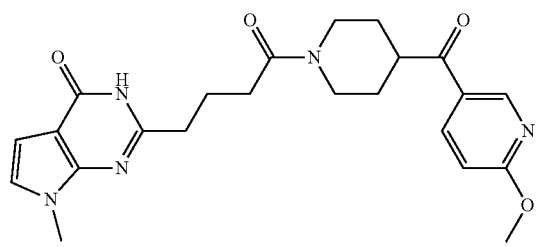 [SMILES: COc1ccc(C(=O)C2CCN(C(=O)CCCc3nc4c(ccn4C)c(=O)[nH]3)CC2)cn1]

Yield: 126 mg (71%) colorless solid;
¹H NMR (400 MHz, DMSO-d₆) δ 11.74 (s, 1H), 8.91 (d, J=2.0 Hz, 1H), 8.23 (dd, J=8.8, 2.4 Hz, 1H), 7.02 (d, J=3.2 Hz, 1H), 6.95 (d, J=8.8 Hz, 1H), 6.39 (d, J=3.2 Hz, 1H), 4.41 (d, J=12.8 Hz, 1H), 4.00-3.88 (m, 4H), 3.71-3.62 (m, 4H), 3.21-3.12 (m, 1H), 2.79-2.70 (m, 1H), 2.69-2.60 (m, 2H), 2.48-2.36 (m, 2H), 1.98-1.89 (m, 2H), 1.84-1.73 (m, 2H), 1.58-1.46 (m, 1H), 1.41-1.28 (m, 1H); LC/MS (B), Rt: 3.03 min; (M+H) 438.3.

7-Methyl-2-{4-oxo-4-[4-(5-phenyl-[1,3,4]oxadiazol-2-yl)-piperidin-1-yl]-butyl}-3,7-dihydro-pyrrolo[2,3-d]pyrimidin-4-one ("C184")

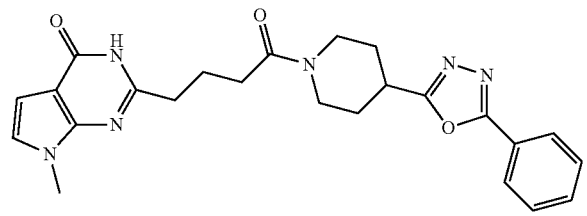 [SMILES: Cn1ccc2c(=O)[nH]c(CCCC(=O)N3CCC(c4nnc(-c5ccccc5)o4)CC3)nc21]

Yield: 134 mg (74%) colorless solid;
¹H NMR (400 MHz, DMSO-d₆) δ 11.75 (s, 1H), 7.99 (d, J=6.4 Hz, 2H), 7.64-7.58 (m, 3H), 7.01 (d, J=3.2 Hz, 1H), 6.39 (d, J=3.6 Hz, 1H), 4.32 (d, J=13.2 Hz, 1H), 3.91 (d, J=13.2 Hz, 1H), 3.67 (s, 3H), 3.40-3.19 (m, 2H), 2.92-2.83 (m, 1H), 2.69-2.61 (m, 2H), 2.47-2.39 (m, 2H), 2.17-2.04 (m, 2H), 1.99-1.91 (m, 2H), 1.82-1.71 (m, 1H), 1.69-1.58 (m, 1H); LC/MS (B), Rt: 3.19 min; (M+H) 447.3.

2-[4-(6-Amino-5-pyrimidin-2-yl-3',4',5',6'-tetrahydro-2'H-[3,4']bipyridinyl-1'-yl)-4-oxo-butyl]-7-methyl-3,7-dihydro-pyrrolo[2,3-d]pyrimidin-4-one ("C183")

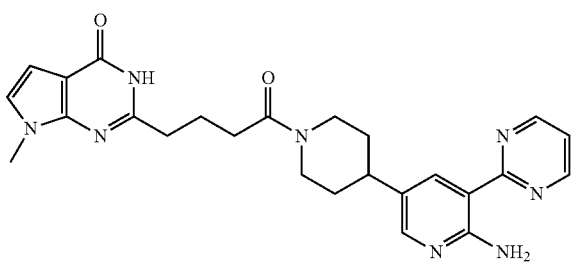 [SMILES: Cn1ccc2c(=O)[nH]c(CCCC(=O)N3CCC(c4cnc(N)c(-c5ncccn5)c4)CC3)nc21]

Yield: 148 mg (72%) colorless solid;
¹H NMR (400 MHz, DMSO-d₆) δ 11.75 (s, 1H), 8.91 (d, J=4.9 Hz, 2H), 8.53 (s, 1H), 8.05 (s, 1H), 7.62 (brs, 2H), 7.41 (t, J=4.4 Hz, 1H), 7.01 (s, 1H), 6.39 (d, J=3.3 Hz, 1H), 4.56 (d, J=13.2 Hz, 1H), 4.01 (d, J=13.2 Hz, 1H), 3.67 (s, 3H), 3.15-3.08 (m, 2H), 2.80-2.63 (m, 3H), 2.47-2.39 (m, 2H), 2.03-1.92 (m, 2H), 1.87-1.76 (m, 2H), 1.62-1.51 (m, 1H), 1.49-1.30 (m, 1H); LC/MS (B), Rt: 2.47 min; (M+H) 473.2.

6-Amino-1'-[4-(7-methyl-4-oxo-4,7-dihydro-3H-pyrrolo[2,3-d]pyrimidin-2-yl)-butyryl]-1',2',3',4',5',6'-hexahydro-[3,4']bipyridinyl-5-carbonitrile ("C182")

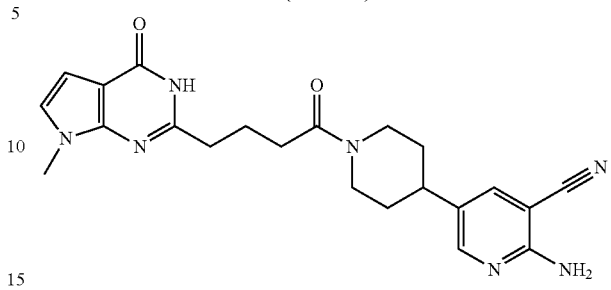

Yield: 129 mg (72%) colorless solid;
¹H NMR (400 MHz, DMSO-d₆) δ 11.74 (s, 1H), 8.13 (s, 1H), 7.71 (s, 1H), 7.00 (d, J=3.2 Hz, 1H), 6.69 (s, 2H), 6.39 (d, J=3.2 Hz, 1H), 4.52 (d, J=13.2 Hz, 1H), 3.96 (d, J=13.2 Hz, 1H), 3.67 (s, 3H), 3.13-3.02 (m, 2H), 2.70-2.60 (m, 3H), 2.47-2.38 (m, 2H), 2.01-1.93 (m, 2H), 1.76-1.68 (m, 2H), 1.58-1.46 (m, 1H), 1.44-1.30 (m, 1H); LC/MS (B), Rt: 2.14 min; (M+H) 420.2.

7-Methyl-2-{4-[4-(1-methyl-1H-pyrazole-4-carbonyl)-piperidin-1-yl]-4-oxo-butyl}-3,7-dihydro-pyrrolo[2,3-d]pyrimidin-4-one ("C190")

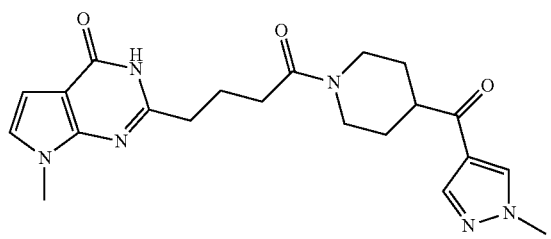 [SMILES: Cn1cc(C(=O)C2CCN(C(=O)CCCc3nc4c(ccn4C)c(=O)[nH]3)CC2)cn1]

Yield: 50 mg (54%) pale yellow solid;
¹H NMR (400 MHz, DMSO-d₆) δ 11.72 (s, 1H), 8.44 (s, 1H), 7.96 (s, 1H), 7.00 (d, J=2.8 Hz, 1H), 6.38 (d, J=3.2 Hz, 1H), 4.44-4.39 (m, 1H), 3.95-3.85 (m, 4H), 3.67 (s, 3H), 3.30-3.20 (m, 1H), 3.18-3.10 (m, 1H), 2.70-2.60 (m, 3H), 2.46-2.35 (m, 2H), 1.98-1.91 (m, 2H), 1.80-1.70 (m, 2H), 1.55-1.41 (m, 1H), 1.40-1.26 (m, 1H); LC/MS (B), Rt: 2.36 min; (M+H) 411.2.

1-Methyl-6-{4-[4-(4-methyl-benzoyl)-piperidin-1-yl]-4-oxo-butyl}-1,5-dihydro-pyrazolo[3,4-d]pyrimidin-4-one ("C234")

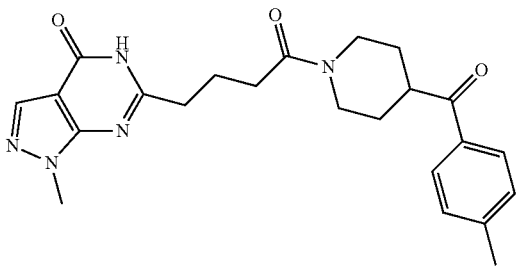 [SMILES: Cc1ccc(C(=O)C2CCN(C(=O)CCCc3nc4c(cnn4C)c(=O)[nH]3)CC2)cc1]

Yield: 65 mg (24%) colorless solid;
¹H NMR (400 MHz, DMSO-d₆) δ 12.02 (s, 1H), 7.98 (s, 1H), 7.91 (d, J=8.4 Hz, 2H), 7.35 (d, J=8.0 Hz, 2H), 4.40 (d, J=13.2 Hz, 1H), 3.99-3.87 (m, 4H), 3.68 (t, J=11.2 Hz, 1H), 3.18 (q, J=8.0 Hz, 1H), 2.80-2.65 (m, 3H), 2.46-2.38 (m, 5H), 2.01-1.91 (m, 2H), 1.82-1.73 (m, 2H), 1.56-1.45 (m, 1H), 1.42-1.28 (m, 1H); LC/MS (B), Rt: 3.49 min; (M+H) 422.2.

2-{4-[4-(4-Methyl-benzoyl)-piperidin-1-yl]-4-oxo-butyl}-3H-pyrrolo[2,1-f][1,2,4]triazin-4-one ("C235")

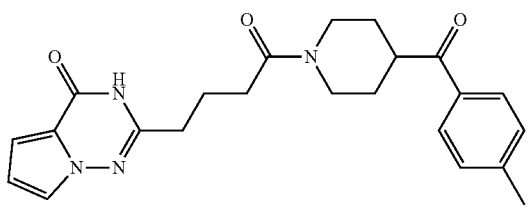 [SMILES: Cc1ccc(C(=O)C2CCN(C(=O)CCCc3nn4cccc4c(=O)[nH]3)CC2)cc1]

Yield: 60 mg (35%) colorless solid;
¹H NMR (400 MHz, DMSO-d₆) δ 11.58 (s, 1H), 7.91 (d, J=8.0 Hz, 2H), 7.53 (dd, J=1.6, 2.8 Hz, 1H), 7.35 (d, J=7.6 Hz, 2H), 6.83 (dd, J=1.6, 4.0 Hz, 1H), 6.49 (dd, J=2.4, 4.2 Hz, 1H), 4.45-4.38 (m, 1H), 3.96-3.89 (m, 1H), 3.75-3.62 (m, 1H), 3.22-3.13 (m, 1H), 2.76-2.68 (m, 1H), 2.56-2.53 (m, 2H), 2.45-2.39 (m, 5H), 1.95-1.89 (m, 2H), 1.83-1.74 (m, 2H), 1.58-1.45 (m, 1H), 1.40-1.26 (m, 1H); LC/MS (B), Rt: 3.98 min; (M+H) 407.3.

6-{4-[4-(4-Chloro-benzoyl)-piperidin-1-yl]-4-oxo-butyl}-1-methyl-1,5-dihydro-pyrazolo[3,4-d]pyrimidin-4-one ("C236")

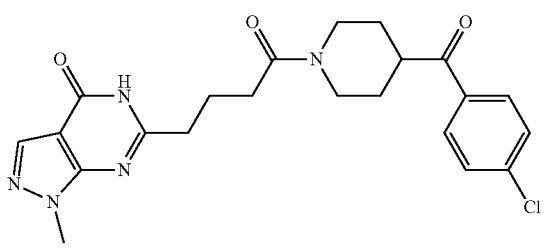 [SMILES: Cn1ncc2c(=O)[nH]c(CCCC(=O)N3CCC(C(=O)c4ccc(Cl)cc4)CC3)nc21]

Yield: 25 mg (10%) colorless solid;
¹H NMR (400 MHz, DMSO-d₆) δ 12.02 (s, 1H), 8.03 (d, J=6.4 Hz, 2H), 7.98 (s, 1H), 7.62 (d, J=6.8 Hz, 2H), 4.40 (d, J=13.2 Hz, 1H), 3.94-3.87 (m, 4H), 3.74-3.66 (m, 1H), 3.18 (t, J=11.2 Hz, 1H), 2.77-2.65 (m, 3H), 2.46-2.39 (m, 2H), 2.00-1.91 (m, 2H), 1.82-1.73 (m, 2H), 1.57-1.43 (m, 1H), 1.40-1.26 (m, 1H); LC/MS (B), Rt: 3.69 min; (M+H) 442.3.

2-{4-[4-(4-Chloro-benzoyl)-piperidin-1-yl]-4-oxo-butyl}-3H-pyrrolo[2,1-f][1,2,4]triazin-4-one ("C237")

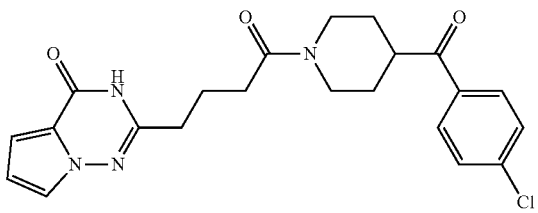 [SMILES: O=C(c1ccc(Cl)cc1)C1CCN(C(=O)CCCc2nn3cccc3c(=O)[nH]2)CC1]

Yield: 110 mg (60%) colorless solid;
¹H NMR (400 MHz, DMSO-d₆) δ 11.58 (s, 1H), 8.02 (d, J=8.8 Hz, 2H), 7.61 (d, J=8.4 Hz, 2H), 7.54-7.51 (m, 1H), 6.83 (dd, J=1.2, 4.2 Hz, 1H), 6.49 (dd, J=2.8, 4.0 Hz, 1H), 4.45-4.34 (m, 1H), 3.96-3.88 (m, 1H), 3.73-3.64 (m, 1H), 3.22-3.11 (m, 1H), 2.79-2.68 (m, 1H), 2.56-2.51 (m, 2H), 2.46-2.35 (m, 2H), 1.98-1.71 (m, 4H), 1.58-1.43 (m, 1H), 1.40-1.26 (m, 1H); LC/MS (B), Rt: 4.23 min; (M+H) 427.0.

6,7-Difluoro-2-{4-[4-(1-methyl-1H-pyrazole-4-carbonyl)-piperidin-1-yl]-4-oxo-butyl}-3H-pyrrolo[2,1-f][1,2,4]triazin-4-one ("C238")

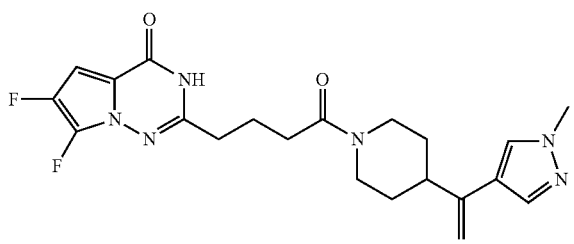 [SMILES: C=C(c1cnn(C)c1)C1CCN(C(=O)CCCc2nn3c(F)c(F)cc3c(=O)[nH]2)CC1]

Yield: 48 mg (32%) colorless solid;
¹H NMR (700 MHz, DMSO-d₆) δ 11.87 (s, 1H), 8.44 (s, 1H), 7.97 (s, 1H), 6.88 (d, J=5.2 Hz, 1H), 4.39 (d, J=13.1, 1H), 3.95-3.86 (m, 4H), 3.23 (t, J=11.5 Hz, 1H), 3.11 (t, J=13.1 Hz, 1H), 2.66 (t, J=12.7 Hz, 1H), 2.57 (t, J=7.4 Hz, 2H), 2.47-2.34 (m, 2H), 1.94-1.86 (m, 2H), 1.79-1.73 (m, 2H), 1.53-1.45 (m, 1H), 1.37-1.28 (m, 1H); LC/MS (A), Rt: 1.73 min; (M+H) 433.2.

2-{4-[4-(4-Methoxy-benzoyl)-piperidin-1-yl]-4-oxo-butyl}-5,6-dimethyl-3H-pyrimidin-4-one ("C239")

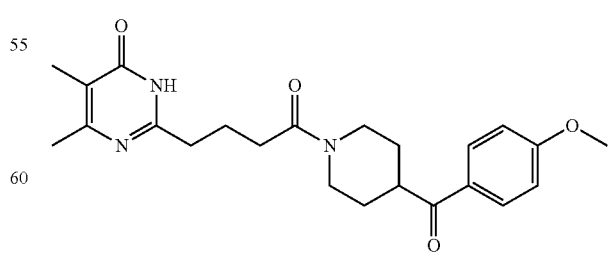

Yield: 60 mg (32%) colorless solid;
¹H NMR (400 MHz, DMSO-d₆) δ 12.10 (s, 1H), 7.95-7.91 (m, 2H), 7.01-6.98 (m, 2H), 4.38-4.30 (m, 1H), 3.89-

3.80 (m, 1H), 3.79 (s, 3H), 3.64-3.53 (m, 1H), 3.17-3.06 (m, 1H), 2.71-2.63 (m, 1H), 2.45-2.38 (m, 1H), 2.37-2.23 (m, 2H), 2.10 (s, 3H), 1.85-1.65 (m, 7H), 1.49-1.37 (m, 1H), 1.35-1.20 (m, 1H); LC/MS (B), Rt: 2.93 min; (M+H) 412.3.

2-{4-[4-(4-Fluoro-benzoyl)-piperidin-1-yl]-4-oxo-butyl}-5,6-dimethyl-3H-pyrimidin-4-one ("C240")

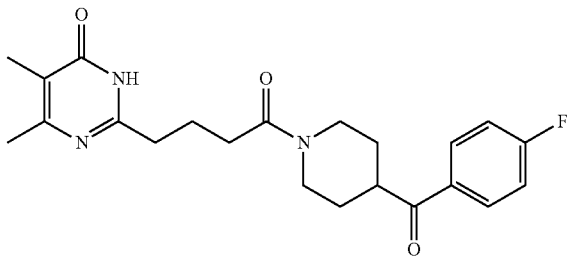 [SMILES: Cc1nc(CCCC(=O)N2CCC(C(=O)c3ccc(F)cc3)CC2)[nH]c(=O)c1C]

Yield: 55 mg (30%) colorless solid;
$^1$H NMR (400 MHz, DMSO-d$_6$) δ 12.17 (s, 1H), 8.12-8.08 (m, 2H), 7.41-7.35 (m, 2H), 4.44-4.38 (m, 1H), 3.96-3.88 (m, 1H), 3.75-3.66 (m, 1H), 3.22-3.12 (m, 1H), 2.79-2.69 (m, 1H), 2.48-2.40 (m, 1H), 2.42-2.30 (m, 2H), 2.12 (s, 3H), 1.91-1.75 (m, 7H), 1.56-1.42 (m, 1H), 1.40-1.26 (m, 1H); LC/MS (B), Rt: 3.02 min; (M+H) 400.2.

2-{4-[4-(6-Methoxy-pyridine-3-carbonyl)-piperidin-1-yl]-4-oxo-butyl}-5,6-dimethyl-3H-pyrimidin-4-one ("C241")

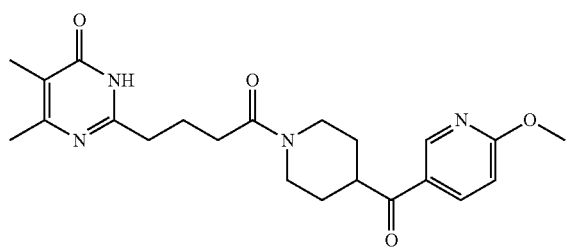

Yield: 55 mg (29%) colorless solid;
$^1$H NMR (400 MHz, DMSO-d$_6$) δ 12.17 (s, 1H), 8.91 (d, J=2.0 Hz, 1H), 8.23 (dd, J=2.8, 8.6 Hz, 1H), 6.95 (d, J=8.4 Hz, 1H), 4.46-4.39 (m, 1H), 3.95 (s, 3H), 3.94-3.88 (m, 1H), 3.70-3.63 (m, 1H), 3.22-3.14 (m, 1H), 2.80-2.68 (m, 1H), 2.50-2.45 (m, 1H), 2.41-2.32 (m, 2H), 2.17 (s, 3H), 1.93-1.75 (m, 7H), 1.68-1.55 (m, 1H), 1.32-1.30 (m, 1H); LC/MS (B), Rt: 2.59 min; (M+H) 413.3.

5,6-Dimethyl-2-{4-[4-(1-methyl-1H-pyrazole-4-carbonyl)-piperidin-1-yl]-4-oxo-butyl}-3H-pyrimidin-4-one ("C242")

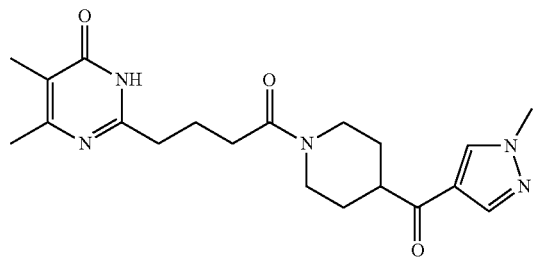

Yield: 70 mg (65%) colorless gum;
$^1$H NMR (400 MHz, DMSO-d$_6$) δ 12.30 (brs, 1H), 8.44 (s, 1H), 7.97 (s, 1H), 4.48-4.41 (m, 1H), 3.98-3.88 (m, 4H), 3.40-3.22 (m, 1H), 3.21-3.07 (m, 1H), 2.72-2.59 (m, 2H), 2.42-2.30 (m, 2H), 2.18 (s, 3H), 1.95-1.73 (m, 7H), 1.58-1.44 (m, 1H), 1.40-1.26 (m, 1H); LC/MS (B), Rt: 1.89 min; (M+H) 386.2.

2-{4-[4-(1-Ethyl-1H-pyrazole-4-carbonyl)-piperidin-1-yl]-4-oxo-butyl}-7-methyl-3,7-dihydro-pyrrolo[2,3-d]pyrimidin-4-one ("C243")

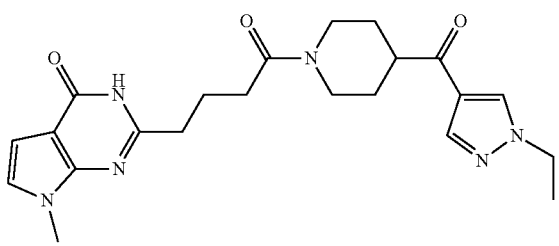 [SMILES: CCn1cc(C(=O)C2CCN(C(=O)CCCc3nc4c(ccn4C)c(=O)[nH]3)CC2)cn1]

Yield: 55 mg (32%) colorless solid;
$^1$H NMR (400 MHz, DMSO-d$_6$) δ 11.74 (s, 1H), 8.50 (s, 1H), 7.98 (s, 1H), 7.02 (d, J=3.2 Hz, 1H), 6.40 (d, J=3.6 Hz, 1H), 4.41-4.47 (m, 1H), 4.17 (q, J=7.2 Hz, 2H), 3.97-3.91 (m, 1H), 3.68 (s, 3H), 3.34-3.22 (m, 1H), 3.20-3.09 (m, 1H), 2.72-2.61 (m, 2H), 2.48-2.39 (m, 2H), 1.99-1.91 (m, 2H), 1.82-1.72 (m, 2H), 1.58-1.26 (m, 5H); LC/MS (B), Rt: 2.59 min; (M+H) 425.2.

2-{4-[4-(1-Isopropyl-1H-pyrazole-4-carbonyl)-piperidin-1-yl]-4-oxo-butyl}-7-methyl-3,7-dihydro-pyrrolo[2,3-d]pyrimidin-4-one ("C244")

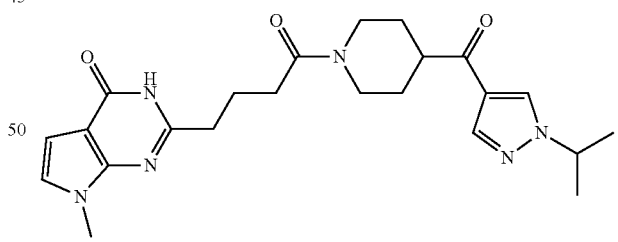

Yield: 58 mg (33%) colorless solid;
$^1$H NMR (400 MHz, DMSO-d$_6$) δ 11.74 (s, 1H), 8.52 (s, 1H), 7.98 (s, 1H), 7.02 (d, J=3.6 Hz, 1H), 6.39 (d, J=3.2 Hz, 1H), 4.55 (hept, J=6.8 Hz, 1H), 4.49-4.41 (m, 1H), 3.98-3.91 (m, 1H), 3.68 (s, 3H), 3.34-3.24 (m, 1H), 3.18-3.10 (m, 1H), 2.72-2.59 (m, 3H), 2.47-2.38 (m, 2H), 1.99-1.90 (m, 2H), 1.82-1.73 (m, 2H), 1.58-1.26 (m, 8H); LC/MS (B), Rt: 2.85 min; (M+H) 439.3.

6-(4-{4-[4-(1,1-Difluoro-ethyl)-benzoyl]-piperidin-1-yl}-4-oxo-butyl)-1-methyl-1,5-dihydro-pyrazolo[3,4-d]pyrimidin-4-one ("C245")

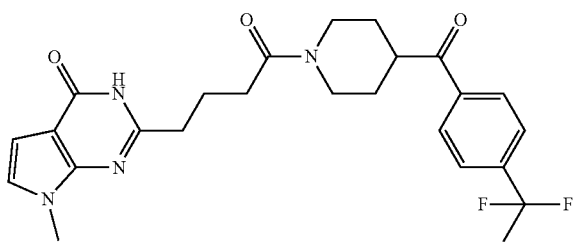 [SMILES: Cn1ccc2c(=O)[nH]c(CCCC(=O)N3CCC(C(=O)c4ccc(C(C)(F)F)cc4)CC3)nc21]

Yield: 69 mg (68%) colorless solid;
$^1$H NMR (500 MHz, DMSO-d$_6$) δ 11.98 (s, 1H), 8.09 (d, J=8.4 Hz, 2H), 7.96 (s, 1H), 7.72 (d, J=8.4 Hz, 2H), 4.44-4.33 (m, 1H), 3.96-3.89 (m, 1H), 3.87 (s, 3H), 3.73 (tt, J=11.2, 3.6 Hz, 1H), 3.24-3.14 (m, 1H), 2.80-2.71 (m, 1H), 2.67 (t, J=7.4 Hz, 2H), 2.45-2.33 (m, 2H), 2.00 (t, J=19.0 Hz, 3H), 1.98-1.92 (m, 2H), 1.85-1.76 (m, 2H), 1.51 (qd, J=13.0, 3.9 Hz, 1H), 1.34 (qd, J=12.5, 4.0 Hz, 1H); LC/MS (A), Rt: 1.97 min; (M+H) 472.2.

6-{4-[4-(3,4-Difluoro-benzoyl)-piperidin-1-yl]-4-oxo-butyl}-1-methyl-1,5-dihydro-pyrazolo[3,4-d]pyrimidin-4-one ("C246")

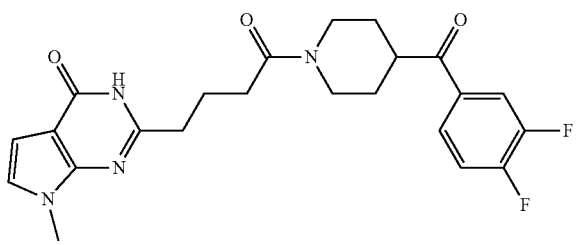

Yield: 47 mg (50%) colorless solid;
$^1$H NMR (500 MHz, DMSO-d$_6$) δ 11.99 (s, 1H), 8.07 (ddd, J=11.3, 7.9, 2.1 Hz, 1H), 7.97 (s, 1H), 7.94-7.90 (m, 1H), 7.62 (dt, J=10.3, 8.3 Hz, 1H), 4.44-4.35 (m, 1H), 3.95-3.89 (m, 1H), 3.88 (s, 3H), 3.71 (tt, J=11.2, 3.5 Hz, 1H), 3.25-3.13 (m, 1H), 2.79-2.71 (m, 1H), 2.68 (t, J=7.4 Hz, 2H), 2.45-2.38 (m, 2H), 1.96 (p, J=7.4 Hz, 2H), 1.86-1.76 (m, 2H), 1.49 (qd, J=12.6, 3.8 Hz, 1H), 1.33 (qd, J=12.5, 4.0 Hz, 1H); LC/MS (A), Rt: 1.88 min; (M+H) 444.2.

2-{4-[4-(4-Chloro-benzoyl)-piperidin-1-yl]-4-oxo-butyl}-3,5,7,8-tetrahydro-pyrano[4,3-d]pyrimidin-4-one trifluoroacetate ("C247")

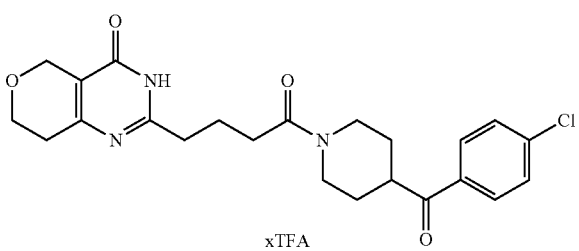 [SMILES: O=C(c1ccc(Cl)cc1)C1CCN(C(=O)CCCc2nc3c(c(=O)[nH]2)COCC3)CC1]

Yield: 54 mg (30%) colorless solid;
$^1$H NMR (400 MHz, Methanol-d$_4$) δ 7.91 (d, J=6.8 Hz, 2H), 7.44 (d, J=6.8 Hz, 2H), 4.43-4.38 (m, 3H), 3.93 (d, J=13.6 Hz, 1H), 3.89-3.83 (m, 2H), 3.72-3.65 (m, 1H), 2.82-2.73 (m, 1H), 2.68-2.57 (m, 4H), 2.49-2.41 (m, 2H), 2.01-1.90 (m, 2H), 1.85-1.76 (m, 2H), 1.61-1.38 (m, 2H); LC/MS (B), Rt: 3.42 min; (M+H) 444.0.

2-{4-[4-(3,4-Difluoro-benzoyl)-piperidin-1-yl]-4-oxo-butyl}-7-methyl-3,7-dihydro-pyrrolo[2,3-d]pyrimidin-4-one ("C248")

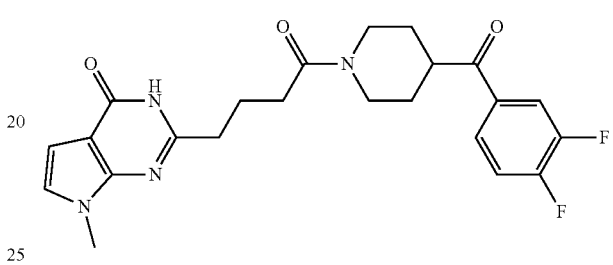

Yield: 77 mg (81%) colorless solid;
$^1$H NMR (400 MHz, DMSO-d$_6$) δ 11.71 (s, 1H), 8.07 (ddd, J=11.3, 7.9, 2.1 Hz, 1H), 8.01-7.83 (m, 1H), 7.62 (dt, J=10.3, 8.3 Hz, 1H), 7.01 (d, J=3.3 Hz, 1H), 6.39 (d, J=3.3 Hz, 1H), 4.40 (d, J=13.1 Hz, 1H), 3.92 (d, J=13.2 Hz, 1H), 3.78-3.64 (m, 4H), 3.18 (t, J=11.9 Hz, 1H), 2.75 (t, J=11.5 Hz, 1H), 2.63 (t, J=7.4 Hz, 2H), 2.41 (td, J=7.3, 2.8 Hz, 2H), 2.00-1.88 (m, 2H), 1.88-1.75 (m, 2H), 1.49 (qd, J=12.9, 4.4 Hz, 1H), 1.33 (qd, J=12.4, 11.9, 3.8 Hz, 1H); LC/MS (A), Rt: 1.94 min; (M+H) 443.2.

2-(4-{4-[4-(1,1-Difluoro-ethyl)-benzoyl]-piperidin-1-yl}-4-oxo-butyl)-7-methyl-3,7-dihydro-pyrrolo[2,3-d]pyrimidin-4-one ("C249")

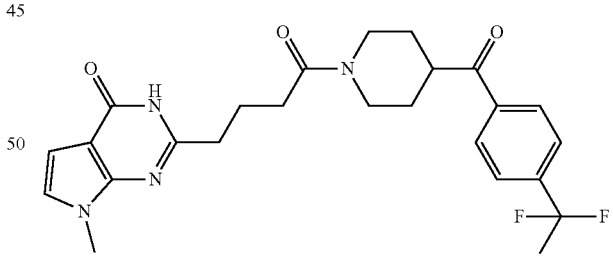

Yield: 67 mg (66%) colorless solid;
$^1$H NMR (400 MHz, DMSO-d$_6$) δ 11.68 (s, 1H), 8.09 (d, J=8.4 Hz, 2H), 7.72 (d, J=8.5 Hz, 2H), 7.00 (d, J=3.3 Hz, 1H), 6.38 (d, J=3.3 Hz, 1H), 4.39 (d, J=13.5 Hz, 1H), 3.91 (d, J=12.6 Hz, 1H), 3.77-3.68 (m, 1H), 3.67 (s, 3H), 3.19 (t, J=11.9 Hz, 1H), 2.76 (t, J=11.5 Hz, 1H), 2.63 (t, J=7.5 Hz, 2H), 2.40 (td, J=7.2, 3.1 Hz, 2H), 2.05-1.90 (m, 5H), 1.87-1.74 (m, 2H), 1.60-1.43 (m, 1H), 1.43-1.28 (m, 1H); LC/MS (A), Rt: 2.03 min; (M+H) 471.2.

127

1-[4-(4-Methoxy-benzoyl)-piperidin-1-yl]-4-phthalazin-1-yl-butan-1-one ("C250")

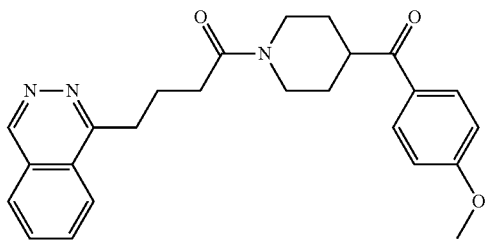 [SMILES: COc1ccc(C(=O)C2CCN(C(=O)CCCc3nncc4ccccc34)CC2)cc1]

Yield: 13 mg (15%) pale yellow solid;
¹H NMR (400 MHz, DMSO-d₆) δ 9.54 (s, 1H), 8.42-8.35 (m, 1H), 8.18-8.12 (m, 1H), 8.08-7.95 (m, 4H), 7.16-6.98 (m, 2H), 4.51-4.39 (m, 1H), 3.98-3.88 (m, 1H), 3.85 (s, 3H), 3.66 (tt, J=11.2, 3.6 Hz, 1H), 3.34 (dd, J=8.7, 6.8 Hz, 2H), 3.26-3.13 (m, 1H), 2.83-2.71 (m, 1H), 2.56-2.48 (m, 2H, overlapped with DMSO-d6), 2.09-1.97 (m, 2H), 1.82-1.71 (m, 2H), 1.58-1.44 (m, 1H), 1.44-1.29 (m, 1H); LC/MS (A), Rt: 1.77 min; (M+H) 418.2.

6-Ethyl-2-{4-[4-(4-methoxy-benzoyl)-piperidin-1-yl]-4-oxo-butyl}-3H-pyrimidin-4-one ("C251")

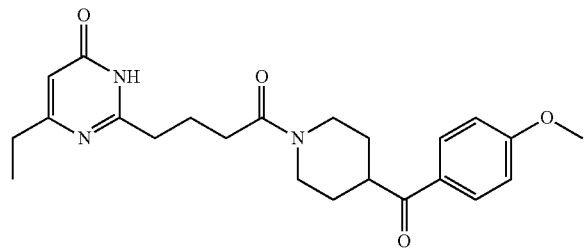 [SMILES: CCc1cc(=O)[nH]c(CCCC(=O)N2CCC(C(=O)c3ccc(OC)cc3)CC2)n1]

Yield: 30 mg (15%) pale brown gum;
¹H NMR (400 MHz, DMSO-d₆) δ 7.98 (d, J=8.8 Hz, 2H), 7.07 (d, J=8.8 Hz, 2H), 6.02 (s, 1H), 4.41 (d, J=12.8 Hz, 1H), 3.89-3.86 (m, 1H), 3.85 (s, 3H), 3.73-3.63 (m, 1H), 3.24-3.12 (m, 1H), 2.78-2.68 (m, 1H), 2.61-2.55 (m, 2H), 2.46-2.34 (m, 4H), 1.93-1.84 (m, 2H), 1.81-1.72 (m, 2H), 1.58-1.44 (m, 1H), 1.41-1.28 (m, 1H), 1.13 (t, J=7.6 Hz, 3H); LC/MS (B), Rt: 3.01 min; (M+H) 412.3.

6-Ethyl-2-{4-[4-(4-fluoro-benzoyl)-piperidin-1-yl]-4-oxo-butyl}-3H-pyrimidin-4-one ("C252")

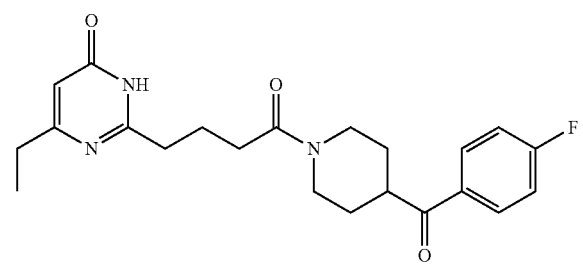 [SMILES: CCc1cc(=O)[nH]c(CCCC(=O)N2CCC(C(=O)c3ccc(F)cc3)CC2)n1]

Yield: 75 mg (39%) pale brown gum;
¹H NMR (400 MHz, DMSO-d₆) δ 8.14-8.06 (m, 2H), 7.38 (t, J=8.8 Hz, 2H), 6.07 (s, 1H), 4.39 (d, J=12.8 Hz, 1H), 3.90 (d, J=13.2 Hz, 1H), 3.77-3.68 (m, 1H), 3.17 (t, J=12.0 Hz, 1H), 2.78-2.69 (m, 1H), 2.62-2.54 (m, 2H), 2.48-2.38 (m, 4H), 1.97-1.77 (m, 4H), 1.57-1.43 (m, 1H), 1.40-1.28 (m, 1H), 1.13 (t, J=7.6 Hz, 3H); LC/MS (B), Rt: 3.16 min; (M+H) 400.0.

6-Ethyl-2-{4-[4-(6-methoxy-pyridine-3-carbonyl)-piperidin-1-yl]-4-oxo-butyl}-3H-pyrimidin-4-one ("C253")

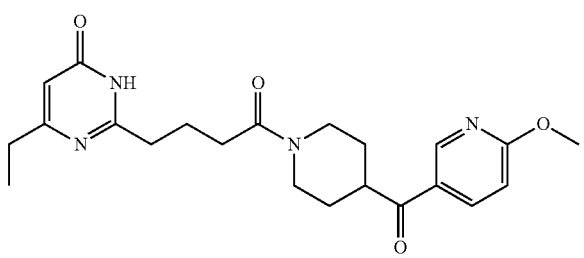 [SMILES: CCc1cc(=O)[nH]c(CCCC(=O)N2CCC(C(=O)c3ccc(OC)nc3)CC2)n1]

Yield: 35 mg (17%) pale brown gum;
¹H NMR (400 MHz, DMSO-d₆) δ 8.91 (d, J=2.4 Hz, 1H), 8.23 (dd, J=2.4, 8.4 Hz, 1H), 6.95 (d, J=8.4 Hz, 1H), 6.05 (s, 1H), 4.40 (d, J=13.2 Hz, 1H), 3.96 (s, 3H), 3.94 (d, J=13.6 Hz, 1H), 3.71-3.62 (m, 1H), 3.22-3.13 (m, 1H), 2.79-2.69 (m, 1H), 2.61-2.54 (m, 2H), 2.48-2.36 (m, 4H), 1.95-1.75 (m, 4H), 1.57-1.43 (m, 1H), 1.40-1.28 (m, 1H), 1.13 (t, J=7.6 Hz, 3H); LC/MS (B), Rt: 2.73 min; (M+H) 413.2.

6-Isopropyl-2-{4-[4-(4-methoxy-benzoyl)-piperidin-1-yl]-4-oxo-butyl}-3H-pyrimidin-4-one trifluoroacetate ("C254")

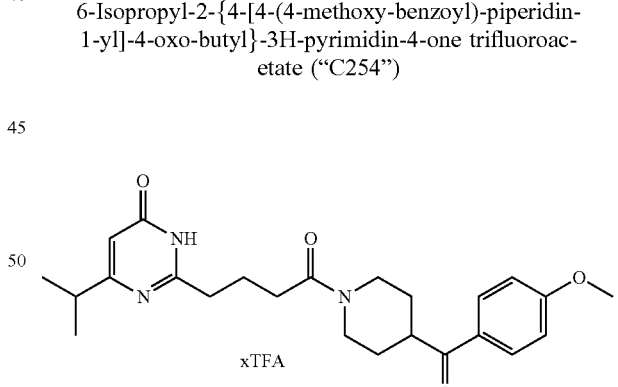

Yield: 120 mg (47%) pale brown gum;
¹H NMR (400 MHz, DMSO-d₆) δ 7.99 (dd, J=2.0, 7.2 Hz, 2H), 7.06 (dd, J=1.6, 7.0 Hz, 2H), 6.05 (s, 1H), 4.40 (d, J=12.8 Hz, 1H), 4.01-3.81 (m, 4H), 3.71-3.61 (m, 1H), 3.23-3.13 (m, 1H), 2.80-2.56 (m, 4H), 2.45-2.38 (m, 2H), 1.97-1.8 (m, 2H), 1.82-1.72 (m, 2H), 1.58-1.43 (m, 1H), 1.40-1.28 (m, 1H), 1.15 (d, J=6.8 Hz, 6H); LC/MS (B), Rt: 3.32 min; (M+H) 426.2.

2-{4-[4-(4-Fluorobenzoyl)-1-piperidyl]-4-oxo-butyl}-4-isopropyl-1H-pyrimidin-6-one trifluoroacetate ("C255")

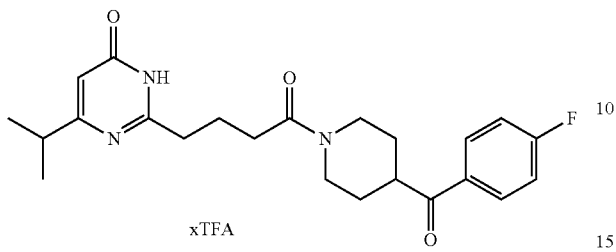

xTFA

Yield: 110 mg (46%) pale brown gum
$^1$H NMR (400 MHz, DMSO-d$_6$) δ 8.12-8.08 (m, 2H), 7.40-7.36 (m, 2H), 6.08 (s, 1H), 4.39 (d, J=13.2 Hz, 1H), 3.90 (d, J=14.0 Hz, 1H), 3.77-3.68 (m, 1H), 3.17 (t, J=11.2 Hz, 1H), 2.81-2.58 (m, 4H), 2.47-2.38 (m, 2H), 1.98-1.87 (m, 2H), 1.85-1.75 (m, 2H), 1.57-1.42 (m, 1H), 1.40-1.28 (m, 1H), 1.15 (d, J=6.8 Hz, 6H). LC/MS (B), Rt: 3.42 min; (M+H) 414.2

4-Isopropyl-2-{4-[4-(6-methoxypyridine-3-carbonyl)-1-piperidyl]-4-oxo-butyl}-1H-pyrimidin-6-one trifluoroacetate ("C256")

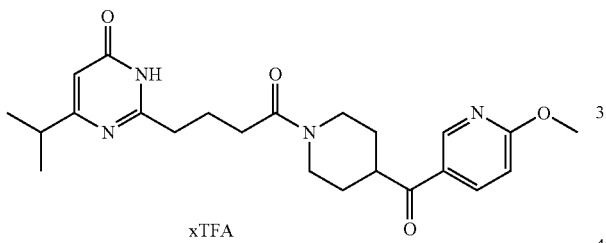

xTFA

Yield: 52 mg (19%) pale brown gum;
$^1$H NMR (400 MHz, DMSO-d$_6$) δ 8.91 (d, J=2.4 Hz, 1H), 8.23 (dd, J=2.4, 8.8 Hz, 1H), 6.95 (d, J=8.8 Hz, 1H), 6.06 (s, 1H), 4.39 (d, J=12.8 Hz, 1H), 4.00-3.85 (m, 4H), 3.72-3.62 (m, 1H), 3.17 (t, J=12.0 Hz, 1H), 2.80-2.55 (m, 4H), 2.47-2.38 (m, 2H), 1.97-1.76 (m, 4H), 1.58-1.43 (m, 1H), 1.41-1.28 (m, 1H), 1.15 (d, J=6.8 Hz, 6H); LC/MS (B), Rt: 3.00 min; (M+H) 427.2.

4-Isopropyl-2-{4-[4-(1-methylpyrazole-4-carbonyl)-1-piperidyl]-4-oxo-butyl}-1H-pyrimidin-6-one trifluoroacetate ("C257")

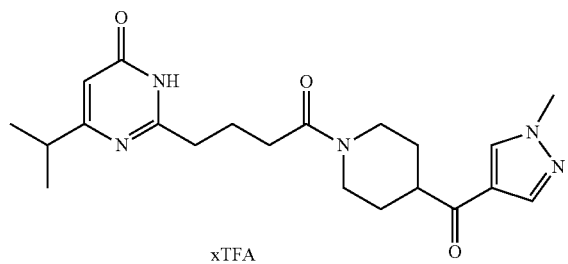 [SMILES: CC(C)c1cc(=O)[nH]c(CCCC(=O)N2CCC(C(=O)c3cnn(C)c3)CC2)n1]

xTFA

Yield: 55 mg (24%) pale brown gum;
$^1$H NMR (400 MHz, DMSO-d$_6$) δ 8.45 (s, 1H), 7.96 (s, 1H), 6.10 (s, 1H), 4.40 (d, J=12.8 Hz, 1H), 3.95-3.85 (m, 4H), 3.29-3.19 (m, 1H), 3.11 (t, J=12.0 Hz, 1H), 2.74-2.58 (m, 4H), 2.44-2.38 (m, 2H), 1.96-1.85 (m, 2H), 1.81-1.72 (m, 2H), 1.57-1.43 (m, 1H), 1.40-1.28 (m, 1H), 1.15 (d, J=6.8 Hz, 6H); LC/MS (B), Rt: 2.31 min; (M+H) 400.2.

4-(1,2-Benzoxazol-3-yl)-1-[4-(4-methoxybenzoyl)-1-piperidyl]butan-1-one ("C258")

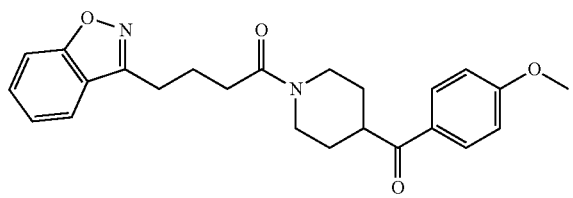 [SMILES: COc1ccc(C(=O)C2CCN(C(=O)CCCc3noc4ccccc34)CC2)cc1]

Yield: 41 mg (31%) colorless solid;
$^1$H NMR (400 MHz, DMSO-d$_6$) δ 8.00 (d, J=8.8 Hz, 2H), 7.93 (d, J=8.0 Hz, 1H), 7.72 (d, J=8.4 Hz, 1H), 7.68-7.63 (m, 1H), 7.43-7.38 (m, 1H), 7.06 (d, J=9.2 Hz, 2H), 4.43 (d, J=12.8 Hz, 1H), 3.96-3.83 (m, 4H), 3.71-3.62 (m, 1H), 3.22-3.12 (m, 1H), 3.08-3.00 (m, 2H), 2.81-2.71 (m, 1H), 2.49-2.42 (m, 2H), 2.07-1.97 (m, 2H), 1.82-1.74 (m, 2H), 1.56-1.29 (m, 2H); LC/MS (B), Rt: 4.57 min; (M+H) 407.0.

4-(1,2-Benzoxazol-3-yl)-1-[4-(4-fluorobenzoyl)-1-piperidyl]butan-1-one ("C259")

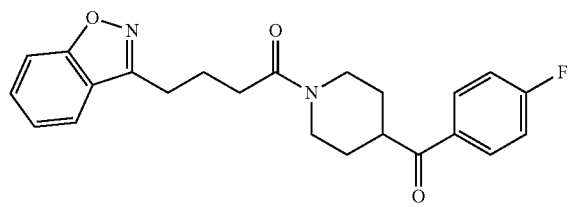 [SMILES: O=C(c1ccc(F)cc1)C1CCN(C(=O)CCCc2noc3ccccc23)CC1]

Yield: 15 mg (12%) colorless solid;
$^1$H NMR (400 MHz, DMSO-d$_6$) δ 8.12-8.09 (m, 2H), 7.92 (d, J=8.0 Hz, 1H), 7.71 (d, J=8.4 Hz, 1H), 7.69-7.62 (m, 1H), 7.43-7.34 (m, 3H), 4.43 (d, J=13.2 Hz, 1H), 3.90 (d, J=13.6 Hz, 1H), 3.77-3.68 (m, 1H), 3.22-3.13 (m, 1H), 3.07-3.00 (m, 2H), 2.81-2.72 (m, 1H), 2.49-2.42 (m, 2H), 2.07-1.97 (m, 2H), 1.85-1.76 (m, 2H), 1.55-1.29 (m, 2H); LC/MS (B), Rt: 4.69 min; (M+H) 395.0.

4-(1,2-Benzoxazol-3-yl)-1-[4-(6-methoxypyridine-3-carbonyl)-1-piperidyl]butan-1-one ("C259a")

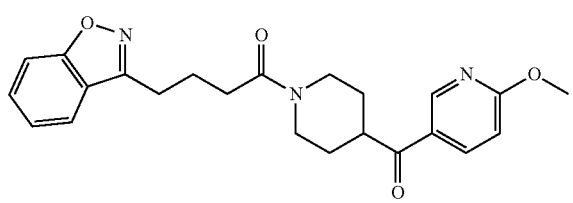 [SMILES: COc1ccc(C(=O)C2CCN(C(=O)CCCc3noc4ccccc34)CC2)cn1]

Yield: 57 mg (43%) colorless solid;
¹H NMR (400 MHz, DMSO-d₆) δ 8.92 (d, J=2.4 Hz, 1H), 8.27-8.21 (m, 1H), 7.92 (d, J=8.0 Hz, 1H), 7.71 (d, J=8.4 Hz, 1H), 7.68-7.62 (m, 1H), 7.42-7.38 (m, 1H), 6.95 (d, J=8.8 Hz, 1H), 4.43 (d, J=13.2 Hz, 1H), 3.95 (s, 3H), 3.93-3.88 (m, 1H), 3.71-3.62 (m, 1H), 3.22-3.12 (m, 1H), 3.07-3.00 (m, 2H), 2.81-2.71 (m, 1H), 2.49-2.42 (m, 2H), 2.08-1.97 (m, 2H), 1.85-1.77 (m, 2H), 1.57-1.29 (m, 2H); LC/MS (B), Rt: 4.26 min; (M+H) 408.0.

4-(1,2-Benzoxazol-3-yl)-1-[4-(1-methylpyrazole-4-carbonyl)-1-piperidyl]butan-1-one ("C260")

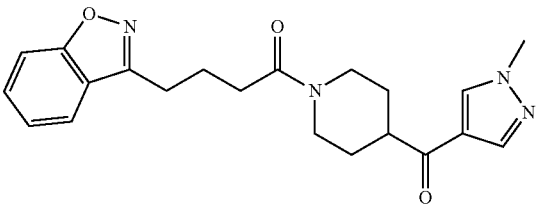 [SMILES: Cn1cc(C(=O)C2CCN(C(=O)CCCc3noc4ccccc34)CC2)cn1]

Yield: 113 mg (30%) off-white gum;
¹H NMR (400 MHz, DMSO-d₆) δ 8.45 (s, 1H), 7.94 (s, 1H), 7.92 (d, J=8.8 Hz, 1H), 7.72 (d, J=8.4 Hz, 1H), 7.69-7.63 (m, 1H), 7.43-7.38 (m, 1H), 4.44 (d, J=13.2 Hz, 1H), 3.95-3.84 (m, 4H), 3.28-3.19 (m, 1H), 3.18-3.07 (m, 1H), 3.06-2.99 (m, 2H), 2.75-2.65 (m, 1H), 2.58-2.40 (m, 2H), 1.96-2.07 (m, 2H), 1.81-1.72 (m, 2H), 1.46-1.29 (m, 2H); LC/MS (B), Rt: 3.47 min; (M+H) 381.0.

4-Ethyl-2-{4-[4-(1-methylpyrazole-4-carbonyl)-1-piperidyl]-4-oxo-butyl}-1H-pyrimidin-6-one ("C261")

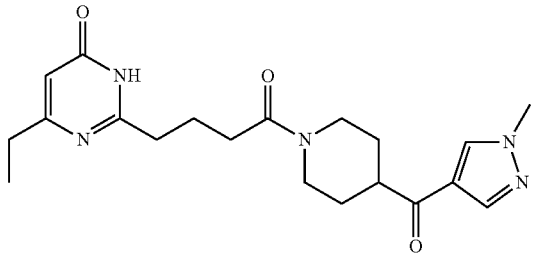 [SMILES: CCc1cc(=O)[nH]c(CCCC(=O)N2CCC(C(=O)c3cnn(C)c3)CC2)n1]

2-{4-[4-(3,4-Difluorobenzoyl)-1-piperidyl]-4-oxo-butyl}-3,5,7,8-tetrahydro-pyrano[4,3-d]pyrimidin-4-one ("C262")

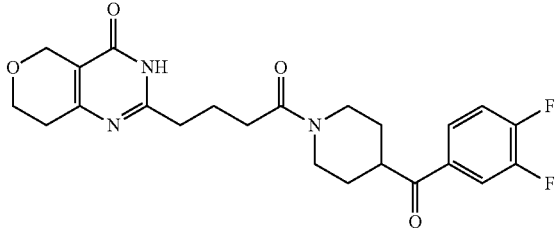 [SMILES: O=C(c1ccc(F)c(F)c1)C1CCN(C(=O)CCCc2nc3c(c(=O)[nH]2)COCC3)CC1]

Yield: 63 mg (63%) colorless solid;
¹H NMR (500 MHz, DMSO-d₆) δ 12.28 (s, 1H), 8.06 (ddd, J=11.3, 7.9, 2.1 Hz, 1H), 7.95-7.87 (m, 1H), 7.61 (dt, J=10.3, 8.3 Hz, 1H), 4.44-4.36 (m, 1H), 4.33 (s, 2H), 3.95-3.88 (m, 1H), 3.83 (t, J=5.6 Hz, 2H), 3.70 (tt, J=11.2, 3.6 Hz, 1H), 3.22-3.11 (m, 1H), 2.79-2.70 (m, 1H), 2.57- 2.51 (m, 4H), 2.43-2.30 (m, 2H), 1.92-1.83 (m, 2H), 1.83-1.76 (m, 2H), 1.48 (qd, J=12.6, 3.9 Hz, 1H), 1.33 (qd, J=12.5, 4.0 Hz, 1H); LC/MS (A), Rt: 1.80 min; (M+H) 446.2.

2-{4-{4-[4-(1,1-Difluoroethyl)benzoyl]-1-piperidyl}-4-oxo-butyl}-3,5,7,8-tetra-hydropyrano[4,3-d]pyrimidin-4-one ("C263")

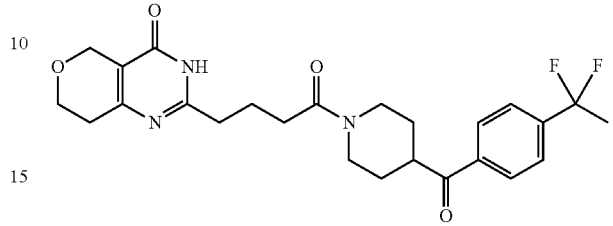

Yield: 53 mg (53%) colorless solid;
¹H NMR (500 MHz, DMSO-d₆) δ 12.28 (s, 1H), 8.09 (d, J=8.4 Hz, 2H), 7.72 (d, J=8.4 Hz, 2H), 4.43-4.36 (m, 1H), 4.34 (s, 2H), 3.95-3.87 (m, 1H), 3.83 (t, J=5.6 Hz, 2H), 3.73 (tt, J=11.2, 3.6 Hz, 1H), 3.23-3.14 (m, 1H), 2.80-2.72 (m, 1H), 2.56-2.51 (m, 4H), 2.43-2.30 (m, 2H), 2.00 (t, J=19.0 Hz, 3H), 1.88 (p, J=7.7 Hz, 2H), 1.84-1.75 (m, 2H), 1.50 (qd, J=12.8, 3.7 Hz, 1H), 1.35 (qd, J=12.6, 4.0 Hz, 1H); LC/MS (A), Rt: 1.90 min; (M+H) 474.2.

1-[4-(1-Methylpyrazole-4-carbonyl)-1-piperidyl]-4-phthalazin-1-yl-butan-1-one ("C266")

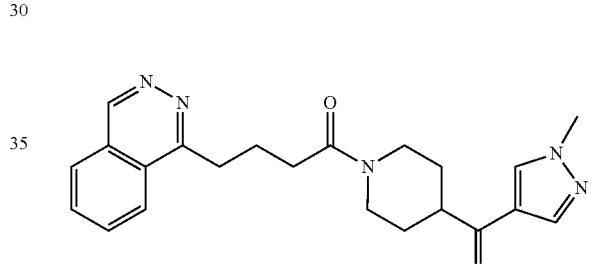

Yield: 23 mg (25%) pale yellow foam;
¹H NMR (500 MHz, DMSO-d₆) δ 9.55 (d, J=0.9 Hz, 1H), 8.45 (s, 1H), 8.39 (d, J=8.1 Hz, 1H), 8.18-8.14 (m, 1H), 8.08-8.00 (m, 2H), 7.97 (d, J=0.7 Hz, 1H), 4.45 (d, J=12.7 Hz, 1H), 3.94 (d, J=13.2 Hz, 1H), 3.89 (s, 3H), 3.38-3.33 (m, 2H), 3.25 (tt, J=11.4, 3.9 Hz, 1H), 3.17-3.10 (m, 1H), 2.72 (td, J=12.6, 2.7 Hz, 1H), 2.56-2.52 (m, 2H), 2.11-2.00 (m, 2H), 1.84-1.73 (m, 2H), 1.50 (qd, J=12.2, 4.1 Hz, 1H), 1.38 (qd, J=12.3, 4.2 Hz, 1H). LC/MS (A), Rt: 1.30/1.36 min; (M+H) 392.2.

7-Fluoro-2-{4-[4-(1-methyl-1H-pyrazole-4-carbonyl)-piperidin-1-yl]-4-oxo-butyl}-3H-pyrrolo[2,1-f][1,2,4]triazin-4-one ("C282")

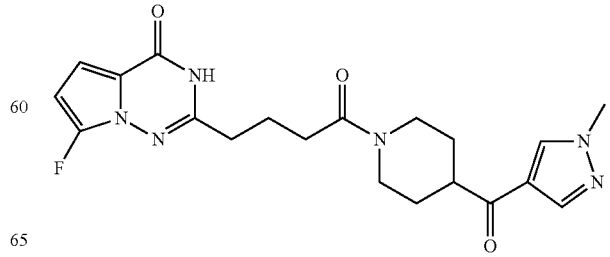

Yield: 25 mg (27%) colorless solid;
¹H NMR (500 MHz, DMSO-d₆) δ 11.60 (s, 1H), 8.43 (s, 1H), 7.95 (d, J=0.4 Hz, 1H), 6.81-6.77 (m, 1H), 6.21 (dd, J=4.6, 3.7 Hz, 1H), 4.44-4.34 (m, 1H), 3.97-3.83 (m, 4H), 3.22 (tt, J=11.4, 3.6 Hz, 1H), 3.15-3.07 (m, 1H), 2.71-2.63 (m, 1H), 2.55 (t, J=7.4 Hz, 2H), 2.41 (td, J=7.2, 2.4 Hz, 2H), 1.91 (p, J=7.4 Hz, 2H), 1.80-1.72 (m, 2H), 1.49 (qd, J=12.7, 3.9 Hz, 1H), 1.34 (qd, J=12.6, 4.1 Hz, 1H); LC/MS (A), Rt: 1.62 min; (M+H) 415.3.

| No. | Name/structure |
| --- | --- |
| "C14" | 3-[4-[-4-(3-Fluoro-4-methoxy-benzoyl)-1-piperidyl]-4-oxo-butyl]-2H-pyrrolo[1,2-a]pyrazin-1-one |
| "C16" | 2-Amino-5-[1-[4-(1-oxo-2H-pyrrolo[1,2-a]pyrazin-3-yl)butanoyl]piperidine-4-carbonyl]pyridine-3-carbonitrile |
| "C17" | 3-[4-[4-(6-Amino-5-pyrimidin-2-yl-pyridine-3-carbonyl)-1-piperidyl]-4-oxo-butyl]-2H-pyrrolo[1,2-a]pyrazin-1-one |
| "C18" | 3-[4-[4-(4-Fluorobenzoyl)-1-piperidyl]-4-oxo-butyl]-2H-pyrrolo[1,2-a]pyrazin-1-one |
| "C20" | 3-[4-[4-[4-(1-Hydroxy-1-methyl-ethyl)benzoyl]-1-piperidyl]-4-oxo-butyl]-2H-pyrrolo[1,2-a]pyrazin-1-one |

-continued

| No. | Name/structure |
|---|---|
| "C21" | 3-[4-[4-(6-Methoxypyridazine-3-carbonyl)-1-piperidyl]-4-oxo-butyl]-2H-pyrrolo[1,2-a]pyrazin-1-one 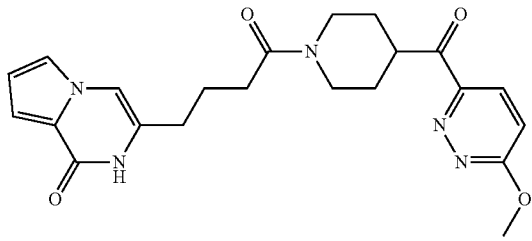 [SMILES: COc1ccc(C(=O)C2CCN(C(=O)CCCc3cn4cccc4c(=O)[nH]3)CC2)nn1] |
| "C23" | 3-[4-[4-(1-Methylpyrazole-3-carbonyl)-1-piperidyl]-4-oxo-butyl]-2H-pyrrolo[1,2-a]pyrazin-1-one 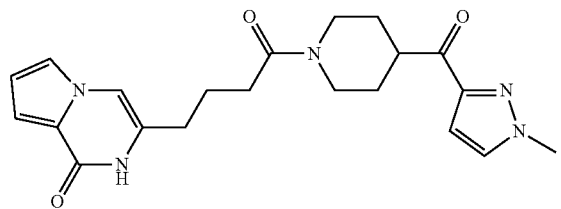 [SMILES: Cn1ccc(C(=O)C2CCN(C(=O)CCCc3cn4cccc4c(=O)[nH]3)CC2)n1] |
| "C24" | 3-[4-[4-(Isoxazole-4-carbonyl)-1-piperidyl]-4-oxo-butyl]-2H-pyrrolo[1,2-a]pyrazin-1-one 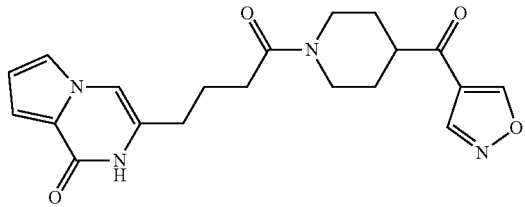 [SMILES: O=C(c1cnoc1)C1CCN(C(=O)CCCc2cn3cccc3c(=O)[nH]2)CC1] |
| "C25" | 3-[4-[4-(1-Methylimidazole-4-carbonyl)-1-piperidyl]-4-oxo-butyl]-2H-pyrrolo[1,2-a]pyrazin-1-one 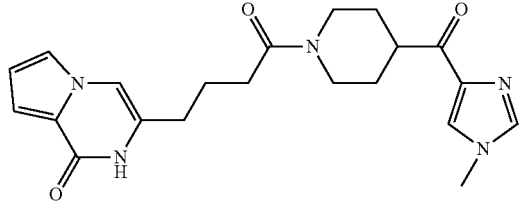 [SMILES: Cn1cnc(C(=O)C2CCN(C(=O)CCCc3cn4cccc4c(=O)[nH]3)CC2)c1] |
| "C26" | 3-[4-[-(3-Methylimidazole-4-carbonyl)-1-piperidyl]-4-oxo-butyl]-2H-pyrrolo[1,2-a]pyrazin-1-one 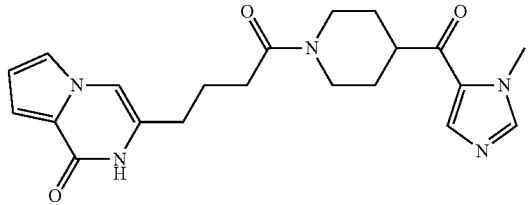 [SMILES: Cn1cncc1C(=O)C1CCN(C(=O)CCCc2cn3cccc3c(=O)[nH]2)CC1] |

-continued

| No. | Name/structure |
|---|---|
| "C27" | 3-[4-[4-(1-Methylimidazole-2-carbonyl)-1-piperidyl]-4-oxo-butyl]-2H-pyrrolo[1,2-a]pyrazin-1-one 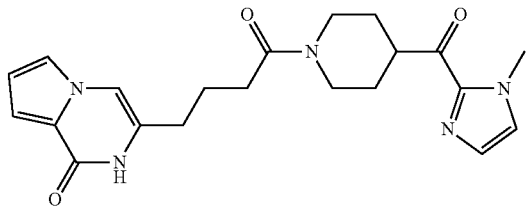 [SMILES: Cn1ccnc1C(=O)C1CCN(C(=O)CCCc2cn3cccc3c(=O)[nH]2)CC1] |
| "C28" | 3-[4-[4-(3-methoxy-6-oxo-pyridazin-1-yl)-1-piperidyl]-4-oxo-butyl]-2H-pyrrolo[1,2-a]pyrazin-1-one 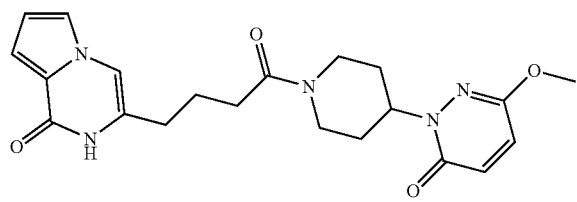 [SMILES: COc1ccc(=O)n(C2CCN(C(=O)CCCc3cn4cccc4c(=O)[nH]3)CC2)n1] |
| "C29" | 3-[4-[4-(3-methyl-6-oxo-pyridazin-1-yl)-1-piperidyl]-4-oxo-butyl]-2H-pyrrolo[1,2-a]pyrazin-1-one 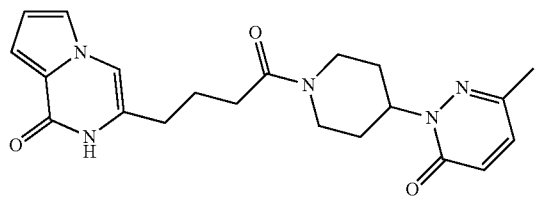 [SMILES: Cc1ccc(=O)n(C2CCN(C(=O)CCCc3cn4cccc4c(=O)[nH]3)CC2)n1] |
| "C30" | 6-(Hydroxymethyl)-3-[4-[4-(4-methoxybenzoyl)-1-piperidyl]-4-oxo-butyl]-2H-pyrrolo[1,2-a]pyrazin-1-one 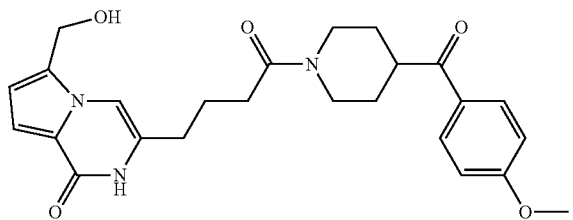 [SMILES: COc1ccc(C(=O)C2CCN(C(=O)CCCc3cn4c(CO)ccc4c(=O)[nH]3)CC2)cc1] |
| "C51" | 6-[4-[4-(6-Methoxypyridazine-3-carbonyl)-1-piperidyl]-4-oxo-butyl]-1-methyl-5H-pyrazolo[3,4-d]pyrimidin-4-one 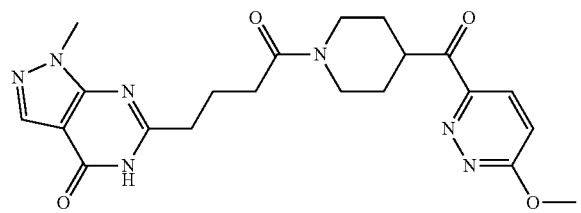 [SMILES: COc1ccc(C(=O)C2CCN(C(=O)CCCc3nc4c(cnn4C)c(=O)[nH]3)CC2)nn1] |

| No. | Name/structure |
|---|---|
| "C53" | 7-Fluoro-2-[4-[4-(4-methoxybenzoyl)-1-piperidyl]-4-oxo-butyl]-3H-pyrrolo[2,1-f][1,2,4]triazin-4-one 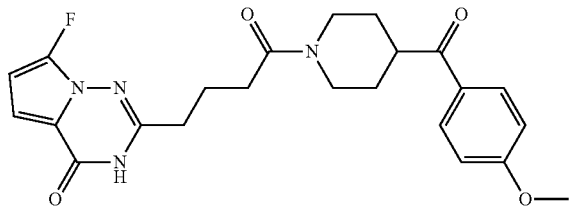 [SMILES: COc1ccc(C(=O)C2CCN(C(=O)CCCc3nn4c(F)ccc4c(=O)[nH]3)CC2)cc1] |
| "C58" | 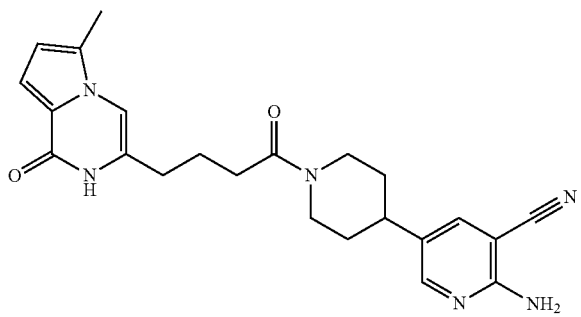 [SMILES: Cc1ccc2c(=O)[nH]c(CCCC(=O)N3CCC(c4cnc(N)c(C#N)c4)CC3)cn12] |
| "C59" | 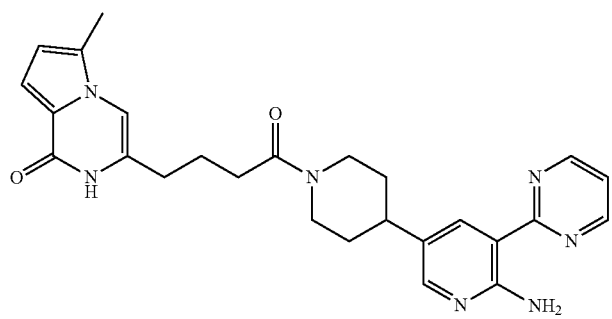 [SMILES: Cc1ccc2c(=O)[nH]c(CCCC(=O)N3CCC(c4cnc(N)c(-c5ncccn5)c4)CC3)cn12] |
| "C60" | 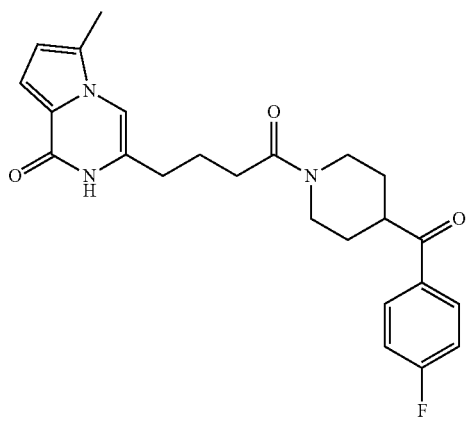 [SMILES: Cc1ccc2c(=O)[nH]c(CCCC(=O)N3CCC(C(=O)c4ccc(F)cc4)CC3)cn12] |

| No. | Name/structure |
|---|---|
| "C61" | 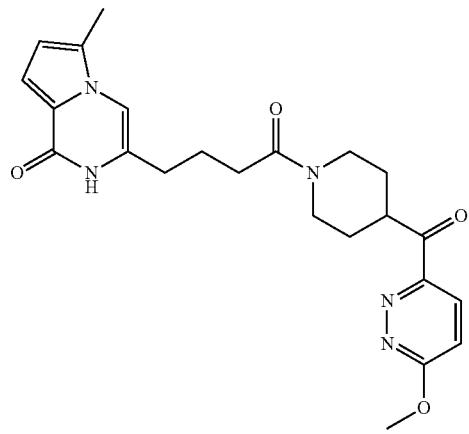 [SMILES: COc1ccc(C(=O)C2CCN(C(=O)CCCc3cn4c(C)ccc4c(=O)[nH]3)CC2)nn1] |
| "C63" | 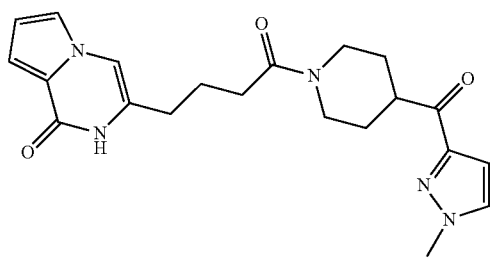 [SMILES: Cn1ccc(C(=O)C2CCN(C(=O)CCCc3cn4cccc4c(=O)[nH]3)CC2)n1] |
| "C64" | 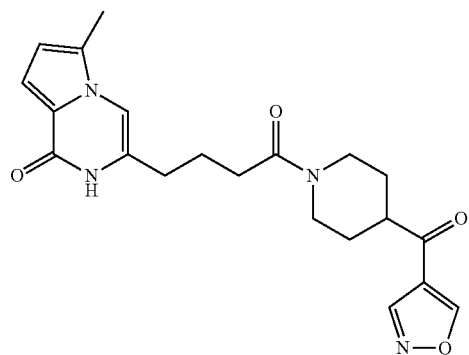 [SMILES: Cc1ccc2c(=O)[nH]c(CCCC(=O)N3CCC(C(=O)c4cnoc4)CC3)cn12] |
| "C65" | 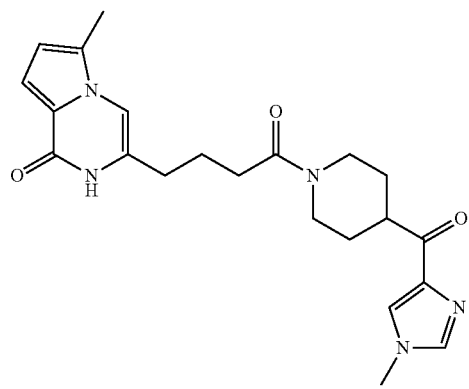 [SMILES: Cc1ccc2c(=O)[nH]c(CCCC(=O)N3CCC(C(=O)c4cn(C)cn4)CC3)cn12] |

| No. | Name/structure |
|---|---|
| "C66" | 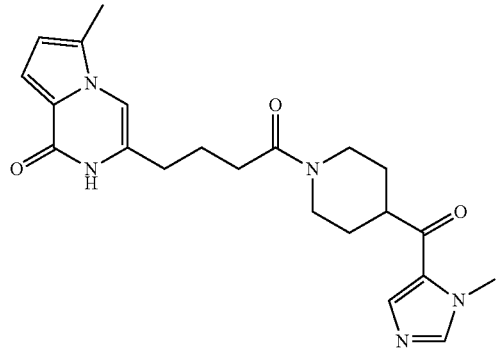 |
| "C67" | 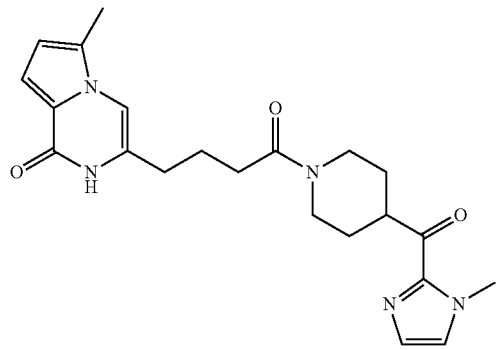 [SMILES: Cc1ccc2c(=O)[nH]c(CCCC(=O)N3CCC(C(=O)c4nccn4C)CC3)cn12] |
| "C68" | 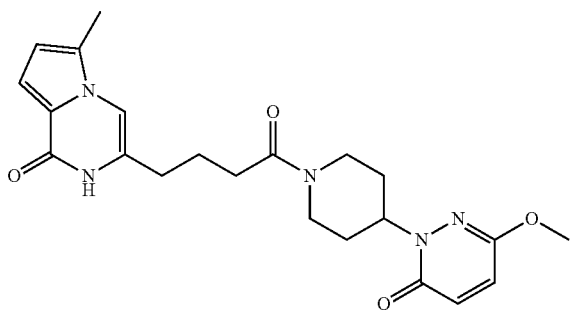 [SMILES: COc1ccc(=O)n(C2CCN(C(=O)CCCc3cn4c(C)ccc4c(=O)[nH]3)CC2)n1] |
| "C69" | 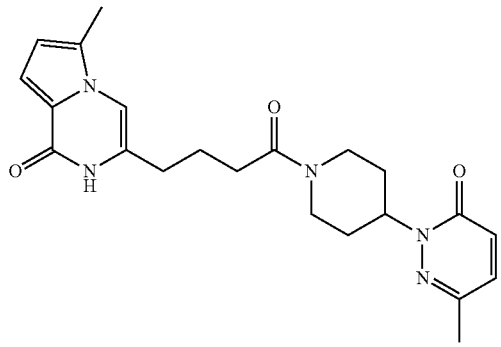 [SMILES: Cc1ccc(=O)n(C2CCN(C(=O)CCCc3cn4c(C)ccc4c(=O)[nH]3)CC2)n1] |

| No. | Name/structure |
|---|---|
| "C70" | (structure) |
| "C72" | (structure) |
| "C73" | (structure) |
| "C74" | (structure) |

| No. | Name/structure |
|---|---|
| "C75" | 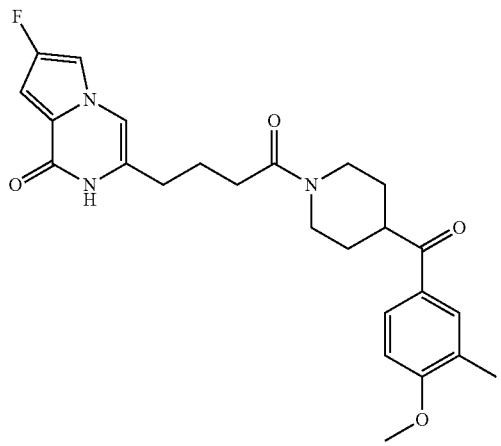 [SMILES: COc1ccc(C(=O)C2CCN(C(=O)CCCc3cn4cc(F)cc4c(=O)[nH]3)CC2)cc1C] |
| "C76" | 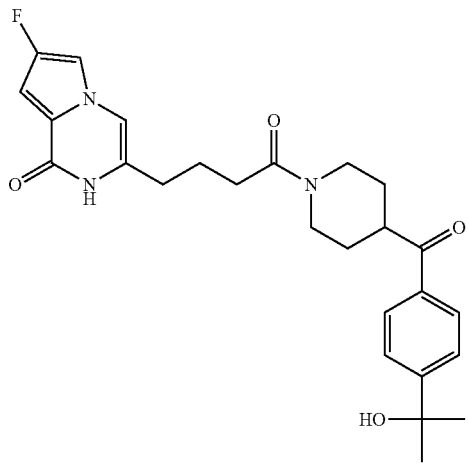 [SMILES: CC(C)(O)c1ccc(C(=O)C2CCN(C(=O)CCCc3cn4cc(F)cc4c(=O)[nH]3)CC2)cc1] |
| "C77" | 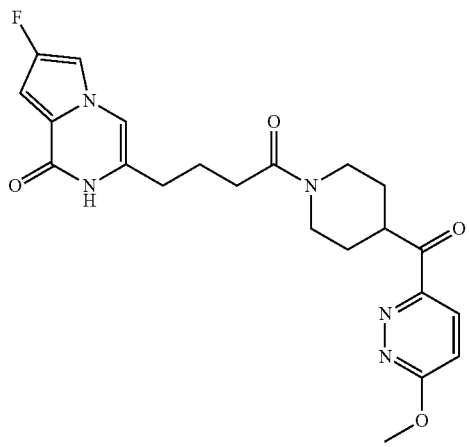 |

| No. | Name/structure |
|---|---|
| "C79" | 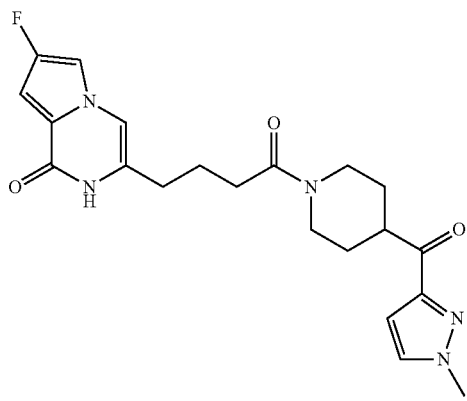 [SMILES: Cn1ccc(C(=O)C2CCN(C(=O)CCCc3cn4cc(F)cc4c(=O)[nH]3)CC2)n1] |
| "C80" | 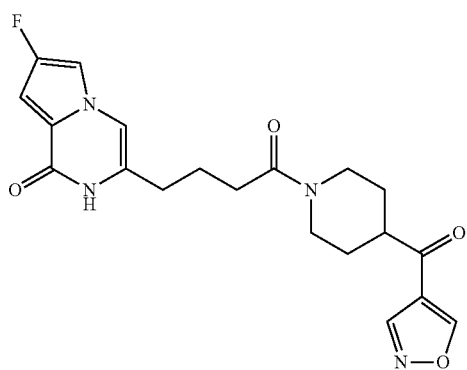 [SMILES: O=C(c1cnoc1)C1CCN(C(=O)CCCc2cn3cc(F)cc3c(=O)[nH]2)CC1] |
| "C81" | 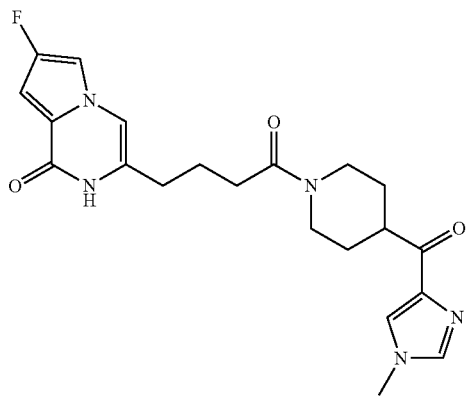 [SMILES: Cn1cnc(C(=O)C2CCN(C(=O)CCCc3cn4cc(F)cc4c(=O)[nH]3)CC2)c1] |
| "C82" | 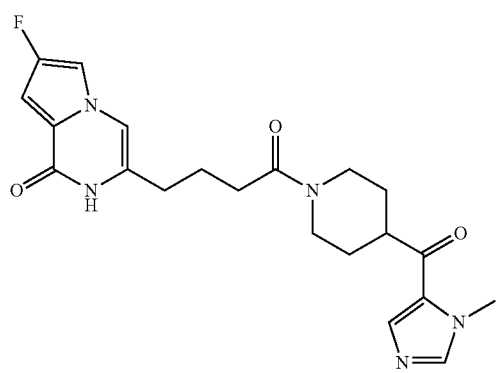 [SMILES: Cn1cncc1C(=O)C1CCN(C(=O)CCCc2cn3cc(F)cc3c(=O)[nH]2)CC1] |

-continued
| No. | Name/structure |
|---|---|
| "C83" | 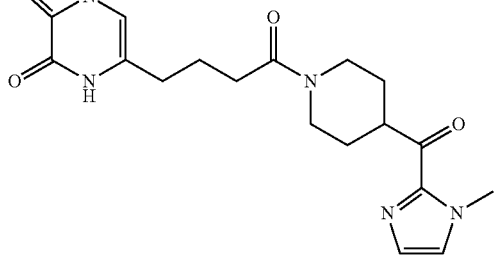 |
| "C84" | 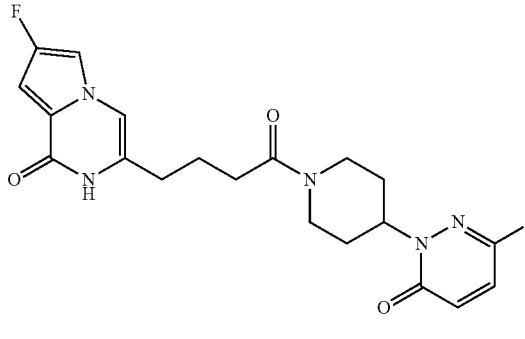 |
| "C85" | 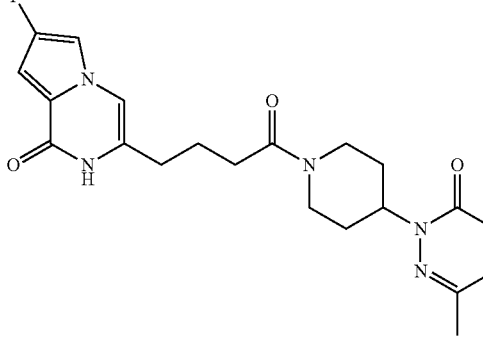 |
| "C86" | 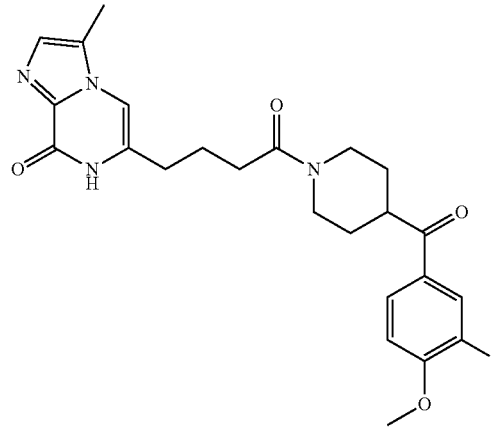 |

-continued
| No. | Name/structure |
|---|---|
| "C87" | 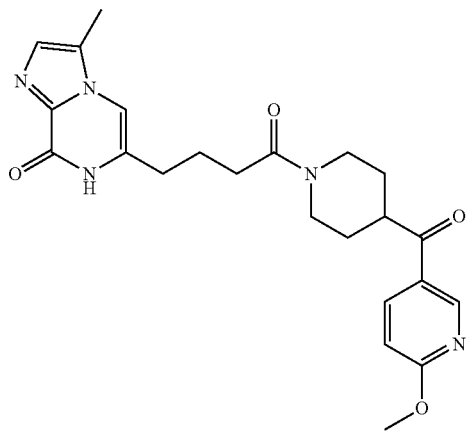 [SMILES: COc1ccc(C(=O)C2CCN(C(=O)CCCc3cn4c(C)cnc4c(=O)[nH]3)CC2)cn1] |
| "C88" | 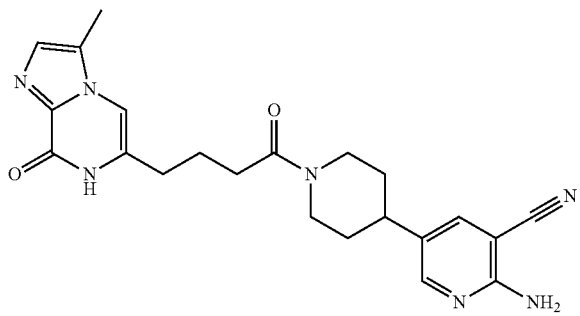 [SMILES: Cc1cnc2c(=O)[nH]c(CCCC(=O)N3CCC(c4cnc(N)c(C#N)c4)CC3)cn12] |
| "C89" | 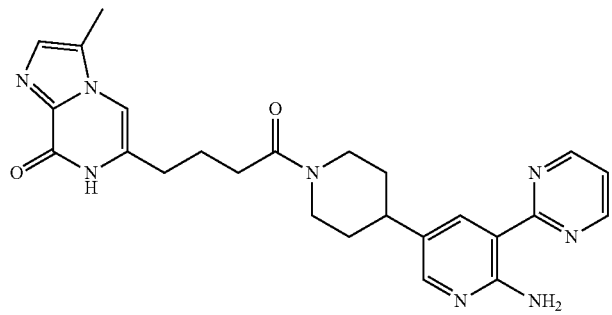 [SMILES: Cc1cnc2c(=O)[nH]c(CCCC(=O)N3CCC(c4cnc(N)c(-c5ncccn5)c4)CC3)cn12] |
| "C90" | 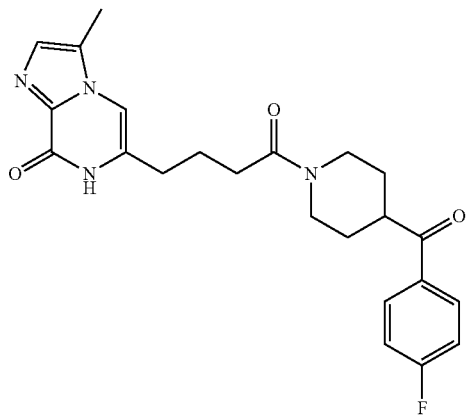 [SMILES: Cc1cnc2c(=O)[nH]c(CCCC(=O)N3CCC(C(=O)c4ccc(F)cc4)CC3)cn12] |

-continued
| No. | Name/structure |
|---|---|
| "C91" | 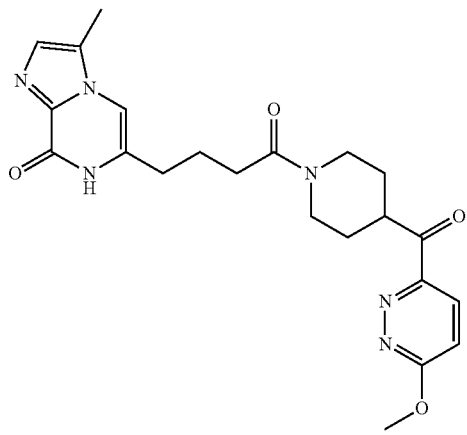 [SMILES: COc1ccc(C(=O)C2CCN(C(=O)CCCc3cn4c(C)cnc4c(=O)[nH]3)CC2)nn1] |
| "C92" | 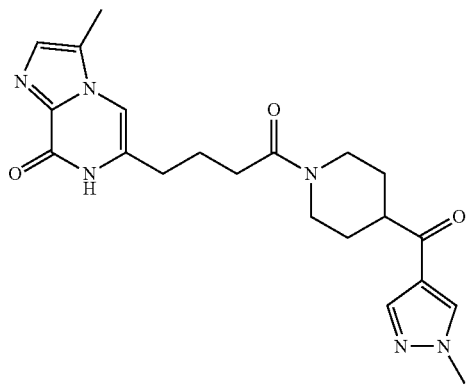 [SMILES: Cc1cnc2c(=O)[nH]c(CCCC(=O)N3CCC(C(=O)c4cnn(C)c4)CC3)cn12] |
| "C93" | 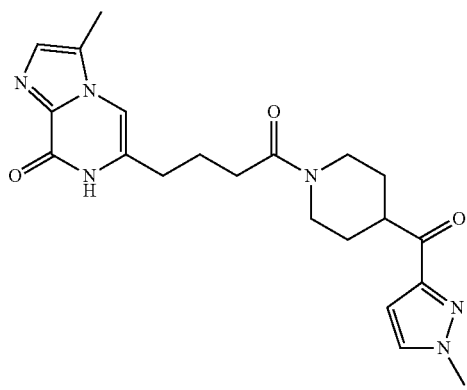 [SMILES: Cc1cnc2c(=O)[nH]c(CCCC(=O)N3CCC(C(=O)c4ccn(C)n4)CC3)cn12] |
| "C94" | 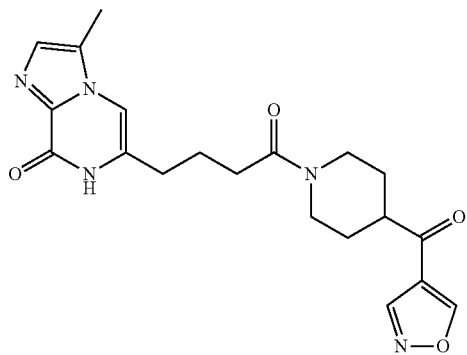 [SMILES: Cc1cnc2c(=O)[nH]c(CCCC(=O)N3CCC(C(=O)c4cnoc4)CC3)cn12] |

| No. | Name/structure |
|---|---|
| "C95" | 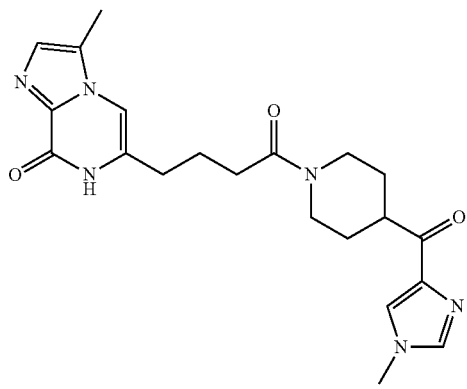 [SMILES: Cc1cnc2c(=O)[nH]c(CCCC(=O)N3CCC(C(=O)c4cn(C)cn4)CC3)cn12] |
| "C96" | 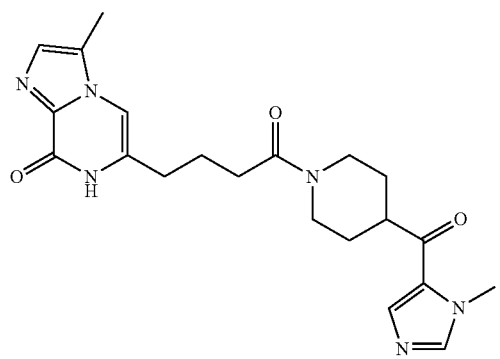 [SMILES: Cc1cnc2c(=O)[nH]c(CCCC(=O)N3CCC(C(=O)c4cncn4C)CC3)cn12] |
| "C97" | 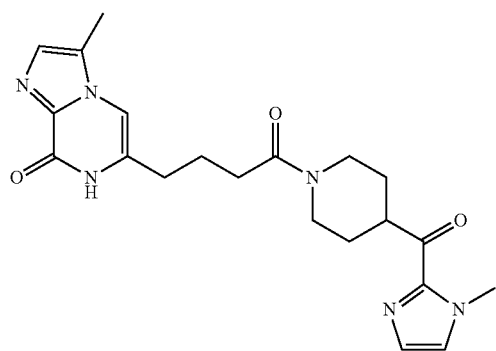 [SMILES: Cc1cnc2c(=O)[nH]c(CCCC(=O)N3CCC(C(=O)c4nccn4C)CC3)cn12] |
| "C98" | 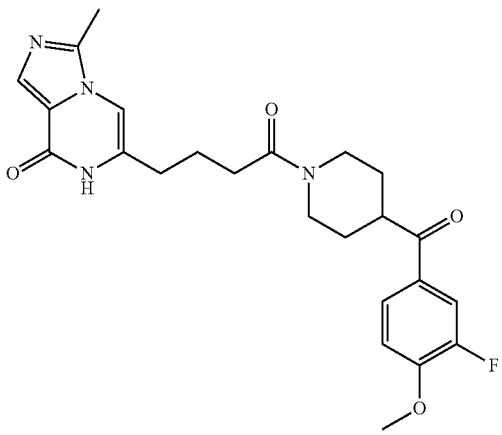 [SMILES: COc1ccc(C(=O)C2CCN(C(=O)CCCc3cn4c(C)ncc4c(=O)[nH]3)CC2)cc1F] |

| No. | Name/structure |
|---|---|
| "C100" | 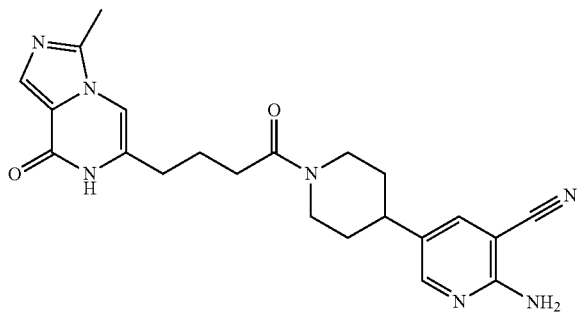 |
| "C101" | 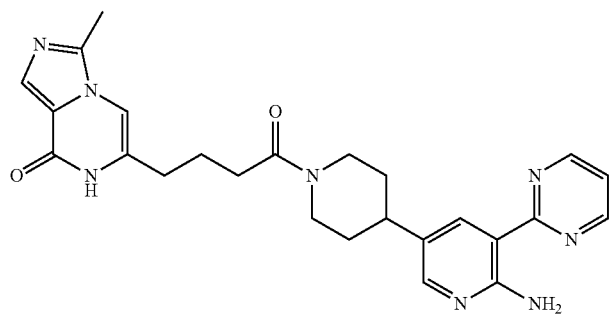 |
| "C102" | 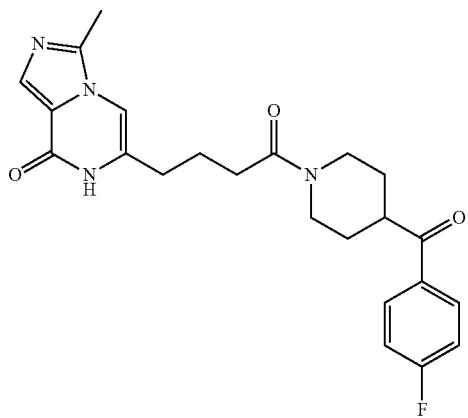 |
| "C103" | 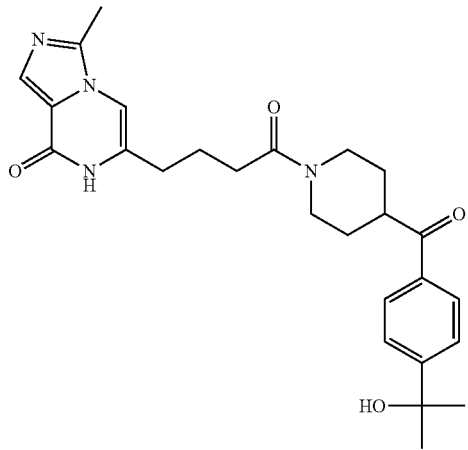 [SMILES: Cc1ncc2c(=O)[nH]c(CCCC(=O)N3CCC(C(=O)c4ccc(C(C)(C)O)cc4)CC3)cn12] |

-continued
| No. | Name/structure |
|---|---|
| "C104" | 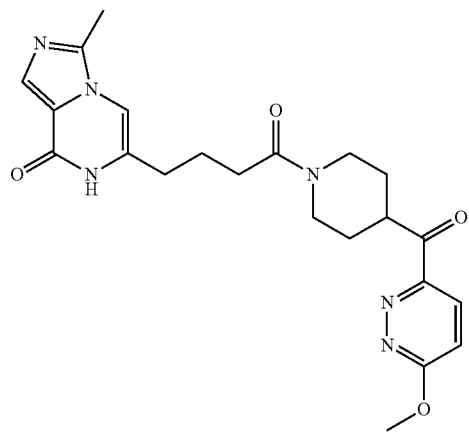 [SMILES: COc1ccc(C(=O)C2CCN(C(=O)CCCc3cn4c(C)ncc4c(=O)[nH]3)CC2)nn1] |
| "C106" | 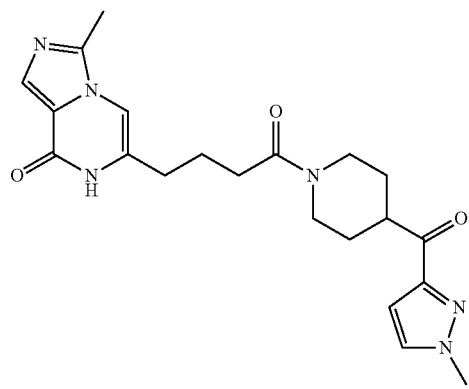 [SMILES: Cc1ncc2c(=O)[nH]c(CCCC(=O)N3CCC(C(=O)c4ccn(C)n4)CC3)cn12] |
| "C107" | 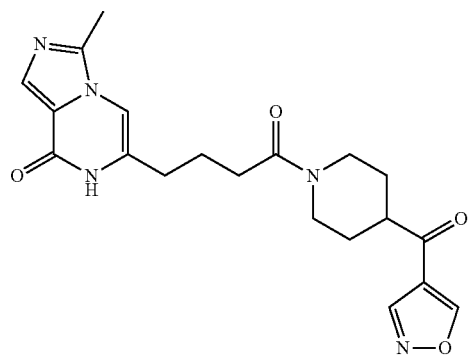 [SMILES: Cc1ncc2c(=O)[nH]c(CCCC(=O)N3CCC(C(=O)c4cnoc4)CC3)cn12] |
| "C108" | 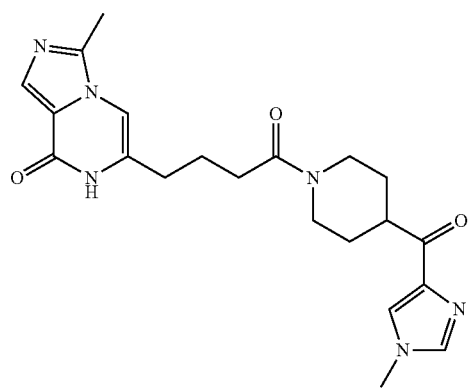 [SMILES: Cc1ncc2c(=O)[nH]c(CCCC(=O)N3CCC(C(=O)c4cn(C)cn4)CC3)cn12] |

| No. | Name/structure |
|---|---|
| "C109" | 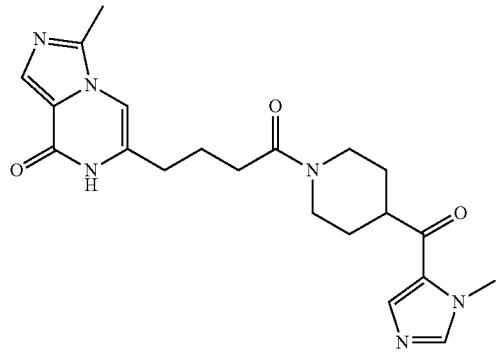 [SMILES: Cc1ncc2c(=O)[nH]c(CCCC(=O)N3CCC(C(=O)c4cncn4C)CC3)cn12] |
| "C110" | 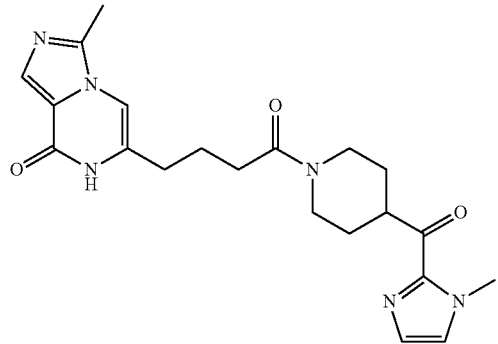 [SMILES: Cc1ncc2c(=O)[nH]c(CCCC(=O)N3CCC(C(=O)c4nccn4C)CC3)cn12] |
| "C111" | 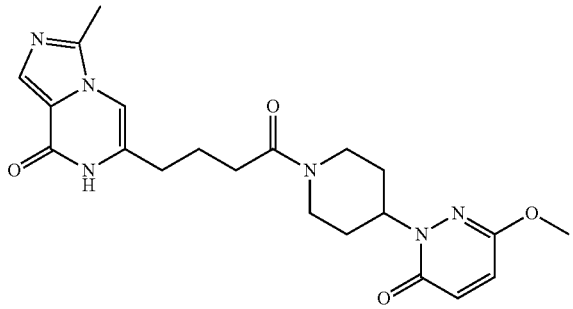 [SMILES: COc1ccc(=O)n(C2CCN(C(=O)CCCc3cn4c(C)ncc4c(=O)[nH]3)CC2)n1] |
| "C112" | 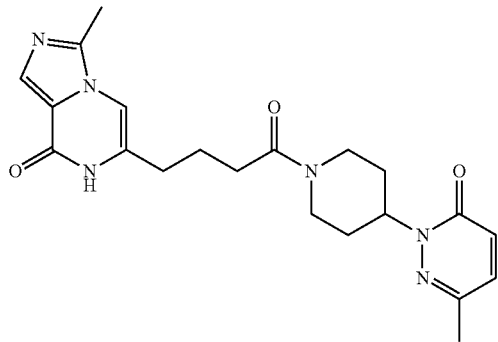 |

| No. | Name/structure |
|---|---|
| "C122" | 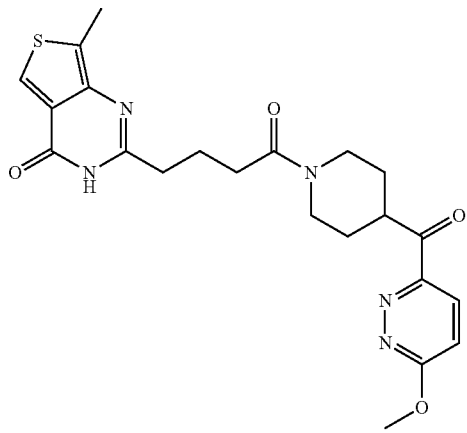 [SMILES: COc1ccc(C(=O)C2CCN(C(=O)CCCc3nc4c(C)scc4c(=O)[nH]3)CC2)nn1] |
| "C124" | 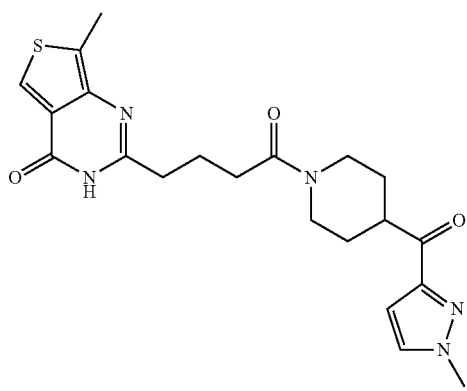 [SMILES: Cc1scc2c(=O)[nH]c(CCCC(=O)N3CCC(C(=O)c4ccn(C)n4)CC3)nc12] |
| "C134" | 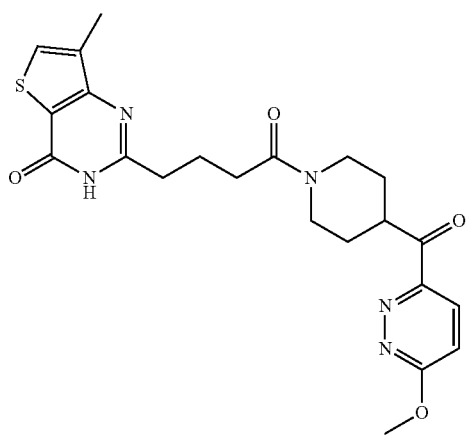 [SMILES: COc1ccc(C(=O)C2CCN(C(=O)CCCc3nc4c(C)csc4c(=O)[nH]3)CC2)nn1] |

| No. | Name/structure |
|---|---|
| "C145" | 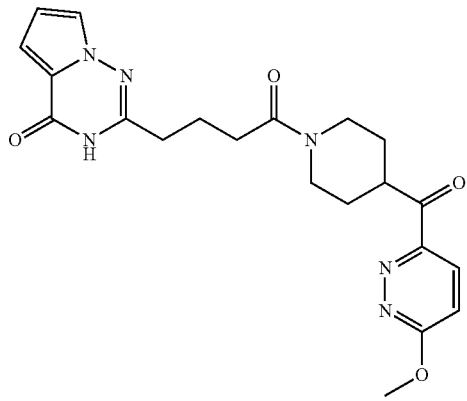 [SMILES: COc1ccc(C(=O)C2CCN(C(=O)CCCc3nn4cccc4c(=O)[nH]3)CC2)nn1] |
| "C156" | 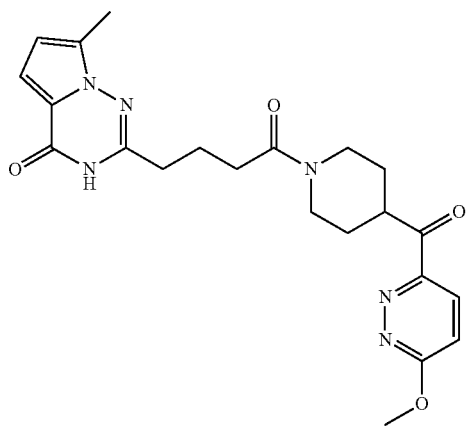 [SMILES: COc1ccc(C(=O)C2CCN(C(=O)CCCc3nn4c(C)ccc4c(=O)[nH]3)CC2)nn1] |
| "C167" | 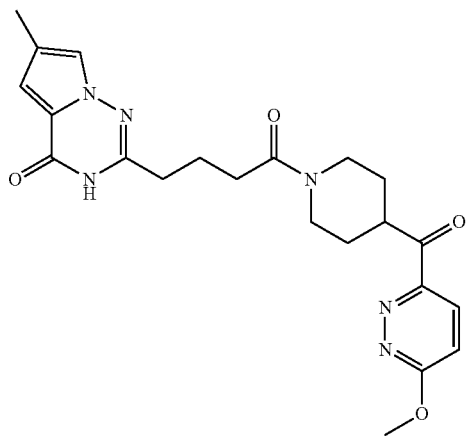 [SMILES: COc1ccc(C(=O)C2CCN(C(=O)CCCc3nn4cc(C)cc4c(=O)[nH]3)CC2)nn1] |

-continued
| No. | Name/structure |
|---|---|
| "C178" | 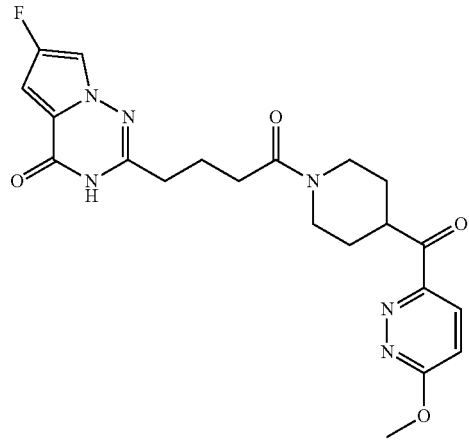 [SMILES: COc1ccc(C(=O)C2CCN(C(=O)CCCc3nn4cc(F)cc4c(=O)[nH]3)CC2)nn1] |
| "C185" | 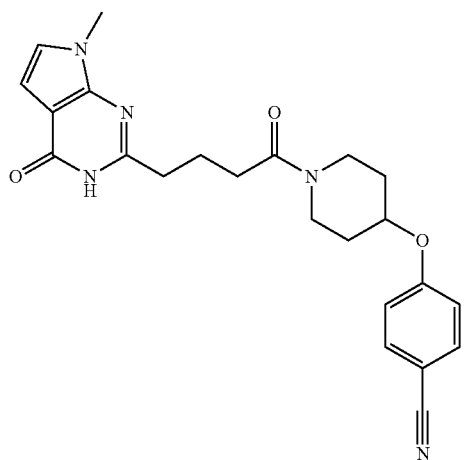 [SMILES: Cn1ccc2c(=O)[nH]c(CCCC(=O)N3CCC(Oc4ccc(C#N)cc4)CC3)nc21] |
| "C187" | 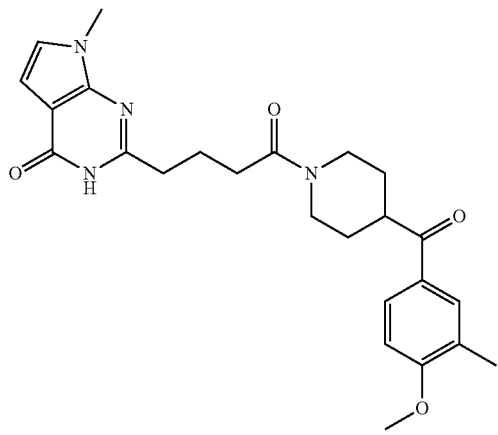 [SMILES: COc1ccc(C(=O)C2CCN(C(=O)CCCc3nc4c(ccn4C)c(=O)[nH]3)CC2)cc1C] |

-continued
| No. | Name/structure |
|---|---|
| "C188" | 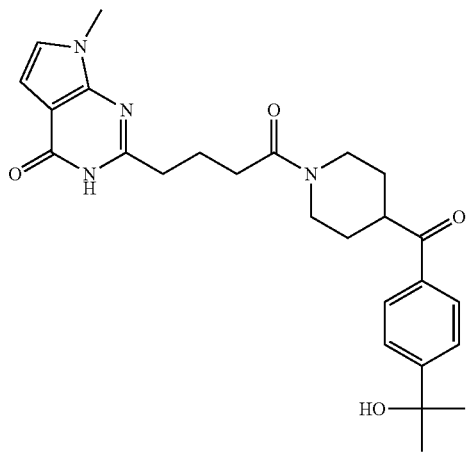 [SMILES: Cn1ccc2c(=O)[nH]c(CCCC(=O)N3CCC(C(=O)c4ccc(C(C)(C)O)cc4)CC3)nc21] |
| "C189" | 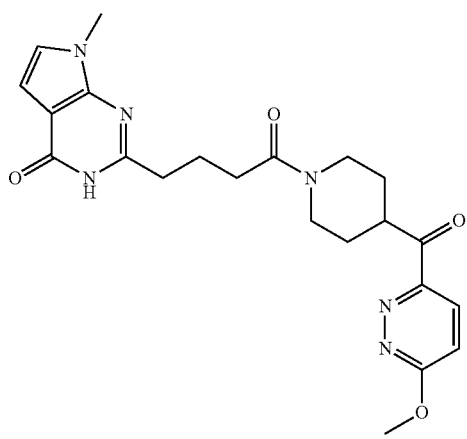 [SMILES: COc1ccc(C(=O)C2CCN(C(=O)CCCc3nc4c(ccn4C)c(=O)[nH]3)CC2)nn1] |
| "C201" | 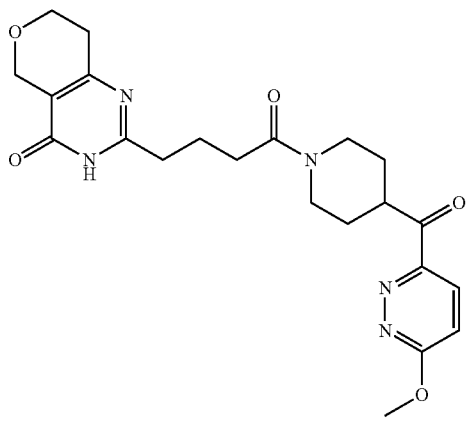 [SMILES: COc1ccc(C(=O)C2CCN(C(=O)CCCc3nc4c(c(=O)[nH]3)COCC4)CC2)nn1] |

| No. | Name/structure |
|---|---|
| "C203" | 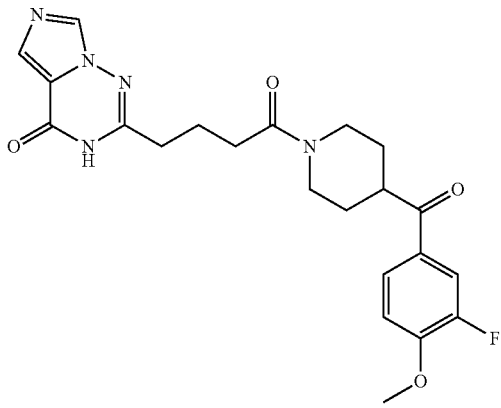 [SMILES: COc1ccc(C(=O)C2CCN(C(=O)CCCc3nn4cncc4c(=O)[nH]3)CC2)cc1F] |
| "C204" | 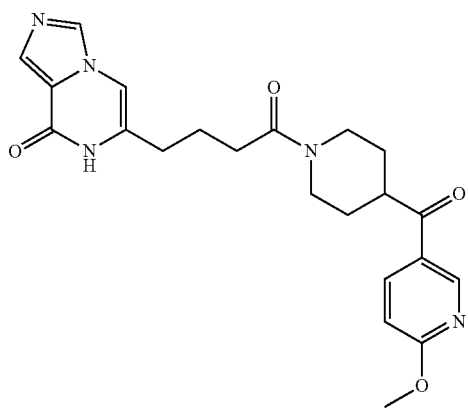 [SMILES: COc1ccc(C(=O)C2CCN(C(=O)CCCc3cn4cncc4c(=O)[nH]3)CC2)cn1] |
| "C205" | 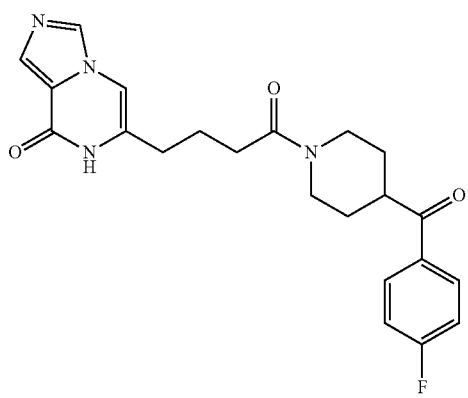 [SMILES: O=C(c1ccc(F)cc1)C1CCN(C(=O)CCCc2cn3cncc3c(=O)[nH]2)CC1] |
| "C206" | 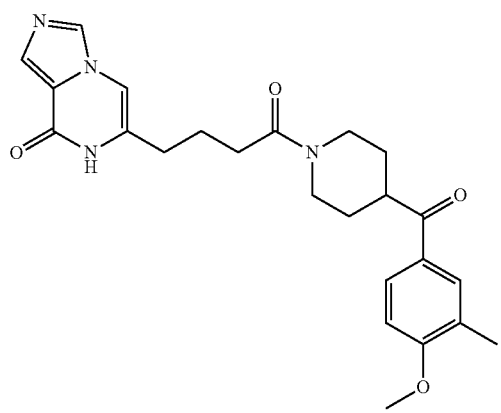 [SMILES: COc1ccc(C(=O)C2CCN(C(=O)CCCc3cn4cncc4c(=O)[nH]3)CC2)cc1C] |

| No. | Name/structure |
|---|---|
| "C264" | 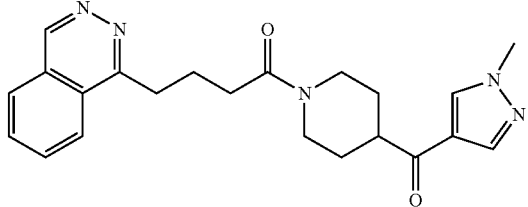 [SMILES: Cn1cc(C(=O)C2CCN(C(=O)CCCc3nncc4ccccc34)CC2)cn1] |
| "C265" | 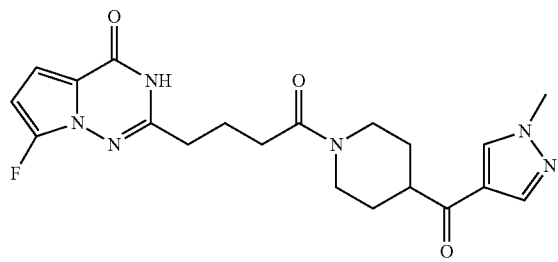 [SMILES: Cn1cc(C(=O)C2CCN(C(=O)CCCc3nn4c(F)ccc4c(=O)[nH]3)CC2)cn1] |
| "C267" | 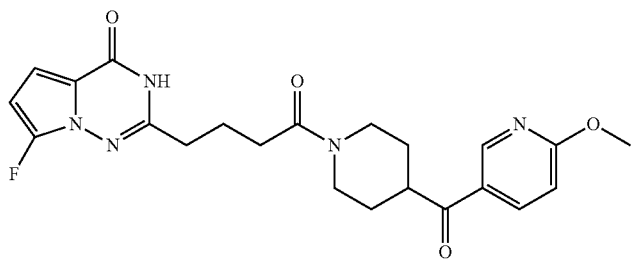 [SMILES: COc1ccc(C(=O)C2CCN(C(=O)CCCc3nn4c(F)ccc4c(=O)[nH]3)CC2)cn1] |
| "C268" | 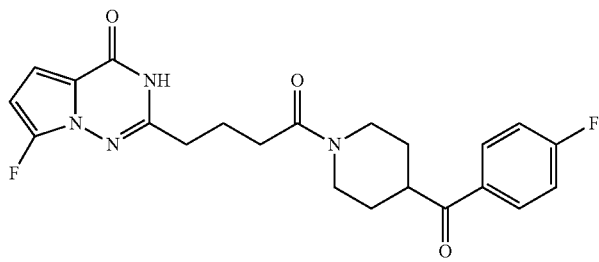 [SMILES: O=C(c1ccc(F)cc1)C1CCN(C(=O)CCCc2nn3c(F)ccc3c(=O)[nH]2)CC1] |
| "C269" | 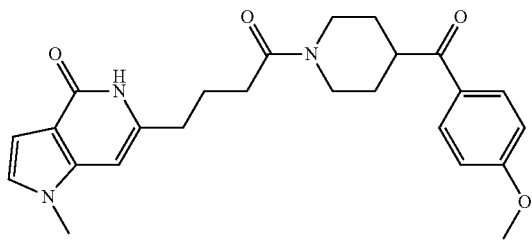 [SMILES: COc1ccc(C(=O)C2CCN(C(=O)CCCc3cc4c(ccn4C)c(=O)[nH]3)CC2)cc1] |
| "C270" | 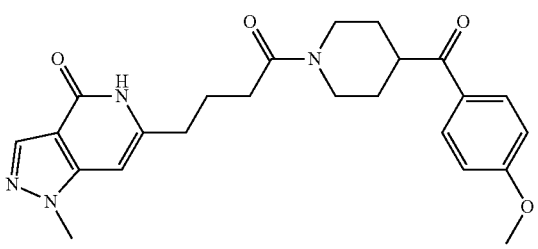 [SMILES: COc1ccc(C(=O)C2CCN(C(=O)CCCc3cc4c(cnn4C)c(=O)[nH]3)CC2)cc1] |

| No. | Name/structure |
|---|---|
| "C271" | 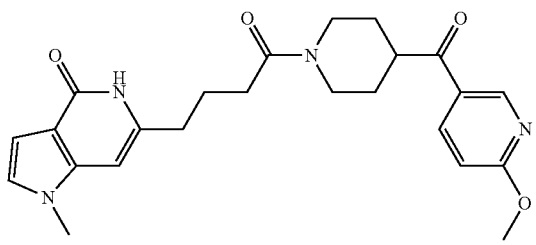 [SMILES: COc1ccc(C(=O)C2CCN(C(=O)CCCc3cc4c(ccn4C)c(=O)[nH]3)CC2)cn1] |
| "C272" | 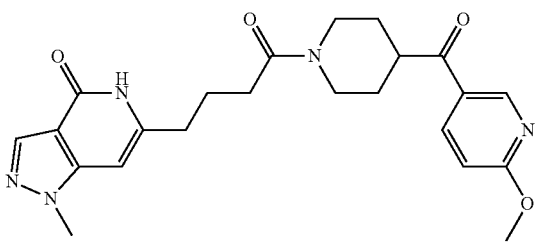 [SMILES: COc1ccc(C(=O)C2CCN(C(=O)CCCc3cc4c(cnn4C)c(=O)[nH]3)CC2)cn1] |
| "C273" | 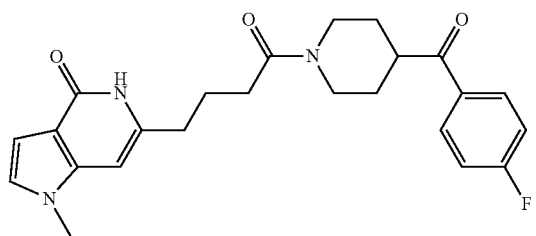 [SMILES: Cn1ccc2c(=O)[nH]c(CCCC(=O)N3CCC(C(=O)c4ccc(F)cc4)CC3)cc21] |
| "C274" | 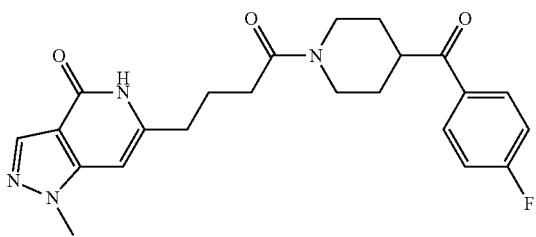 [SMILES: Cn1ncc2c(=O)[nH]c(CCCC(=O)N3CCC(C(=O)c4ccc(F)cc4)CC3)cc21] |
| "C275" | 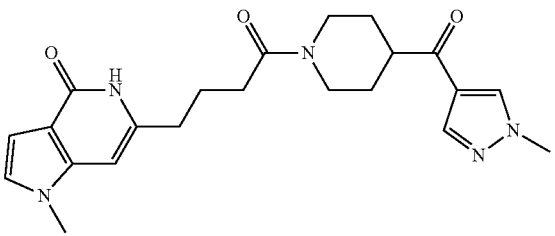 [SMILES: Cn1cc(C(=O)C2CCN(C(=O)CCCc3cc4c(ccn4C)c(=O)[nH]3)CC2)cn1] |
| "C276" | 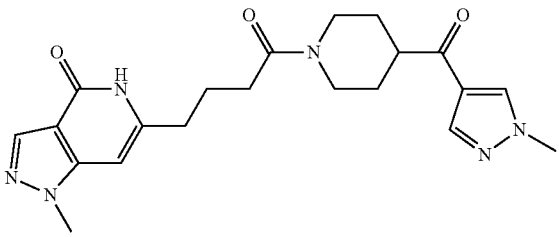 [SMILES: Cn1cc(C(=O)C2CCN(C(=O)CCCc3cc4c(cnn4C)c(=O)[nH]3)CC2)cn1] |

| No. | Name/structure |
|---|---|
| "C277" | (structure) |
| "C278" | (structure) |
| "C279" | (structure) |
| "C280" | (structure) |
| "C281" | (structure) |

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of $NaH_2PO_4 \cdot 2H_2O$, 28.48 g of Na₂HPO₄.12H₂O and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

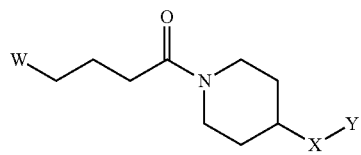

in which
W denotes

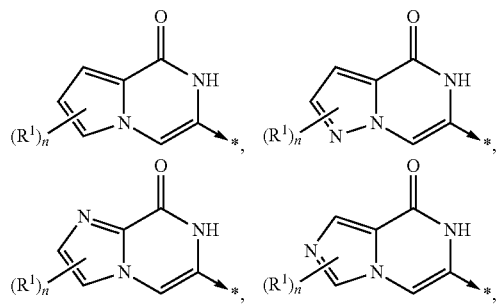

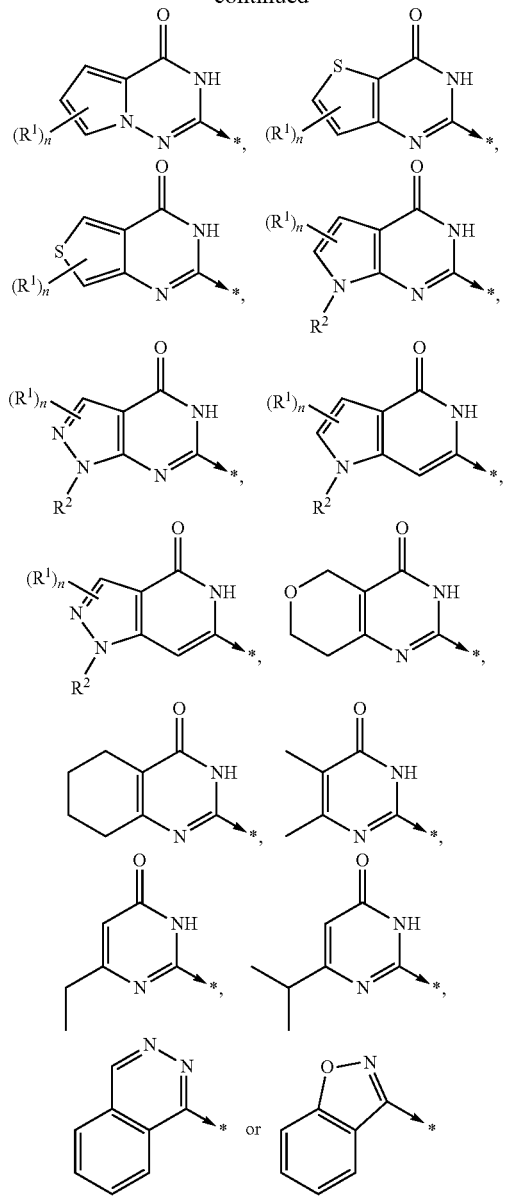

wherein * indicates the point of attachment to the propylene moiety,
X denotes O, CO or is absent,
Y denotes Ar or Het¹,
R¹ denotes H, F, Cl, CN, CH₃, CF₃, CHF₂, CH₂OH or OCH₃,
R² denotes H or CH₃,
Ar denotes phenyl, which is unsubstituted, or mono-, di- or trisubstituted by Hal, NO₂, CN, A, OR³, S(O)ₘR³, N(R³)₂, COA, COOR³, CON(R³)₂, SO₂N(R³)₂, NR³COR³, NR³SO₂A, NR³CON(R³)₂ and/or Het²,
Het¹ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by Hal, NO₂, Ar¹, CN, A, OR³, N(R³)₂, CON (R³)₂, Het² and/or =O,
Het² denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by Hal, NO$_2$, Ar$^1$, CN, A, OR$^3$, N(R$^3$)$_2$, CON(R$^3$)$_2$ and/or =O, Ar$^1$ denotes phenyl, which is unsubstituted, or mono-, di- or trisubstituted by Hal, NO$_2$, CN, A, OR$^3$, S(O)$_m$R$^3$, N(R$^3$)$_2$, COA, COOR$^3$, CON(R$^3$)$_2$, NR$^3$COR$^3$ and/or NR$^3$SO$_2$A, A denotes unbranched or branched alkyl with 1-8 C-Atoms, wherein one or two non-adjacent CH- and/or CH$_2$-groups may each be replaced by N- or O-atoms and wherein 1-7 H-atoms may each be replaced by F, Cl or OH, R$^3$ denotes H or unbranched or branched alkyl with 1, 2, 3 or 4 C-Atoms, Hal denotes F, Cl, Br or I, m denotes 0, 1 or 2, n denotes 1 or 2, and pharmaceutically acceptable salts, tautomers and stereoisomers thereof, including mixtures thereof in all ratios.

2. The compound according to claim 1 in which W denotes

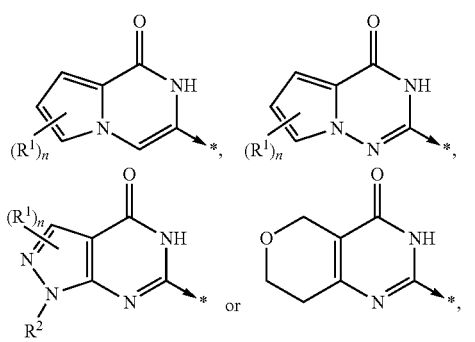

and pharmaceutically acceptable solvates, salts, tautomers and stereoisomers thereof, including mixtures thereof in all ratios.

3. The compound according to claim 1 in which
Ar denotes phenyl, which is unsubstituted, or mono-, di- or trisubstituted by Hal, CN, A and/or OR$^3$,
and pharmaceutically acceptable solvates, salts, tautomers and stereoisomers thereof, including mixtures thereof in all ratios.

4. The compound according to claim 1, in which
Het$^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by Ar$^1$, CN, A, OR$^3$, N(R$^3$)$_2$, Het$^2$ and/or =O,
and pharmaceutically acceptable salts, tautomers and stereoisomers thereof, including mixtures thereof in all ratios.

5. The compound according to claim 1, in which
Het$^2$ denotes pyrimidyl,
and pharmaceutically acceptable salts, tautomers and stereoisomers thereof, including mixtures thereof in all ratios.

6. The compound according to claim 1, in which
Ar$^1$ denotes phenyl,
and pharmaceutically acceptable salts, tautomers and stereoisomers thereof, including mixtures thereof in all ratios.

7. The compound according to claim 1, in which W denotes

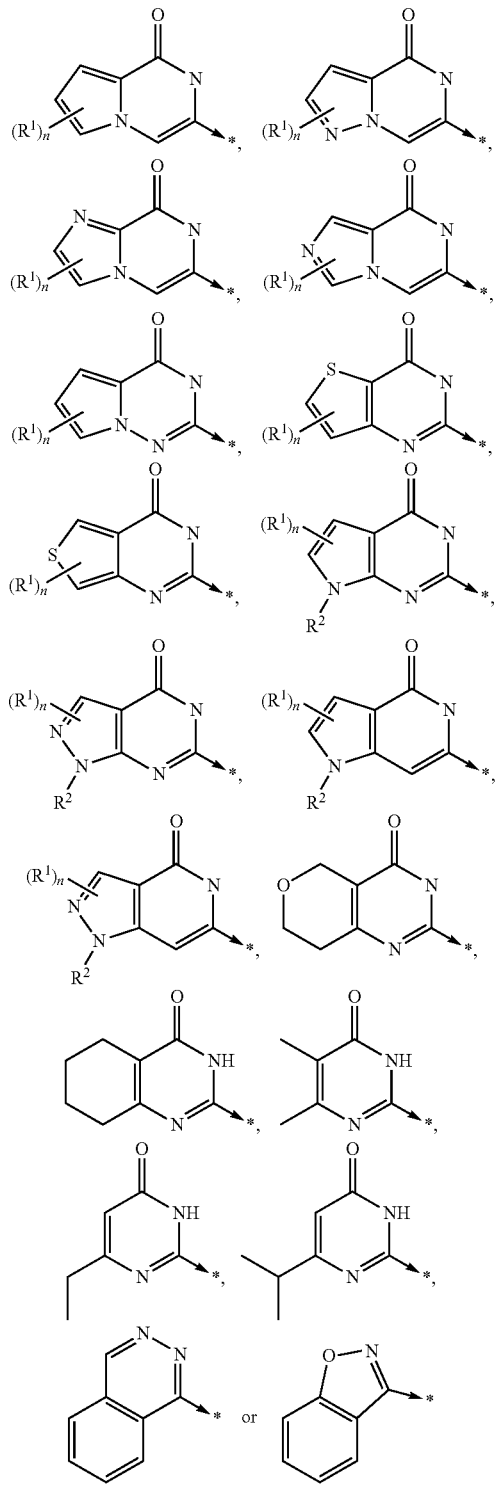

wherein * indicates the point of attachment to the propylene moiety,

X denotes O, CO or is absent,

Y denotes Ar or Het$^1$, $R^1$ denotes H, F, Cl, CN, $CH_3$, $CF_3$, $CHF_2$, $CH_2OH$ or $OCH_3$, $R^2$ denotes H or $CH_3$, Ar denotes phenyl, which is unsubstituted, or mono-, di- or trisubstituted by Hal, CN, A and/or $OR^3$, $Het^1$ denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl or pyridazinyl, each of which is unsubstituted or mono- or disubstituted by $Ar^1$, CN, A, $OR^3$, $N(R^3)_2$, $Het^2$ and/or =O, $Het^2$ denotes pyrimidyl, $Ar^1$ denotes phenyl, A denotes unbranched or branched alkyl with 1-8 C-Atoms, wherein one or two non-adjacent CH- and/or $CH_2$-groups may be replaced by N- or O-atoms and wherein 1-7 H-atoms may be replaced by F, Cl and/or OH, $R^3$ denotes H or unbranched or branched alkyl with 1, 2, 3 or 4 C-Atoms, Hal denotes F, Cl, Br or I, n denotes 1 or 2, and pharmaceutically acceptable salts, tautomers and stereoisomers thereof, including mixtures thereof in all ratios.

8. The compound according to claim 1, in which W denotes

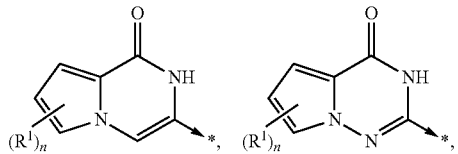

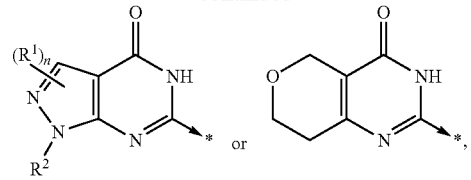

wherein * indicates the point of attachment to the propylene moiety,

X denotes CO or is absent,

Y denotes Ar or $Het^1$, $R^1$ denotes H, F or $CH_3$, $R^2$ denotes H or $CH_3$, Ar denotes phenyl, which is mono- or disubstituted by Hal and/or $OR^3$, $Het^1$ denotes pyrazolyl or pyridyl, each of which is unsubstituted or mono- or disubstituted by A, $OR^3$, $N(R^3)_2$ and/or $Het^2$, $Het^2$ denotes pyrimidyl, A denotes unbranched or branched alkyl with 1-8 C-Atoms, $R^3$ denotes H or unbranched or branched alkyl with 1, 2, 3 or 4 C-Atoms, Hal denotes F, Cl, Br or I, n denotes 1, and pharmaceutically acceptable salts, tautomers and stereoisomers thereof, including mixtures thereof in all ratios.

9. The compound according to claim 1, wherein said compound is selected from the following compounds group

| No. | Name |
|---|---|
| "C1" | 3-{4-[4-(4-Methoxy-benzoyl)-piperidin-1-yl]-4-oxo-butyl}-6-methyl-2H-pyrrolo[1,2-a]pyrazin-1-one |
| "C2" | 3-{4-[4-(4-Methoxy-benzoyl)-piperidin-1-yl]-4-oxo-butyl}-2H-pyrrolo[1,2-a]pyrazin-1-one |
| "C3" | 3-{4-[4-(4-Methoxy-3-methyl-benzoyl)-piperidin-1-yl]-4-oxo-butyl}-6-methyl-2H-pyrrolo[1,2-a]pyrazin-1-one |
| "C4" | 3-{4-[4-(4-Methoxy-3-methyl-benzoyl)-piperidin-1-yl]-4-oxo-butyl}-2H-pyrrolo[1,2-a]pyrazin-1-one |
| "C5" | 4-{1-[4-(1-Oxo-1,2-dihydro-pyrrolo[1,2-a]pyrazin-3-yl)-butyryl]-piperidin-4-yloxy}-benzonitrile |
| "C6" | 3-{4-Oxo-4-[4-(5-phenyl-[1,3,4]oxadiazol-2-yl)-piperidin-1-yl]-butyl}-2H-pyrrolo[1,2-a]pyrazin-1-one |
| "C7" | 4-{1-[4-(6-Methyl-1-oxo-1,2-dihydro-pyrrolo[1,2-a]pyrazin-3-yl)-butyryl]-piperidin-4-yloxy}-benzonitrile |
| "C8" | 3-{4-[4-(4-Methoxy-benzoyl)-piperidin-1-yl]-4-oxo-butyl}-7-methyl-2H-pyrrolo[1,2-a]pyrazin-1-one |
| "C9" | 6-Fluoro-3-{4-[4-(4-methoxy-benzoyl)-piperidin-1-yl]-4-oxo-butyl}-2H-pyrrolo[1,2-a]pyrazin-1-one |
| "C10" | 6-{4-[4-(4-Methoxy-benzoyl)-piperidin-1-yl]-4-oxo-butyl}-7H-imidazo[1,5-a]pyrazin-8-one |
| "C11" | 6-Chloro-3-{4-[4-(4-methoxy-benzoyl)-piperidin-1-yl]-4-oxo-butyl}-2H-pyrrolo[1,2-a]pyrazin-1-one |
| "C12" | 6-{4-[4-(4-Methoxy-benzoyl)-piperidin-1-yl]-4-oxo-butyl}-2-methyl-5H-pyrazolo[1,5-a]pyrazin-4-one |
| "C13" | 6-{4-[4-(4-Methoxy-benzoyl)-piperidin-1-yl]-4-oxo-butyl}-7H-imidazo[1,2-a]pyrazin-8-one |
| "C14" | 3-[4-[4-(3-Fluoro-4-methoxy-benzoyl)-1-piperidyl]-4-oxo-butyl]-2H-pyrrolo[1,2-a]pyrazin-1-one |
| "C15" | 3-[4-[4-(6-Methoxypyridine-3-carbonyl)-1-piperidyl]-4-oxo-butyl]-2H-pyrrolo[1,2-a]pyrazin-1-one |
| "C16" | 2-Amino-5-[1-[4-(1-oxo-2H-pyrrolo[1,2-a]pyrazin-3-yl)butanoyl]piperidine-4-carbonyl]pyridine-3-carbonitrile |
| "C17" | 3-[4-[4-(6-Amino-5-pyrimidin-2-yl-pyridine-3-carbonyl)-1-piperidyl]-4-oxo-butyl]-2H-pyrrolo[1,2-a]pyrazin-1-one |
| "C18" | 3-[4-[4-(4-Fluorobenzoyl)-1-piperidyl]-4-oxo-butyl]-2H-pyrrolo[1,2-a]pyrazin-1-one |

-continued

| No. | Name |
|---|---|
| "C20" | 3-[4-[4-[4-(1-Hydroxy-1-methyl-ethyl)benzoyl]-1-piperidyl]-4-oxo-butyl]-2H-pyrrolo[1,2-a]pyrazin-1-one |
| "C21" | 3-[4-[4-(6-Methoxypyridazine-3-carbonyl)-1-piperidyl]-4-oxo-butyl]-2H-pyrrolo[1,2-a]pyrazin-1-one |
| "C22" | 3-[4-[4-(1-Methylpyrazole-4-carbonyl)-1-piperidyl]-4-oxo-butyl]-2H-pyrrolo[1,2-a]pyrazin-1-one |
| "C23" | 3-[4-[4-(1-Methylpyrazole-3-carbonyl)-1-piperidyl]-4-oxo-butyl]-2H-pyrrolo[1,2-a]pyrazin-1-one |
| "C24" | 3-[4-[4-(Isoxazole-4-carbonyl)-1-piperidyl]-4-oxo-butyl]-2H-pyrrolo[1,2-a]pyrazin-1-one |
| "C25" | 3-[4-[4-(1-Methylimidazole-4-carbonyl)-1-piperidyl]-4-oxo-butyl]-2H-pyrrolo[1,2-a]pyrazin-1-one |
| "C26" | 3-[4-[4-(3-Methylimidazole-4-carbonyl)-1-piperidyl]-4-oxo-butyl]-2H-pyrrolo[1,2-a]pyrazin-1-one |
| "C27" | 3-[4-[4-(1-Methylimidazole-2-carbonyl)-1-piperidyl]-4-oxo-butyl]-2H-pyrrolo[1,2-a]pyrazin-1-one |
| "C28" | 3-[4-[4-(3-methoxy-6-oxo-pyridazin-1-yl)-1-piperidyl]-4-oxo-butyl]-2H-pyrrolo[1,2-a]pyrazin-1-one |
| "C29" | 3-[4-[4-(3-methyl-6-oxo-pyridazin-1-yl)-1-piperidyl]-4-oxo-butyl]-2H-pyrrolo[1,2-a]pyrazin-1-one |
| "C30" | 6-(Hydroxymethyl)-3-[4-[4-(4-methoxybenzoyl)-1-piperidyl]-4-oxo-butyl]-2H-pyrrolo[1,2-a]pyrazin-1-one |
| "C31" | 7-Fluoro-3-[4-[4-(4-methoxybenzoyl)-1-piperidyl]-4-oxo-butyl]-2H-pyrrolo[1,2-a]pyrazin-1-one |
| "C32" | 6-[4-[4-(4-Methoxybenzoyl)-1-piperidyl]-4-oxo-butyl]-3-methyl-7H-imidazo[1,2-a]pyrazin-8-one |
| "C33" | 6-[4-[4-(4-Methoxybenzoyl)-1-piperidyl]-4-oxo-butyl]-3-methyl-7H-imidazo[1,5-a]pyrazin-8-one |
| "C34" | 2-[4-[4-(4-Methoxybenzoyl)-1-piperidyl]-4-oxo-butyl]-7-methyl-3H-thieno[3,4-d]pyrimidin-4-one |
| "C35" | 2-[4-[4-(4-Methoxybenzoyl)-1-piperidyl]-4-oxo-butyl]-7-methyl-3H-thieno[3,2-d]pyrimidin-4-one |
| "C36" | 2-[4-[4-(4-Methoxybenzoyl)-1-piperidyl]-4-oxo-butyl]-3H-pyrrolo[2,1-f][1,2,4]triazin-4-one |
| "C37" | 2-[4-[4-(4-Methoxybenzoyl)-1-piperidyl]-4-oxo-butyl]-7-methyl-3H-pyrrolo[2,1-f][1,2,4]triazin-4-one |
| "C38" | 2-[4-[4-(4-Methoxybenzoyl)-1-piperidyl]-4-oxo-butyl]-6-methyl-3H-pyrrolo[2,1-f][1,2,4]triazin-4-one |
| "C39" | 6-Fluoro-2-[4-[4-(4-methoxybenzoyl)-1-piperidyl]-4-oxo-butyl]-3H-pyrrolo[2,1-f][1,2,4]triazin-4-one |
| "C40" | 2-[4-[4-(4-Methoxybenzoyl)-1-piperidyl]-4-oxo-butyl]-7-methyl-3H-pyrrolo[2,3-d]pyrimidin-4-one |
| "C41" | 6-[4-[4-(4-Methoxybenzoyl)-1-piperidyl]-4-oxo-butyl]-1-methyl-5H-pyrazolo[3,4-d]pyrimidin-4-one |
| "C42" | 6-[4-[4-(3-Fluoro-4-methoxy-benzoyl)-1-piperidyl]-4-oxo-butyl]-1-methyl-5H-pyrazolo[3,4-d]pyrimidin-4-one |
| "C43" | 6-[4-[4-(6-Methoxypyridine-3-carbonyl)-1-piperidyl]-4-oxo-butyl]-1-methyl-5H-pyrazolo[3,4-d]pyrimidin-4-one |
| "C44" | 2-Amino-5-[1-[4-(1-methyl-4-oxo-5H-pyrazolo[3,4-d]pyrimidin-6-yl)butanoyl]-4-piperidyl]pyridine-3-carbonitrile |
| "C45" | 6-[4-[4-(6-Amino-5-pyrimidin-2-yl-3-pyridyl)-1-piperidyl]-4-oxo-butyl]-1-methyl-5H-pyrazolo[3,4-d]pyrimidin-4-one |
| "C46" | 1-Methyl-6-[4-oxo-4-[4-(5-phenyl-1,3,4-oxadiazol-2-yl)-1-piperidyl]butyl]-5H-pyrazolo[3,4-d]pyrimidin-4-one |
| "C47" | 4-[[1-[4-(1-Methyl-4-oxo-5H-pyrazolo[3,4-d]pyrimidin-6-yl)butanoyl]-4-piperidyl]oxy]benzonitrile |
| "C48" | 6-[4-[4-(4-Fluorobenzoyl)-1-piperidyl]-4-oxo-butyl]-1-methyl-5H-pyrazolo[3,4-d]pyrimidin-4-one |
| "C49" | 6-[4-[4-(4-Methoxy-3-methyl-benzoyl)-1-piperidyl]-4-oxo-butyl]-1-methyl-5H-pyrazolo[3,4-d]pyrimidin-4-one |
| "C50" | 6-[4-[4-(1-Hydroxy-1-methyl-ethyl)benzoyl]-1-piperidyl]-4-oxo-butyl]-1-methyl-5H-pyrazolo[3,4-d]pyrimidin-4-one |
| "C51" | 6-[4-[4-(6-Methoxypyridazine-3-carbonyl)-1-piperidyl]-4-oxo-butyl]-1-methyl-5H-pyrazolo[3,4-d]pyrimidin-4-one |
| "C52" | 2-[4-[4-(4-Methoxybenzoyl)-1-piperidyl]-4-oxo-butyl]-3,4a,5,7,8,8a-hexahydropyrano[4,3-d]pyrimidin-4-one |
| "C53" | 7-Fluoro-2-[4-[4-(4-methoxybenzoyl)-1-piperidyl]-4-oxo-butyl]-3H-pyrrolo[2,1-f][1,2,4]triazin-4-one |
| "C54" | 7-Methyl-2-{4-oxo-4-[4-(5-phenyl-[1,3,4]oxadiazol-2-yl)-piperidin-1-yl]-butyl}-3H-thieno[3,2-d]pyrimidin-4-one |
| "C55" | 2-{4-[4-(3-Fluoro-4-methoxy-benzoyl)-piperidin-1-yl]-4-oxo-butyl}-7-methyl-3H-thieno[3,2-d]pyrimidin-4-one |
| "C56" | 6-Amino-1'-[4-(7-methyl-4-oxo-3,4-dihydro-thieno[3,2-d]pyrimidin-2-yl)-butyryl]-1',2',3',4',5',6'-hexahydro-[3,4']bipyridinyl-5-carbonitrile |
| "C57" | 3-{4-[4-(6-Methoxy-pyridine-3-carbonyl)-piperidin-1-yl]-4-oxo-butyl}-6-methyl-2H-pyrrolo[1,2-a]pyrazin-1-one |

-continued

| No. | Name |
|---|---|
| "C62" | 6-Methyl-3-{4-[4-(1-methyl-1H-pyrazole-4-carbonyl)-piperidin-1-yl]-4-oxo-butyl}-2H-pyrrolo[1,2-a]pyrazin-1-one |
| "C71" | 7-Fluoro-3-{4-[4-(6-methoxy-pyridine-3-carbonyl)-piperidin-1-yl]-4-oxo-butyl}-2H-pyrrolo[1,2-a]pyrazin-1-one |
| "C78" | 7-Fluoro-3-{4-[4-(1-methyl-1H-pyrazole-4-carbonyl)-piperidin-1-yl]-4-oxo-butyl}-2H-pyrrolo[1,2-a]pyrazin-1-one |
| "C99" | 6-{4-[4-(6-Methoxy-pyridine-3-carbonyl)-piperidin-1-yl]-4-oxo-butyl}-3-methyl-7H-imidazo[1,5-a]pyrazin-8-one |
| "C105" | 3-Methyl-6-{4-[4-(1-methyl-1H-pyrazole-4-carbonyl)-piperidin-1-yl]-4-oxo-butyl}-7H-imidazo[1,5-a]pyrazin-8-one |
| "C113" | 2-{4-[4-(3-Fluoro-4-methoxy-benzoyl)-piperidin-1-yl]-4-oxo-butyl}-7-methyl-3H-thieno[3,4-d]pyrimidin-4-one |
| "C114" | 2-{4-[4-(4-Methoxy-3-methyl-benzoyl)-piperidin-1-yl]-4-oxo-butyl}-7-methyl-3H-thieno[3,4-d]pyrimidin-4-one |
| "C115" | 6-Amino-1'-[4-(7-methyl-4-oxo-3,4-dihydro-thieno[3,4-d]pyrimidin-2-yl)-butyryl]-1',2',3',4',5',6'-hexahydro-[3,4']bipyridinyl-5-carbonitrile |
| "C116" | 2-[4-(6-Amino-5-pyrimidin-2-yl-3',4',5',6'-tetrahydro-2'H-[3,4']bipyridinyl-1'-yl)-4-oxo-butyl]-7-methyl-3H-thieno[3,4-d]pyrimidin-4-one |
| "C117" | 7-Methyl-2-{4-oxo-4-[4-(5-phenyl-[1,3,4]oxadiazol-2-yl)-piperidin-1-yl]-butyl}-3H-thieno[3,4-d]pyrimidin-4-one |
| "C118" | 4-{1-[4-(7-Methyl-4-oxo-3,4-dihydro-thieno[3,4-d]pyrimidin-2-yl)-butyryl]-piperidin-4-yloxy}-benzonitrile |
| "C119" | 2-{4-[4-(4-Fluoro-benzoyl)-piperidin-1-yl]-4-oxo-butyl}-7-methyl-3H-thieno[3,4-d]pyrimidin-4-one |
| "C120" | 2-{4-[4-(4-Methoxy-3-methyl-benzoyl)-piperidin-1-yl]-4-oxo-butyl}-7-methyl-3H-thieno[3,4-d]pyrimidin-4-one |
| "C121" | 2-(4-{4-[4-(1-Hydroxy-1-methyl-ethyl)-benzoyl]-piperidin-1-yl}-4-oxo-butyl)-7-methyl-3H-thieno[3,4-d]pyrimidin-4-one |
| "C123" | 7-Methyl-2-{4-[4-(1-methyl-1H-pyrazole-4-carbonyl)-piperidin-1-yl]-4-oxo-butyl}-3H-thieno[3,4-d]pyrimidin-4-one |
| "C126" | 2-{4-[4-(6-Methoxypyridine-3-carbonyl)-1-piperidyl]-4-oxo-butyl}-7-methyl-3H-thieno[3,2-d]pyrimidin-4-one |
| "C128" | 2-{4-[4-(6-Amino-5-pyrimidin-2-yl-3-pyridyl)-1-piperidyl]-4-oxo-butyl}-7-methyl-3H-thieno[3,2-d]pyrimidin-4-one |
| "C130" | 4-{{1-[4-(7-Methyl-4-oxo-3H-thieno[3,2-d]pyrimidin-2-yl)butanoyl]-4-piperidyl}oxy}benzonitrile |
| "C131" | 2-{4-[4-(4-Fluorobenzoyl)-1-piperidyl]-4-oxo-butyl}-7-methyl-3H-thieno[3,2-d]pyrimidin-4-one |
| "C132" | 2-{4-[4-(4-Methoxy-3-methyl-benzoyl)-1-piperidyl]-4-oxo-butyl}-7-methyl-3H-thieno[3,2-d]pyrimidin-4-one |
| "C133" | 2-{4-{4-[4-(1-Hydroxy-1-methyl-ethyl)benzoyl]-1-piperidyl}-4-oxo-butyl}-7-methyl-3H-thieno[3,2-d]pyrimidin-4-one |
| "C135" | 7-Methyl-2-{4-[4-(1-methyl-1H-pyrazole-4-carbonyl)-piperidin-1-yl]-4-oxo-butyl}-3H-thieno[3,2-d]pyrimidin-4-one |
| "C136" | 2-{4-[4-(3-Fluoro-4-methoxy-benzoyl)-piperidin-1-yl]-4-oxo-butyl}-3H-pyrrolo[2,1-f][1,2,4]triazin-4-one |
| "C137" | 2-{4-[4-(6-Methoxy-pyridine-3-carbonyl)-piperidin-1-yl]-4-oxo-butyl}-3H-pyrrolo[2,1-f][1,2,4]triazin-4-one |
| "C138" | 6-Amino-1'-[4-(4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |
| "C139" | 2-[4-(6-Amino-5-pyrimidin-2-yl-3',4',5',6'-tetrahydro-2'H-[3,4']bipyridinyl-1'-yl)-4-oxo-butyl]-3H-pyrrolo[2,1-f][1,2,4]triazin-4-one |
| "C140" | 2-{4-Oxo-4-[4-(5-phenyl-[1,3,4]oxadiazol-2-yl)-piperidin-1-yl]-butyl}-3H-pyrrolo[2,1-f][1,2,4]triazin-4-one |
| "C141" | 4-{1-[4-(4-Oxo-3,4-dihydro-pyrrolo[2,1-f][1,2,4]triazin-2-yl)-butyryl]-piperidin-4-yloxy}-benzonitrile |
| "C142" | 2-{4-[4-(4-Fluoro-benzoyl)-piperidin-1-yl]-4-oxo-butyl}-3H-pyrrolo[2,1-f][1,2,4]triazin-4-one |
| "C143" | 2-{4-[4-(4-Methoxy-3-methyl-benzoyl)-piperidin-1-yl]-4-oxo-butyl}-3H-pyrrolo[2,1-f][1,2,4]triazin-4-one |
| "C144" | 2-(4-{4-[4-(1-Hydroxy-1-methyl-ethyl)-benzoyl]-piperidin-1-yl}-4-oxo-butyl)-3H-pyrrolo[2,1-f][1,2,4]triazin-4-one |
| "C146" | 2-{4-[4-(1-Methyl-1H-pyrazole-4-carbonyl)-piperidin-1-yl]-4-oxo-butyl}-3H-pyrrolo[2,1-f][1,2,4]triazin-4-one |
| "C147" | 2-{4-[4-(3-Fluoro-4-methoxy-benzoyl)-piperidin-1-yl]-4-oxo-butyl}-7-methyl-3H-pyrrolo[2,1-f][1,2,4]triazin-4-one |
| "C148" | 2-{4-[4-(6-Methoxy-pyridine-3-carbonyl)-piperidin-1-yl]-4-oxo-butyl}-7-methyl-3H-pyrrolo[2,1-f][1,2,4]triazin-4-one |
| "C149" | 6-Amino-1'-[4-(7-methyl-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |

-continued

| No. | Name |
|---|---|
| "C150" | 2-[4-(6-Amino-5-pyrimidin-2-yl-3',4',5',6'-tetrahydro-2'H-[3,4']bipyridinyl-1'-yl)-4-oxo-butyl]-7-methyl-3H-pyrrolo[2,1-f][1,2,4]triazin-4-one |
| "C151" | 7-Methyl-2-{4-oxo-4-[4-(5-phenyl-[1,3,4]oxadiazol-2-yl)-piperidin-1-yl]-butyl}-3H-pyrrolo[2,1-f][1,2,4]triazin-4-one |
| "C152" | 4-{1-[4-(7-Methyl-4-oxo-3,4-dihydro-pyrrolo[2,1-f][1,2,4]triazin-2-yl)-butyryl]-piperidin-4-yloxy}-benzonitrile |
| "C153" | 2-{4-[4-(4-Fluoro-benzoyl)-piperidin-1-yl]-4-oxo-butyl}-7-methyl-3H-pyrrolo[2,1-f][1,2,4]triazin-4-one |
| "C154" | 2-{4-[4-(4-Methoxy-3-methyl-benzoyl)-piperidin-1-yl]-4-oxo-butyl}-7-methyl-3H-pyrrolo[2,1-f][1,2,4]triazin-4-one |
| "C155" | 2-(4-{4-[4-(1-Hydroxy-1-methyl-ethyl)-benzoyl]-piperidin-1-yl}-4-oxo-butyl)-7-methyl-3H-pyrrolo[2,1-f][1,2,4]triazin-4-one |
| "C157" | 7-Methyl-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C158" | 2-{4-[4-(3-Fluoro-4-methoxy-benzoyl)-piperidin-1-yl]-4-oxo-butyl}-6-methyl-3H-pyrrolo[2,1-f][1,2,4]triazin-4-one |
| "C159" | 2-{4-[4-(6-Methoxy-pyridine-3-carbonyl)-piperidin-1-yl]-4-oxo-butyl}-6-methyl-3H-pyrrolo[2,1-f][1,2,4]triazin-4-one |
| "C160" | 6-Amino-1'-[4-(6-methyl-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |
| "C161" | 2-[4-(6-Amino-5-pyrimidin-2-yl-3',4',5',6'-tetrahydro-2'H-[3,4']bipyridinyl-1'-yl)-4-oxo-butyl]-6-methyl-3H-pyrrolo[2,1-f][1,2,4]triazin-4-one |
| "C162" | 6-Methyl-2-{4-oxo-4-[4-(5-phenyl-[1,3,4]oxadiazol-2-yl)-piperidin-1-yl]-butyl}-3H-pyrrolo[2,1-f][1,2,4]triazin-4-one |
| "C163" | 4-{1-[4-(6-Methyl-4-oxo-3,4-dihydro-pyrrolo[2,1-f][1,2,4]triazin-2-yl)-butyryl]-piperidin-4-yloxy}-benzonitrile |
| "C164" | 2-{4-[4-(4-Fluoro-benzoyl)-piperidin-1-yl]-4-oxo-butyl}-6-methyl-3H-pyrrolo[2,1-f][1,2,4]triazin-4-one |
| "C165" | 2-{4-[4-(4-Methoxy-3-methyl-benzoyl)-piperidin-1-yl]-4-oxo-butyl}-6-methyl-3H-pyrrolo[2,1-f][1,2,4]triazin-4-one |
| "C166" | 2-(4-{4-[4-(1-Hydroxy-1-methyl-ethyl)-benzoyl]-piperidin-1-yl}-4-oxo-butyl)-6-methyl-3H-pyrrolo[2,1-f][1,2,4]triazin-4-one |
| "C168" | 6-Methyl-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C169" | 6-Fluoro-2-{4-[4-(3-fluoro-4-methoxy-benzoyl)-piperidin-1-yl]-4-oxo-butyl}-3H-pyrrolo[2,1-f][1,2,4]triazin-4-one |
| "C170" | 6-Fluoro-2-{4-[4-(6-methoxy-pyridine-3-carbonyl)-piperidin-1-yl]-4-oxo-butyl}-3H-pyrrolo[2,1-f][1,2,4]triazin-4-one |
| "C171" | 6-Amino-1'-[4-(6-fluoro-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |
| "C172" | 2-[4-(6-Amino-5-pyrimidin-2-yl-3',4',5',6'-tetrahydro-2'H-[3,4']bipyridinyl-1'-yl)-4-oxo-butyl]-6-fluoro-3H-pyrrolo[2,1-f][1,2,4]triazin-4-one |
| "C173" | 6-Fluoro-2-{4-oxo-4-[4-(5-phenyl-[1,3,4]oxadiazol-2-yl)-piperidin-1-yl]-butyl}-3H-pyrrolo[2,1-f][1,2,4]triazin-4-one |
| "C174" | 4-{1-[4-(6-Fluoro-4-oxo-3,4-dihydro-pyrrolo[2,1-f][1,2,4]triazin-2-yl)-butyryl]-piperidin-4-yloxy}-benzonitrile |
| "C175" | 6-Fluoro-2-{4-[4-(4-fluoro-benzoyl)-piperidin-1-yl]-4-oxo-butyl}-3H-pyrrolo[2,1-f][1,2,4]triazin-4-one |
| "C177" | 6-Fluoro-2-(4-{4-[4-(1-hydroxy-1-methyl-ethyl)-benzoyl]-piperidin-1-yl}-4-oxo-butyl)-3H-pyrrolo[2,1-f][1,2,4]triazin-4-one |
| "C179" | 6-Fluoro-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C180" | 2-{4-[4-(3-Fluoro-4-methoxy-benzoyl)-piperidin-1-yl]-4-oxo-butyl}-7-methyl-3,7-dihydro-pyrrolo[2,3-d]pyrimidin-4-one |
| "C181" | 2-{4-[4-(6-Methoxy-pyridine-3-carbonyl)-piperidin-1-yl]-4-oxo-butyl}-7-methyl-3,7-dihydro-pyrrolo[2,3-d]pyrimidin-4-one |
| "C182" | 6-Amino-1'-[4-(7-methyl-4-oxo-4,7-dihydro-3H-pyrrolo[2,3-d]pyrimidin-2-yl)-butyryl]-1',2',3',4',5',6'-hexahydro-[3,4']bipyridinyl-5-carbonitrile |
| "C183" | 2-[4-(6-Amino-5-pyrimidin-2-yl-3',4',5',6'-tetrahydro-2'H-[3,4']bipyridinyl-1'-yl)-4-oxo-butyl]-7-methyl-3,7-dihydro-pyrrolo[2,3-d]pyrimidin-4-one |
| "C184" | 7-Methyl-2-{4-oxo-4-[4-(5-phenyl-[1,3,4]oxadiazol-2-yl)-piperidin-1-yl]-butyl}-3,7-dihydro-pyrrolo[2,3-d]pyrimidin-4-one |
| "C186" | 2-{4-[4-(4-Fluoro-benzoyl)-piperidin-1-yl]-4-oxo-butyl}-7-methyl-3,7-dihydro-pyrrolo[2,3-d]pyrimidin-4-one |
| "C190" | 7-Methyl-2-{4-[4-(1-methyl-1H-pyrazole-4-carbonyl)-piperidin-1-yl]-4-oxo-butyl}-3,7-dihydro-pyrrolo[2,3-d]pyrimidin-4-one |
| "C191" | 1-Methyl-5-{4-[4-(1-methyl-1H-pyrazole-4-carbonyl)-piperidin-1-yl]-4-oxo-butyl}-1,6-dihydro-pyrazolo[4,3-d]pyrimidin-7-one |

| No. | Name |
|---|---|
| "C192" | 2-{4-[4-(3-Fluoro-4-methoxy-benzoyl)-piperidin-1-yl]-4-oxo-butyl}-3,5,7,8-tetrahydro-pyrano[4,3-d]pyrimidin-4-one |
| "C193" | 2-{4-[4-(6-Methoxy-pyridine-3-carbonyl)-piperidin-1-yl]-4-oxo-butyl}-3,5,7,8-tetrahydro-pyrano[4,3-d]pyrimidin-4-one |
| "C194" | 6-Amino-1'-[4-(4-oxo-3,5,7,8-tetrahydro-4H-pyrano[4,3-d]pyrimidin-2-yl)-butyryl]-1',2',3',4',5',6'-hexahydro-[3,4']bipyridinyl-5-carbonitrile |
| "C195" | 2-[4-(6-Amino-5-pyrimidin-2-yl-3',4',5',6'-tetrahydro-2'H-[3,4']bipyridinyl-1'-yl)-4-oxo-butyl]-3,5,7,8-tetrahydro-pyrano[4,3-d]pyrimidin-4-one |
| "C196" | 2-{4-Oxo-4-[4-(5-phenyl-[1,3,4]oxadiazol-2-yl)-piperidin-1-yl]-butyl}-3,5,7,8-tetrahydro-pyrano[4,3-d]pyrimidin-4-one |
| "C197" | 4-{1-[4-(4-Oxo-3,5,7,8-tetrahydro-4H-pyrano[4,3-d]pyrimidin-2-yl)-butyryl]-piperidin-4-yloxy}-benzonitrile |
| "C198" | 2-{4-[4-(4-Fluoro-benzoyl)-piperidin-1-yl]-4-oxo-butyl}-3,5,7,8-tetrahydro-pyrano[4,3-d]pyrimidin-4-one |
| "C199" | 2-{4-[4-(4-Methoxy-3-methyl-benzoyl)-piperidin-1-yl]-4-oxo-butyl}-3,5,7,8-tetrahydro-pyrano[4,3-d]pyrimidin-4-one |
| "C200" | 2-(4-{4-[4-(1-Hydroxy-1-methyl-ethyl)-benzoyl]-piperidin-1-yl}-4-oxo-butyl)-3,5,7,8-tetrahydro-pyrano[4,3-d]pyrimidin-4-one |
| "C202" | 2-{4-[4-(1-Methyl-1H-pyrazole-4-carbonyl)-piperidin-1-yl]-4-oxo-butyl}-3,5,7,8-tetrahydro-pyrano[4,3-d]pyrimidin-4-one |
| "C207" | 6-{4-[4-(1-Methylpyrazole-4-carbonyl)-1-piperidyl]-4-oxo-butyl}-7H-imidazo[1,5-a]pyrazin-8-one |
| "C208" | 6-Fluoro-3-{4-[4-(1-methyl-1H-pyrazole-4-carbonyl)-piperidin-1-yl]-4-oxo-butyl}-2H-pyrrolo[1,2-a]pyrazin-1-one |
| "C209" | 2-Methyl-6-{4-[4-(1-methyl-1H-pyrazole-4-carbonyl)-piperidin-1-yl]-4-oxo-butyl}-5H-pyrazolo[1,5-a]pyrazin-4-one |
| "C210" | 3-{4-[4-(1-Isopropyl-1H-pyrazole-4-carbonyl)-piperidin-1-yl]-4-oxo-butyl}-2H-pyrrolo[1,2-a]pyrazin-1-one |
| "C211" | 3-{4-[4-(1-Isopropyl-1H-pyrazole-4-carbonyl)-piperidin-1-yl]-4-oxo-butyl}-6-methyl-2H-pyrrolo[1,2-a]pyrazin-1-one |
| "C212" | 6-Fluoro-3-{4-[4-(1-isopropyl-1H-pyrazole-4-carbonyl)-piperidin-1-yl]-4-oxo-butyl}-2H-pyrrolo[1,2-a]pyrazin-1-one |
| "C213" | 6-{4-[4-(1-Ethyl-1H-pyrazole-4-carbonyl)-piperidin-1-yl]-4-oxo-butyl}-1-methyl-1,5-dihydro-pyrazolo[3,4-d]pyrimidin-4-one |
| "C214" | 2-{4-[4-(1-Ethyl-1H-pyrazole-4-carbonyl)-piperidin-1-yl]-4-oxo-butyl}-3H-pyrrolo[2,1-f][1,2,4]triazin-4-one |
| "C215" | 2-{4-[4-(1-Ethyl-1H-pyrazole-4-carbonyl)-piperidin-1-yl]-4-oxo-butyl}-6-fluoro-3H-pyrrolo[2,1-f][1,2,4]triazin-4-one |
| "C216" | 2-{4-[4-(1-Ethyl-1H-pyrazole-4-carbonyl)-piperidin-1-yl]-4-oxo-butyl}-7-methyl-3H-thieno[3,4-d]pyrimidin-4-one |
| "C217" | 6-{4-[4-(1-Isopropyl-1H-pyrazole-4-carbonyl)-piperidin-1-yl]-4-oxo-butyl}-2-methyl-5H-pyrazolo[1,5-a]pyrazin-4-one |
| "C218" | 6-{4-[4-(1-Isopropyl-1H-pyrazole-4-carbonyl)-piperidin-1-yl]-4-oxo-butyl}-1-methyl-1,5-dihydro-pyrazolo[3,4-d]pyrimidin-4-one |
| "C219" | 2-{4-[4-(1-Isopropyl-1H-pyrazole-4-carbonyl)-piperidin-1-yl]-4-oxo-butyl}-3H-pyrrolo[2,1-f][1,2,4]triazin-4-one |
| "C220" | 2-{4-[4-(1-Isopropyl-1H-pyrazole-4-carbonyl)-piperidin-1-yl]-4-oxo-butyl}-6-methyl-3H-pyrrolo[2,1-f][1,2,4]triazin-4-one |
| "C221" | 6-Fluoro-2-{4-[4-(1-isopropyl-1H-pyrazole-4-carbonyl)-piperidin-1-yl]-4-oxo-butyl}-3H-pyrrolo[2,1-f][1,2,4]triazin-4-one |
| "C222" | 2-{4-[4-(1-Ethyl-1H-pyrazole-4-carbonyl)-piperidin-1-yl]-4-oxo-butyl}-7-methyl-3H-pyrrolo[2,1-f][1,2,4]triazin-4-one |
| "C223" | 2-{4-[4-(1-Isopropyl-1H-pyrazole-4-carbonyl)-piperidin-1-yl]-4-oxo-butyl}-7-methyl-3H-pyrrolo[2,1-f][1,2,4]triazin-4-one |
| "C224" | 2-{4-[4-(1-Ethyl-1H-pyrazole-4-carbonyl)-piperidin-1-yl]-4-oxo-butyl}-7-methyl-3H-thieno[3,2-d]pyrimidin-4-one |
| "C225" | 2-{4-[4-(1-Isopropyl-1H-pyrazole-4-carbonyl)-piperidin-1-yl]-4-oxo-butyl}-7-methyl-3H-thieno[3,2-d]pyrimidin-4-one |
| "C226" | 2-{4-[4-(1-Isopropyl-1H-pyrazole-4-carbonyl)-piperidin-1-yl]-4-oxo-butyl}-7-methyl-3H-thieno[3,4-d]pyrimidin-4-one |
| "C227" | 2-{4-[4-(4-Methoxy-benzoyl)-piperidin-1-yl]-4-oxo-butyl}-5,6,7,8-tetrahydro-3H-quinazolin-4-one |
| "C228" | 2-{4-[4-(1-Ethyl-1H-pyrazole-4-carbonyl)-piperidin-1-yl]-4-oxo-butyl}-3,5,7,8-tetrahydro-pyrano[4,3-d]pyrimidin-4-one |
| "C229" | 2-{4-[4-(1-Isopropyl-1H-pyrazole-4-carbonyl)-piperidin-1-yl]-4-oxo-butyl}-3,5,7,8-tetrahydro-pyrano[4,3-d]pyrimidin-4-one |
| "C230" | 2-{4-[4-(1-Methyl-1H-pyrazole-4-carbonyl)-piperidin-1-yl]-4-oxo-butyl}-5,6,7,8-tetrahydro-3H-quinazolin-4-one |
| "C231" | 6-{4-[4-(6-Methoxy-pyridine-3-carbonyl)-piperidin-1-yl]-4-oxo-butyl}-2-methyl-5H-pyrazolo[1,5-a]pyrazin-4-one |
| "C232" | 6-Amino-1'-[4-(4-oxo-3,4,5,6,7,8-hexahydro-quinazolin-2-yl)-butyryl]-1',2',3',4',5',6'-hexahydro-[3,4']bipyridinyl-5-carbonitrile |
| "C233" | 2-{4-[4-(1-Ethyl-1H-pyrazole-4-carbonyl)-piperidin-1-yl]-4-oxo-butyl}-6-methyl-3H-pyrrolo[2,1-f][1,2,4]triazin-4-one |

| No. | Name |
|---|---|
| "C234" | 1-Methyl-6-{4-[4-(4-methyl-benzoyl)-piperidin-1-yl]-4-oxo-butyl}-1,5-dihydro-pyrazolo[3,4-d]pyrimidin-4-one |
| "C235" | 2-{4-[4-(4-Methyl-benzoyl)-piperidin-1-yl]-4-oxo-butyl}-3H-pyrrolo[2,1-f][1,2,4]triazin-4-one |
| "C236" | 6-{4-[4-(4-Chloro-benzoyl)-piperidin-1-yl]-4-oxo-butyl}-1-methyl-1,5-dihydro-pyrazolo[3,4-d]pyrimidin-4-one |
| "C237" | 2-{4-[4-(4-Chloro-benzoyl)-piperidin-1-yl]-4-oxo-butyl}-3H-pyrrolo[2,1-f][1,2,4]triazin-4-one |
| "C238" | 6,7-Difluoro-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C239" | 2-{4-[4-(4-Methoxy-benzoyl)-piperidin-1-yl]-4-oxo-butyl}-5,6-dimethyl-3H-pyrimidin-4-one |
| "C240" | 2-{4-[4-(4-Fluoro-benzoyl)-piperidin-1-yl]-4-oxo-butyl}-5,6-dimethyl-3H-pyrimidin-4-one |
| "C241" | 2-{4-[4-(6-Methoxy-pyridine-3-carbonyl)-piperidin-1-yl]-4-oxo-butyl}-5,6-dimethyl-3H-pyrimidin-4-one |
| "C242" | 5,6-Dimethyl-2-{4-[4-(1-methyl-1H-pyrazole-4-carbonyl)-piperidin-1-yl]-4-oxo-butyl}-3H-pyrimidin-4-one |
| "C243" | 2-{4-[4-(1-Ethyl-1H-pyrazole-4-carbonyl)-piperidin-1-yl]-4-oxo-butyl}-7-methyl-3,7-dihydro-pyrrolo[2,3-d]pyrimidin-4-one |
| "C244" | 2-{4-[4-(1-Isopropyl-1H-pyrazole-4-carbonyl)-piperidin-1-yl]-4-oxo-butyl}-7-methyl-3,7-dihydro-pyrrolo[2,3-d]pyrimidin-4-one |
| "C245" | 6-(4-{4-[4-(1,1-Difluoro-ethyl)-benzoyl]-piperidin-1-yl}-4-oxo-butyl)-1-methyl-1,5-dihydro-pyrazolo[3,4-d]pyrimidin-4-one |
| "C246" | 6-{4-[4-(3,4-Difluoro-benzoyl)-piperidin-1-yl]-4-oxo-butyl}-1-methyl-1,5-dihydro-pyrazolo[3,4-d]pyrimidin-4-one |
| "C247" | 2-{4-[4-(4-Chloro-benzoyl)-piperidin-1-yl]-4-oxo-butyl}-3,5,7,8-tetrahydro-pyrano[4,3-d]pyrimidin-4-one |
| "C248" | 2-{4-[4-(3,4-Difluoro-benzoyl)-piperidin-1-yl]-4-oxo-butyl}-7-methyl-3,7-dihydro-pyrrolo[2,3-d]pyrimidin-4-one |
| "C249" | 2-(4-{4-[4-(1,1-Difluoro-ethyl)-benzoyl]-piperidin-1-yl}-4-oxo-butyl)-7-methyl-3,7-dihydro-pyrrolo[2,3-d]pyrimidin-4-one |
| "C250" | 1-[4-(4-Methoxy-benzoyl)-piperidin-1-yl]-4-phthalazin-1-yl-butan-1-one |
| "C251" | 6-Ethyl-2-{4-[4-(4-methoxy-benzoyl)-piperidin-1-yl]-4-oxo-butyl}-3H-pyrimidin-4-one |
| "C252" | 6-Ethyl-2-{4-[4-(4-fluoro-benzoyl)-piperidin-1-yl]-4-oxo-butyl}-3H-pyrimidin-4-one |
| "C253" | 6-Ethyl-2-{4-[4-(6-methoxy-pyridine-3-carbonyl)-piperidin-1-yl]-4-oxo-butyl}-3H-pyrimidin-4-one |
| "C254" | 6-Isopropyl-2-{4-[4-(4-methoxy-benzoyl)-piperidin-1-yl]-4-oxo-butyl}-3H-pyrimidin-4-one |
| "C255" | 2-{4-[4-(4-Fluorobenzoyl)-1-piperidyl]-4-oxo-butyl}-4-isopropyl-1H-pyrimidin-6-one |
| "C256" | 4-Isopropyl-2-{4-[4-(6-methoxypyridine-3-carbonyl)-1-piperidyl]-4-oxo-butyl}-1H-pyrimidin-6-one |
| "C257" | 4-Isopropyl-2-{4-[4-(1-methylpyrazole-4-carbonyl)-1-piperidyl]-4-oxo-butyl}-1H-pyrimidin-6-one |
| "C258" | 4-(1,2-Benzoxazol-3-yl)-1-[4-(4-methoxybenzoyl)-1-piperidyl]butan-1-one |
| "C259" | 4-(1,2-Benzoxazol-3-yl)-1-[4-(4-fluorobenzoyl)-1-piperidyl]butan-1-one |
| "C259a" | 4-(1,2-Benzoxazol-3-yl)-1-[4-(6-methoxypyridine-3-carbonyl)-1-piperidyl]butan-1-one |
| "C260" | 4-(1,2-Benzoxazol-3-yl)-1-[4-(1-methylpyrazole-4-carbonyl)-1-piperidyl]butan-1-one |
| "C261" | 4-Ethyl-2-{4-[4-(1-methylpyrazole-4-carbonyl)-1-piperidyl]-4-oxo-butyl}-1H-pyrimidin-6-one |
| "C262" | 2-{4-[4-(3,4-Difluorobenzoyl)-1-piperidyl]-4-oxo-butyl}-3,5,7,8-tetrahydropyrano[4,3-d]pyrimidin-4-one |
| "C263" | 2-{4-{4-[4-(1,1-Difluoroethyl)benzoyl]-1-piperidyl}-4-oxo-butyl}-3,5,7,8-tetrahydropyrano[4,3-d]pyrimidin-4-one |
| "C266" | 1-[4-(1-Methylpyrazole-4-carbonyl)-1-piperidyl]-4-phthalazin-1-yl-butan-1-one | and pharmaceutically acceptable solvates, salts, tautomers and stereoisomers thereof, including mixtures thereof in all ratios.

10. A medicament composition comprising at least one compound of the formula I according to claim 1 and/or at least one pharmaceutically acceptable salt, solvate, tautomer or stereoisomer thereof, including mixtures thereof in all ratios, and an pharmaceutically acceptable carrier, excipient or vehicle.

11. A medicament composition according to claim 10, further comprising at least one further medicament active ingredient.

12. A kit consisting of separate packs of
   (a) an effective amount of a compound of the formula I according to claim 1 and/or a pharmaceutically acceptable salt, solvate, tautomer or stereoisomer thereof, including mixtures thereof in all ratios, and
   (b) an effective amount of a further medicament active ingredient.

13. The compound according to claim 1, wherein said compound is selected from the following compounds

| No. | Name |
| --- | --- |
| "C1" | 3-{4-[4-(4-Methoxy-benzoyl)-piperidin-1-yl]-4-oxo-butyl}-6-methyl-2H-pyrrolo[1,2-a]pyrazin-1-one |
| "C2" | 3-{4-[4-(4-Methoxy-benzoyl)-piperidin-1-yl]-4-oxo-butyl}-2H-pyrrolo[1,2-a]pyrazin-1-one |
| "C3" | 3-{4-[4-(4-Methoxy-3-methyl-benzoyl)-piperidin-1-yl]-4-oxo-butyl}-6-methyl-2H-pyrrolo[1,2-a]pyrazin-1-one |
| "C4" | 3-{4-[4-(4-Methoxy-3-methyl-benzoyl)-piperidin-1-yl]-4-oxo-butyl}-2H-pyrrolo[1,2-a]pyrazin-1-one |
| "C5" | 4-{1-[4-(1-Oxo-1,2-dihydro-pyrrolo[1,2-a]pyrazin-3-yl)-butyryl]-piperidin-4-yloxy}-benzonitrile |
| "C6" | 3-{4-Oxo-4-[4-(5-phenyl-[1,3,4]oxadiazol-2-yl)-piperidin-1-yl]-butyl}-2H-pyrrolo[1,2-a]pyrazin-1-one |
| "C7" | 4-{1-[4-(6-Methyl-1-oxo-1,2-dihydro-pyrrolo[1,2-a]pyrazin-3-yl)-butyryl]-piperidin-4-yloxy}-benzonitrile |
| "C8" | 3-{4-[4-(4-Methoxy-benzoyl)-piperidin-1-yl]-4-oxo-butyl}-7-methyl-2H-pyrrolo[1,2-a]pyrazin-1-one |
| "C9" | 6-Fluoro-3-{4-[4-(4-methoxy-benzoyl)-piperidin-1-yl]-4-oxo-butyl}-2H-pyrrolo[1,2-a]pyrazin-1-one |
| "C10" | 6-{4-[4-(4-Methoxy-benzoyl)-piperidin-1-yl]-4-oxo-butyl}-7H-imidazo[1,5-a]pyrazin-8-one |
| "C11" | 6-Chloro-3-{4-[4-(4-methoxy-benzoyl)-piperidin-1-yl]-4-oxo-butyl}-2H-pyrrolo[1,2-a]pyrazin-1-one |
| "C12" | 6-{4-[4-(4-Methoxy-benzoyl)-piperidin-1-yl]-4-oxo-butyl}-2-methyl-5H-pyrazolo[1,5-a]pyrazin-4-one |
| "C13" | 6-{4-[4-(4-Methoxy-benzoyl)-piperidin-1-yl]-4-oxo-butyl}-7H-imidazo[1,2-a]pyrazin-8-one |
| "C14" | 3-[4-[4-(3-Fluoro-4-methoxy-benzoyl)-1-piperidyl]-4-oxo-butyl]-2H-pyrrolo[1,2-a]pyrazin-1-one |
| "C15" | 3-[4-[4-(6-Methoxypyridine-3-carbonyl)-1-piperidyl]-4-oxo-butyl]-2H-pyrrolo[1,2-a]pyrazin-1-one |
| "C16" | 2-Amino-5-[1-[4-(1-oxo-2H-pyrrolo[1,2-a]pyrazin-3-yl)butanoyl]piperidine-4-carbonyl]pyridine-3-carbonitrile |
| "C17" | 3-[4-[4-(6-Amino-5-pyrimidin-2-yl-pyridine-3-carbonyl)-1-piperidyl]-4-oxo-butyl]-2H-pyrrolo[1,2-a]pyrazin-1-one |
| "C18" | 3-[4-[4-(4-Fluorobenzoyl)-1-piperidyl]-4-oxo-butyl]-2H-pyrrolo[1,2-a]pyrazin-1-one |
| "C20" | 3-[4-[4-(1-Hydroxy-1-methyl-ethyl)benzoyl]-1-piperidyl]-4-oxo-butyl]-2H-pyrrolo[1,2-a]pyrazin-1-one |
| "C21" | 3-[4-[4-(6-Methoxypyridazine-3-carbonyl)-1-piperidyl]-4-oxo-butyl]-2H-pyrrolo[1,2-a]pyrazin-1-one |
| "C22" | 3-[4-[4-(1-Methylpyrazole-4-carbonyl)-1-piperidyl]-4-oxo-butyl]-2H-pyrrolo[1,2-a]pyrazin-1-one |
| "C23" | 3-[4-[4-(1-Methylpyrazole-3-carbonyl)-1-piperidyl]-4-oxo-butyl]-2H-pyrrolo[1,2-a]pyrazin-1-one |
| "C24" | 3-[4-[4-(Isoxazole-4-carbonyl)-1-piperidyl]-4-oxo-butyl]-2H-pyrrolo[1,2-a]pyrazin-1-one |
| "C25" | 3-[4-[4-(1-Methylimidazole-4-carbonyl)-1-piperidyl]-4-oxo-butyl]-2H-pyrrolo[1,2-a]pyrazin-1-one |
| "C26" | 3-[4-[4-(3-Methylimidazole-4-carbonyl)-1-piperidyl]-4-oxo-butyl]-2H-pyrrolo[1,2-a]pyrazin-1-one |
| "C27" | 3-[4-[4-(1-Methylimidazole-2-carbonyl)-1-piperidyl]-4-oxo-butyl]-2H-pyrrolo[1,2-a]pyrazin-1-one |
| "C28" | 3-[4-[4-(3-methoxy-6-oxo-pyridazin-1-yl)-1-piperidyl]-4-oxo-butyl]-2H-pyrrolo[1,2-a]pyrazin-1-one |
| "C29" | 3-[4-[4-(3-methyl-6-oxo-pyridazin-1-yl)-1-piperidyl]-4-oxo-butyl]-2H-pyrrolo[1,2-a]pyrazin-1-one |
| "C30" | 6-(Hydroxymethyl)-3-[4-[4-(4-methoxybenzoyl)-1-piperidyl]-4-oxo-butyl]-2H-pyrrolo[1,2-a]pyrazin-1-one |
| "C31" | 7-Fluoro-3-[4-[4-(4-methoxybenzoyl)-1-piperidyl]-4-oxo-butyl]-2H-pyrrolo[1,2-a]pyrazin-1-one |
| "C32" | 6-[4-[4-(4-Methoxybenzoyl)-1-piperidyl]-4-oxo-butyl]-3-methyl-7H-imidazo[1,2-a]pyrazin-8-one |
| "C33" | 6-[4-[4-(4-Methoxybenzoyl)-1-piperidyl]-4-oxo-butyl]-3-methyl-7H-imidazo[1,5-a]pyrazin-8-one |
| "C34" | 2-[4-[4-(4-Methoxybenzoyl)-1-piperidyl]-4-oxo-butyl]-7-methyl-3H-thieno[3,4-d]pyrimidin-4-one |
| "C35" | 2-[4-[4-(4-Methoxybenzoyl)-1-piperidyl]-4-oxo-butyl]-7-methyl-3H-thieno[3,2-d]pyrimidin-4-one |
| "C36" | 2-[4-[4-(4-Methoxybenzoyl)-1-piperidyl]-4-oxo-butyl]-3H-pyrrolo[2,1-f][1,2,4]triazin-4-one |
| "C37" | 2-[4-[4-(4-Methoxybenzoyl)-1-piperidyl]-4-oxo-butyl]-7-methyl-3H-pyrrolo[2,1-f][1,2,4]triazin-4-one |
| "C38" | 2-[4-[4-(4-Methoxybenzoyl)-1-piperidyl]-4-oxo-butyl]-6-methyl-3H-pyrrolo[2,1-f][1,2,4]triazin-4-one |
| "C39" | 6-Fluoro-2-[4-[4-(4-methoxybenzoyl)-1-piperidyl]-4-oxo-butyl]-3H-pyrrolo[2,1-f][1,2,4]triazin-4-one |
| "C40" | 2-[4-[4-(4-Methoxybenzoyl)-1-piperidyl]-4-oxo-butyl]-7-methyl-3H-pyrrolo[2,3-d]pyrimidin-4-one |
| "C41" | 6-[4-[4-(4-Methoxybenzoyl)-1-piperidyl]-4-oxo-butyl]-1-methyl-5H-pyrazolo[3,4-d]pyrimidin-4-one |
| "C42" | 6-[4-[4-(3-Fluoro-4-methoxy-benzoyl)-1-piperidyl]-4-oxo-butyl]-1-methyl-5H-pyrazolo[3,4-d]pyrimidin-4-one |
| "C43" | 6-[4-[4-(6-Methoxypyridine-3-carbonyl)-1-piperidyl]-4-oxo-butyl]-1-methyl-5H-pyrazolo[3,4-d]pyrimidin-4-one |
| "C44" | 2-Amino-5-[1-[4-(1-methyl-4-oxo-5H-pyrazolo[3,4-d]pyrimidin-6-yl)butanoyl]-4-piperidyl]pyridine-3-carbonitrile |
| "C45" | 6-[4-[4-(6-Amino-5-pyrimidin-2-yl-3-pyridyl)-1-piperidyl]-4-oxo-butyl]-1-methyl-5H-pyrazolo[3,4-d]pyrimidin-4-one |
| "C46" | 1-Methyl-6-[4-oxo-4-[4-(5-phenyl-1,3,4-oxadiazol-2-yl)-1-piperidyl]butyl]-5H-pyrazolo[3,4-d]pyrimidin-4-one |
| "C47" | 4-[[1-[4-(1-Methyl-4-oxo-5H-pyrazolo[3,4-d]pyrimidin-6-yl)butanoyl]-4-piperidyl]oxy]benzonitrile |
| "C48" | 6-[4-[4-(4-Fluorobenzoyl)-1-piperidyl]-4-oxo-butyl]-1-methyl-5H-pyrazolo[3,4-d]pyrimidin-4-one |
| "C49" | 6-[4-[4-(4-Methoxy-3-methyl-benzoyl)-1-piperidyl]-4-oxo-butyl]-1-methyl-5H-pyrazolo[3,4-d]pyrimidin-4-one |
| "C50" | 6-[4-[4-[4-(1-Hydroxy-1-methyl-ethyl)benzoyl]-1-piperidyl]-4-oxo-butyl]-1-methyl-5H-pyrazolo[3,4-d]pyrimidin-4-one |
| "C51" | 6-[4-[4-(6-Methoxypyridazine-3-carbonyl)-1-piperidyl]-4-oxo-butyl]-1-methyl-5H-pyrazolo[3,4-d]pyrimidin-4-one |
| "C52" | 2-[4-[4-(4-Methoxybenzoyl)-1-piperidyl]-4-oxo-butyl]-3,4a,5,7,8,8a-hexahydropyrano[4,3-d]pyrimidin-4-one |
| "C53" | 7-Fluoro-2-[4-[4-(4-methoxybenzoyl)-1-piperidyl]-4-oxo-butyl]-3H-pyrrolo[2,1-f][1,2,4]triazin-4-one |
| "C54" | 7-Methyl-2-{4-oxo-4-[4-(5-phenyl-[1,3,4]oxadiazol-2-yl)-piperidin-1-yl]-butyl}-3H-thieno[3,2-d]pyrimidin-4-one |
| "C55" | 2-{4-[4-(3-Fluoro-4-methoxy-benzoyl)-piperidin-1-yl]-4-oxo-butyl}-7-methyl-3H-thieno[3,2-d]pyrimidin-4-one |
| "C56" | 6-Amino-1'-[4-(7-methyl-4-oxo-3,4-dihydro-thieno[3,2-d]pyrimidin-2-yl)-butyryl]-1',2',3',4',5',6'-hexahydro-[3,4']bipyridinyl-5-carbonitrile |
| "C57" | 3-{4-[4-(6-Methoxy-pyridine-3-carbonyl)-piperidin-1-yl]-4-oxo-butyl}-6-methyl-2H-pyrrolo[1,2-a]pyrazin-1-one |
| "C62" | 6-Methyl-3-{4-[4-(1-methyl-1H-pyrazole-4-carbonyl)-piperidin-1-yl]-4-oxo-butyl}-2H-pyrrolo[1,2-a]pyrazin-1-one |
| "C71" | 7-Fluoro-3-{4-[4-(6-methoxy-pyridine-3-carbonyl)-piperidin-1-yl]-4-oxo-butyl}-2H-pyrrolo[1,2-a]pyrazin-1-one |
| "C78" | 7-Fluoro-3-{4-[4-(1-methyl-1H-pyrazole-4-carbonyl)-piperidin-1-yl]-4-oxo-butyl}-2H-pyrrolo[1,2-a]pyrazin-1-one |
| "C99" | 6-{4-[4-(6-Methoxy-pyridine-3-carbonyl)-piperidin-1-yl]-4-oxo-butyl}-3-methyl-7H-imidazo[1,5-a]pyrazin-8-one | and pharmaceutically acceptable solvates, salts, tautomers and stereoisomers thereof, including mixtures thereof in all ratios.

14. The compound according to claim 1, wherein said compound is selected from the following compounds

| No. | Name |
|---|---|
| "C105" | 3-Methyl-6-{4-[4-(1-methyl-1H-pyrazole-4-carbonyl)-piperidin-1-yl]-4-oxo-butyl}-7H-imidazo[1,5-a]pyrazin-8-one |
| "C113" | 2-{4-[4-(3-Fluoro-4-methoxy-benzoyl)-piperidin-1-yl]-4-oxo-butyl}-7-methyl-3H-thieno[3,4-d]pyrimidin-4-one |
| "C114" | 2-{4-[4-(4-Methoxy-3-methyl-benzoyl)-piperidin-1-yl]-4-oxo-butyl}-7-methyl-3H-thieno[3,4-d]pyrimidin-4-one |
| "C115" | 6-Amino-1'-[4-(7-methyl-4-oxo-3,4-dihydro-thieno[3,4-d]pyrimidin-2-yl)-butyryl]-1',2',3',4',5',6'-hexahydro-[3,4']bipyridinyl-5-carbonitrile |
| "C116" | 2-[4-(6-Amino-5-pyrimidin-2-yl-3',4',5',6'-tetrahydro-2'H-[3,4']bipyridinyl-1'-yl)-4-oxo-butyl]-7-methyl-3H-thieno[3,4-d]pyrimidin-4-one |
| "C117" | 7-Methyl-2-{4-oxo-4-[4-(5-phenyl-[1,3,4]oxadiazol-2-yl)-piperidin-1-yl]-butyl}-3H-thieno[3,4-d]pyrimidin-4-one |
| "C118" | 4-{1-[4-(7-Methyl-4-oxo-3,4-dihydro-thieno[3,4-d]pyrimidin-2-yl)-butyryl]-piperidin-4-yloxy}-benzonitrile |
| "C119" | 2-{4-[4-(4-Fluoro-benzoyl)-piperidin-1-yl]-4-oxo-butyl}-7-methyl-3H-thieno[3,4-d]pyrimidin-4-one |
| "C120" | 2-{4-[4-(4-Methoxy-3-methyl-benzoyl)-piperidin-1-yl]-4-oxo-butyl}-7-methyl-3H-thieno[3,4-d]pyrimidin-4-one |
| "C121" | 2-(4-{4-[4-(1-Hydroxy-1-methyl-ethyl)-benzoyl]-piperidin-1-yl}-4-oxo-butyl)-7-methyl-3H-thieno[3,4-d]pyrimidin-4-one |
| "C123" | 7-Methyl-2-{4-[4-(1-methyl-1H-pyrazole-4-carbonyl)-piperidin-1-yl]-4-oxo-butyl}-3H-thieno[3,4-d]pyrimidin-4-one |
| "C126" | 2-{4-[4-(6-Methoxypyridine-3-carbonyl)-1-piperidyl]-4-oxo-butyl}-7-methyl-3H-thieno[3,2-d]pyrimidin-4-one |
| "C128" | 2-{4-[4-(6-Amino-5-pyrimidin-2-yl-3-pyridyl)-1-piperidyl]-4-oxo-butyl}-7-methyl-3H-thieno[3,2-d]pyrimidin-4-one |
| "C130" | 4-{{1-[4-(7-Methyl-4-oxo-3H-thieno[3,2-d]pyrimidin-2-yl)butanoyl]-4-piperidyl}oxy}benzonitrile |
| "C131" | 2-{4-[4-(4-Fluorobenzoyl)-1-piperidyl]-4-oxo-butyl}-7-methyl-3H-thieno[3,2-d]pyrimidin-4-one |
| "C132" | 2-{4-[4-(4-Methoxy-3-methyl-benzoyl)-1-piperidyl]-4-oxo-butyl}-7-methyl-3H-thieno[3,2-d]pyrimidin-4-one |
| "C133" | 2-{4-{4-[4-(1-Hydroxy-1-methyl-ethyl)benzoyl]-1-piperidyl}-4-oxo-butyl}-7-methyl-3H-thieno[3,2-d]pyrimidin-4-one |
| "C135" | 7-Methyl-2-{4-[4-(1-methyl-1H-pyrazole-4-carbonyl)-piperidin-1-yl]-4-oxo-butyl}-3H-thieno[3,2-d]pyrimidin-4-one |
| "C136" | 2-{4-[4-(3-Fluoro-4-methoxy-benzoyl)-piperidin-1-yl]-4-oxo-butyl}-3H-pyrrolo[2,1-f][1,2,4]triazin-4-one |
| "C137" | 2-{4-[4-(6-Methoxy-pyridine-3-carbonyl)-piperidin-1-yl]-4-oxo-butyl}-3H-pyrrolo[2,1-f][1,2,4]triazin-4-one |
| "C138" | 6-Amino-1'-[4-(4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |
| "C139" | 2-[4-(6-Amino-5-pyrimidin-2-yl-3',4',5',6'-tetrahydro-2'H-[3,4']bipyridinyl-1'-yl)-4-oxo-butyl]-3H-pyrrolo[2,1-f][1,2,4]triazin-4-one |
| "C140" | 2-{4-Oxo-4-[4-(5-phenyl-[1,3,4]oxadiazol-2-yl)-piperidin-1-yl]-butyl}-3H-pyrrolo[2,1-f][1,2,4]triazin-4-one |
| "C141" | 4-{1-[4-(4-Oxo-3,4-dihydro-pyrrolo[2,1-f][1,2,4]triazin-2-yl)-butyryl]-piperidin-4-yloxy}-benzonitrile |
| "C142" | 2-{4-[4-(4-Fluoro-benzoyl)-piperidin-1-yl]-4-oxo-butyl}-3H-pyrrolo[2,1-f][1,2,4]triazin-4-one |
| "C143" | 2-{4-[4-(4-Methoxy-3-methyl-benzoyl)-piperidin-1-yl]-4-oxo-butyl}-3H-pyrrolo[2,1-f][1,2,4]triazin-4-one |
| "C144" | 2-(4-{4-[4-(1-Hydroxy-1-methyl-ethyl)-benzoyl]-piperidin-1-yl}-4-oxo-butyl)-3H-pyrrolo[2,1-f][1,2,4]triazin-4-one |
| "C146" | 2-{4-[4-(1-Methyl-1H-pyrazole-4-carbonyl)-piperidin-1-yl]-4-oxo-butyl}-3H-pyrrolo[2,1-f][1,2,4]triazin-4-one |
| "C147" | 2-{4-[4-(3-Fluoro-4-methoxy-benzoyl)-piperidin-1-yl]-4-oxo-butyl}-7-methyl-3H-pyrrolo[2,1-f][1,2,4]triazin-4-one |
| "C148" | 2-{4-[4-(6-Methoxy-pyridine-3-carbonyl)-piperidin-1-yl]-4-oxo-butyl}-7-methyl-3H-pyrrolo[2,1-f][1,2,4]triazin-4-one |
| "C149" | 6-Amino-1'-[4-(7-methyl-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |
| "C150" | 2-[4-(6-Amino-5-pyrimidin-2-yl-3',4',5',6'-tetrahydro-2'H-[3,4']bipyridinyl-1'-yl)-4-oxo-butyl]-7-methyl-3H-pyrrolo[2,1-f][1,2,4]triazin-4-one |
| "C151" | 7-Methyl-2-{4-oxo-4-[4-(5-phenyl-[1,3,4]oxadiazol-2-yl)-piperidin-1-yl]-butyl}-3H-pyrrolo[2,1-f][1,2,4]triazin-4-one |
| "C152" | 4-{1-[4-(7-Methyl-4-oxo-3,4-dihydro-pyrrolo[2,1-f][1,2,4]triazin-2-yl)-butyryl]-piperidin-4-yloxy}-benzonitrile |
| "C153" | 2-{4-[4-(4-Fluoro-benzoyl)-piperidin-1-yl]-4-oxo-butyl}-7-methyl-3H-pyrrolo[2,1-f][1,2,4]triazin-4-one |
| "C154" | 2-{4-[4-(4-Methoxy-3-methyl-benzoyl)-piperidin-1-yl]-4-oxo-butyl}-7-methyl-3H-pyrrolo[2,1-f][1,2,4]triazin-4-one |
| "C155" | 2-(4-{4-[4-(1-Hydroxy-1-methyl-ethyl)-benzoyl]-piperidin-1-yl}-4-oxo-butyl)-7-methyl-3H-pyrrolo[2,1-f][1,2,4]triazin-4-one |
| "C157" | 7-Methyl-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C158" | 2-{4-[4-(3-Fluoro-4-methoxy-benzoyl)-piperidin-1-yl]-4-oxo-butyl}-6-methyl-3H-pyrrolo[2,1-f][1,2,4]triazin-4-one |
| "C159" | 2-{4-[4-(6-Methoxy-pyridine-3-carbonyl)-piperidin-1-yl]-4-oxo-butyl}-6-methyl-3H-pyrrolo[2,1-f][1,2,4]triazin-4-one |
| "C160" | 6-Amino-1'-[4-(6-methyl-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |
| "C161" | 2-[4-(6-Amino-5-pyrimidin-2-yl-3',4',5',6'-tetrahydro-2'H-[3,4']bipyridinyl-1'-yl)-4-oxo-butyl]-6-methyl-3H-pyrrolo[2,1-f][1,2,4]triazin-4-one |
| "C162" | 6-Methyl-2-{4-oxo-4-[4-(5-phenyl-[1,3,4]oxadiazol-2-yl)-piperidin-1-yl]-butyl}-3H-pyrrolo[2,1-f][1,2,4]triazin-4-one |
| "C163" | 4-{1-[4-(6-Methyl-4-oxo-3,4-dihydro-pyrrolo[2,1-f][1,2,4]triazin-2-yl)-butyryl]-piperidin-4-yloxy}-benzonitrile |
| "C164" | 2-{4-[4-(4-Fluoro-benzoyl)-piperidin-1-yl]-4-oxo-butyl}-6-methyl-3H-pyrrolo[2,1-f][1,2,4]triazin-4-one |
| "C165" | 2-{4-[4-(4-Methoxy-3-methyl-benzoyl)-piperidin-1-yl]-4-oxo-butyl}-6-methyl-3H-pyrrolo[2,1-f][1,2,4]triazin-4-one |
| "C166" | 2-(4-{4-[4-(1-Hydroxy-1-methyl-ethyl)-benzoyl]-piperidin-1-yl}-4-oxo-butyl)-6-methyl-3H-pyrrolo[2,1-f][1,2,4]triazin-4-one |
| "C168" | 6-Methyl-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C169" | 6-Fluoro-2-{4-[4-(3-fluoro-4-methoxy-benzoyl)-piperidin-1-yl]-4-oxo-butyl}-3H-pyrrolo[2,1-f][1,2,4]triazin-4-one |
| "C170" | 6-Fluoro-2-{4-[4-(6-methoxy-pyridine-3-carbonyl)-piperidin-1-yl]-4-oxo-butyl}-3H-pyrrolo[2,1-f][1,2,4]triazin-4-one |
| "C171" | 6-Amino-1'-[4-(6-fluoro-4-oxo-3,4-dihydro-pyrrolo[2,1-f][1,2,4]triazin-2-yl)-butyryl]-1',2',3',4',5',6'-hexahydro-[3,4']bipyridinyl-5-carbonitrile |
| "C172" | 2-[4-(6-Amino-5-pyrimidin-2-yl-3',4',5',6'-tetrahydro-2'H-[3,4']bipyridinyl-1'-yl)-4-oxo-butyl]-6-fluoro-3H-pyrrolo[2,1-f][1,2,4]triazin-4-one |
| "C173" | 6-Fluoro-2-{4-oxo-4-[4-(5-phenyl-[1,3,4]oxadiazol-2-yl)-piperidin-1-yl]-butyl}-3H-pyrrolo[2,1-f][1,2,4]triazin-4-one |
| "C174" | 4-{1-[4-(6-Fluoro-4-oxo-3,4-dihydro-pyrrolo[2,1-f][1,2,4]triazin-2-yl)-butyryl]-piperidin-4-yloxy}-benzonitrile |
| "C175" | 6-Fluoro-2-{4-[4-(4-fluoro-benzoyl)-piperidin-1-yl]-4-oxo-butyl}-3H-pyrrolo[2,1-f][1,2,4]triazin-4-one |
| "C177" | 6-Fluoro-2-(4-{4-[4-(1-hydroxy-1-methyl-ethyl)-benzoyl]-piperidin-1-yl}-4-oxo-butyl)-3H-pyrrolo[2,1-f][1,2,4]triazin-4-one |
| "C179" | 6-Fluoro-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C180" | 2-{4-[4-(3-Fluoro-4-methoxy-benzoyl)-piperidin-1-yl]-4-oxo-butyl}-7-methyl-3,7-dihydro-pyrrolo[2,3-d]pyrimidin-4-one |
| "C181" | 2-{4-[4-(6-Methoxy-pyridine-3-carbonyl)-piperidin-1-yl]-4-oxo-butyl}-7-methyl-3,7-dihydro-pyrrolo[2,3-d]pyrimidin-4-one |
| "C182" | 6-Amino-1'-[4-(7-methyl-4-oxo-4,7-dihydro-3H-pyrrolo[2,3-d]pyrimidin-2-yl)-butyryl]-1',2',3',4',5',6'-hexahydro-[3,4']bipyridinyl-5-carbonitrile |
| "C183" | 2-[4-(6-Amino-5-pyrimidin-2-yl-3',4',5',6'-tetrahydro-2'H-[3,4']bipyridinyl-1'-yl)-4-oxo-butyl]-7-methyl-3,7-dihydro-pyrrolo[2,3-d]pyrimidin-4-one |
| "C184" | 7-Methyl-2-{4-oxo-4-[4-(5-phenyl-[1,3,4]oxadiazol-2-yl)-piperidin-1-yl]-butyl}-3,7-dihydro-pyrrolo[2,3-d]pyrimidin-4-one |
| "C186" | 2-{4-[4-(4-Fluoro-benzoyl)-piperidin-1-yl]-4-oxo-butyl}-7-methyl-3,7-dihydro-pyrrolo[2,3-d]pyrimidin-4-one |
| "C190" | 7-Methyl-2-{4-[4-(1-methyl-1H-pyrazole-4-carbonyl)-piperidin-1-yl]-4-oxo-butyl}-3,7-dihydro-pyrrolo[2,3-d]pyrimidin-4-one |
| "C191" | 1-Methyl-5-{4-[4-(1-methyl-1H-pyrazole-4-carbonyl)-piperidin-1-yl]-4-oxo-butyl}-1,6-dihydro-pyrazolo[4,3-d]pyrimidin-7-one |
| "C192" | 2-{4-[4-(3-Fluoro-4-methoxy-benzoyl)-piperidin-1-yl]-4-oxo-butyl}-3,5,7,8-tetrahydro-pyrano[4,3-d]pyrimidin-4-one | and pharmaceutically acceptable solvates, salts, tautomers and stereoisomers thereof, including mixtures thereof in all ratios.

15. The compound according to claim 1, wherein said compound is selected from the following compounds

| No. | Name |
|---|---|
| "C193" | 2-{4-[4-(6-Methoxy-pyridine-3-carbonyl)-piperidin-1-yl]-4-oxo-butyl}-3,5,7,8-tetrahydro-pyrano[4,3-d]pyrimidin-4-one |
| "C194" | 6-Amino-1'-[4-(4-oxo-3,5,7,8-tetrahydro-4H-pyrano[4,3-d]pyrimidin-2-yl)-butyryl]-1',2',3',4',5',6'-hexahydro-[3,4']bipyridinyl-5-carbonitrile |
| "C195" | 2-[4-(6-Amino-5-pyrimidin-2-yl-3',4',5',6'-tetrahydro-2'H-[3,4']bipyridinyl-1'-yl)-4-oxo-butyl]-3,5,7,8-tetrahydro-pyrano[4,3-d]pyrimidin-4-one |
| "C196" | 2-{4-Oxo-4-[4-(5-phenyl-[1,3,4]oxadiazol-2-yl)-piperidin-1-yl]-butyl}-3,5,7,8-tetrahydro-pyrano[4,3-d]pyrimidin-4-one |
| "C197" | 4-{1-[4-(4-Oxo-3,5,7,8-tetrahydro-4H-pyrano[4,3-d]pyrimidin-2-yl)-butyryl]-piperidin-4-yloxy}-benzonitrile |
| "C198" | 2-{4-[4-(4-Fluoro-benzoyl)-piperidin-1-yl]-4-oxo-butyl}-3,5,7,8-tetrahydro-pyrano[4,3-d]pyrimidin-4-one |
| "C199" | 2-{4-[4-(4-Methoxy-3-methyl-benzoyl)-piperidin-1-yl]-4-oxo-butyl}-3,5,7,8-tetrahydro-pyrano[4,3-d]pyrimidin-4-one |
| "C200" | 2-(4-{4-[4-(1-Hydroxy-1-methyl-ethyl)-benzoyl]-piperidin-1-yl}-4-oxo-butyl)-3,5,7,8-tetrahydro-pyrano[4,3-d]pyrimidin-4-one | and pharmaceutically acceptable solvates, salts, tautomers and stereoisomers thereof, including mixtures thereof in all ratios.

16. The compound according to claim 1, wherein said compound is selected from the following compounds

| No. | Name |
|---|---|
| "C202" | 2-{4-[4-(1-Methyl-1H-pyrazole-4-carbonyl)-piperidin-1-yl]-4-oxo-butyl}-3,5,7,8-tetrahydro-pyrano[4,3-d]pyrimidin-4-one |
| "C207" | 6-{4-[4-(1-Methylpyrazole-4-carbonyl)-1-piperidyl]-4-oxo-butyl}-7H-imidazo[1,5-a]pyrazin-8-one |
| "C208" | 6-Fluoro-3-{4-[4-(1-methyl-1H-pyrazole-4-carbonyl)-piperidin-1-yl]-4-oxo-butyl}-2H-pyrrolo[1,2-a]pyrazin-1-one |
| "C209" | 2-Methyl-6-{4-[4-(1-methyl-1H-pyrazole-4-carbonyl)-piperidin-1-yl]-4-oxo-butyl}-5H-pyrazolo[1,5-a]pyrazin-4-one |
| "C210" | 3-{4-[4-(1-Isopropyl-1H-pyrazole-4-carbonyl)-piperidin-1-yl]-4-oxo-butyl}-2H-pyrrolo[1,2-a]pyrazin-1-one |
| "C211" | 3-{4-[4-(1-Isopropyl-1H-pyrazole-4-carbonyl)-piperidin-1-yl]-4-oxo-butyl}-6-methyl-2H-pyrrolo[1,2-a]pyrazin-1-one |
| "C212" | 6-Fluoro-3-{4-[4-(1-isopropyl-1H-pyrazole-4-carbonyl)-piperidin-1-yl]-4-oxo-butyl}-2H-pyrrolo[1,2-a]pyrazin-1-one |
| "C213" | 6-{4-[4-(1-Ethyl-1H-pyrazole-4-carbonyl)-piperidin-1-yl]-4-oxo-butyl}-1-methyl-1,5-dihydro-pyrazolo[3,4-d]pyrimidin-4-one |
| "C214" | 2-{4-[4-(1-Ethyl-1H-pyrazole-4-carbonyl)-piperidin-1-yl]-4-oxo-butyl}-3H-pyrrolo[2,1-f][1,2,4]triazin-4-one |
| "C215" | 2-{4-[4-(1-Ethyl-1H-pyrazole-4-carbonyl)-piperidin-1-yl]-4-oxo-butyl}-6-fluoro-3H-pyrrolo[2,1-f][1,2,4]triazin-4-one |
| "C216" | 2-{4-[4-(1-Ethyl-1H-pyrazole-4-carbonyl)-piperidin-1-yl]-4-oxo-butyl}-7-methyl-3H-thieno[3,4-d]pyrimidin-4-one |
| "C217" | 6-{4-[4-(1-Isopropyl-1H-pyrazole-4-carbonyl)-piperidin-1-yl]-4-oxo-butyl}-2-methyl-5H-pyrazolo[1,5-a]pyrazin-4-one |
| "C218" | 6-{4-[4-(1-Isopropyl-1H-pyrazole-4-carbonyl)-piperidin-1-yl]-4-oxo-butyl}-1-methyl-1,5-dihydro-pyrazolo[3,4-d]pyrimidin-4-one |
| "C219" | 2-{4-[4-(1-Isopropyl-1H-pyrazole-4-carbonyl)-piperidin-1-yl]-4-oxo-butyl}-3H-pyrrolo[2,1-f][1,2,4]triazin-4-one |
| "C220" | 2-{4-[4-(1-Isopropyl-1H-pyrazole-4-carbonyl)-piperidin-1-yl]-4-oxo-butyl}-6-methyl-3H-pyrrolo[2,1-f][1,2,4]triazin-4-one |
| "C221" | 6-Fluoro-2-{4-[4-(1-isopropyl-1H-pyrazole-4-carbonyl)-piperidin-1-yl]-4-oxo-butyl}-3H-pyrrolo[2,1-f][1,2,4]triazin-4-one |
| "C222" | 2-{4-[4-(1-Ethyl-1H-pyrazole-4-carbonyl)-piperidin-1-yl]-4-oxo-butyl}-7-methyl-3H-pyrrolo[2,1-f][1,2,4]triazin-4-one |
| "C223" | 2-{4-[4-(1-Isopropyl-1H-pyrazole-4-carbonyl)-piperidin-1-yl]-4-oxo-butyl}-7-methyl-3H-pyrrolo[2,1-f][1,2,4]triazin-4-one |
| "C224" | 2-{4-[4-(1-Ethyl-1H-pyrazole-4-carbonyl)-piperidin-1-yl]-4-oxo-butyl}-7-methyl-3H-thieno[3,2-d]pyrimidin-4-one |
| "C225" | 2-{4-[4-(1-Isopropyl-1H-pyrazole-4-carbonyl)-piperidin-1-yl]-4-oxo-butyl}-7-methyl-3H-thieno[3,2-d]pyrimidin-4-one |
| "C226" | 2-{4-[4-(1-Isopropyl-1H-pyrazole-4-carbonyl)-piperidin-1-yl]-4-oxo-butyl}-7-methyl-3H-thieno[3,4-d]pyrimidin-4-one |
| "C227" | 2-{4-[4-(4-Methoxy-benzoyl)-piperidin-1-yl]-4-oxo-butyl}-5,6,7,8-tetrahydro-3H-quinazolin-4-one |
| "C228" | 2-{4-[4-(1-Ethyl-1H-pyrazole-4-carbonyl)-piperidin-1-yl]-4-oxo-butyl}-3,5,7,8-tetrahydro-pyrano[4,3-d]pyrimidin-4-one |
| "C229" | 2-{4-[4-(1-Isopropyl-1H-pyrazole-4-carbonyl)-piperidin-1-yl]-4-oxo-butyl}-3,5,7,8-tetrahydro-pyrano[4,3-d]pyrimidin-4-one |
| "C230" | 2-{4-[4-(1-Methyl-1H-pyrazole-4-carbonyl)-piperidin-1-yl]-4-oxo-butyl}-5,6,7,8-tetrahydro-3H-quinazolin-4-one |
| "C231" | 6-{4-[4-(6-Methoxy-pyridine-3-carbonyl)-piperidin-1-yl]-4-oxo-butyl}-2-methyl-5H-pyrazolo[1,5-a]pyrazin-4-one |
| "C232" | 6-Amino-1'-[4-(4-oxo-3,4,5,6,7,8-hexahydro-quinazolin-2-yl)-butyryl]-1',2',3',4',5',6'-hexahydro-[3,4']bipyridinyl-5-carbonitrile |
| "C233" | 2-{4-[4-(1-Ethyl-1H-pyrazole-4-carbonyl)-piperidin-1-yl]-4-oxo-butyl}-6-methyl-3H-pyrrolo[2,1-f][1,2,4]triazin-4-one |
| "C234" | 1-Methyl-6-{4-[4-(4-methyl-benzoyl)-piperidin-1-yl]-4-oxo-butyl}-1,5-dihydro-pyrazolo[3,4-d]pyrimidin-4-one |
| "C235" | 2-{4-[4-(4-Methyl-benzoyl)-piperidin-1-yl]-4-oxo-butyl}-3H-pyrrolo[2,1-f][1,2,4]triazin-4-one |
| "C236" | 6-{4-[4-(4-Chloro-benzoyl)-piperidin-1-yl]-4-oxo-butyl}-1-methyl-1,5-dihydro-pyrazolo[3,4-d]pyrimidin-4-one |
| "C237" | 2-{4-[4-(4-Chloro-benzoyl)-piperidin-1-yl]-4-oxo-butyl}-3H-pyrrolo[2,1-f][1,2,4]triazin-4-one |
| "C238" | 6,7-Difluoro-2-{4-[4-(1-methyl-1H-pyrazole-4-carbonyl)-piperidin-1-yl]-4-oxo-butyl}-3H-pyrrolo[2,1-f][1,2,4]triazin-4-one |
| "C239" | 2-{4-[4-(4-Methoxy-benzoyl)-piperidin-1-yl]-4-oxo-butyl}-5,6-dimethyl-3H-pyrimidin-4-one |
| "C240" | 2-{4-[4-(4-Fluoro-benzoyl)-piperidin-1-yl]-4-oxo-butyl}-5,6-dimethyl-3H-pyrimidin-4-one |
| "C241" | 2-{4-[4-(6-Methoxy-pyridine-3-carbonyl)-piperidin-1-yl]-4-oxo-butyl}-5,6-dimethyl-3H-pyrimidin-4-one |
| "C242" | 5,6-Dimethyl-2-{4-[4-(1-methyl-1H-pyrazole-4-carbonyl)-piperidin-1-yl]-4-oxo-butyl}-3H-pyrimidin-4-one |
| "C243" | 2-{4-[4-(1-Ethyl-1H-pyrazole-4-carbonyl)-piperidin-1-yl]-4-oxo-butyl}-7-methyl-3,7-dihydro-pyrrolo[2,3-d]pyrimidin-4-one |
| "C244" | 2-{4-[4-(1-Isopropyl-1H-pyrazole-4-carbonyl)-piperidin-1-yl]-4-oxo-butyl}-7-methyl-3,7-dihydro-pyrrolo[2,3-d]pyrimidin-4-one |
| "C245" | 6-(4-{4-[4-(1,1-Difluoro-ethyl)-benzoyl]-piperidin-1-yl}-4-oxo-butyl)-1-methyl-1,5-dihydro-pyrazolo[3,4-d]pyrimidin-4-one |
| "C246" | 6-{4-[4-(3,4-Difluoro-benzoyl)-piperidin-1-yl]-4-oxo-butyl}-1-methyl-1,5-dihydro-pyrazolo[3,4-d]pyrimidin-4-one |
| "C247" | 2-{4-[4-(4-Chloro-benzoyl)-piperidin-1-yl]-4-oxo-butyl}-3,5,7,8-tetrahydro-pyrano[4,3-d]pyrimidin-4-one |
| "C248" | 2-{4-[4-(3,4-Difluoro-benzoyl)-piperidin-1-yl]-4-oxo-butyl}-7-methyl-3,7-dihydro-pyrrolo[2,3-d]pyrimidin-4-one |
| "C249" | 2-(4-{4-[4-(1,1-Difluoro-ethyl)-benzoyl]-piperidin-1-yl}-4-oxo-butyl)-7-methyl-3,7-dihydro-pyrrolo[2,3-d]pyrimidin-4-one |
| "C250" | 1-[4-(4-Methoxy-benzoyl)-piperidin-1-yl]-4-phthalazin-1-yl-butan-1-one |
| "C251" | 6-Ethyl-2-{4-[4-(4-methoxy-benzoyl)-piperidin-1-yl]-4-oxo-butyl}-3H-pyrimidin-4-one |
| "C252" | 6-Ethyl-2-{4-[4-(4-fluoro-benzoyl)-piperidin-1-yl]-4-oxo-butyl}-3H-pyrimidin-4-one |
| "C253" | 6-Ethyl-2-{4-[4-(6-methoxy-pyridine-3-carbonyl)-piperidin-1-yl]-4-oxo-butyl}-3H-pyrimidin-4-one |
| "C254" | 6-Isopropyl-2-{4-[4-(4-methoxy-benzoyl)-piperidin-1-yl]-4-oxo-butyl}-3H-pyrimidin-4-one |
| "C255" | 2-{4-[4-(4-Fluorobenzoyl)-1-piperidyl]-4-oxo-butyl}-4-isopropyl-1H-pyrimidin-6-one |
| "C256" | 4-Isopropyl-2-{4-[4-(6-methoxypyridine-3-carbonyl)-1-piperidyl]-4-oxo-butyl}-1H-pyrimidin-6-one |
| "C257" | 4-Isopropyl-2-{4-[4-(1-methylpyrazole-4-carbonyl)-1-piperidyl]-4-oxo-butyl}-1H-pyrimidin-6-one |
| "C258" | 4-(1,2-Benzoxazol-3-yl)-1-[4-(4-methoxybenzoyl)-1-piperidyl]butan-1-one |
| "C259" | 4-(1,2-Benzoxazol-3-yl)-1-[4-(4-fluorobenzoyl)-1-piperidyl]butan-1-one |
| "C259a" | 4-(1,2-Benzoxazol-3-yl)-1-[4-(6-methoxypyridine-3-carbonyl)-1-piperidyl]butan-1-one |
| "C260" | 4-(1,2-Benzoxazol-3-yl)-1-[4-(1-methylpyrazole-4-carbonyl)-1-piperidyl]butan-1-one |
| "C261" | 4-Ethyl-2-{4-[4-(1-methylpyrazole-4-carbonyl)-1-piperidyl]-4-oxo-butyl}-1H-pyrimidin-6-one |
| "C262" | 2-{4-[4-(3,4-Difluorobenzoyl)-1-piperidyl]-4-oxo-butyl}-3,5,7,8-tetrahydropyrano[4,3-d]pyrimidin-4-one |
| "C263" | 2-{4-{4-[4-(1,1-Difluoroethyl)benzoyl]-1-piperidyl}-4-oxo-butyl}-3,5,7,8-tetrahydropyrano[4,3-d]pyrimidin-4-one |
| "C266" | 1-[4-(1-Methylpyrazole-4-carbonyl)-1-piperidyl]-4-phthalazin-1-yl-butan-1-one | and pharmaceutically acceptable solvates, salts, tautomers and stereoisomers thereof, including mixtures thereof in all ratios.

17. The compound 3-{4-[3-(4-Methoxy-benzoyl)-azetidin-1-yl]-4-oxo-butyl}-2H-pyrrolo[1,2-a]pyrazin-1-one ("D1")

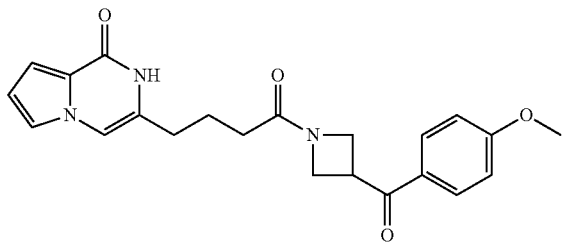 [SMILES: COc1ccc(C(=O)C2CN(C(=O)CCCc3cn4cccc4c(=O)[nH]3)C2)cc1]

and pharmaceutically acceptable solvates, salts, tautomers and stereoisomers thereof, including mixtures thereof in all ratios.

18. A method for the treatment of cancer, multiple sclerosis, cardiovascular diseases, central nervous system injury and different forms of inflammation, comprising administering to a patient a compound according to claim 1, wherein treatment refers to alleviation of, or slowing further progression worsening of, symptoms of the disorder or disease.

19. The method according to claim 18, wherein said method is for the treatment of diseases selected from the group cancer of head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

20. A process for the preparation of compounds of the formula I according to claim 1 and pharmaceutically acceptable salts, solvates, tautomers and stereoisomers thereof, said process comprising:
reacting a compound of formula II

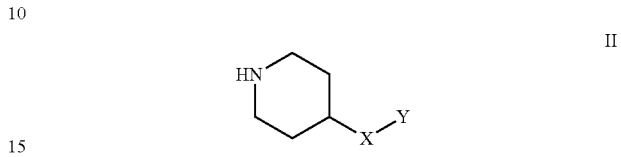

in which X and Y have the meanings indicated in claim 1, with a compound of formula III

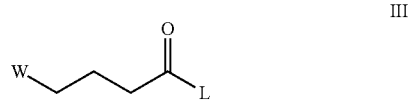

in which W has the meanings indicated in claim 1,
and L denotes Cl, Br, I or a free or reactively functionally modified OH group,
and/or
a base or acid of the formula I is converted into one of its salts.

* * * * *